US011168344B2

(12) United States Patent
Igawa et al.

(10) Patent No.: US 11,168,344 B2
(45) Date of Patent: Nov. 9, 2021

(54) METHODS FOR PRODUCING POLYPEPTIDES BY REGULATING POLYPEPTIDE ASSOCIATION

(71) Applicant: Chugai Seiyaku Kabushiki Kaisha, Tokyo (JP)

(72) Inventors: Tomoyuki Igawa, Shizuoka (JP); Hiroyuki Tsunoda, Shizuoka (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 960 days.

(21) Appl. No.: 15/782,256

(22) Filed: Oct. 12, 2017

(65) Prior Publication Data
US 2018/0051307 A1    Feb. 22, 2018

Related U.S. Application Data

(63) Continuation of application No. 11/910,128, filed as application No. PCT/JP2006/306803 on Mar. 31, 2006, now Pat. No. 10,011,858.

(30) Foreign Application Priority Data

Mar. 31, 2005 (JP) ................... 2005-101105
Dec. 28, 2005 (JP) ................... 2005-378266

(51) Int. Cl.
A61K 39/00 (2006.01)
C12P 21/02 (2006.01)
C07K 16/18 (2006.01)

(52) U.S. Cl.
CPC ............. C12P 21/02 (2013.01); C07K 16/18 (2013.01); *A61K 2039/505* (2013.01); *C07K 2317/31* (2013.01)

(58) Field of Classification Search
CPC .............................................. A61K 2039/505
See application file for complete search history.

(56) References Cited

U.S. PATENT DOCUMENTS

| | | |
|---|---|---|
| 4,208,479 A | 6/1980 | Zuk et al. |
| 4,444,878 A | 4/1984 | Paulus |
| 4,474,893 A | 10/1984 | Reading |
| 5,126,250 A | 6/1992 | McDonough et al. |
| 5,322,678 A | 6/1994 | Morgan et al. |
| 5,496,549 A | 3/1996 | Yamazaki et al. |
| 5,591,828 A | 1/1997 | Bosslet et al. |
| 5,639,641 A | 6/1997 | Pedersen et al. |
| 5,670,373 A | 9/1997 | Kishimoto |
| 5,744,446 A | 4/1998 | Lollar et al. |
| 5,795,965 A | 8/1998 | Tsuchiya et al. |
| 5,837,821 A | 11/1998 | Wu |
| 5,859,205 A | 1/1999 | Adair et al. |
| 5,877,291 A | 3/1999 | Mezes et al. |
| 5,945,311 A | 8/1999 | Lindhofer et al. |
| 5,990,286 A | 11/1999 | Khawli et al. |
| 6,005,091 A | 12/1999 | Blackburn et al. |
| 6,010,902 A | 1/2000 | Ledbetter et al. |
| 6,126,980 A | 10/2000 | Smith et al. |
| 6,129,914 A | 10/2000 | Weiner |
| 6,132,992 A | 10/2000 | Ledbetter et al. |
| 6,183,744 B1 | 2/2001 | Goldenberg |
| 6,323,000 B2 | 11/2001 | Briggs et al. |
| 6,329,511 B1 | 12/2001 | Vasquez et al. |
| 6,342,220 B1 | 1/2002 | Adams et al. |
| 6,368,596 B1 | 4/2002 | Ghetie et al. |
| 6,485,943 B2 | 11/2002 | Stevens et al. |
| 6,677,436 B1 | 1/2004 | Sato et al. |
| 6,683,157 B2 | 1/2004 | Briggs et al. |
| 6,699,686 B1 | 3/2004 | Brocard et al. |
| 6,723,319 B1 | 4/2004 | Ito et al. |
| 6,737,056 B1 | 5/2004 | Presta |
| 6,884,879 B1 | 4/2005 | Baca et al. |
| 6,913,747 B1 | 7/2005 | Co et al. |
| 7,018,632 B2 | 3/2006 | Lindhofer et al. |
| 7,033,590 B1 | 4/2006 | Scheiflinger et al. |
| 7,052,873 B2 | 5/2006 | Tsuchiya |
| 7,122,637 B2 | 10/2006 | Presta |
| 7,217,797 B2 | 5/2007 | Hinton et al. |
| 7,276,585 B2 | 10/2007 | Lazar et al. |
| 7,538,196 B2 | 5/2009 | Jung |
| 7,615,213 B2 | 11/2009 | Kasaian et al. |
| 7,732,149 B2 | 6/2010 | Kojima et al. |
| 8,062,635 B2 | 11/2011 | Hattori et al. |
| 8,217,147 B2 | 7/2012 | Stavenhagen et al. |

(Continued)

FOREIGN PATENT DOCUMENTS

| | | |
|---|---|---|
| AU | 755822 | 3/1999 |
| AU | 2009290162 | 4/2010 |

(Continued)

OTHER PUBLICATIONS

Ratten et al. (Protein Eng. Apr. 1998; 11 (4): 303-9).*
Müller et al. (FEBS Lett. Jan. 30, 1998; 422 (2): 259-64).*
Mazor et al. (MAbs. 2015; 7 (2): 377-89).*
Golay et al. (J. Immunol. Apr. 1, 2016; 196 (7): 3199-211).*
U.S. Appl. No. 15/024,063, Igawa et al., filed Mar. 23, 2016.
U.S. Appl. No. 10/575,905, Hattori et al., filed Apr. 30, 2007 (abandoned).
U.S. Appl. No. 11/910,836, Hattori et al., filed Jan. 12, 2009 (abandoned).
U.S. Appl. No. 13/434,643, Hattori et al., filed Mar. 29, 2012 (abandoned).
U.S. Appl. No. 14/921,590, Hattori et al., filed Oct. 23, 2015 (abandoned).
U.S. Appl. No. 15/172,727, Hattori et al., filed Jun. 3, 2016 (abandoned).

(Continued)

Primary Examiner — Stephen L Rawlings
(74) Attorney, Agent, or Firm — Fish & Richardson P.C.

(57) ABSTRACT

In the course of the present invention, it was discovered that one could regulate association between polypeptides by modifying amino acid residues that form the interface during the association to amino acids carrying the same type of charge. In this context, the present invention enables efficient formation of heterologous molecules. For example, the present invention can be suitably applied to the preparation of bispecific antibodies.

39 Claims, 32 Drawing Sheets

Specification includes a Sequence Listing.

(56) References Cited

U.S. PATENT DOCUMENTS

| | | |
|---|---|---|
| 8,592,562 B2 | 11/2013 | Kannan et al. |
| 8,597,911 B2 | 12/2013 | Miyazaki et al. |
| 8,637,641 B2 | 1/2014 | Dahiyat et al. |
| 9,096,651 B2 | 8/2015 | Igawa et al. |
| 9,228,017 B2 | 1/2016 | Igawa et al. |
| 9,334,331 B2 | 5/2016 | Igawa et al. |
| 9,527,926 B2 | 12/2016 | Ho et al. |
| 9,556,279 B2 | 1/2017 | Niwa et al. |
| 9,637,557 B2 | 5/2017 | Scheer et al. |
| 9,670,269 B2 | 6/2017 | Igawa et al. |
| 9,688,762 B2 | 6/2017 | Igawa et al. |
| 9,828,429 B2 | 11/2017 | Igawa et al. |
| 9,975,966 B2 | 5/2018 | Nezu et al. |
| 10,011,858 B2 | 7/2018 | Igawa et al. |
| 10,066,018 B2 | 9/2018 | Igawa et al. |
| 10,150,808 B2 | 12/2018 | Kuramochi et al. |
| 10,253,091 B2 | 4/2019 | Igawa et al. |
| 10,435,458 B2 | 10/2019 | Kuramochi et al. |
| 10,450,381 B2 | 10/2019 | Igawa et al. |
| 10,934,344 B2 | 3/2021 | Igawa et al. |
| 2001/0001663 A1 | 5/2001 | Kishimoto et al. |
| 2001/0006796 A1 | 7/2001 | Briggs et al. |
| 2002/0028178 A1 | 3/2002 | Hanna et al. |
| 2002/0062010 A1 | 5/2002 | Arathoon et al. |
| 2002/0142374 A1 | 10/2002 | Gallo et al. |
| 2002/0147326 A1 | 10/2002 | Chaiklin et al. |
| 2002/0155537 A1 | 10/2002 | Carter et al. |
| 2002/0164339 A1 | 11/2002 | Do et al. |
| 2002/0164668 A1 | 11/2002 | Durham et al. |
| 2002/0187150 A1 | 12/2002 | Mihara et al. |
| 2002/0193571 A1 | 12/2002 | Carter et al. |
| 2002/0197706 A1 | 12/2002 | Nadkarni et al. |
| 2003/0073161 A1 | 4/2003 | Briggs et al. |
| 2003/0082612 A1 | 5/2003 | Snodgrass et al. |
| 2003/0148409 A1 | 8/2003 | Rossi et al. |
| 2003/0187225 A1 | 10/2003 | Penichet et al. |
| 2003/0190311 A1 | 10/2003 | Dall'Acqua et al. |
| 2003/0207346 A1 | 11/2003 | Arathoon et al. |
| 2003/0219441 A1 | 11/2003 | Thorpe et al. |
| 2003/0224397 A1 | 12/2003 | Lowman et al. |
| 2004/0071706 A1 | 4/2004 | Ito et al. |
| 2004/0081651 A1 | 4/2004 | Karpusas et al. |
| 2004/0091475 A1 | 5/2004 | Tsuchiya et al. |
| 2004/0219643 A1 | 11/2004 | Winter et al. |
| 2004/0236080 A1 | 11/2004 | Aburatani et al. |
| 2004/0242847 A1 | 12/2004 | Fukushima et al. |
| 2005/0095243 A1 | 5/2005 | Chan et al. |
| 2005/0130224 A1 | 6/2005 | Saito et al. |
| 2005/0142133 A1 | 6/2005 | Lazar et al. |
| 2005/0142635 A1 | 6/2005 | Tsuchiya et al. |
| 2005/0164352 A1 | 7/2005 | Lauder et al. |
| 2005/0191293 A1 | 9/2005 | Deshpande et al. |
| 2005/0244403 A1 | 11/2005 | Lazar et al. |
| 2005/0261229 A1 | 11/2005 | Gillies |
| 2005/0266425 A1 | 12/2005 | Zauderer et al. |
| 2006/0019342 A1 | 1/2006 | Dall Acqua et al. |
| 2006/0024298 A1 | 2/2006 | Lazar et al. |
| 2006/0057149 A1 | 3/2006 | Johnson et al. |
| 2006/0058511 A1 | 3/2006 | Tanikawa et al. |
| 2006/0063228 A1 | 3/2006 | Kasaian et al. |
| 2006/0074225 A1 | 4/2006 | Chamberlain |
| 2006/0134105 A1 | 6/2006 | Lazar et al. |
| 2006/0134709 A1 | 6/2006 | Stavenhagen et al. |
| 2006/0134805 A1 | 6/2006 | Berg et al. |
| 2006/0141456 A1 | 6/2006 | Edwards et al. |
| 2006/0159673 A1 | 7/2006 | Kojima |
| 2006/0160184 A1 | 7/2006 | Hoogenboom et al. |
| 2006/0189794 A1 | 8/2006 | Tsuchiya et al. |
| 2006/0194280 A1 | 8/2006 | Dillon et al. |
| 2006/0204493 A1 | 9/2006 | Huang et al. |
| 2006/0222643 A1 | 10/2006 | Tsunoda et al. |
| 2006/0269989 A1 | 11/2006 | Miyazaki et al. |
| 2006/0275282 A1 | 12/2006 | Moore et al. |
| 2006/0275301 A1 | 12/2006 | Ozaki et al. |
| 2006/0292147 A1 | 12/2006 | Yoshizaki et al. |
| 2007/0003556 A1 | 1/2007 | Tsuchiya et al. |
| 2007/0036785 A1 | 2/2007 | Kishimoto et al. |
| 2007/0041978 A1 | 2/2007 | Hattori et al. |
| 2007/0054354 A1 | 3/2007 | Humphreys et al. |
| 2007/0059312 A1 | 3/2007 | Baca et al. |
| 2007/0087381 A1 | 4/2007 | Kojima |
| 2007/0110757 A1 | 5/2007 | Wei et al. |
| 2007/0134234 A1 | 6/2007 | Smith et al. |
| 2007/0148163 A1 | 6/2007 | Takahashi et al. |
| 2007/0148164 A1 | 6/2007 | Farrington et al. |
| 2007/0148167 A1 | 6/2007 | Strohl |
| 2007/0212357 A1 | 9/2007 | Pons et al. |
| 2007/0280951 A1 | 12/2007 | Kimura et al. |
| 2007/0281327 A1 | 12/2007 | Nakano et al. |
| 2008/0009038 A1 | 1/2008 | Ohtomo et al. |
| 2008/0063635 A1 | 3/2008 | Takahashi et al. |
| 2008/0075712 A1 | 3/2008 | Hattori et al. |
| 2008/0166756 A1 | 7/2008 | Tsuchiya et al. |
| 2008/0206229 A1 | 8/2008 | Ono et al. |
| 2008/0274110 A1 | 11/2008 | Ozaki et al. |
| 2009/0028854 A1 | 1/2009 | Igawa et al. |
| 2009/0117097 A1 | 5/2009 | Igawa et al. |
| 2009/0208416 A1 | 8/2009 | Moretta et al. |
| 2009/0214535 A1 | 8/2009 | Igawa et al. |
| 2009/0221803 A1 | 9/2009 | Dall'Acqua et al. |
| 2009/0263392 A1 | 10/2009 | Igawa et al. |
| 2009/0297501 A1 | 12/2009 | Igawa et al. |
| 2009/0324589 A1 | 12/2009 | Igawa et al. |
| 2010/0003254 A1 | 1/2010 | Hattori et al. |
| 2010/0004429 A1 | 1/2010 | Kai et al. |
| 2010/0008907 A1 | 1/2010 | Nishimoto et al. |
| 2010/0015133 A1 | 1/2010 | Igawa |
| 2010/0055092 A1 | 3/2010 | Hasegawa et al. |
| 2010/0239577 A1 | 9/2010 | Igawa et al. |
| 2010/0291072 A1 | 11/2010 | Lowman et al. |
| 2010/0298542 A1 | 11/2010 | Igawa et al. |
| 2010/0331527 A1 | 12/2010 | Davis et al. |
| 2011/0076275 A1 | 3/2011 | Igawa et al. |
| 2011/0111406 A1 | 5/2011 | Igawa et al. |
| 2011/0129459 A1 | 6/2011 | Kuramochi et al. |
| 2011/0236374 A1 | 9/2011 | Shitara et al. |
| 2011/0245473 A1 | 10/2011 | Igawa et al. |
| 2012/0009188 A1 | 1/2012 | Behrens |
| 2012/0028304 A1 | 2/2012 | Dahiyat et al. |
| 2012/0065379 A1 | 3/2012 | Igawa et al. |
| 2012/0071634 A1 | 3/2012 | Igawa et al. |
| 2012/0149876 A1 | 6/2012 | Kreudensiein et al. |
| 2012/0237517 A1 | 9/2012 | Hattori et al. |
| 2012/0238729 A1 | 9/2012 | Kuramochi et al. |
| 2013/0011866 A1 | 1/2013 | Igawa et al. |
| 2013/0018174 A1 | 1/2013 | Igawa et al. |
| 2013/0030156 A1 | 1/2013 | Apostolou et al. |
| 2013/0039913 A1 | 2/2013 | Labrijn |
| 2013/0052196 A1 | 2/2013 | Apostolou et al. |
| 2013/0085199 A1 | 4/2013 | Tamori et al. |
| 2013/0101581 A1 | 4/2013 | Kuramochi et al. |
| 2013/0195849 A1 | 8/2013 | Spreter et al. |
| 2013/0330345 A1 | 12/2013 | Igawa et al. |
| 2014/0037632 A1 | 2/2014 | Igawa et al. |
| 2014/0051833 A1 | 2/2014 | Fischer et al. |
| 2014/0112883 A1 | 4/2014 | Ponath et al. |
| 2014/0112914 A1 | 4/2014 | Nezu et al. |
| 2014/0154270 A1 | 6/2014 | Wang et al. |
| 2014/0303356 A1 | 10/2014 | Gramer et al. |
| 2014/0370018 A1 | 12/2014 | Igawa et al. |
| 2014/0370020 A1 | 12/2014 | Kuramochi et al. |
| 2014/0377253 A1 | 12/2014 | Harding et al. |
| 2015/0118184 A1 | 4/2015 | Kawai |
| 2015/0274809 A1 | 10/2015 | Igawa et al. |
| 2015/0284465 A1 | 10/2015 | Igawa et al. |
| 2015/0315278 A1 | 11/2015 | Igawa et al. |
| 2016/0024147 A1 | 1/2016 | Tustian et al. |
| 2016/0159915 A1 | 6/2016 | Igawa et al. |
| 2016/0168259 A1 | 6/2016 | Igawa et al. |
| 2016/0222129 A1 | 8/2016 | Igawa et al. |
| 2016/0229915 A1 | 8/2016 | Igawa et al. |
| 2017/0022287 A1 | 1/2017 | Igawa et al. |
| 2017/0022293 A1 | 1/2017 | Igawa et al. |
| 2018/0057607 A1 | 3/2018 | Igawa et al. |

(56) References Cited

U.S. PATENT DOCUMENTS

| | | |
|---|---|---|
| 2018/0142027 A1 | 5/2018 | Igawa et al. |
| 2018/0162902 A1 | 6/2018 | Igawa et al. |
| 2018/0244800 A1 | 8/2018 | Hattori et al. |
| 2019/0062368 A1 | 2/2019 | Igawa et al. |
| 2019/0112390 A1 | 4/2019 | Hattori et al. |
| 2019/0211081 A1 | 7/2019 | Igawa et al. |
| 2019/0315884 A1 | 10/2019 | Igawa |
| 2019/0330268 A1 | 10/2019 | Tanaka et al. |
| 2019/0352334 A1 | 11/2019 | Igawa et al. |
| 2019/0359728 A1 | 11/2019 | Hattori et al. |
| 2020/0087380 A1 | 3/2020 | Kuramochi et al. |
| 2020/0207805 A1 | 7/2020 | Igawa et al. |
| 2020/0277402 A1 | 9/2020 | Hattori et al. |
| 2021/0040147 A1 | 2/2021 | Igawa et al. |

FOREIGN PATENT DOCUMENTS

| | | |
|---|---|---|
| CA | 2 203 182 | 5/1996 |
| CA | 2 331 641 | 11/1999 |
| CA | 2 019 559 | 1/2002 |
| CA | 2 443 294 | 10/2002 |
| CA | 2 523 577 | 11/2004 |
| CA | 2 531 482 | 1/2005 |
| CA | 2 549 467 | 7/2005 |
| CA | 2 560 953 | 9/2005 |
| CA | 2 603 264 | 10/2006 |
| CA | 2 625 773 | 4/2007 |
| CA | 2 626 688 | 4/2007 |
| CA | 2 647 846 | 10/2007 |
| CA | 2 700 986 | 4/2009 |
| CA | 2 819 530 | 6/2012 |
| CN | 101198698 | 6/2008 |
| CN | 102471378 | 5/2012 |
| CN | 102782131 | 11/2012 |
| CN | 102946906 | 2/2013 |
| CN | 103429737 | 12/2013 |
| CN | 103833852 | 6/2014 |
| CN | 101874042 | 9/2018 |
| DE | 198 19 846 | 11/1999 |
| EP | 0 369 566 | 5/1990 |
| EP | 437 622 | 7/1991 |
| EP | 0 329 185 | 4/1994 |
| EP | 0 637 593 | 2/1995 |
| EP | 0 404 097 | 9/1996 |
| EP | 0 774 511 | 5/1997 |
| EP | 0 783 893 | 7/1997 |
| EP | 0 811 691 | 12/1997 |
| EP | 1 069 185 | 1/2001 |
| EP | 1 220 923 | 7/2002 |
| EP | 1 327 681 | 7/2003 |
| EP | 1 510 943 | 3/2005 |
| EP | 0 979 281 | 7/2005 |
| EP | 1 605 058 | 12/2005 |
| EP | 1 693 448 | 8/2006 |
| EP | 1 701 979 | 9/2006 |
| EP | 1 773 391 | 4/2007 |
| EP | 1 847 602 | 10/2007 |
| EP | 1 870 458 | 12/2007 |
| EP | 1 870 459 | 12/2007 |
| EP | 1 876 236 | 1/2008 |
| EP | 1 900 814 | 3/2008 |
| EP | 2 006 381 | 12/2008 |
| EP | 2 009 101 | 12/2008 |
| EP | 2 031 064 | 3/2009 |
| EP | 1 505 148 | 4/2009 |
| EP | 2 107 115 | 10/2009 |
| EP | 2 194 066 | 6/2010 |
| EP | 2 196 541 | 6/2010 |
| EP | 2 202 245 | 6/2010 |
| EP | 2 206 775 | 7/2010 |
| EP | 2 236 604 | 10/2010 |
| EP | 2 275 443 | 1/2011 |
| EP | 1 688 488 | 8/2011 |
| EP | 2 409 991 | 1/2012 |
| EP | 2 238 985 | 8/2012 |
| EP | 2 522 724 | 11/2012 |
| EP | 2 526 963 | 11/2012 |
| EP | 2 543 727 | 1/2013 |
| EP | 2 644 698 | 10/2013 |
| EP | 2 647 707 | 10/2013 |
| EP | 2 905 290 | 8/2015 |
| EP | 2 914 634 | 9/2015 |
| EP | 3 199 628 A | 8/2017 |
| JP | S63-52890 | 3/1988 |
| JP | 2-028200 | 1/1990 |
| JP | H02-145187 | 6/1990 |
| JP | H03-500644 | 2/1991 |
| JP | H05-184383 | 7/1993 |
| JP | H05-199894 | 8/1993 |
| JP | H05-203652 | 8/1993 |
| JP | H05-213775 | 8/1993 |
| JP | H05-304992 | 11/1993 |
| JP | 07-67688 | 3/1995 |
| JP | 7-503622 | 4/1995 |
| JP | 8-500979 | 2/1996 |
| JP | 8-510555 | 11/1996 |
| JP | 09-506001 | 6/1997 |
| JP | 10-505231 | 5/1998 |
| JP | 10-165184 | 6/1998 |
| JP | 10-511085 | 10/1998 |
| JP | 11-500915 | 1/1999 |
| JP | 11-500916 | 1/1999 |
| JP | 11-71288 | 3/1999 |
| JP | 11-506310 | 6/1999 |
| JP | 3032287 | 4/2000 |
| JP | 2001-506135 | 5/2001 |
| JP | 2001-513999 | 9/2001 |
| JP | 2001-518930 | 10/2001 |
| JP | 2001-523971 | 11/2001 |
| JP | 2002-514406 | 5/2002 |
| JP | 2002-518041 | 6/2002 |
| JP | 2002-543822 | 12/2002 |
| JP | 2002-544173 | 12/2002 |
| JP | 2003-055398 | 2/2003 |
| JP | 2003-509049 | 3/2003 |
| JP | 2003-515323 | 5/2003 |
| JP | 2004-086862 | 3/2004 |
| JP | 2004-511426 | 4/2004 |
| JP | 2004-321100 | 11/2004 |
| JP | 2005-501514 | 1/2005 |
| JP | 2005-101105 | 3/2005 |
| JP | 2005-535341 | 11/2005 |
| JP | 2005-378266 | 12/2005 |
| JP | 2005-537009 | 12/2005 |
| JP | 2008-512995 | 5/2008 |
| JP | 2008-523140 | 7/2008 |
| JP | 2008-538920 | 11/2008 |
| JP | 2009-500458 | 1/2009 |
| JP | 2010-522701 | 7/2010 |
| JP | 2011-508604 | 3/2011 |
| JP | 2012-504970 | 3/2012 |
| JP | 2012-510281 | 5/2012 |
| JP | 2012-515160 | 7/2012 |
| JP | 2012-522527 | 9/2012 |
| JP | 2012-531439 | 12/2012 |
| JP | 5144499 | 2/2013 |
| JP | 2013-515509 | 5/2013 |
| JP | 2013-529084 | 7/2013 |
| JP | 2013-529190 | 7/2013 |
| JP | 2013-165716 | 8/2013 |
| JP | 5334319 | 11/2013 |
| JP | 5484060 | 5/2014 |
| JP | 2015-510764 | 4/2015 |
| JP | 5717624 | 5/2015 |
| JP | 2015-130883 | 7/2015 |
| JP | 5787446 | 9/2015 |
| JP | 5912436 | 4/2016 |
| JP | 2016-69329 | 5/2016 |
| JP | 6175590 | 8/2017 |
| JP | 6534615 | 6/2019 |
| KR | 2009/0107091 | 10/2009 |
| KR | 2010/0056467 | 5/2010 |
| KR | 2010/0074221 | 7/2010 |
| KR | 2012/0123055 | 11/2012 |

(56) References Cited

FOREIGN PATENT DOCUMENTS

| | | |
|---|---|---|
| KR | 2013/0102113 | 9/2013 |
| KR | 2013/0102640 | 9/2013 |
| KR | 2013/0130765 | 12/2013 |
| KR | 2014/0084249 | 7/2014 |
| MX | 9905856 A | 7/2000 |
| NO | 20062087 | 7/2006 |
| RU | 94028282 | 7/1996 |
| RU | 2232773 | 7/2004 |
| RU | 2266298 | 12/2005 |
| RU | 2337107 | 10/2008 |
| RU | 2339696 | 11/2008 |
| RU | 2009/149451 | 7/2011 |
| RU | 2427588 | 8/2011 |
| RU | 2012/112067 | 10/2013 |
| SG | 11201701119 R | 3/2017 |
| TW | 2007/14313 | 4/2007 |
| TW | 2007/22517 | 6/2007 |
| TW | 2012/49872 | 12/2012 |
| TW | I452135 | 9/2014 |
| TW | I452136 | 9/2014 |
| TW | 2016/19193 | 6/2016 |
| WO | WO 89/01343 | 2/1989 |
| WO | WO 91/01335 | 2/1991 |
| WO | WO 1991/008770 | 6/1991 |
| WO | WO 1992/019759 | 11/1992 |
| WO | WO 93/11161 | 6/1993 |
| WO | WO 94/05690 | 3/1994 |
| WO | WO 94/13804 | 6/1994 |
| WO | WO 95/01571 | 1/1995 |
| WO | WO 95/14710 | 6/1995 |
| WO | WO 95/33844 | 12/1995 |
| WO | WO 96/01653 | 1/1996 |
| WO | WO 96/04925 | 2/1996 |
| WO | WO 96/07754 | 3/1996 |
| WO | WO 96/11020 | 4/1996 |
| WO | WO 96/12503 | 5/1996 |
| WO | WO 96/16673 | 6/1996 |
| WO | WO 96/26964 | 9/1996 |
| WO | WO 96/27011 | 9/1996 |
| WO | WO 96/34892 | 11/1996 |
| WO | WO 97/09351 | 3/1997 |
| WO | WO 97/10354 | 3/1997 |
| WO | WO 97/31108 | 8/1997 |
| WO | WO 98/03546 | 1/1998 |
| WO | WO 98/28331 | 7/1998 |
| WO | WO 98/41641 | 9/1998 |
| WO | WO 98/42378 | 10/1998 |
| WO | WO 98/50431 | 11/1998 |
| WO | WO 99/02567 | 1/1999 |
| WO | WO 99/03495 | 1/1999 |
| WO | WO 99/10494 | 3/1999 |
| WO | WO 99/018212 | 4/1999 |
| WO | WO 99/51743 | 10/1999 |
| WO | WO 99/58572 | 11/1999 |
| WO | WO 99/67359 | 12/1999 |
| WO | WO 00/44788 | 8/2000 |
| WO | WO 00/67795 | 11/2000 |
| WO | WO 00/69462 | 11/2000 |
| WO | WO 01/19992 | 3/2001 |
| WO | WO 01/30854 | 5/2001 |
| WO | WO 01/36486 | 5/2001 |
| WO | WO 01/44282 | 6/2001 |
| WO | WO 01/64713 | 9/2001 |
| WO | WO 01/66737 | 9/2001 |
| WO | WO 01/70775 | 9/2001 |
| WO | WO 01/74388 | 10/2001 |
| WO | WO 01/79494 | 10/2001 |
| WO | WO 01/82899 | 11/2001 |
| WO | WO 01/90192 | 11/2001 |
| WO | WO 01/97858 | 12/2001 |
| WO | WO 02/04021 | 1/2002 |
| WO | WO 02/06838 | 1/2002 |
| WO | WO 02/22212 | 3/2002 |
| WO | WO 02/30463 | 4/2002 |
| WO | WO 02/33072 | 4/2002 |
| WO | WO 02/33073 | 4/2002 |
| WO | WO 02/060919 | 8/2002 |
| WO | WO 02/072605 | 9/2002 |
| WO | WO 02/078612 | 10/2002 |
| WO | WO 03/000883 | 1/2003 |
| WO | WO 03/012069 | 2/2003 |
| WO | WO 03/020949 | 3/2003 |
| WO | WO 03/033654 | 4/2003 |
| WO | WO 03/035835 | 5/2003 |
| WO | WO 03/042231 | 5/2003 |
| WO | WO 03/074679 | 9/2003 |
| WO | WO 03/087163 | 10/2003 |
| WO | WO 03/091424 | 11/2003 |
| WO | WO 03/104425 | 12/2003 |
| WO | WO 03/105757 | 12/2003 |
| WO | WO 2004/009618 | 1/2004 |
| WO | WO 2004/016740 | 2/2004 |
| WO | WO 2004/019966 | 3/2004 |
| WO | WO 2004/020579 | 3/2004 |
| WO | WO 2004/033499 | 4/2004 |
| WO | WO 2004/060919 | 7/2004 |
| WO | WO 2004/065611 | 8/2004 |
| WO | WO 2004/068931 | 8/2004 |
| WO | WO 2004/081048 | 9/2004 |
| WO | WO 2004/087763 | 10/2004 |
| WO | WO 2004/096273 | 11/2004 |
| WO | WO 2004/097041 | 11/2004 |
| WO | WO 2004/111233 | 12/2004 |
| WO | WO 2004/113387 | 12/2004 |
| WO | WO 2005/000900 | 1/2005 |
| WO | WO 2005/005604 | 1/2005 |
| WO | WO 2005/025615 | 3/2005 |
| WO | WO 2005/035753 | 4/2005 |
| WO | WO 2005/035754 | 4/2005 |
| WO | WO 2005/035756 | 4/2005 |
| WO | WO 2005/047327 | 5/2005 |
| WO | WO 2005/056604 | 6/2005 |
| WO | WO 2005/056606 | 6/2005 |
| WO | WO 2005/059106 | 6/2005 |
| WO | WO 2005/062916 | 7/2005 |
| WO | WO 2005/067620 | 7/2005 |
| WO | WO 2005/092925 | 10/2005 |
| WO | WO 2005/107784 | 11/2005 |
| WO | WO 2005/112564 | 12/2005 |
| WO | WO 2005/121180 | 12/2005 |
| WO | WO 2005/123126 | 12/2005 |
| WO | WO 2006/004663 | 1/2006 |
| WO | WO 2006/019447 | 2/2006 |
| WO | WO 2006/029879 | 3/2006 |
| WO | WO 2006/030200 | 3/2006 |
| WO | WO 2006/030220 | 3/2006 |
| WO | WO 2006/033386 | 3/2006 |
| WO | WO 2006/047340 | 5/2006 |
| WO | WO 2006/047350 | 5/2006 |
| WO | WO 2006/050491 | 5/2006 |
| WO | WO 2006/065208 | 6/2006 |
| WO | WO 2006/067913 | 6/2006 |
| WO | WO 2006/071877 | 7/2006 |
| WO | WO 2006/075668 | 7/2006 |
| WO | WO 2006/106903 | 10/2006 |
| WO | WO 2006/106905 | 10/2006 |
| WO | WO 2006/109592 | 10/2006 |
| WO | WO 2006/113767 | 10/2006 |
| WO | WO 2006/116260 | 11/2006 |
| WO | WO 2006/121852 | 11/2006 |
| WO | WO 2007/009065 | 1/2007 |
| WO | WO 2007/024535 | 3/2007 |
| WO | WO 2007/060411 | 5/2007 |
| WO | WO 2007/108559 | 9/2007 |
| WO | WO 2007/110205 | 10/2007 |
| WO | WO 2007/114319 | 10/2007 |
| WO | WO 2007/114325 | 10/2007 |
| WO | WO 2007/147901 | 12/2007 |
| WO | WO 2008/043822 | 4/2008 |
| WO | WO 2008/090960 | 7/2008 |
| WO | WO 2008/092117 | 7/2008 |
| WO | WO 2008/118970 | 10/2008 |
| WO | WO 2008/119353 | 10/2008 |
| WO | WO 2008/145141 | 12/2008 |

(56) References Cited

FOREIGN PATENT DOCUMENTS

| | | |
|---|---|---|
| WO | WO 2008/145142 | 12/2008 |
| WO | WO 2009/012394 | 1/2009 |
| WO | WO 2009/036209 | 3/2009 |
| WO | WO 2009/041062 | 4/2009 |
| WO | WO 2009/041613 | 4/2009 |
| WO | WO 2009/041621 | 4/2009 |
| WO | WO 2009/041643 | 4/2009 |
| WO | WO 2009/041734 | 4/2009 |
| WO | WO 2009/052439 | 4/2009 |
| WO | WO 2009/053368 | 4/2009 |
| WO | WO 2009/072604 | 6/2009 |
| WO | WO 2009/079649 | 6/2009 |
| WO | WO 2009/084659 | 7/2009 |
| WO | WO 2009/089004 | 7/2009 |
| WO | WO 2009/100309 | 8/2009 |
| WO | WO 2009/125825 | 10/2009 |
| WO | WO 2009/139822 | 11/2009 |
| WO | WO 2010/035769 | 4/2010 |
| WO | WO 2010/042904 | 4/2010 |
| WO | WO 2010/063746 | 6/2010 |
| WO | WO 2010/064090 | 6/2010 |
| WO | WO 2010/080065 | 7/2010 |
| WO | WO 2010/106180 | 9/2010 |
| WO | WO 2010/107109 | 9/2010 |
| WO | WO 2010/107110 | 9/2010 |
| WO | WO 2010/115589 | 10/2010 |
| WO | WO 2010/129304 | 11/2010 |
| WO | WO 2010/151792 | 12/2010 |
| WO | WO 2011/090088 | 2/2011 |
| WO | WO 2011/025964 | 3/2011 |
| WO | WO 2011/037158 | 3/2011 |
| WO | WO 2011/078332 | 6/2011 |
| WO | WO 2011/090754 | 7/2011 |
| WO | WO 2011/090762 | 7/2011 |
| WO | WO 2011/091177 | 7/2011 |
| WO | WO 2011/091181 | 7/2011 |
| WO | WO 2011/108502 | 9/2011 |
| WO | WO 2011/108714 | 9/2011 |
| WO | WO 2011/111007 | 9/2011 |
| WO | WO 2011/125674 | 10/2011 |
| WO | WO 2011/131746 | 10/2011 |
| WO | WO 2011/133886 | 10/2011 |
| WO | WO 2011/143545 | 11/2011 |
| WO | WO 2012/020096 | 2/2012 |
| WO | WO 2012/067176 | 5/2012 |
| WO | WO 2012/073985 | 6/2012 |
| WO | WO 2012/131555 | 10/2012 |
| WO | WO 2012/145238 | 10/2012 |
| WO | WO 2013/060867 | 5/2013 |
| WO | WO 2013/065708 | 5/2013 |
| WO | WO 2013/124450 | 8/2013 |
| WO | WO 2013/131866 | 9/2013 |
| WO | WO 2013/136186 | 9/2013 |
| WO | WO 2013/157954 | 10/2013 |
| WO | WO 2013/158856 | 10/2013 |
| WO | WO 2013/181543 | 12/2013 |
| WO | WO 2014/028354 | 2/2014 |
| WO | WO 2014/051433 | 4/2014 |
| WO | WO 2014/054804 | 4/2014 |
| WO | WO 2014/067011 | 5/2014 |
| WO | WO 2015/046467 | 4/2015 |
| WO | WO 2015/046554 | 4/2015 |
| WO | WO 2015/063339 | 5/2015 |
| WO | WO 2015/156268 | 10/2015 |
| WO | WO 2015/174439 | 11/2015 |
| WO | WO 2015/194233 | 12/2015 |
| WO | WO 2016/047722 | 3/2016 |
| WO | WO 2016/159213 | 10/2016 |
| WO | WO 2016/166014 | 10/2016 |
| WO | WO 2016/171202 | 10/2016 |
| WO | WO 2017/115773 | 7/2017 |
| WO | WO 2017/129585 | 8/2017 |
| WO | WO 2017/159287 | 9/2017 |
| WO | WO 2017/188356 | 11/2017 |
| WO | WO 2018/181870 | 10/2018 |

OTHER PUBLICATIONS

U.S. Appl. No. 15/402,580, Hattori et al., filed Jan. 10, 2017 (abandoned).
U.S. Appl. No. 15/701,630, Hattori et al., filed Sep. 12, 2017 (abandoned).
U.S. Appl. No. 15/963,345, Hattori et al., filed Apr. 26, 2018.
U.S. Appl. No. 14/019,117, Igawa et al., filed Sep. 5, 2013.
U.S. Appl. No. 14/019,712, Igawa et al., filed Sep. 6, 2013 (abandoned).
U.S. Appl. No. 15/132,996, Igawa et al., filed Apr. 19, 2016.
U.S. Appl. No. 15/288,965, Igawa et al., filed Oct. 7, 2016.
U.S. Appl. No. 12/295,039, Igawa et al., filed Jan. 20, 2009.
U.S. Appl. No. 15/725,692, Igawa et al., filed Oct. 5, 2017.
U.S. Appl. No. 15/614,842, Igawa et al., filed Jun. 6, 2017.
U.S. Appl. No. 13/257,145, Igawa et al., filed Nov. 22, 2011 (abandoned).
U.S. Appl. No. 14/680,250, Igawa et al., filed Apr. 7, 2015.
U.S. Appl. No. 14/962,293, Igawa et al., filed Dec. 8, 2015.
U.S. Appl. No. 13/497,269, Kuramochi et al., filed Jun. 1, 2012.
U.S. Appl. No. 13/582,073, Kuramochi et al., filed Dec. 20, 2012.
U.S. Appl. No. 15/490,936, Igawa et al., filed Apr. 19, 2017.
U.S. Appl. No. 13/518,861, Igawa et al., filed Oct. 4, 2012 (abandoned).
U.S. Appl. No. 15/617,008, Igawa et al., filed Jun. 8, 2017 (abandoned).
U.S. Appl. No. 14/351,654, Kuramochi et al., filed Apr. 14, 2014.
U.S. Appl. No. 15/562,186, Igawa et al., filed Sep. 27, 2017.
U.S. Appl. No. 15/875,847, Igawa et al., filed Jan. 19, 2018.
U.S. Appl. No. 16/061,454, Tanaka et al., filed Jun. 12, 2018.
U.S. Appl. No. 15/963,221, Nezu et al., filed Apr. 26, 2018.
U.S. Appl. No. 15/963,221, filed Apr. 26, 2018, Nezu et al.
U.S. Appl. No. 15/963,345, filed Apr. 26, 2018, Hattori et al.
U.S. Appl. No. 16/011,858, filed Jun. 12, 2018, Tanaka et al.
Canfield et al., "The Binding Affinity of Human IgG for its High Affinity Fc Receptor Is Determined by Multiple Amino Acids in the CH2 Domain and Is Modulated by the Hinge Region," J Exp Med, Jun. 1, 1991, 173(6):1483-91.
Dall'Acqua et al., "Properties of Human IgGls Engineered for Enhanced Binding to the Neonatal Fc Receptor (FcRn)," J Biol Chem, Aug. 18, 2006, 281(33):23514-24. Epub Jun. 21, 2006.
EPO Register Extract EP 1915397 (document submitted in EP opposition and posted by EPO on Feb. 2, 2018); 4 pages.
Hotzel et al., "A strategy for risk mitigation of antibodies with fast clearance," mAbs, Nov.-Dec. 2012, 4(6):753-60. doi: 10.4161/mabs.22189.
Ryman et al., "Pharmacokinetics of Monoclonal Antibodies," CPT Pharmacometrics Syst Pharmacol, Sep. 2017, 6(9):576-588. doi: 10.1002/psp4.12224. Epub Jul. 29, 2017.
Summary of information about antibodies in Examples of patent (document submitted in EP opposition and posted by EPO on Apr. 13, 2018); 3 pages.
Written Submissions by Opponent 1 (Alexion Pharmaceuticals, Inc.) in Opposition of EP 2006381 dated Apr. 13, 2018, 19 pages.
Written Submissions by Opponent 2 (Novo Nordisk A/S) in Opposition of EP 2006381 dated Apr. 13, 2018, 14 pages.
Written Submissions by Opponent 3 (name Unknown) in Opposition of EP 2006381 dated Apr. 13, 2018, 16 pages.
Wu et al., "Ultra-potent Antibodies Against Respiratory Syncytial Virus: Effects of Binding Kinetics and Binding Valence on Viral Neutralization," J Mol Biol, Jul. 1, 2005, 350(1):126-44.
Yarilin, "Fundamentals of Immunology", M:Medicina, 1999:169-74 (with English translation) 14 pages.
U.S. Appl. No. 15/963,345, Hattori et al., filed Apr. 26, 2018 (abandoned).
U.S. Appl. No. 16/226,798, Hattori et al., filed Dec. 20, 2018.
U.S. Appl. No. 14/019,117, Igawa et al., filed Sep. 5, 2013 (abandoned).
U.S. Appl. No. 16/298,032, Igawa et al., filed Mar. 11, 2019.
U.S. Appl. No. 15/875,847, Igawa et al., filed Jan. 19, 2018 (abandoned).
U.S. Appl. No. 16/155,673, Igawa et al., filed Oct. 9, 2018.
U.S. Appl. No. 16/093,495, Saeki et al., filed Oct. 12, 2018.

(56) References Cited

OTHER PUBLICATIONS

U.S. Appl. No. 16/083,975, Kinoshita et al., filed Sep. 11, 2018.
Davie, "A Brief Historical Review of the Waterfall/Cascade of Blood Coagulation," J Biol Chem, Dec. 19, 2003, 278(51):50819-32. Epub Oct. 21, 2003.
Decision of the Opposition Division in EP 2 275 443, dated Apr. 26, 2018 (submitted on May 24, 2019 by the Patentee during EPO Opposition Procedure for EP 2 202 245), 29 pages.
Declaration of Dr. Anette Henriksen, signed Apr. 17, 2019 (submitted by the Opponent during EPO opposition procedure for EP 2 006 381).
Declaration of Taichi Kuramochi (submitted on May 24, 2019 by the Patentee during EPO Opposition Procedure for EP 2 202 245), 11 pages.
Feige et al., "An Unfolded $C_H1$ Domain Controls the Assembly and Secretion of IgG Antibodies," Mol Cell, Jun. 12, 2009, 34(5):569-79. doi: 10.1016/j.molcel.2009.04.028.
Granted claims of EP 2 275 443 (submitted on May 24, 2019 by the Patentee during EPO Opposition Procedure for EP 2 202 245), 1 page.
Horne et al., "Noncovalent Association of Heavy and Light Chains of Human Immunoglobulins," J Immunol, Aug. 1982, 129(2):660-4.
Kabat et al., "Sequences of proteins of immunological interest," 1991, vol. 1, $5^{th}$ edition, DIANE Publishing, pp. 647-652 and 661-669.
Moiseenko, "Monoclonal Antibodies in the Treatment of Malignant Tumors," Practical Oncology, 2003, 4(3):148-56 (with English translation).
Muller et al., "The first constant domain (CH1 and CL) of an antibody used as. heterodimerization domain for bispecific miniantibodies," FEBS Lett, Jan. 30, 1998, 422(2):259-64.
Supplemental Material to Raposo et al., "Epitope-specific antibody response is controlled by immunoglobulin VH polymorphisms," J Exp Med, Mar. 10, 2014, 211(3):405-11. doi: 10.1084/jem.20130968. Epub Feb. 17, 2014 (submitted on May 24, 2019 during the Patentee during EPO Opposition Procedure for EP 2 202 245), 4 pages.
Labrijn et al., "Therapeutic IgG4 antibodies engage in Fab-arm exchange with endogenous human IgG4 in vivo," Nat Biotechnol, Aug. 2009, 27(8):767-771.
Lund et al., "Multiple interactions of IgG with its core oligosaccharide can modulate recognition by complement and human Fc gamma receptor I and influence the synthesis of its oligosaccharide chains," The Journal of Immunology, Dec. 1, 1996, 157(11):4963-4969.
Wu et al., "Humanization of a Murine Monoclonal Antibody by Simultaneous Optimization of Framework and CDR Residues," J Mol Biol, Nov. 19, 1999, 294(1):151-162.
U.S. Appl. No. 16/496,089, filed Sep. 20, 2019, Shima et al.
U.S. Appl. No. 16/536,385, filed Aug. 9, 2019, Hattori et al.
Do et al., "A rapid method for determining dynamic binding capacity of resins for the purification of proteins," Protein Expr Purif, Aug. 2008, 60(2):147-50. doi: 10.1016/j.pep.2008.04.009. Epub May 3, 2008.
Pabst et al., "Engineering of novel Staphylococcal Protein A ligands to enable milder elution pH and high dynamic binding capacity," J Chromatogr A, Oct. 3, 2014, 1362:180-5. doi: 10.1016/j.chroma.2014.08.046. Epub Aug. 19, 2014.
Pabst et al., "Evaluation of recent Protein A stationary phase innovations for capture of biotherapeutics," J Chromatogr A, Jun. 15, 2018, 1554:45-60. doi: 10.1016/j.chroma.2018.03.060. Epub Apr. 7, 2018.
U.S. Appl. No. 16/226,798, Hattori et al., filed Dec. 20, 2018 (abandoned).
U.S. Appl. No. 16/536,385, Hattori et al., filed Aug. 9, 2019.
U.S. Appl. No. 15/132,996, Igawa et al., filed Oct. 22, 2019.
U.S. Appl. No. 15/288,965, Igawa et al., filed Oct. 7, 2016 (abandoned).
U.S. Appl. No. 16/459,791, Igawa et al., filed Jul. 2, 2019.
U.S. Appl. No. 16/155,673, Igawa et al., filed Oct. 9, 2018 (abandoned).
U.S. Appl. No. 16/448,088, Igawa et al., filed Jun. 21, 2019.
U.S. Appl. No. 16/692,676, Kuramochi et al., filed Nov. 22, 2019.
U.S. Appl. No. 16/496,089, Shima et al., filed Sep. 20, 2019.
U.S. Appl. No. 16/692,676, filed Nov. 22, 2019, Kuramochi et al.
U.S. Appl. No. 16/298,032, filed Mar. 11, 2019.
Choi et al., "Crystal structures of immunoglobulin Fc heterodimers reveal the molecular basis for heterodimer formation," Mol Immunol, Jun. 2015, 65(2):377-83. doi: 10.1016/j.molimm.2015.02.017. Epub Mar. 2, 2015.
Feige et al., "How antibodies fold," Trends Biochem Sci, Apr. 2010, 35(4):189-98. doi: 10.1016/j.tibs.2009.11.005. Epub Dec. 21, 2009.
Goulet et al., "Kinetic mechanism of controlled Fab-arm exchange for the formation of bispecific immunoglobulin G1 antibodies," J Biol Chem, Jan. 12, 2018, 293(2):651-661. doi:10.1074/jbc.RA117.000303. Epub Nov. 17, 2017.
Rispens et al., "Mechanism of Immunoglobulin G4 Fab-arm Exchange," J Am Chem Soc, Jul. 6, 2011, 133(26):10302-11. doi: 10.1021/ja203638y. Epub Jun. 15, 2011.
U.S. Appl. No. 15/701,630, Hattori et al., filed Sep. 12, 2017.
U.S. Appl. No. 14/741,786, Igawa et al., filed Jun. 17, 2015.
U.S. Appl. No. 15/617,008, Igawa et al., filed Jun. 8, 2017.
U.S. Appl. No. 11/910,128, Igawa et al., filed Oct. 7, 2008.
U.S. Appl. No. 15/467,654, Nezu et al., filed Mar. 23, 2017.
U.S. Appl. No. 16/536,385, Hattori et al., filed Aug. 9, 2019 (abandoned).
U.S. Appl. No. 16/825,513, Hattori et al., filed Mar. 20, 2020 (abandoned).
U.S. Appl. No. 17/130,736, Hattori et al., filed Dec. 22, 2020.
U.S. Appl. No. 16/448,088, Igawa et al., filed Jun. 21, 2019 (abandoned).
U.S. Appl. No. 16/815,089, Igawa et al., filed Mar. 11, 2020 (abandoned).
U.S. Appl. No. 17/076,938, Igawa et al., filed Oct. 22, 2020.
U.S. Appl. No. 17/076,938, filed Oct. 22, 2020, Igawa et al.
U.S. Appl. No. 17/130,736, filed Dec. 22, 2020, Hattori et al.
Dall'Acqua et al., "Contribution of Domain Interface Residues to the Stability of Antibody $C_H3$ Domain Homodimers," Biochemistry, Jun. 30, 1998, 37(26):9266-9273. doi: 10.1021/bi980270i. PMID: 9649307.
Declaration of Christian Beil, signed Jun. 18, 2020, submitted by the opponent in Opposition of EP 3 050 963, 6 pages.
Feng et al., "Glypican-3 antibodies: A new therapeutic target for liver cancer," FEBS Lett, Jan. 21, 2014, 588(2):377-382. doi: 10.1016/j.febslet.2013.10.002. Epub Oct. 15, 2013.
Helguera et al., "Antibody-Cytokine Fusion Proteins for the Therapy of Cancer," Methods Mol Med, 2005, 109:347-373. doi: 10.1385/1-59259-862-5:347. PMID: 15585931.
Hugo et al., "Functional aspects of co-variant surface charges in an antibody fragment," Protein Sci, Nov. 2002, 11(11):2697-2705. doi: 10.1110/ps.0209302. PMID: 12381851; PMCID: PMC2373727.
Otomo et al., "Structure of the heterodimeric complex between CAD domains of CAD and ICAD," Nat Struct Biol, Aug. 2000, 7(8):658-662. doi: 10.1038/77957. PMID: 10932250.
Raghavan et al., "Fc Receptors and Their Interactions with Immunoglobulins," Annu Rev Cell Dev Biol, Nov. 1996, 12:181-220.
Reference table: IMGT exon, EU and Kabat numbering of residues within the human IgG1 sequence; retrieved from http://www.imgt.org/IMGTScientificChart/Numbering/Hu_IGHGnber.html on Jun. 1, 2020, 4 pages (cited by the opponents in the Opposition procedure in the corresponding European Patent No. 3 050 963, which was notified to the patentee on Jul. 3, 2020).
Shirakawa et al., "Glypican-3 is a useful diagnostic marker for a component of hepatocellular carcinoma in human liver cancer," Int J Oncol, Mar. 2009, 34(3):649-656.
Taylor et al., "A new era for hemophilia B treatment," Blood, Apr. 7, 2016, 127(14):1734-1736.
U.S. Appl. No. 11/373,063, filed Mar. 10, 2006, Ozaki et al.
U.S. Appl. No. 15/875,847, filed Jan. 19, 2018, Igawa et al.
Geneseq Accession No. AEM45140, Feb. 22, 2007, "Light chain constant region of therapeutic human IgG antibody" 1 page.

(56) References Cited

OTHER PUBLICATIONS

Golay et al., "Mechanism of action of therapeutic monoclonal antibodies: Promises and pitfalls of in vitro and in vivo assays," Archives of Biochemistry and Biophysics 526: 146-153, Feb. 25, 2012.
Jaeger, "Clinical Immunology and Allergology," 2nd edition, translation from German, M.: Medicina, 1990, 3 volume ;2:484-5.
Kabat et al., "Identical V Region Amino Acid Sequences and Segments of Sequences in Antibodies of Different Specificities," Journal of Immunology. Sep. 1, 1991; 147(5):1709-19.
Kim et al., "Antibody light chain variable domains and their biophysically improved versions for human immunotherapy," mAbs. Jan.-Feb. 2014; 6(1):219-35. doi: 10.4161/mabs.26844.
Li et al., "Framework selection can influence pharmacokinetics of a humanized therapeutic antibody through differences in molecule charge," mAbs. 2014;6(5):1255-64. doi: 10.4161/mabs.29809. Epub Oct. 30, 2014.
Narhi et al., "Asn to Lys mutations at three sites which are N-glycosylated in the mammalian protein decrease the aggregation of Escherichia coli-derived erythropoietin," Protein Eng., Feb. 2001;14(2) :135-40.
Paul, "Immunology" ed. by W. Paul, a Russian translation of English book, M.: Mir, 1987-1988, vol. 3, pp. 248-251.
Roitt et al., Immunology, M., Mir, (2000), pp. 110, 150, and 537-539 (in Russian, with what is believed to be a published English equivalent of those pages).
Stancovski et al., "Mechanistic Aspects of the Opposing Effects of Monoclonal Antibodies to the ERBB2 Receptor on Tumor Growth," Proceedings of the National Academy of Sciences, 88:8691-8695, Oct. 1, 1991.
Yarilin, Immunology Basics, M:Medicina, 1999:169-74 (with English translation) 14 pages.
Yarilin, Fundamentals of Immunology M:Medicina, 1999, pp. 169-172, 354-358 (with English translation) 21 pages.
U.S. Appl. No. 16/825,513, Hattori et al., filed Mar. 20, 2020.
U.S. Appl. No. 16/815,089, Igawa et al., filed Mar. 11, 2020.
U.S. Appl. No. 16/815,089, filed Mar. 11, 2020, Igawa et al.
U.S. Appl. No. 16/825,513, filed Mar. 20, 2020, Hattori et al.
U.S. Appl. No. 61/467,727, filed Mar. 25, 2011, Blein et al.
Adlersberg et al., "The Immunoglobulin Hinge (Interdomain) Region," Ric Clin Lab, Jul.-Sep. 1976, 6(3):191-205.
Annex 1—Analysis of the Examples of EP 2 787 078 (document submitted in opposition of EP 2 787 078 on Feb. 28, 2020), 3 pages.
Arguments filed on Oct. 12, 2016 in U.S. Appl. No. 14/351,654 (document submitted in opposition of EP 2 787 078 on Feb. 25, 2020), 10 pages.
Claims filed on Sep. 5, 2018 in U.S. Appl. No. 14/351,654 (document submitted in opposition of EP 2 787 078 on Feb. 28, 2020), 7 pages.
Filmus et al., "Protein family review—Glypicans," Genome Biol, May 22, 2008, 9(5):224. doi:10.1186/gb-2008-9-5-224.
Singer et al., Chapter 1.3 "Structure of Proteins," Genes & Genomes, 1998, pp. 63-64 (in Russian, which what are believed to be corresponding pages from an English version of Genes & Genomes, pp. 67-70).
Wenig et al., "Structure of the streptococcal endopeptidase IdeS, a cysteine proteinase with strict specificity for IgG," Proc Natl Acad Sci USA, Dec. 14, 2004, 101:17371-17376.
USPTO Final Office Action in U.S. Appl. No. 14/351,654, dated Apr. 14, 2016, 12 pages.
U.S. Appl. No. 15/490,936, Igawa et al., filed Apr. 17, 2017.
U.S. Appl. No. 16/093,495, filed Oct. 12, 2018, Saeki et al.
U.S. Appl. No. 16/226,798, filed Dec. 20, 2018, Hattori et al.
Abe et al., "Novel Protein A Resin: Synthetic Polymer Matrix Design Impact on Antibody Binding Capacity," JSR Technical Review No. 119, 2012, p. 1-5 [online], [retrieved on Feb. 17, 2017], retrieved from the internet: <URL:http://www.jsr.co.jp/pdf/rd/tec119-1.pdf > (with English translation).
Cruse et al., Atlas of Immunology, CRC Press LLC, 2004, Chapter 3 "Antigens and Immunogens," p. 109.

Decision of the EPO Opposition Division for EP 2 006 381 on Jul. 25, 2018, 17 pages.
GE Healthcare Life Sciences, Dynamic binding capacity study on MabSelect SuReTM LX for capturing high-titer monoclonal antibodies, Application note 28/9875-25-AA, 2011, [online], [retrieved on Feb. 17, 2017], retrieved from the internet;,http://www.processdevelopmentforum.com/images/articles/28/9875-25_AA_AN_DBC_study_on_MabSelect_SuRe_LX_final.pdf.
Geneseq Accession No. ARZ17615, Aug. 21, 2008, "Human antibody IgG2 heavy chain constant region SEQ ID No. 36".
Sequence alignments and modification scheme (document filed during Oral Proceedings in EPO opposition for EP 2 006 381 mentioned in minutes of the Oral Proceedings posted by EPO on Jul. 25, 2018); 3 pages.
Van Den Abbeele et al., "Antigen-Binding Site Protection During Radiolabeling Leads to a Higher Immunoreactive Fraction," J Nucl Med, Jan. 1991, 32(1):116-22.
"Hemostatic Therapy Guideline for Inhibitor-negative Hemophilia Patients," Japanese Journal of Thrombosis and Hemostasis, 2013, 24(6):619-639 (with English translation).
"Hemostatic Therapy Guideline for Inhibitor-positive Hemophilia Patients," Japanese Journal of Thrombosis and Hemostasis, 2013, 24(6):640-658 (with English translation).
ALPROLIX Intravenous, 2019, 16 pages (with English translation).
Astermark et al., "When to start and when to stop primary prophylaxis in patients with severe haemophilia," Blood, Jan. 15, 2007, 109(2):546-51. Epub Sep. 21, 2006.
Collins et al., "Implications of coagulation factor VIII and IX pharmaco-kinetics in the prophylactic treatment of haemophilia," Haemophilia, Jan. 2011, 17(1):2-10. doi: 10.1111/j.1365-2516.2010.02370.x. Epub Aug. 22, 2010.
Coppola et al., "Acquired Inhibitors of Coagulation Factors: Part I—Acquired Hemophilia A," Semin Thromb Hemost, Jul. 2012, 38(5):433-46. doi: 10.1055/s-0032-1315757. Epub Jun. 27, 2012.
Franchini et al., "Acquired haemophilia A: A 2013 update," Thromb Haemost, Dec. 2013, 110(6):1114-20. doi:10.1160/TH13-05-0363. Epub Sep. 5, 2013.
Guidelines for the management of hemophilia, World Federation of Hemophilia, 2005, 52 pages.
Hagiwara et al., "Effect of Emicizumab in improving coagulation ability in the presence of minor amount of Factor IX," Japanese Journal of Thrombosis and Hemostasis, 2017, 28(2):190 0-012 (with English translation).
Kruse-Jarres, "Inhibitors: our greatest challenge. Can we minimize the incidence?," Haemophilia, Jan. 2013, 19(Suppl 1):2-7. doi: 10.1111/hae. 12049.
Lillicrap, "von Willebrand disease: advances in pathogenetic understanding, diagnosis, and therapy," Blood, Nov. 28, 2013, 122(23):3735-40. doi: 10.1182/blood-2013-06-498303. Epub Sep. 24, 2013.
Minami et al., "Bispecific Antibody ACE910 Improves Coagulation Function in Plasma of Patients with Factor XI-Deficiency," Japanese Journal of Thrombosis and Hemostasis, 2015, 26(2):188 0-024 (with English translation).
Miyata, "Factor Ix Abnormality—Molecular defects of Factor IX," Japanese Journal of Thrombosis and Hemostasis, 1991, 2(1):1-11 (with English translation).
Muto et al., "Anti-factor IXa/X bispecific antibody (ACE910): hemostatic potency against ongoing bleeds in a hemophilia A model and the possibility of routine supplementation," J Thromb Haemost, Feb. 2014, 12(2):206-213. doi: 10. 1111/jth.12474.
Muto et al., "Anti-factor IXa/X bispecific antibody ACE910 prevents joint bleeds in a long-term primate model of acquired hemophilia A," Blood, Nov. 13, 2014, 124(20):3165-71. doi: 10. 1182/blood-2014-07-585737. Epub Oct. 1, 2014.
Nishimura et al., "Factor IX Fukuoka. Substitution of $ASN^{92}$ by His in the second epidermal growth factor-like domain results in defective interaction with factors VIIIa/X," J Biol Chem, 1993, 268(32):24041-24046.
Nogami, "Bispecific Antibody that Substitutes for Factor VIII in the Treatment of Childhood Hemophilia A," The Japanese Journal of Pediatric Hematology/Oncology, 2016, 53(2):69-74 (with English translation).

(56) References Cited

OTHER PUBLICATIONS

Shima et al., "Factor VIII-Mimetic Function of Humanized Bispecific Antibody in Hemophilia A," N Engl J Med, May 26, 2016, 374(21):2044-2053. doi: 10.1052/NEJMoa1511769.
Shima, "The Forefront and Prospects of Hemophilia Treatment," J Jpn Pediatr Soc, Mar. 1, 2017, 121(3):543-552 (with English translation).
Tarantino et al., "Safety of human plasma-derived clotting factor products and their role in haemostasis in patients with haemophilia meeting report," Haemophilia, Sep. 2007, 13(5):663-9.
Uchida et al., "A first-in-human phase 1 study of ACE910, a novel factor VIII-mimetic bispecific antibody, in healthy subjects," Blood, Mar. 2016, 127(13):1633-1641. doi: 10.1182/blood-2015-06-650226. Epub Dec. 1, 2015.
U.S. Appl. No. 10/595,905, Hattori et al., filed Apr. 30, 2007 (abandoned).
U.S. Appl. No. 16/448,088, filed Jun 21, 2019, Igawa et al.
U.S. Appl. No. 16/459,791, filed Jul. 2, 2019, Igawa et al.
Barrabes et al., "Effect of sialic acid content on glycoprotein p/ analyzed by two-dimensional electrophoresis," Electrophoresis, Sep. 2010, 31(17):2903-12. doi: 10.1002/elps.200900764.
Mariuzza et al., "The Structural Basis of Antigen-Antibody Recognition," Annu. Rev. Biophys. Biophys. Chem., Jun. 1987, 16:139-159.
U.S. Appl. No. 16/083,975, filed Sep. 11, 2018, Kinoshita et al.
U.S. Appl. No. 16/155,673, filed Oct. 9, 2018, Igawa et al.
Sampei et al, "Non—antigen-contacting region of an asymmetric bispecific antibody to factors IXa/X significantly affects factor VIII-mimetic activity," mAbs, 2015, 7(1):120-8. doi: 10.4161/19420862.2015.989028.
USPTO Restriction Requirement in U.S. Appl. No. 11/910,128, dated Jun. 9, 2011, 10 pages.
USPTO Non-Final Office Action in U.S. Appl. No. 11/910,128, dated Apr. 25, 2012, 21 pages.
USPTO Notice of Non-Responsive Amendment in U.S. Appl. No. 11/910,128, dated Mar. 6, 2013, 7 pages.
USPTO Applicant-Initiated Interview Summary in U.S. Appl. No. 11/910,128, dated Apr. 4, 2013, 3 pages.
USPTO Final Office Action in U.S. Appl. No. 11/910,128, dated Sep. 10, 2013, 12 pages.
USPTO Restriction Requirement in U.S. Appl. No. 11/910,128, dated Apr. 6, 2015, 8 pages.
USPTO Non-Final Office Action in U.S. Appl. No. 11/910,128, dated Sep. 18, 2015, 22 pages.
USPTO Final Office Action in U.S. Appl. No. 11/910,128, dated May 17, 2016, 35 pages.
USPTO Applicant-Initiated Interview Summary in U.S. Appl. No. 11/910,128, dated Sep. 8, 2016, 4 pages.
USPTO Non-Final Office Action in U.S. Appl. No. 11/910,128, dated Nov. 28, 2016, 17 pages.
USPTO Notice of Allowance in U.S. Appl. No. 11/910,128, dated Aug. 8, 2017, 15 pages.
USPTO Notice of Allowance in U.S. Appl. No. 11/910,128, dated Aug. 30, 2017, 15 pages.
USPTO Corrected Notice of Allowability in U.S. Appl. No. 11/910,128, dated Nov. 3, 2017, 21 pages.
USPTO Notice of Allowance in U.S. Appl. No. 11/910,128, dated Feb. 16, 2018, 8 pages.
U.S. Appl. No. 13/518,861, filed Jun. 22, 2012, Igawa et al.
U.S. Appl. No. 13/582,073, filed Aug. 31, 2012, Kuramochi et al.
U.S. Appl. No. 13/885,421, filed May 15, 2013, Igawa et al.
U.S. Appl. No. 14/019,117, filed Sep. 5, 2013, Igawa et al.
U.S. Appl. No. 14/019,712, filed Sep. 6, 2013, Igawa et al.
U.S. Appl. No. 14/921,590, filed Oct. 23, 2015, Hattori et al.
U.S. Appl. No. 15/172,727, filed Apr. 3, 2016, Hattori et al.
U.S. Appl. No. 15/402,580, filed Jan. 10, 2017, Hattori et al.
U.S. Appl. No. 15/467,654, filed Mar. 23, 2017, Nezu et al.
U.S. Appl. No. 15/490,936, filed Apr. 19, 2017, Igawa et al.
U.S. Appl. No. 15/562,186, filed Sep. 27, 2017, Igawa et al.
U.S. Appl. No. 15/614,842, filed Jun. 6, 2017, Igawa et al.
U.S. Appl. No. 15/617,008, filed Jun. 8, 2017, Igawa et al.
U.S. Appl. No. 15/701,630, filed Sep. 12, 2017, Hattori et al.
U.S. Appl. No. 15/725,692, filed Oct. 5, 2017, Igawa et al.
"Hemophilia and von Willebrand's disease: 2. Management. Association of Hemophilia Clinic Directors of Canada," CMAJ., 153(2):147-157, Jul. 15, 1995.
"National Haemophilia Foundation (NHF) Medical and Scientific Advisory Council (MASAC) Recommendations Concerning Prophylaxis," MedicalBulletin, No. 193, 1 page (1994).
Abe et al., "Purification of monoclonal antibodies with light-chain heterogeneity produced by mouse hybridomas raised with NS-1 myelomas: application of hydrophobic interaction high-performance liquid chromatography," J. Biochem. Biophys. Methods, Oct. 1993, 27:215-227.
Abe et al., "Surrogate thrombopoietin," Immunology Letters, Apr. 1998, 61:73-78.
Adams et al., "Humanization of a recombinant monoclonal antibody to produce a therapeutic HER dimenzationinhibitor, pertuzumab," Cancer Immunol. Immunother., Jun. 2006, 55:717-727.
Algonomics—Tripole® applications [online] [retrieved on Feb. 29, 2012]. Retrieved from the Internet: http://web.archive.org/web20090221052902/http://www.algonomics.com/proteinengineering/tripole_applications.php, 2 pages (Feb. 21, 2009).
Allard et al., "Antigen binding properties of highly purified bispecific antibodies," Mol Immunol., Oct. 1992;29(10):1219-27.
Allen et al., "Interchain disulfide bonding in human IgG2 antibodies probed by site-directed mutagenesis," Biochemistry, Apr. 15, 2009, 48(17):3755-66.
Almagro et al., "Humanization of antibodies," Front Biosci., Jan. 1, 2008, 13:1619-33.
Amann et al., "Therapeutic window of an EpCAM/CD3-specific BiTE antibody in mice is determined by a subpopulation of EpCAM-expressing lymphocytes that is absent in humans," Cancer Immunol Immunother. Jan. 2009: 58 (1) :95-109. Epub Jul. 2, 2008.
Amersdorfer et al., GenPept Accession No. AAC26541, "anti BoNT/A Hc scFv antibody [synthetic construct]," Aug. 1, 2001, 1 page.
Amersham Biosciences, "Affinity Chromatography: Principles and Methods," Edition AD, pp. 16-18, 137 (2002).
Amersham Biosciences, "Protein Purification Handbook, " Edition AC, 98 pages (2001).
Andris-Widhopf et al., "Methods for the generation of chicken monoclonal antibody fragments by phage display," Journal of Immunological Methods, Aug. 28, 2000, 242:159-181.
Angal et al., "A single amino acid substitution abolishes the heterogeneity of chimeric mouse/human (IgG4) antibody," Mol. Immunol., Jan. 1, 1993, 30:105-108.
Armour et al., "Recombinant human IgG molecules lacking Fcgamma receptor I binding and monocyte triggering activities," Eur. J. Immunol., Aug. 1, 1999, 29(8):2613-24.
Arndt et al., "Factors influencing the dimer to monomer transition of an antibody single-chain Fv fragment," Biochemistry, Sep. 15, 1998, 37(37):12918-26.
Arndt et al., "Generation of a highly stable, internalizing anti-DC22 single-chain Fv fragment for targeting non-Hodgkin's lymphoma," Int. J. Cancer, Dec. 10, 2003, 107(5):822-829.
Arndt et al., "Helix-stabilized Fv (hsFv) antibody fragments: substituting the constant domains of a Fab fragment for a heterodimeric coiled-coil domain," J. Mol. Biol., Sep. 7, 2001, 312:221-228.
Aslan et al., "Engineering a novel, stable dimeric streptavidin with lower isoelectric point," J. Biotechnol., Feb. 1, 2007, 128(2):213-25.
Asselta et al., "Factor V Deficiency," Semin. Thromb. Hemost., Jun. 2009, 35:382-389.
Atwell et al., "Stable heterodimers from remodeling the domain interface of a homodimer using a phage display library," J. Mol. Biol., Jul. 1997, 270:26-35.
Baerga-Ortiz et al., "Two different proteins that compete for binding to thrombin have opposite kinetic and thermodynamic profiles," Protein Sci., Jan. 1, 2004, 13(1):166-76.
Bajaj et al., "A Monoclonal Antibody to Factor IX That Inhibits the Factor VIII:Ca Potentiation of Factor X Activation," J. Biol. Chem., Sep. 25, 1985;260(21):11574-11580.

(56) References Cited

OTHER PUBLICATIONS

Baker et al., "Conversion of a T cell antagonist into an agonist by repairing a defect in the TCR/peptide/MHC interface: implications for TCR signaling," Immunity, Oct. 1, 2000, 13:475-484.
Ballmaier et al., "c-mpl mutations are the cause of congenital amegakaryocytic thrombocytopenia," Jan. 1, 2001, Blood, 97:139-146.
Bartelds et al., "Clinical response to adalimumab: relationship to anti-adalimumab antibodies and serum adalimumab concentrations in rheumatoid arthritis," Ann Rheum. Dis., Feb. 14, 2007, 66:921-926.
Batra et al., "Pharmacokinetics and biodistribution of genetically engineered antibodies," Curr Opin Biotechnol., Dec. 2002;13(6):603-8.
Bayry et al., "Immuno affinity purification of foot and mouth disease virus type specific antibodies using recombinant protein adsorbed to polystyrene wells," J. Virol. Methods, Aug. 31, 1999, 81:21-30.
Bebbington et al., "High-Level Expression of a Recombinant Antibody from Myeloma Cells Using a Glutamine Synthetase Gene as an Amplifiable Selectable Marker," Biotechnology (N Y), Feb. 1992;10:169-175.
Bender et al., "Immunogenicity, efficacy and adverse events of adalimumab in RA patients," Rheumatol. Int., Jan. 1, 2007, 27:269-274.
Bendig M. M., "Humanization of Rodent Monoclonal Antibodies by CDR Grafting," Methods: A Companion to Methods in Enzymology, 1995; 8:83-93.
Bessos et al., "The characterization of a panel of monoclonal antibodies to human coagulation factor IX," Thrombosis Research, Dec. 15, 1985;40:863-867.
Bian et al., "Discovery of promiscuous HLA-II-restricted T cell epitopes with TEPITOPE," Methods, Dec. 2004;34(4):468-75.
Binz et al., "Engineering novel binding proteins from nonimmunoglobulin domains," Nat. Biotechnol., Oct. 1, 2005, 23:1257-68.
Blazar, "Infusion of Anti-B7.1 (CD80) and Anti-B7.2 (CD86) Monoclonal Antibodies Inhibits Murine Graft-Versus-Host Disease Lethality in Part via Direct Effects on CD4+ and CD8+ T Cells," J. Immunol., Oct. 15, 1996, 157:3250-59.
Bolton-Maggs et al., "Haemophilias A and B," The Lancet, May 24, 2003;361:1801-9.
Borrebaeck et al., "Antibody evolution beyond Nature," Nat Biotechnol., Dec. 2002;20(12):1189-90.
Bos et al., "Enhanced Transfection of a Bacterial Plasmid into Hybridoma Cells by Electroporation: Application for the Selection of Hybrid Hybridoma (Quadroma) Cell Lines," Hybridoma, Feb. 1992;11:41-51.
Bowen, Haemophilia A and haemophilia B: molecular insights, Mol Pathol., Feb. 2002;55(1):1-18.
Bowie et al., "Deciphering the Message in Protein Sequences: Tolerance to Amino Acid Substitutions," Science, Mar. 16, 1990, 247:1306-1310.
Branden and Tooze, "Recognition of Foreign Molecules by the Immune System," Introduction to Protein Structure, 2d Ed., Garland Publishing, pp. 299-323 (1999).
Brandstetter et al., "X-ray structure of clotting factor IXa: active site and module structure related to Xase activity and hemophilia B," Proc Natl Acad Sci U S A, Oct. 10, 1995;92(21):9796-800.
Brennan et al., "Preparation of Bispecific Antibodies by Chemical Recombination of Monoclonal Immunoglobulin G1 Fragments," Science, Jul. 5, 1985;229:81-3.
Brenner et al., "Errors in genome annotation," Trends in Genetics, Apr. 1999;15:132-133.
Brinkman et al. "Phospholipid-binding domain of factor Viii is involved in endothelial cell-mediated activation of factor X by factor IXa," Arterioscler. Thromb. Vasc. Biol., Mar. 1, 2002;22(3):511-6.
Brinkmann et al., "FTY720: targeting G-protein-coupled receptors for sphingosine 1-phosphate in transplantation and autoimmunity," Curr. Opin. Immunol., Oct. 1, 2002, 14:569-575.
Brown et al., "Tolerance of single, but not multiple, amino acid replacements in antibody $V_H$ CDR2: a means of minimizing B cell wastage from somatic hypermutation?," J. Immunol., May 1, 1996, 156(9):3285-91.
Bruenke et al., "A recombinant bispecific single-chain Fv antibody against HLA class II and FcγRIII (CD16) triggers effective lysis of lymphoma cells," Br. J. Haematol., Apr. 1, 2004, 125:167-179.
Buque et al., "Trial Watch: Immunomodulatory monoclonal antibodies for oncological indications," Oncoimmunology, Mar. 2, 2015;4(4):e1008814. eCollection 2015.
Burges et al., "Effective relief of malignant ascites in patients with advanced ovarian cancer by a trifunctional anti-EpCAM x anti-CD3 antibody: a phase I/II study," Clin. Cancer Res., Jul. 1, 2007, 13(13):3899-905.
Burgess et al., "Possible dissociation of the heparin-binding and mitogenic activities of heparin-binding (acidic fibroblast) growth factor-1 from its receptor-binding activities by site-directed mutagenesis of a single lysine residue," J Cell Biol., Nov. 1990;111(5 Pt 1):2129-38.
CALBIOCHEM® Buffers, "A guide for the preparation and use of buffers in biological systems," by Chandra Mohan, Ph.D., Copyright © 2003 EMD Biosciences, Inc., an Affiliate of Merck KGaA, Darmstadt, Germany, 37 pages.
Campoli et al., "Immunotherapy of Malignant Disease with Tumor Antigen-Specific Monoclonal Antibodies," Clin Cancer Res. Jan. 1, 2010:16 (1): 11-20. doi: 10. 1158/ 1078-0432. CCR-09-2345. Epub Dec. 22, 2009.
Carter, "Bispecific human IgG by design," J. Immunol. Methods, Feb. 1, 2001, 248:7-15.
Casset et al., "A peptide mimetic of an anti-CD4 monoclonal antibody by rational design," Biochemical and Biophysical Research Communications, Jul. 18, 2003, 307:198-205.
Cekaite et al., "Protein Arrays: A versatile toolbox for target identification and monitoring of patient immune responses," Methods Mol. Biol., 360:335-348 (2007).
Chamow et al., "A humanized, bispecific immunoadhesin-antibody that retargets CD3+ effectors to kill HIV-1-infected cells," J. Immunol., Nov. 1, 1994, 153(9):4268-80.
Chan et al., "Therapeutic antibodies for autoimmunity and inflammation," Nat Rev Immunol. May 2010 ;10(5):301-16. do i: 10.1038/ nri 2761.
Chappel et al., "Identification of a secondary Fc gamma RI binding site within a genetically engineered human IgG antibody," J Biol Chem., Nov. 25, 1993;268(33):25124-31.
Chappel et al., "Identification of the Fc gamma receptor class I binding site in human IgG through the use of recombinant IgG1/ IgG2 hybrid and point-mutated antibodies," Proc Natl Acad Sci U S A., Oct. 15, 1991;88(20):9036-40.
Chatellier et al., "Functional mapping of conserved residues located at the VL and VH domain interface of a Fab," J. Mol. Biol., Nov. 22, 1996, 264(1):1-6.
Chau et al., "HuM291(Nuvion), a humanized Fc receptor-nonbinding antibody against CD3, anergizes peripheral blood T cells as partial agonist of the T cell receptor," Transplantation., Apr. 15, 2001, 71(7):941-50.
Chen et al., "Defective secretion of an immunoglobulin caused by mutations in the heavy chain complementarity determining region 2," J. Exp. Med., Aug. 1, 1994, 180(2):577-86.
Chen et al., "Generation and analysis of random point mutations in an antibody CDR2 sequence: many mutated antibodies lose their ability to bind antigen," J. Exp. Med., Sep. 1, 1992, 176(3):855-66.
Chen et al., "Selection and analysis of an optimized anti-VEGF antibody: crystal structure of an affinity-matured Fab in complex with antigen," Journal of Molecular Biology, Nov. 5, 1999, 293:865-881.
Chirino et al., "Minimizing the immunogenicity of protein therapeutics," Drug Discov. Today., Jan. 15, 2004, 9:82-90.
Choi et al., "Engineering of Immunoglobulin Fc Heterodimers Using Yeast Surface-Displayed Combinatorial Fc Library Screening," PLoS One, Dec. 16, 2015;10(12):e0145349. doi: 10.1371/ journal.pone.0145349. eCollection 2015.
Chowdhury et al., "Engineering scFvs for improved stability," Methods Mol. Biol., 207:237-54 (2003).

(56) References Cited

OTHER PUBLICATIONS

Chu et al., "Accumulation of succinimide in a recombinant monoclonal antibody in mildly acidic buffers under elevated temperatures," Pharm. Res., Jun. 1, 2007, 24(6):1145-56.
Clackson et al., "Making antibody fragments using phage display libraries," Nature, Aug. 15, 1991, 352:624-628.
Clark, "CD22, a B Cell-Specific Receptor, Mediates Adhesion and Signal Transduction," J. Immunol., Jun. 1, 1993, 150:4715-4718.
Co et al., "A Humanized Antibody Specific for the Platelet Integrin gpIIb/IIIa," J. Immunol., Mar. 15, 1994, 152:2968-2976.
Cochlovius et al., "Treatment of human B cell lymphoma xenografts with a CD3 x CD19 diabody and T cells," The Journal of Immunology, Jul. 15, 2000, 165:888-895.
Cole et al., "Human IgG2 variants of chimeric anti-CD3 are nonmitogenic to T cells," J. Immunol., Oct. 1, 1997, 159(7):3613-21.
Coloma et al., "Position effects of variable region carbohydrate on the affinity and in vivo behavior of an anti-(1→6) dextran antibody," J Immunol., Feb. 15, 1999;162(4):2162-70.
Comper et al., "Charge selectivity in kidney ultrafiltration," Kidney Int., May 1, 1995, 47:1242-51.
Cordoba et al., "Non-enzymatic hinge region fragmentation of antibodies in solution," J. Chromatogr. B. Analyt. Technol. Biomed. Life Sci., Apr. 25, 2005, 818(2):115-21.
Couto et al., "Anti-BA46 Monoclonal Antibody Mc3: Humanization Using a Novel Positional Consensus and in Vivo and in Vitro Characterization," Cancer Research, Apr. 15, 1995, 55:1717-1722.
Creighton, "Protein folding," Biochem. J., Aug. 15, 1990, 270(1):1-16.
Dahlback, "Blood coagulation," Lancet, May 6, 2000, 355(9215):1627-32.
Dall'Acqua et al., "Antibody humanization by framework shuffling," Methods, May 31, 2005, 36(1):43-60.
Dall'Acqua et al., "Increasing the affinity of a human IgG1 for the neonatal Fc receptor: biological consequences," J. Immunol., Nov. 1, 2002;169(9):5171-80.
Dall'Acqua et al., "Modulation of the effector functions of a human IgG1 through engineering of its hinge region," J. Immunol., Jul. 15, 2006, 177(2):1129-38.
Damschroder et al., "Framework shuffling of antibodies to reduce immunogenicity and manipulate functional and biophysical properties," Mol. Immunol., Apr. 30, 2007, 44(11):3049-60.
Daniel et al., "Induction of Apoptosis in Human Lymphocytes by Human Anti-HLA Class I. Antibodies," Transplantation, Apr. 27, 2003, 75:1380-1386.
Datta-Mannan et al., "Monoclonal antibody clearance. Impact of modulating the interaction of IgG with the neonatal Fc receptor," J Biol Chem., Jan. 19, 2007, 282(3):1709-17.
Davie et al., "The coagulation cascade: Initiation, maintenance, and regulation," Biochemistry, Oct. 29, 1991;30(43):10363-70.
Davies et al., "Antibody VH domains as small recognition units," Biotechnology (N.Y.), May 1, 1995, 13(5):475-9.
De Felice et al., "Differential regulatory role of monomorphic and polymorphic determinants of histocompatibility leukocyte antigen class I antigens in monoclonal antibody OKT3-induced T cell proliferation," J. Immunol., Oct. 15, 1987, 139:2683-2689.
De Groot et al., "De-immunization of therapeutic proteins by T-cell epitope modification," Dev. Biol. (Basel), Jan. 2005, 122:171-94.
De Jonge et al., "Production and Characterization of Bispecific Single-Chain Antibody Fragments," Mol. Immunol., Dec. 1, 1995, 32:1405-1412.
Deen et al., "Structural determinants of glomerular permeability," Am. J. Physiol. Renal. Physiol., Oct. 1, 2001, 281:F579-F596.
Dejonge et al., "In vivo retargeting of T cell effector function by recombinant bispecific single chain Fv (anti-DC3 x anti-idiotype) induces long term survival of the murine BCL1 lymphoma model," J. Immunol., Aug. 1, 1998, 161(3):1454-1461.
Del Rio et al., "An Engineered Penicillin Acylase with Altered Surface Charge Is More Stable in Alkaline pH," Ann. NY Acad. Sci., Oct. 1, 1996, 799:61-64.

Denardo et al., "Anti-HLA-DR/anti-DOTA Diabody Construction in a Modular Gene Design Platform: Bispecific Antibodies for Pretargeted Radioimmunotherapy," Cancer Biother. Radiopharm., Dec. 1, 2001, 16:525-535.
Deng et al., "An Agonist Murine Monoclonal Antibody to the Human c-Mpl Receptor Stimulates Megakaryocytopoiesis," Blood, Sep. 15, 1998, 92:1981-1988.
Depascalis et al., "Grafting of "abbreviated" complementarity-determining regions containing specificity-determining residues essential for ligand contact to engineer a less immunogenic humanized monoclonal antibody," J Immunol., Sep. 15, 2002;169(6):3076-84.
Desplancq et al., "Multimerization behaviour of single chain Fv variants for the tumour-binding antibody B72.3," Protein Engineering, Aug. 1, 1994, 7(8):1027-1033.
Dhiman et al., "Gene expression microarrays: a 21st century tool for directed vaccine design," Vaccine, Oct. 12, 2001;20(1-2):22-30.
Diaz et al., "Effects of engineering charged amino acids in the CH3 domains on antibody heavy chain dimerization," Philippine Science Letters. 2011;4(1):48-55.
Dillon et al., "Structural and functional characterization of disulfide isoforms of the human IgG2 subclass," J. Biol. Chem., Jun. 6, 2008, 283(23):16206-15.
Dumont et al., "Monomeric Fc fusions: impact on pharmacokinetic and biological activity of protein therapeutics," BioDrugs., May 1, 2006, 20(3):151-60.
Ebert et al., "Expression of Metallothionein II in Intestinal Metaplasia, Dysplasia, and Gastric Cancer," Cancer Res., Apr. 1, 2000, 60:1995-2001.
Edelman et al., "The covalent structure of an entire gammaG immunoglobulin molecule," Proc Natl Acad Sci U S A., May 1969;63(1):78-85.
Eijsink et al., "Rational engineering of enzyme stability," Journal of Biotechnology, Sep. 30, 2004, 113:105-120.
Ejima et al, "Effects of Acid Exposure on the Conformation, Stability, and Aggregation of Monoclonal Antibodies," Proteins. Mar. 1, 2007;66(4):954-62.
Elliott et al., "Activation of the Erythropoietin (EPO) Receptor by Bivalent Anti-EPO Receptor Antibodies," J. Biol. Chem., Oct. 4, 1996, 271:24691-24697.
Ewert et al., "Biophysical properties of human antibody variable domains," J. Mol. Biol., Jan. 17, 2003, 325:531-553.
Ewert et al., "Stability improvement of antibodies for extracellular and intracellular applications: CDR grafting to stable frameworks and structure-based framework engineering," Methods, Oct. 31, 2004, 34:184-199.
Ewert et al., "Structure-based improvement of the biophysical properties of immunoglobulin $V_H$ domains with a generalizable approach," Biochemistry, Feb. 18, 2003, 42:1517-1528.
Fay et al., "Chapter 2B Nonenzymatic cofactors: factor VIII," Comprehensive Biochemistry, Jun. 23, 1986, 13:35-37.
Fay et al., "The size of human factor VIII heterodimers and the effects produced by thrombin," Biochim Biophys Acta., Jun. 23, 1986, 871(3):268-78.
Fay, "Activation of factor VIII and mechanisms of cofactor action," Blood Rev., Mar. 2004;18(1):1-15.
Fayen et al., "Negative signaling by anti-HLA class I antibodies is dependent upon two triggering events," Int. Immunol., Sep. 1, 1998, 10:1347-1358.
Figini et al., "In vitro assembly of repertoires of antibody chains on the surface of phage by renaturation," J Mol Biol., May 27, 1994;239(1):68-78.
Francois et al., "Construction of a Bispecific Antibody Reacting with the α- and β-Chains of the Human IL-2 Receptor," J. Immunol., May 15, 1993;150:4610-9.
Fujii, "Antibody affinity maturation by random mutagenesis," Methods Mol. Biol., 248:345-59 (2004).
Funaro et al., "Monoclonal antibodies and therapy of human cancers," Biotechnol. Adv., Aug. 31, 2000, 18:385-401.
Gelderman et al., "The inhibitory effect of CD46, CD55, and CD59 on complement activation after immunotherapeutic treatment of cervical carcinoma cells with monoclonal antibodies or bispecific monoclonal antibodies," Lab Invest., Apr. 1, 2002, 82(4):483-93.

(56) References Cited

OTHER PUBLICATIONS

Gen Bank Accession No. AAG00910.2, "recombinant IgG2 heavy chain, partial [*Homo sapiens*]," May 14, 2001, 1 page.
Genestier et al., "Caspase-dependent Ceramide Production in Fas- and HLA Class I-mediated Peripheral T Cell Apoptosis," J. Biol. Chem., Feb. 27, 1998, 273:5060-5066.
Genestier et al., "Antibodies to HLA Class 1 α1 Domain Trigger Apoptosis of CD40-Activated Human B Lymphocytes," Blood, Jul. 15, 1997, 90:726-735.
Genestier et al., "Fas-Independent Apoptosis of Activated T Cells Induced by Antibodies to the HLA Class I α1 Domain," Blood, Nov. 1, 1997, 90:3629-3639.
Genestier et al., "T cell sensitivity to HLA class I-mediated apoptosis is dependent on interleukin-2 and interleukin-4," Eur. J. Immunol., Feb. 1, 1997, 27:495-499.
Gerstner et al., "Sequence plasticity in the antigen-binding site of a therapeutic anti-HER2 antibody," J. Mol. Biol., Aug. 30, 2002, 321(5):851-62.
Gessner et al., "The IgG Fc receptor family," Ann. Hematol., Jun. 1, 1998, 76:231-248.
Ghetie et al., "FcRn: the MHC class I-related receptor that is more than an IgG transporter," Immunol. Today, Dec. 1, 1997, 18:592-598.
Ghetie et al., "Homodimerization of tumor-reactive monoclonal antibodies markedly increases their ability to induce growth arrest or apoptosis of tumor cells," Proc. Natl. Acad. Sci. USA, Jul. 8, 1997, 94:7509-7514.
Ghetie et al., "Increasing the serum persistence of an IgG fragment by random mutagenesis," Nature Biotechnology, Jul. 1, 1997, 15:637-640.
Ghetie et al., "Multiple roles for the major histocompatibility complex class I-related receptor FcRn," Annu. Rev. Immunol., Apr. 18, 2000, 18:739-766.
Gobburu et al., "Pharmacokinetics/dynamics of 5c8, a monoclonal antibody to CD154 (CD40 ligand) suppression of an immune response in monkeys," J. Pharmacol. Exp. Ther., Aug. 1, 1998, 286:925-930.
Goding, "Monoclonal Antibodies: Principles and Practice," Academic Press, second Ed., 125:129 (1986).
Goel et al., "$^{99m}$Tc-Labeled Divalent and Tetravalent CC49 Single-Chain Fv's: Novel Imaging Agents for Rapid In Vivo Localization of Human Colon Carcinoma," J. Nucl. Med., Oct. 1, 2001, 42:1519-1527.
Goel et al., "Genetically Engineered Tetravalent Single-Chain Fv of the Pancarcinoma Monoclonal Antibody CC49: Improved Biodistribution and Potential for Therapeutic Application," Cancer Res., Dec. 15, 2000, 60:6964-6971.
Goldstein et al., "Cytolytic and Cytostatic Properties of an Anti-Human FcγRI (CD64) x Epidermal Growth Factor Bispecific Fusion Protein," J. Immunol., Jan. 15, 1997, 158:872-879.
Gonzales et al., "Minimizing the immunogenicity of antibodies for clinical application," Tumour Biol., Jan.-Feb. 2005;26(1):31-43.
Goode et al., "The glomerular basement membrane charge-selectivity barrier: an oversimplified concept?," Nephrol. Dial. Transplant., Sep. 1996, 11:1714-16.
Goto et al., "A Novel Membrane Antigen Selectively Expressed on Terminally Differentiated Human B Cells," Blood, Sep. 15, 1994, 84:1922-1930.
Gramer et al., "Production of stable bispecific IgG1 by controlled Fab-arm exchange: scalability from bench to large-scale manufacturing by application of standard approaches," MAbs., Nov.-Dec. 2013;5(6):962-73. doi: 10.4161/mabs.26233. Epub Aug. 22, 2013.
Graves et al., "Molecular modeling and preclinical evaluation of the humanized NR-LU-13 antibody," Clin. Cancer Res., Apr. 1, 1999, 5(4):899-908.
Greenwood et al., "Structural motifs involved in human IgG antibody effector functions," Eur J Immunol., May 1993;23(5):1098-104.
Griffin et al., "Analysis of heavy and light chain sequences of conventional camelid antibodies from Camelus dromedarius and Camelus bactrianus species," J Immunol Methods, Mar. 2014;405:35-46. doi: 10.1016/j.jim.2014.01.003. Epub Jan. 18, 2014.
Grosse-Hovest et al., "A recombinant bispecific single-chain antibody induces targeted, supra-agonistic CD28-stimulation and tumor cell killing", European Journal of Immunology, May 2003;33(5):1334-40.
Gruber et al., "Efficient tumor cell lysis mediated by a bispecific single chain antibody expressed in *Escherichia coli*," Journal of Immunology, Jun. 1, 1994, 152(11):5368-5374.
Gunasekaran et al., "Enhancing antibody Fc heterodimer formation through electrostatic steering effects: applications to bispecific molecules and monovalent IgG," J. Biol. Chem., Jun. 18, 2010;285(25):19637-46. doi: 10.1074/jbc.M110.117382. Epub Apr. 16, 2010.
Gunawardane et al., "Agonistic Human Antibodies Binding to Lecithin-Cholesterol Acyltransferase Modulate High Density Lipoprotein Metabolism," J Biol Chem. Feb. 5, 2016;291(6):2799-811. doi: 10.1074/jbc.M115.672790. Epub Dec. 7, 2015.
Gupta et al., "Affinity chromatography and co-chromatography of bispecific monoclonal antibody immunoconjugates," J. Biochem. Biophys. Methods, May 31, 2002, 51(3):203-216.
Guyre et al., "Increased potency of Fc-receptor-targeted antigens," Cancer Immunol. Immunother., Nov. 1, 1997, 45(3-4):146-8.
Haagen et al., "Unprimed CD4+ and CD8+ T cells can be rapidly activated by a CD3 x CD19 bispecific antibody to proliferate and become cytotoxic," Cancer Immunol Immunother., Dec. 1994;39(6):391-6.
Hamers-Casterman et al., "Naturally occurring antibodies devoid of light chains," Nature, Jun. 3, 1993;363(6428):446-8.
Hämmerling et al., "Use of Hybrid Antibody with Anti-γG and Anti-Ferritin Specificities in Locating Cell Surface Antigens by Electron Microscopy," J. Exp. Med., Dec. 1, 1968;128:1461-73.
Hanson et al., "Catalytic antibodies and their applications," Curr. Opin. Biotechnol., Dec. 31, 2005, 16(6):631-636.
Hattori, Introduction of ART-Ig and application to hemophilia A treatment, Chugai Seiyaku ni Okeru Dokuji no Kakushinteki Kotai Gijutsu. Dec. 2012; 18: 42-57 (with English translation).
He et al., "Humanization and pharmacokinetics of a monoclonal antibody with specificity for both E- and P-selectin," J. Immunol., Jan. 15, 1998, 160(2):1029-35.
Helfrich et al., "A rapid and versatile method for harnessing scFv antibody fragments with various biological effector functions," J. Immunol. Methods, Apr. 3, 2000, 237(1-2):131-45.
Hess et al., "Cancer therapy with trifunctional antibodies: linking innate and adaptive immunity," Future Oncol. Jan. 2012: 8(1):73-85. doi: 10.2217/ fon.11.138.
Hinton et al., "An engineered human IgG1 antibody with longer serum half-life," J. Immunol., Jan. 1, 2006;176:346-56.
Hinton et al., "Engineered human IgG antibodies with longer serum half-lives in primates," J Biol Chem., Feb. 20, 2004;279(8):6213-6. Epub Dec. 29, 2003.
Hird et al., "Tumour localisation with a radioactively labelled reshaped human monoclonal antibody," Br J Cancer, Nov. 1991;64(5):911-4.
Hoad et al. "Characterization of monoclonal antibodies to human factor X.Xa: Initial observations with a quantitative ELISA procedure," J. Immunol. Methods, Feb. 15, 1991;136(2):269-78.
Holliger et al., "'Diabodies': Small bivalent and bispecific antibody fragments," Proc. Natl. Acad. Sci. USA, Jul. 15, 1993, 90(14):6444-6448.
Hombach et al., "A CD16/CD30 bispecific monoclonal antibody induces lysis of Hodgkin's cells by unstimulated natural killer cells in vitro and in vivo," Int J Cancer, Nov. 11, 1993, 55:830-6.
Hong et al., "Enhanced cellular uptake and transport of polyclonal immunoglobulin G and fab after their cationization," J Drug Target., Jan. 1, 2000;8(2):67-77.
Hoogenboom et al., "Multi-subunit proteins on the surface of filamentous phage: methodologies for displaying antibody (Fab) heavy and light chains," Nucleic Acids Res., Aug. 11, 1991, 19:4133-4137.
Hoyer, L.W., "The factor VIII complex: structure and function," Blood, Jul. 1, 1981, 58(1):1-13.

(56) References Cited

OTHER PUBLICATIONS

Hozumi et al., "Evidence for somatic rearrangement of immunoglobulin genes coding for variable and constant regions," Proc. Natl. Acad. Sci. USA, Oct. 1, 1976, 73(10):3628-3632.
Hsia et al., "Treatment of acquired factor X inhibitor by plasma exchange with concomitant intravenous immunoglobulin and corticosteroids," Am. J. Hematol., Apr. 2008;83:318-20.
Hu et al., "Development and characterization of a novel fusion protein composed of a human IgG1 heavy chain constant region and a single-chain fragment variable antibody against Venezuelan equine encephalitis virus," J Biochem., Jan. 1, 2003, 133(1):59-66.
Hu et al., "Minibody: A Novel Engineered Anti-Carcinoembryonic Antigen Antibody Fragment (Single-Chain Fv-$C_H3$) Which Exhibits Rapid, High-Level Targeting of Xenografts," Cancer Res., Jul. 1, 1996, 56:3055-3061.
Hudson et al., "High avidity scFv multimers; diabodies and triabodies," J. Immunol. Methods, Dec. 10, 1999, 231:177-189.
Huse et al., "Generation of a Large Combinatorial Library of the Immunoglobulin Repertoire in Phage Lambda," Science, Dec. 8, 1989;246:1275-81.
Hwang et al., "Use of human germline genes in a CDR homology-based approach to antibody humanization," Methods, May 31, 2005, 36:35-42.
Ibragimova et al., "Stability of the beta-sheet of the WW domain: A molecular dynamics simulation study," Biophys J., Oct. 1999;77(4):2191-8.
Igawa et al., "Antibody recycling by engineered pH-dependent antigen binding improves the duration of antigen neutralization," Nat. Biotechnol., Nov. 1, 2010, 28(11):1203-7.
Igawa et al., "Engineering the variable region of therapeutic IgG antibodies," MAbs, May 1, 2011, 3(3):243-52.
Igawa et al., "Reduced elimination of IgG antibodies by engineering the variable region," Protein Eng. Des. Sel., Feb. 15, 2010, 23(5):385-92.
Igawa et al., "VH/VL interface engineering to promote selective expression and inhibit conformational isomerization of thrombopoietin receptor agonist single-chain diabody," Protein Eng Des Sel., Aug. 2010;23(8):667-77. doi: 10.1093/protein/gzq034. Epub Jun. 24, 2010.
IMGT Scientific charts depicting the correspondence between EU and Kabat numberings for the human IgG constant region, created May 17, 2001 and last updated Aug. 13, 2014, 2 pages.
Ito et al., "The His-probe method: effects of histidine residues introduced into the complementarity-determining regions of antibodies on antigen-antibody interactions at different pH values," FEBS Lett., Aug. 31, 1992, 309:85-88.
Iwahashi et al., "CDR substitutions of a humanized monoclonal antibody (CC49): contributions of individual CDRs to antigen binding and immunogenicity," Mol Immunol., Oct.-Nov. 1999;36(15-16):1079-91.
Iwai et al., "Therapeutic Agents for Gastric Cancer," Igan Chiryoyaku, Yakkyoku, Jan. 5, 2016:67(1)138-41 (with English translation).
Jackman et al., "Development of a two-part strategy to identify a therapeutic human bispecific antibody that inhibits IgE receptor signaling," J Biol Chem., Jul. 2, 2010;285(27): 20850-9. doi: 10.1074/jbc.M110.113910. Epub May 5, 2010.
Jäger et al., "Folding and assembly of an antibody Fv fragment, a heterodimer stabilized by antigen," Journal of Molecular Biology, Feb. 5, 1999, 285:2005-2019.
Jain et al., "Engineering antibodies for clinical applications," Trends Biotechnol., Jul. 31, 2007, 25(7):307-16.
Janeway et al., "Structure of the Antibody Molecule and Immunoglobulin Genes," Immunobiology, 3$^{rd}$ Edition, Garland Press, 3:1-3:11 (1997).
Janeway et al., Immunobiology, 5th edition. 2001 :Extract from Chapter 3, pp. 93-122.
Janeway et al., Immunobiology, 5th edition. 2001 :Extract from Chapter 4, pp. 123-154.
Jefferis et al., "Interaction sites on human IgG-Fc for FcγR: current models," Immunol Lett. Jun. 3, 2002:82(1-2):57-65.
Jefferis et al., "Recognition sites on human IgG for Fc gamma receptors: the role of glycosylation," Immunol. Lett., Jan. 2, 1995, 44(2-3):111-7.
Jendeberg et al., "Engineering of Fc(1) and Fc(3) from human immunoglobulin G to analyse subclass specificity for staphylococcal protein A," J. Immunol. Methods., Feb. 14, 1997, 201(1):25-34.
Jirholt et al., "Exploiting sequence space: shuffling in vivo formed complementarity determining regions into a master framework," Gene., Jul. 30, 1998;215(2):471-6.
Johnson et al., "Cation exchange-HPLC and mass spectrometry reveal C-terminal amidation of an IgG1 heavy chain,"Anal. Biochem., Jan. 1, 2007, 360:75-83.
Johnson et al., "Kabat database and its applications: 30 years after the first variability plot," Nucleic Acids Res., Jan. 1, 2000;28(1):214-8.
Jones et al., "Growth factor receptor interplay and resistance in cancer," Endocr Relat Cancer. Dec. 2006 :13 Supp 1 1:S45-51.
Jones et al., "Identification and removal of a promiscuous CD4+ T cell epitope from the C1 domain of factor VIII," Thromb. Haemost., May 1, 2005, 3:991-1000.
Ju et al., "Conversion of the interleukin 1 receptor antagonist into an agonist by site-specific mutagenesis," Proc. Natl. Acad. Sci. U.S.A., Apr. 1, 1991, 88:2658-2662.
Jung et al., "The importance of framework residues H6, H7 and H10 in antibody heavy chains: experimental evidence for a new structural subclassification of antibody V(H) domains," J. Mol. Biol., Jun. 8, 2001;309(3):701-16.
Kabat et al., Sequence of Proteins of Immunological Interest, 5$^{th}$ Edition 1991, p. 690 and p. 693.
Kabat et al., Sequences of Proteins of Immunological Interest, National Institute of Health, Publ'n No. 91-3242, vol. 1 p. 647-60 (5th ed. 1991).
Kabsch et al., "On the use of sequence homologies to predict protein structure: identical pentapeptides can have completely different conformations," Proc Natl Acad Sci U S A., Feb. 1984;81(4):1075-8.
Kai et al., "Switching constant domains enhances agonist activities of antibodies to a thrombopoietin receptor," Nat. Biotechnol., Feb. 1, 2008, 26(2):209-11.
Kang et al., "Linkage of recognition and replication functions by assembling combinatorial antibody Fab libraries along phage surfaces," Proc. Natl. Acad. Sci.USA, May 15, 1991;88:4363-6.
Karpovsky et al., "Production of Target-Specific Effector Cells Using Hetero-Cross-Linked Aggregates Containing Anti-Target Cell and Anti-Fcγ Receptor Antibodies," J. Exp. Med., Dec. 1, 1984;160:1686-701.
Kashmiri et al., "Generation, characterization, and in vivo studies of humanized anticarcinoma antibody CC49," Hybridoma, Oct. 1995, 14:461-473.
Katayose et al., "MUC1-specific targeting immunotherapy with bispecific antibodies: inhibition of xenografted human bile duct carcinoma growth," Cancer Res., Sep. 15, 1996, 56(18):4205-12.
Kenanova et al., "Tailoring the pharmacokinetics and positron emission tomography imaging properties of anti-carcinoembryonic antigen single-chain Fv-Fc antibody fragments," Cancer Res., Jan. 15, 2005;65(2):622-31.
Kerschbaumer et al., "An antibody specific for coagulation factor IX enhances the activity of the intrinsic factor X-activating complex," J. Biol. Chem., Sep. 24, 2004, 279(39):40445-50.
Khalifa et al., "Effects on interaction kinetics of mutations at the VH-VL interface of Fabs depend on the structural context," J. Mol. Recognit., May-Jun. 2000;13(3):127-39.
Khawli et al., "Improved tumor localization and radioimaging with chemically modified monoclonal antibodies," Cancer Biother. Radiopharm., Jun. 1996, 11:203-215.
Kikuchi et al., "A bivalent single-chain Fv fragment against CD47 induces apoptosis for leukemic cells," Biochem. Biophys. Res. Commun., Mar. 19, 2004, 315:912-918.
Kim et al., "Antibody Engineering for the Development of Therapeutic Antibodies," Mol. Cells, Aug. 1, 2005, 20:17-29.

(56) References Cited

OTHER PUBLICATIONS

Kim et al., "Chemical modification to reduce renal uptake of disulfide-bonded variable region fragment of anti-tac monoclonal antibody labeled with 99mTc," Bioconjugate Chem., May 17, 1999, 10(3):447-453.
Kim et al., "Lowering of pI by acylation improves the renal uptake of 99mTc-labeled anti-Tac dsFv: effect of different acylating reagents," Nucl. Med. Biol., Nov. 30, 2002, 29:795-801.
Kim et al., "Mammalian type I interferon receptors consists of two subunits: IFNaR1 and IFNaR2," Gene, Sep. 1, 1997;196:279-86.
Kim et al., "Mapping the site on human IgG for binding of the Mhc class I-related receptor, FcRn," Eur. J. Immunol., Sep. 1999;29(9):2819-25.
Kimura et al., "2D7 diabody bound to the α2 domain of HLA class I efficiently induces caspase-independent cell death against malignant and activated lymphoid cells," Biochem. Biophys. Res. Commun., Dec. 24, 2004, 325:1201-1209.
Kipriyanov and Little, "Generation of Recombinant Antibodies," Molecular Biotechnology, Jun. 1, 1999, 12:173-201.
Kipriyanov et al., "Bispecific CD3 x CD19 diabody for T cell-mediated lysis of malignant human B cells," In. J. Cancer, Aug. 31, 1998, 77:763-772.
Kipriyanov et al., "Bispecific tandem diabody for tumor therapy with imprived antigen binding and pharmacokinetics," J Mol Biol., Oct. 15, 1999;293(1):41-56.
Kipriyanov et al., "Effect of Domain Order on the Activity of Bacterially Produced Bispecific Single-chain Fv Antibodies," J. Mol. Biol., Jun. 27, 2003;330(1):99-111.
Kitazawa et al., "A bispecific antibody to factors IXa and X restores factor VIII hemostatic activity in a hemophilia A model," Nat. Med., Oct. 2012;18(10):1570-4. doi:10.1038/nm.2942. Epub Sep. 30, 2012.
Klein et al., "Progress in overcoming the chain association issue in bispecific heterodimeric IgG antibodies," MAbs., Nov.-Dec. 2012;4(6):653-63. doi: 10.4161/mabs.21379. Epub Aug. 27, 2012.
Klinger et al., "Harnessing T cells to fight cancer with BiTE((R)) antibody constructs—past developments and future directions," Immunol. Rev., Mar. 2016 :270(1):193-208. doi:10.1111/imr.12393.
Kobayashi et al., "A monoclonal antibody specific for a distinct region of hen egg-white lysozyme," Mol. Immunol., Apr. 1, 1982, 19:619-30.
Kobayashi et al., "The pharmacokinetic characteristics of glycolated humanized anti-Tac Fabs are determined by their isoelectric points," Cancer Res., Jan. 15, 1999, 59:422-430.
Komissarov et al., "Site-specific mutagenesis of a recombinant anti-single-stranded DNA Fab. Role of heavy chain complementarity-determining region 3 residues in antigen interaction," J. Biol. Chem., Oct. 24, 1997, 272(43):26864-70.
Kong et al., "A Single Residue, Aspartic Acid 95, in the δ Opioid Receptor Specifies Selective High Affinity Agonist Binding," The Journal of Biological Chemistry, Nov. 5, 1993, 268(31):23056-23058.
Kontermann, "Dual targeting strategies with bispecific antibodies," MAbs. Mar.-Apr. 2012 ;4(2):182-97. doi: 10.4161/mabs.4.2.19000. Epub Mar. 1, 2012.
Kontermann, R., "Recombinant bispecific antibodies for cancer therapy," Acta Pharmacol Sin., Jan. 2005;26(1):1-9.
Korn et al., "Recombinant bispecific antibodies for the targeting of adenoviruses to CEA-expressing tumour cells: a comparative analysis of bacterially expressed single-chain diabody and tandem scFv," J Gene Med., Jun. 2004;6(6):642-651.
Kortt et al., "Dimeric and trimeric antibodies: high avidity scFvs for cancer targeting," Biomol. Eng., Oct. 15, 2001, 18:95-108.
Kranenborg et al., "Development and characterization of anti-renal cell carcinoma x antichelate bispecific monoclonal antibodies for two-phase targeting of renal cell carcinoma," Cancer Res., Dec. 1, 1995, 55:5864s-5867s.
Krebber et al., "Reliable cloning of functional antibody variable domains from hybridomas and spleen cell repertoires employing a reengineered phage display system," J. Immunol. Methods, Feb. 14, 1997, 201:35-55.

Kreitman et al., "Cytotoxic Activity of Disulfide-stabilized Recombinant Immunotoxin RFB4(dsFv)-PE38 (BL22) toward Fresh Malignant Cells from Patients with B-Cell Leukemias," Clin. Cancer Res., Apr. 1, 2000, 6:1476-1487.
Kreutz et al., "Efficient bispecific monoclonal antibody purification using gradient thiophilic affinity chromatography," J. Chromatogr. B, Sep. 4, 1998, 714:161-170.
Kriangkum et al., "Bispecific and bifunctional single chain recombinant antibodies," Biomol. Eng., Sep. 31, 2001, 18(2):31-40.
Kroesen et al., "Phase I study of intravenously applied bispecific antibody in renal cell cancer patients receiving subcutaneous interleukin 2," Br. J. Cancer, Oct. 1994;70:652-61.
Kufer et al., "A revival of bispecific antibodies," Trends Biotechnol., May 1, 2004, 22(5):238-44.
Kulkarni et al., "Construction of a Single-Chain Antibody Derived From 5H7, A Monoclonal Antibody Specific for a Death Signaling Domain of Human Class I Major Histocompatibility Complex," Transplant. Proc., Jun. 30, 1998, 30:1081.
Kulkarni et al., "Programmed Cell Death Signaling via Cell-Surface Expression of a Single-Chain Antibody Transgene," Transplantation, Mar. 27, 2000, 69:1209-1217.
Kumar et al., "Molecular cloning and expression of the fabs of human autoantibodies in *Escherichia coli*," The Journal of Biological Chemistry, Nov. 10, 2000, 275:35129-35136.
Kumar et al., "The second PDZ domain of INAD is a type I domain involved in binding to eye protein kinase C. Mutational analysis and naturally occurring variants," J Biol Chem., Jul. 6, 2001;276(27):24971-7.
Kurfis et al., "Role of Arg182 in the second extracellular loop of angiotensin II receptor AT2 in ligand binding," Biochem Biophys Res Commun., Oct. 5, 1999;263:816-9.
Kurokawa et al., "Enhanced Fibrinolysis by a Bispecific Monoclonal Antibody Reactive to Fibrin and Tissue Plasminogen Activator," Bio/Technology, Nov. 1989;7:1163-7.
Kurucz et al., "Retargeting of CTL by an efficiently refolded bispecific single-chain Fv dimer produced in bacteria," The Journal of Immunology, May 1, 1995, 154:4576-4582.
Labrijn et al., "Controlled Fab-arm exchange for the generation of stable bispecific IgG1," Nat Protoc. Oct. 2014; 9(10): 2450-63. doi: 10.1038/nprot.2014.169. Epub Sep. 25, 2014.
Labrijn et al., "Efficient generation of stable bispecific IgG1 by controlled Fab-arm exchange," Pro Natl Acad Sci U S A., Mar. 26, 2013;110(13):5145-50. doi: 10.1073/pnas.1220145110. Epub Mar. 11, 2013.
Labrijn et al., "Species-specific determinants in the IgG CH3 domain enable Fab-arm exchange by affecting the noncovalent CH3-CH3 interaction strength," J Immunol., Sep. 15, 2011;187(6):3238-46. doi: 10.4049/jimmunol.1003336. Epub Aug. 12, 2011.
Lacroix-Desmazes et al, "Dynamics of factor VIII interactions determine its immunologic fate in hemophilia A," Blood. Jul. 15, 2008;112(2):240-9. doi: 10.1182/blood-2008-02-124941. Epub May 9, 2008.
Lansdorp et al., "Purification and analysis of bispecific tetrameric antibody complexes," Mol. Immunol., Jul. 31, 1990, 27:659-666.
Lapan et al., "Interaction of the A1 Subunit of Factor VIIIa and the Serine Protease Domain of Factor X Identified by Zero-length Cross-linking," Thromb. Haemost., Sep. 1998;80:418-22.
Larkin et al., "Combined Nivolumab and Ipilimumab or Monotherapy in Untreated Melanoma," N. Engl. J. Med., Jul. 2, 2015:373(1):23-34. doi:10.1056/NEJMoa1504030. Epub May 31, 2015.
Lazar et al., "Transforming growth factor alpha: mutation of aspartic acid 47 and leucine 48 results in different biological activities," Mol Cell Biol., Mar. 1988;8(3):1247-52.
Le Doussal et al., "Bispecific Monoclonal Antibody-Mediated Targeting of an Indium-111-Labeled DTPA Dimer to Primary Colorectal Tumors: Pharmacokinetics, Biodistribution, Scintigraphy and Immune Response," J. Nucl. Med., Oct. 1993;34:1662-71.
Le Gall et al., "Effect of linker sequences between the antibody variable domains on the formation, stability and biological activity of a bispecific tandem diabody," Protein Eng Des Sel., Apr. 2004;17(4):357-66. Epub May 4, 2004.

(56) References Cited

OTHER PUBLICATIONS

Lebégue et al., "Production and characterization of hybrid monoclonal antibodies with IgG1/IgG3 double isotype," C R Acad Sci III., 1990;310(9):377-82.

Lebrun et al., "Antibodies to the Extracellular Receptor Domain Restore the Hormone-insensitive Kinase and Conformation of the Mutant Insulin Receptor Valine 382," J. Biol. Chem., May 25, 1993, 268:11272-11277.

Ledbetter et al., "Agonistic Activity of a CD4O-Specific Single-Chain Fv Constructed from the Variable Regions of mAb G28-5," Critical Reviews in Immunology, 17:427-435 (1997).

Lenting et al., "The life cycle of coagulation factor VIII in view of its structure and function", Blood, Dec. 1, 1998;92(11):3983-96.

Leong et al., "Adapting pharmacokinetic properties of a humanized anti-interleukin-8 antibody for therapeutic applications using site-specific pegylation," Cytokine, Nov. 1, 2001, 16(3):106-19.

Li et al., "Construction and characterization of a humanized anti-human CD3 monoclonal antibody 12F6 with effective immunoregulation functions," Immunology, 2005 Dec;116(4):487-98.

Li et al., "The Epitope Specificity and Tissue Reactivity of Four Murine Monoclonal Anti-CD22 Antibodies," Cell. Immunol., Jan. 1, 1989, 118(1):85-99.

Life Technologies (Invitrogen: "ecdysone analogue" and pIND plasmid), Aug. 10, 2012, 2 pages.

Lin et al., "Preclinical pharmacokinetics, interspecies scaling, and tissue distribution of a humanized monoclonal antibody against vascular endothelial growth factor," J Pharmacol Exp Ther., Jan. 1, 1999, 288(1):371-8.

Lin et al., "Structure-function relationships in glucagon: properties of highly purified des-His-1-, monoiodo-, and (des-Asn-28, Thr-29)(homoserine lactone-27)-glucagon," Biochemistry, Apr. 22, 1975;14(8):1559-63.

Lindhofer et al., "Preferential Species-Restricted Heavy/Light Chain Pairing in Rat/Mouse Quadromas," J. Immunol., Jul. 1, 1995, 155:219-225.

Lindsay, "Chapter 4: Determination of the Kinetics and Mechanism of tg-FIX Activation by Factor XIa," Doctoral Dissertation, 49-75 (2004).

Link et al., "Production and Characterization of a Bispecific IgG Capable of Inducing T-Cell-Mediated Lysis of Malignant B Cells," Blood, Jun. 15, 1993;81:3343-9.

Little et al., "Of mice and men: hybridoma and recombinant antibodies," Immunol. Today, Aug. 1, 2000, 21:364-370.

Liu et al., "Functional interactions between arginine-133 and aspartate-88 in the human reduced folate carrier: evidence for a charge-pair association," Biochem J.,Sep. 1, 2001;358(Pt 2):511-6.

Liu et al., "Heterogeneity of monoclonal antibodies," J. Pharm. Sci., Jul. 1, 2008, 97(7):2426-47.

Lloyd et al., "The production of a bispecific anti-CEA, anti-hapten (4-amino-phthalate) hybrid-hybridoma," J Natl Med Assoc., Oct. 1991;83(10):901-4.

Lobo et al., "Antibody pharmacokinetics and pharmacodynamics," J. Pharm. Sci., Nov. 1, 2004, 93:2645-68.

Löfqvist et al., "Haemophilia prophylaxis in young patients—a long-term follow-up," J. Intern. Med., May 1997;241:395-400.

Lu et al., "Di-diabody: a novel tetravalent bispecific antibody molecule by design," J. Immunol. Methods, Aug. 2003;279:219-32.

Lu et al., "Fab-scFv fusion protein: an efficient approach to production of bispecific antibody fragments," J. Immunol. Methods, Sep. 15, 2002;267:213-26.

Lund et al., "Expression and characterization of truncated forms of humanized L243 IgG1 Architectural features can influence synthesis of its oligosaccharide chains and affect superoxide production triggered through human Fcgamma receptor I," Eur. J. Biochem., Dec. 2000, 267(24):7246-57.

MacCallum et al., "Antibody-antigen interactions: contact analysis and binding site topography," J. Mol. Biol., Oct. 11, 1996, 262:732-45.

Mack et al., "A small bispecific antibody construct expressed as a functional single-chain molecule with high tumor cell cytotoxicity," Proc. Natl. Acad. Sci. USA, Jul. 18, 1995, 92(15):7021-7025.

Maeda et al., "pH-dependent receptor/ligand dissociation as a determining factor for intracellular sorting of ligands for epidermal growth factor receptors in rat hepatocytes," J. Control Release, Jul. 18, 2002, 82(1):71-82.

Maini et al., "Double-blind randomized controlled clinical trial of the interleukin-6 receptor antagonist, tocilizumab, in European patients with rheumatoid arthritis who had an incomplete response to methotrexate," Arthritis Rheum., Sep. 1, 2006, 54:2817-29.

Maity et al., "Equilibrium unfolding of dimeric and engineered monomeric forms of Cro (F58W) repressor and the effect of added salts: evidence for the formation of folded monomer induced by sodium perchlorate," Arch Biochem Biophys., Feb. 1, 2005;434(1):93-107.

Male et al., "Antibodies" Immunology, 7th Edition (2006), published by Elsevier Ltd., pp. 59-86.

Mallender et al., "Construction, expression and activity of a bivalent bispecific single-chain antibody," J. Biol. Chem., Jan. 7, 1994, 269(1):199-206.

Manz et al., Bioanalytical Chemistry, World Scientific Publishing Co., 1 page (2003).

Manzke et al., "Single-step purification of bispecific monoclonal antibodies for immunotherapeutic use by hydrophobic interaction chromatography," J. Immunol. Methods, Oct. 13, 1997;208:65-73.

Marshall et al., "Rational design and engineering of therapeutic proteins," Drug Discov Today, Mar. 1, 2003;8(5):212-21.

Marti et al., "Inverse electrostatic effect: electrostatic repulsion in the unfolded state stabilizes a leucine zipper," Biochemistry, Oct. 5, 2004, 43(39):12436-47.

Martin et al., "Crystal structure at 2.8 A of an FcRn/heterodimeric Fc complex: mechanism of pH-dependent binding," Mol. Cell, Apr. 30, 2001, 7:867-877.

Martinez et al., "Disulfide connectivity of human immunoglobulin G2 structural isoforms," Jul. 15, 2008;47(28):7496-508. doi: 10.1021/bi800576c. Epub Jun. 13, 2008.

Marvin et al., "Recombinant approaches to IgG-like bispecific antibodies," Acta Pharmacol Sin., Jun. 2005;26:649-58.

Marvin et al., "Redesigning an antibody fragment for faster association with its antigen," Biochemistry, Jun. 17, 2003, 42:7077-83.

Massino et al., "Quantitative analysis of the products of IgG chain recombination in hybrid hybridomas based on affinity chromatography and radioimmunoassay," J. Immunol. Methods, Feb. 14, 1997;201:57-66.

Matsuoka et al., "A Monoclonal Antibody to the a2 Domain of Murine Major Histocompatibility Complex Class I that Specifically Kills Activated Lymphocytes and Blocks Liver Damage in the Concanavalin A Hepatitis Model," J. Exp. Med., Aug. 4, 2003, 198:497-503.

Matsuoka et al., "A Novel Type of Cell Death of Lymphocytes Induced by a Monoclonal Antibody without Participation of Complement," J. Exp. Med., Jun. 1, 1995, 181:2007-2015.

Maxfield et al., "Endocytic recycling," Nat. Rev. Mol. Cell Biol., Feb. 1, 2004, 5(2):121-32.

Mccafferty et al., "Phage antibodies: filamentous phage displaying antibody variable domains," Nature, Dec. 6, 1990;348:552-4.

Mcguinness et al., "Phage diabody repertoires for selection of large number of bispecific antibody fragments," Nature Biotechnology, Sep. 1, 1996, 14(9):1149-1154.

Mcphee et al., "Engineering human immunodeficiency virus 1 protease heterodimers as macromolecular inhibitors of viral maturation," Proc Natl Acad Sci U S A., Oct. 15, 1996;93(21):11477-81.

Medesan et al., "Delineation of the amino acid residues involved in transcytosis and catabolism of mouse IgG1," J Immunol., Mar. 1, 1997;158(5):2211-7.

Medline Plus Drug Information: Dexamethasone Oral www.nlm.nih.gov/medlineplus/druginfo/meddmaster/a682792.html, downloaded Jul. 19, 2007; last revised Apr. 1, 2003 (4 pages).

Menegatti et al., "Factor X Deficiency," Semin. Thromb. Hemost., Jun. 2009;35:407-15.

(56) References Cited

OTHER PUBLICATIONS

Meng et al., "The evaluation of recombinant, chimeric, tetravalent antihuman CD22 antibodies," Clinical Cancer Research, Feb. 15, 2004, 10:1274-1281.

Merchant et al., "An efficient route to human bispecific IgG," Nat Biotechnol., Jul. 1998;16(7):677-81.

Mertens et al., "Factor VIII-Factor IX Interactions: Molecular Sites Involved in Enzyme-Cofactor Complex Assembly," Thromb. Haemost., Aug. 1999;82:209-17.

Mezzanzanica et al., "Human Ovarian Carcinoma Lysis by Cytotoxic T Cells Targeted by Bispecific Monoclonal Antibodies: Analysis of the Antibody Components," Int J Cancer. Apr. 1988 15:41(4):609-15.

Michaelsen et al., "A mutant human IgG molecule with only one C1q binding site can activate complement and induce lysis of target cells," Eur J Immunol., Jan. 2006;36(1):129-38.

Milstein et al., "Hybrid hybridomas and their use in immunohistochemistry," Nature, Oct. 6-12, 1983;305:537-40.

Miyazaki et al., "Generation of bispecific IgG, which mimics the cofactor function of blood coagulation factor VIII," Seikagaku, Poster sessions (2P-B-161) (2006).

Moore et al., "Kinetics and thermodynamics of dimer formation and dissociation for a recombinant humanized monoclonal antibody to vascular endothelial growth factor," Biochemistry, Oct. 19, 1999, 38:13960-13967.

Morell et al., "Metabolic properties of IgG subclasses in man," J. Clin. Invest., Apr. 1970, 49(4):673-80.

Morimoto et al., "Single-step purification of F(ab')2 fragments of mouse monoclonal antibodies (immunoglobulins G1) by hydrophobic interaction high performance liquid chromatography using TSKgel Phenyl-Spw," J. Biochem. Biophys. Methods, Jan. 1, 1992, 24:107-117.

Morrison, "Two heads are better than one," Nat Biotechnol. Nov. 2007;25(11):1233-4.

Murata et al., "Anti-Digoxin Fab Variants Generated by Phage Display," Mol Biotechnol. Jun. 2013 :54 (2) :269- 77. doi : 10.1007/s12033-012-9564-1.

Murtaugh et al., "A combinatorial histidine scanning library approach to engineer highly pH-dependent protein switches," Protein Sci., Sep. 1, 2011, 20(9):1619-31 doi:10.1002/pro 696.

Nakano et al. "Anti-glypican 3 antibodies cause ADCC against human hepatocellular carcinoma cells," Biochem Biophys Res Conrnun. Jan. 9, 2009:378 (2) :279-84. doi: 10.1016/j.bbrc.2008.11.033. Epub Nov. 18, 2008.

Natsume et al., "Improving effector functions of antibodies for cancer treatment: Enhancing ADCC and CDC," Drug Des Devel Ther. Sep. 21, 2009 :3:7-16.

Nesterova et al., "Glypican-3 as a novel target for an antibody-drug conjugate," AACR Abstract No. 656, Los Angeles, CA (Apr. 4-18, 2007).

Newman et al, "Modification of the Fc Region of a Primatized IgG Antibody to Human CD4 Retains Its Ability to Modulate CD4 Receptors but Does Not Deplete CD4 T Cells in Chimpanzees," Clin Immunol. Feb. 2001;98(2):164-74.

Ngo et al., "Computational Complexity, Protein Structure Prediction, and the Levinthal Paradox," The Protein Folding Problem and Tertiary Structure Prediction, Merz, Jr. et al. Editors, Birkhauser Boston, 433-506 (1994).

Nieba et al., "Disrupting the hydrophobic patches at the antibody variable/constant domain interface: improved in vivo folding and physical characterization of an engineered scFv fragment," Protein Eng., Apr. 1997;10(4):435-44.

Nilsson et al., "Induction of split tolerance and clinical cure in high-responding hemophiliacs with factor IX antibodies," Proc. Natl. Acad. Sci. U S A., Dec. 1986;83:9169-73.

Nilsson et al., "Twenty-five years' experience of prophylactic treatment in severe haemophilia A and B," J. Intern. Med., Jul. 1992;232:25-32.

Nimmerjahn et al., "Fcγ receptors as regulators of immune responses," Nat Rev Immunol. Jan. 2008; 8(1):34-47.

Nishii, "CD22 antibody therapy," Current Therapy, 20:47-50 (2001) (English translation included).

Nishimoto et al., "Humanized anti-interleukin-6 receptor antibody treatment of multicentric Castleman disease," Blood, Oct. 15, 2005, 106:2627-32.

Nishimoto et al., "Interleukin 6: from bench to bedside," Nat. Clin. Pract. Rheumatol., Nov. 1, 2006, 2:619-626.

Nitta et al., "Preliminary trial of specific targeting therapy against malignant glioma," Lancet, Feb. 17, 1990;335:368-371.

Nohaile et al., "Altering dimerization specificity by changes in surface electrostatics," Pro Natl Acad Sci U S A., Mar. 13, 2001;98(6):3109-14. Epub Feb. 27, 2001.

O'Shea et al., "Peptide 'Velcro': design of a heterodimeric coiled coil," Curr Biol., Oct. 1, 1993;3(10):658-67.

Ohtomo et al., "Molecular Cloning and Characterization of a Surface Antigen Preferentially Overexpressed on Multiple Myeloma Cells," Biochem. Biophys. Res. Commun., May 19, 1999, 258:583-591.

Oka, "Development of Novel Immunotoxin Using Recombinant Alpha-Sarcin and Its Application Treatment of Hematopoietic Tumor," Sankyo Seimei Kagaku Kenkyu Shinko Zaidan Kenkyu Hokokushu, 12:46-56 (1998) (English translation included).

Okubo et al. "The production and characterization of four monoclonal antibodies to human factor X," Nara Med Assoc., Sep. 1987;38(1):20-28.

Onda et al., "Lowering the Isoelectric Point of the Fv Portion of Recombinant Immunotoxins Leads to Decreased Nonspecific Animal Toxicity without Affecting Antitumor Activity," Cancer Res., Jul. 1, 2001, 61:5070-77.

Ono et al., "The humanized anti-HM1.24 antibody effectively kills multiple myeloma cells by human effector cell-mediated cytotoxicity," Mol. Immunol., Apr. 30, 1999, 36:387-395.

Orita et al., "A novel therapeutic approach for thrombocytopenia by minibody agonist of the thrombopoietin receptor," Blood, Jan. 15, 2005, 105:562-566.

Ozaki et al., "A Recombinant HLA Class I-Specific Single Chain Fv Diabody Induces Cell Death in Human Lymphoid Malignancies," Nov. 2003, Blood, 102:933a, Abstract No. 3474.

Ozaki et al., "Humanized Anti-HM1.24 Antibody Mediates Myeloma Cell Cytotoxicity That Is Enhanced by Cytokine Stimulation of Effector Cells," Blood, Jun. 1, 1999, 93:3922-3930.

Ozaki et al., "Immunotherapy of Multiple Myeloma With a Monoclonal Antibody Directed Against a Plasma Cell-Specific Antigen, HM1.24," Blood, Oct. 15, 1997, 90:3179-3186.

Ozhegov et al., Tolkovyi Slovar Russkogo iazyka: 2004, p. 292 (with an English translation of the relevant passage defining "control").

Padlan et al., "Antibody Fab assembly: the interface residues between CH1 and CL," Mol Immunol., Sep. 1, 1986, 23(9):951-60.

Pakula et al., "Genetic Analysis of Protein Stability and Function," Annu. Rev. Genet., Dec. 1989, 23:289-310.

Palacios et al., "IL-3-dependent mouse clones that express B-220 surface antigen, contain Ig genes in germ-line configuration, and generate B lymphocytes in vivo," Cell, Jul. 1, 1985, 41:727-734.

Pan et al., "Blocking neuropilin-1 function has an additive effect with anti-VEGF to inhibit tumor growth," Cancer Cell, Jan. 2007;11(1):53-67.

Panka et al., "Variable region framework differences result in decreased or increased affinity of variant anti-digoxin antibodies," Proc. Natl. Acad. Sci. U.S.A., May 1, 1988, 85(9):3080-4.

Pardridge et al., "Enhanced cellular uptake and in vivo biodistribution of a monoclonal antibody following cationization," J Pharm Sci., Aug. 1995;84(8):943-8.

Pardridge et al., "Enhanced endocytosis in cultured human breast carcinoma cells and in vivo biodistribution in rats of a humanized monoclonal antibody after cationization of the protein," J. Pharmacol. Exp. Ther., Jul. 1, 1998, 286(1):548-54.

Paul et al., "Immunologiya", M.:Mir, 1987-1988, vol. 1, p. 231 (with English translation).

Paul, "Structure and function of immunoglobulins," Fundamental Immunology, Third Edition, 292-295 (1993).

Paul, Fundamental Immunology, $3^{rd}$ edition, p. 242 (1993).

(56) References Cited

OTHER PUBLICATIONS

Pavlinkova et al., "Charge-modified single chain antibody constructs of monoclonal antibody CC49: Generation, characterization, pharmacokinetics, and biodistribution analysis," Nucl. Med. Biol., Jan. 31, 1999, 26:27-34.
Pavlou et al., "The therapeutic antibodies market to 2008," Eur. J. Pharm. Biopharm., Apr. 30, 2005, 59:389-396.
Peipp et al., "Bispecific antibodies targeting cancer cells," Biochem. Soc. Trans., Aug. 2002, 30:507-511.
Pejchal et al., "A Conformational Switch in Human Immunodeficiency Virus gp41 Revealed by the Structures of Overlapping Epitopes Recognized by Neutralizing Antibodies," J Virol. Sep. 2009;83(17):8451-62. doi:10.1128/JVI.00685-09. Epub Jun. 10, 2009.
Peters et al., "Engineering an improved IgG4 molecule with reduced disulfide bond heterogeneity and increased Fab domain thermal stability," J Biol Chem. Jul. 13, 2012; 287(29): 24525-33. doi: 10.1074/jbc.M112.369744. Epub May 18, 2012.
Petkova et al., Enhanced half-life of genetically engineered human IgG1 antibodies in a humanized FcRn mouse model: potential application in humorally mediated autoimmune disease, Int. Immunol. Dec. 2006;18(12):1759-69. Epub 2006.
Pettersen et al., "The TCR-Binding Region of the HLA Class I $\alpha_2$ Domain Signals Rapid Fas-Independent Cell Death: A Direct Pathway for T Cell-Mediated Killing of Target Cells?" J. Immunol., May 1, 1998, 160:4343-4352.
Piétri-Rouxel et al., "The biochemical effect of the naturally occurring Trp64→Arg mutation on human β3-adrenoceptor activity," Eur. J. Biochem., Aug. 1, 1997, 247:1174-1179.
Piper et al., "Interferon therapy in primary care," Primary Care Update for Ob/Gyns, Jul. 2001;8(4):163-69.
Plückthun et al., "New protein engineering approaches to multivalent and bispecific antibody fragments," Immunotechnology, Jun. 30, 1997, 3:83-105.
Poduslo et al., "Polyamine modification increases the permeability of proteins at the blood-nerve and blood-brain barriers," J. Neurochem., Apr. 1, 1996, 66:1599-1609.
Pokkuluri et al., "A domain flip as a result of a single amino-acid substitution," Structure, Aug. 15, 1998;6(8):1067-73.
Pons et al., "Energetic analysis of an antigen/antibody interface: alanine scanning mutagenesis and double mutant cycles on the HyHEL-10/lysozyme interaction," Protein Sci., May 1999, 8(5):958-68.
Portolano et al., "Lack of Promiscuity in Autoantigen-Specific H and L Chain Combinations as Revealed by Human H and L Chain "Roulette"," J. Immunol., Feb. 1, 1993, 150(3):880-887.
Presta et al., "Molecular engineering and design of therapeutic antibodies," Curr. Opin. Immunol., Aug. 31, 2008, 20(4):460-70. doi: 10.1016/j.coi.2008.06.012.
Presta, "Engineering of therapeutic antibodies to minimize immunogenicity and optimize function," Adv. Drug Deliv. Rev., Aug. 7, 2006, 58(5-6):640-56.
Price et al., "Tissue factor and tissue factor pathway inhibitor," Anaesthesia, May 2004;59:483-92.
Pritsch et al., "Can Immunoglobulin CH1 Constant Region Domain Modulate Antigen Binding Affinity of Antibodies?," J Clin Invest. Nov. 15, 1996;98(10):2235-43.
Queen et al., "A humanized antibody that binds to the interleukin 2 receptor," Proc. Natl. Acad. Sci. U.S.A., Dec. 1, 1989, 86(24):10029-10033.
Radaev et al., "The Structure of a Human Type III Fcγ Receptor in Complex with Fc," J Biol Chem. May 11, 2001 :276 (19) :16469-77. Epub Jan. 31, 2001.
Raffen et al., "Reengineering immunoglobulin domain interactions by introduction of charged residues," Protein Eng. Apr. 1998;11:303-9.
Rajagopal et al., "A form of anti-Tac (Fv) which is both single-chain and disulfide stabilized: comparison with its single-chain and disulfide-stabilized homologs," Protein Engineering, Dec. 1, 1997, 10(12):1453-1459.

Rajpal et al., "A general method for greatly improving the affinity of antibodies by using combinatorial libraries," Proc. Natl. Acad. Sci. USA, Jun. 14, 2005, 102:8466-71.
Raposo et al., "Epitope-specific antibody response is controlled by immunoglobulin Vh polymorphisms," J Exp Med. Mar. 10, 2014:211(3):405-11.doi:10.1084/jem.20130968. Epub Feb. 17, 2014.
Rathanaswami et al., "Demonstration of an in vivo generated sub-picomolar affinity fully human monoclonal antibody to interleukin-8," Biochem. Biophys. Res. Commun., Sep. 9, 2005, 334:1004-13.
Reddy et al., "Elimination of Fc receptor-dependent effector functions of a modified IgG4 monoclonal antibody to human CD4," J. Immunol., Feb. 15, 2000, 164(4):1925-33.
Reichert et al., "Development trends for monoclonal antibody cancer therapeutics," Nat. Rev. Drug Discov., May 1, 2007, 6(5):349-56.
Reichert et al., "Monoclonal antibody successes in the clinic," Nat. Biotechnol., Sep. 1, 2005, 23:1073-78.
Reimann et al., "A humanized form of a CD4-specific monoclonal antibody exhibits decreased antigenicity and prolonged plasma half-life in rhesus monkeys while retaining its unique biological and antiviral properties," AIDS Res Hum Retroviruses, Jul. 20, 1997;13(11):933-43.
Reist et al., "Human IgG2 constant region enhances in vivo stability of anti-tenascin antibody 81C6 compared with its murine parent," Clin Cancer Res., Oct. 1998;4(10):2495-502.
Ridgway et al., "'Knobs-into-holes' engineering of antibody $C_H3$ domains for heavy chain heterodimerization," Protein Eng., Jul. 1, 1996, 9:617-621.
Riechelmann et al., "Adoptive therapy of head and neck squamous cell carcinoma with antibody coated immune cells: a pilot clinical trial," Cancer Immunol Immunother. Sep. 2007 :56 (9):1397-406. Epub Feb. 2, 2007.
Rispens et al., "Dynamics of inter-heavy chain interactions in human immunoglobulin G (IgG) subclasses studied by kinetic Fab arm exchange," J Biol Chem., Feb. 28, 2014;289(9):6098-109. doi: 10.1074/jbc.M113.541813. Epub Jan. 14, 2014.
Roguska et al., "Humanization of murine monoclonal antibodies through variable domain resurfacing," Proc Natl Acad Sci U.S.A., Feb. 1, 1994, 91:969-73.
Roitt et al., Immunology, M., Mir, (2000), pp. 110-111 (in Russian, with what is believed to be a published English equivalent of those pages taken from Roitt et al., "Antibody Structure and Function," Immunology, Fifth Ed., (1998), pp. 80-81).
Roitt et al., Immunology, M., Mir, 5th Edition (2000), pp. 97-113 (in Russian. What are believed to be corresponding pages from an English language edition of Immunology are cited as. Desig. ID 755 (Male et al.).
Roopenian et al., "FcRn: the neonatal Fc receptor comes of age," Nat Rev Immunol., 7(9):715-25 (Sep. 2007).
Rossi et al., "Development of New Multivalent-bispecific Agents for Pretargeting Tumor Localization and Therapy," Clin. Cancer Res., Sep. 1, 2003, 9:3886s-3896s.
Rothe et al., "Ribosome display for improved biotherapeutic molecules," Expert Opin. Biol. Ther., Feb. 1, 2006, 6:177-187.
Rothe et al., Recombinant proteins in rheumatology—recent advances, N Biotechnol. Sep. 2011;28(5):502-10.doi:10.1016/ j.nbt.2011.03. 019. Epub Apr. 5, 2011.
Rothlisberger et al., "Domain interactions in the Fab fragment: a comparative evaluation of the single-chain Fv and Fab format engineered with variable domains of different stability," J Mol. Biol., Apr. 8, 2005, 347(4):773-89.
Rousch et al., "Somatostatin displayed on filamentous phage as a receptor-specific agonist," Br. J. Pharmacol., Sep. 1, 1998, 125:5-16.
Rudikoff et al., "Single amino acid substitution altering antigen-binding specificity," Proc. Natl. Acad. Sci. U.S.A., Mar. 1, 1982, 79(6):1979-83.
Ruef et al., "A bispecific antifibrin-antiplatelet urokinase conjugate (BAAUC) induces enhanced clot lysis and inhibits platelet aggregation," Thromb. Haemost., Jul. 1999;82(1):109-14.
Ruf et al., "Pharmacokinetics and in vivo stability of intraperitoneally administered therapeutic antibody catumaxomab," J. Clin. Oncol., 26 (May 20 suppl) (2008), abstr 14006.

(56) References Cited

OTHER PUBLICATIONS

Ruggeri et al., "von Willebrand factor and von Willebrand disease," Blood. Oct. 1987;70(4):895-904.

Saito et al., "Establishment of Factor VIII Mimetic Antibodies and Their In Vitro Activities in Hemophilia A," 2006 National Hemophilia Foundation Symposia, 1 page.

Saito et al., "Factor VIII Mimetic Antibody: (1) Establishment and Characterization of Anti-factor IX/anti-factor X Bispecific Antibodies," 2005 International Society of Thrombosis and Haemostasis, vol. 3, Issue Supplement s1, p. OR160.

Salfeld et al., "Isotype selection in antibody engineering," Nat. Biotechnol., Dec. 1, 2007, 25:1369-72.

Sal-Man et al., "Arginine mutations within a transmembrane domain of Tar, an *Escherichia coli* aspartate receptor, can drive homodimer dissociation and heterodimer association in vivo," Biochem J., Jan. 1, 2005;385(Pt 1):29-36.

Sampei et al., "Identification and multidimensional optimization of an asymmetric bispecific IgG antibody mimicking the function of factor VIII cofactor activity," PLoS One, 2013;8(2):e57479. doi: 10.1371/journal.pone.0057479. Epub Feb. 28, 2013.

Sarkar et al., "Rational cytokine design for increased lifetime and enhanced potency using pH-activated "histidine switching"," Nat Biotechnol., Sep. 2002;20(9):908-13. Epub Aug. 5, 2002.

Sarmay et al., "Mapping and comparison of the interaction sites on the Fc region of IgG responsible for triggering antibody dependent cellular cytotoxicity (ADCC) through different types of human Fc gamma receptor," Mol. Immunol., May 1, 1992, 29(5):633-9.

Sato et al., "CD22 Is Both a Positive and Negative Regulator of B Lymphocyte Antigen Receptor Signal Transduction: Altered Signaling in CD22-Deficient Mice," Immunity, Dec. 1, 1996, 5:551-562.

Sato et al., "Properties of Two VEGF Receptors, Flt-1 and KDR, in Signal Transduction," Ann N.Y. Acad. Sci, May 2000;902:201-207, discussion 205-7.

Sato et al., "Reshaping a human antibody to inhibit the interleukin 6-dependent tumor cell growth," Cancer Res., Feb. 15, 1993, 53:851-856.

Schaefer et al., "Immunoglobulin domain crossover as a generic approach for the production of bispecific IgG antibodies," Proc Natl Acad Sci U S A., Jul. 5, 2011;108(27):11187-92. doi: 10.1073/pnas.1019002108. Epub Jun. 20, 2011.

Schaeffer et al., "The Rat Glomerular Filtration Barrier Does Not Show Negative Charge Selectivity," Microcirculation, Jan. 1, 2002, 9:329-342.

Scheurle et al., "Cancer Gene Discovery Using Digital Differential Display," Cancer Res., Aug. 1, 2000, 60:4037-4043.

Schlereth et al., "T-cell activation and B-cell depletion in chimpanzees treated with a bispecific anti-CD19/anti-CD3 single-chain antibody construct," Cancer Immunol Immunother. May 2006 :55(5) :503-14. Epub Jul. 20, 2005.

Schmidt et al., "Structure-function relationships in factor IX and factor IXa," Trends Cardiovasc Med., Jan. 2003;13(1):39-45.

Schmidt et al., Human Physiology, Moscow, 2:431-436 (1996), and English equivalent: Schmidt et al., "Hemostatis and Coagulation," Human Physiology, R.F. Schmidt, G. Thews (Eds.), Second, Completely Revised Edition, 418-423, Springer-Verlag, 1989.

Schmidt et al., Human Physiology, Moscow, 3:764 (1996), and English equivalent: Schmidt et al., "Enzymes of the pancreatic juice," Human Physiology, R.F. Schmidt, G. Thews (Eds.), Second, Completely Revised Edition, 716, Springer-Verlag, 1989.

Schmitz et al., "Phage display: a molecular tool for the generation of antibodies—a review," Placenta., Mar. 1, 2000, 21 Suppl A:S106-12.

Schuurman et al., "Normal human immunoglobulin G4 is bispecific: it has two different antigen-combining sites," Immunology, Aug. 1999;97(4):693-8.

Schuurman et al., "The inter-heavy chain disulfide bonds of IgG4 are in equilibrium with intra-chain disulfide bonds," Mol Immunol., Jan. 2001;38(1):1-8.

Schwartz et al., "A superactive insulin: [B10-aspartic acid]insulin(human)," Proc Natl Acad Sci. U S A., Sep. 1987;84(18):6408-11.

Sebastian et al., "Treatment of non-small cell lung cancer patients with the trifunctional monoclonal antibody catumaxomab (anti-EpCAM x anti-CD3): a phase I study," Cancer Immunol Immunother. Oct. 2007 :56 (10) :1637-44. Epub Apr. 5, 2007.

Segal et al., "Bispecific antibodies in cancer therapy," Curr Opin Immunol., Oct. 1999;11(5):558-62.

Segal et al., "Introduction: bispecific antibodies," J. Immunol. Methods, Feb. 1, 2001;248:1-6.

Seimetz et al., "Development and approval of the trifunctional antibody catumaxomab (anti-EpCAM x anti-CD3) as a targeted cancer immunotherapy," Cancer Treat Rev. Oct. 2010 :36(6):458-67.doi:10.1016/j.ctrv.2010.03.001 Epub Mar. 27, 2010.

Shalaby et al., "Development of Humanized Bispecific Antibodies Reactive with Cytotoxic Lymphocytes and Tumor Cells Overexpressing the HER2 Protooncogene," J. Exp. Med Jan. 1, 1992, 175:217-225.

Sharifi et al., "Improving monoclonal antibody pharmacokinetics via chemical modification," Q J Nucl Med., Dec. 1998;42(4):242-9.

Shaul, "Exploring the charge space of protein-protein association: a proteomic study," Proteins, Aug. 15, 2005, 60:341-352.

Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., Mar. 2, 2001, 276:6591-6604 (Epub Nov. 28, 2000).

Shima et al., "Factor VIII Mimetic Antibody: (2) In Vitro Assessment of Cofactor Activity in Hemophilia A," 2005 International Society of Thrombosis and Haemostasis, vol. 3, Issue Supplement s1, p. P0038.

Shima et al., "Factor VIII Taitei Kotai (2), Ketsuyubyo A Kanja Katsueki ni okeru in vitro Gyoko Kassei no Kento", Rinsho Ketsueki, Aug. 30, 2005;46(8):777 (#WS-36-5) (with English translation).

Shima, M., "Bispecific antibodies to coagulation factors IXa and X mimic the function of factor VIII," 2006 World Federation of Haemophilia (Haemophilia, 12(Suppl. 2):98 (2006)).

Shimba et al., "Comparative thermodynamic analyses of the Fv, Fab* and Fab fragments of anti-dansyl mouse monoclonal antibody," FEBS Letters, 360:247-250 (1995).

Shirahata, Minna ni yakudatsu ketsuyubyo no kiso to rinsho. Iyaku (Medicine and Drug) Journal Co., Ltd., 280-9 (2009) (including English translation).

Shire et al., "Challenges in the development of high protein concentration formulations," Journal of Pharmaceutical Sciences, Jun. 1, 2004, 93(6):1390-1402.

Singer et al., Genes & Genomes, 1991; Chapter 1, pp. 67-69.

Singer et al., Genes & Genomes, 1998; Chapter 1, pp. 63-64.

Sinha et al., "Electrostatics in protein binding and function," Curr Protein Pept Sci., Dec. 2002;3(6):601-14.

Sinha et al., "Molecular dynamics simulation of a high-affinity antibody-protein complex: the binding site is a mosaic of locally flexible and preorganized rigid regions," Cell Biochem Biophys., Oct. 1, 2005, 43:253-273.

Skerra, "Use of the tetracycline promoter for the tightly regulated production of a murine antibody fragment in *Escherichia coli*," Gene, Dec. 30, 1994, 151:131-135.

Smans et al., "Bispecific antibody-mediated lysis of primary cultures of ovarian carcinoma cells using multiple target antigens," Int. J. Cancer, Oct. 8, 1999, 83:270-277.

Smith et al., "The challenges of genome sequence annotation or 'The devil is in the details'," Nature Biotechnology, Nov. 1997;15:1222-1223.

Smith et al., "Inhibition of T Cell Activation by a Monoclonal Antibody Reactive Against the α3 Domain of Human MHC Class I Molecules," J. Immunol., Aug. 1, 1994, 153:1054-1067.

Smith, "Creative Expression. Mammalian Expression Vectors and Systems," The Scientist Magazine, Feb. 2, 1998, 3 pages.

Smith-Gill et al., "Contributions of immunoglobulin heavy and light chains to antibody specificity for lysozyme and two haptens," The Journal of Immunology, Dec. 15, 1987, 139:4135-4144.

(56) References Cited

OTHER PUBLICATIONS

Smolen et al., "Interleukin-6: a new therapeutic target," Arthritis Res Ther., 2006;8 Suppl 2:S5. Epub Jul. 28, 2006.
Soeda et al., "Factor VIII Taitei Kotai (1) Ko FIXa/FX bispecific Kotai no Sakusei oyobi characterization," Rinsho Ketsueki, Aug. 30, 2005, 46(8):728 (including English translation).
Soeda et al., "Phage library-ho ni yori Sakusei shita Ko-FIXa/Ko-FX bispecific Kotai no FVIII Taitei Sayo," Jpn J Thromb Hemost., Oct. 1, 2005, 16(5):526 (including English translation).
Song et al., "Light chain of natural antibody plays a dominant role in protein antigen binding," Biochemical and Biophysical Research Communications, Feb. 16, 2000, 268:390-394.
Souyri, M., "Mpl: from an acute myeloproliferative virus to the isolation of the long sought thrombopoietin," Seminars in Hematology, Jul. 1998, 35(3):222-231.
Spiess et al., "Bispecific antibodies with natural architecture produced by co-culture of bacteria expressing two distinct half-antibodies," Nat Biotechnol., Aug. 2013; 31(8):753-8. doi: 10.1038/nbt.2621. Epub Jul. 7, 2013.
Staerz et al., "Hybrid antibodies can target sites for attack by T cells," Nature. Apr. 18-24, 1985:314(6012):628-31.
Staerz et al., "Hybrid hybridoma producing a bispecific monoclonal antibody that can focus effector T-cell activity," Proc Natl Acad Sci U.S.A., Mar. 1, 1986, 83:1453-7.
Stickney et al., "Bifunctional Antibody: A Binary Radiopharmaceutical Delivery System for Imaging Colorectal Carcinoma," Cancer Res., Dec. 15, 1991;51:6650-5.
Strand et al., "Biologic therapies in rheumatology: lessons learned, future directions," Nat. Rev. Drug Discov., Jan. 1, 2007, 6:75-92.
Sun et al., "Coexpression of Gas6/Ax1 in human ovarian cancers," Oncology, Jun. 1, 2004, 66(6):450-7.
Suresh et al., "Advantages of bispecific hybridomas in one-step immunocytochemistry and immunoassays," Proc. Natl. Acad. Sci. U S A., Oct. 1986;83:7989-93.
Suresh et al., "Bispecific monoclonal antibodies from hybrid hybridomas," Methods Enzymol., Dec. 31, 1986;121:210-228.
Tabrizi et al., "Elimination mechanisms of therapeutic monoclonal antibodies," Drug Discov Today, Jan. 2006;11(1-2):81-8.
Tahtis et al., "Biodistribution Properties of [111]Indium-labeled C-Functionalized trans-Cyclohexyl Diethylenetriaminepentaacetic Acid Humanized 3S193 Diabody and F(ab')₂ Constructs in a Breast Carcinoma Xenograft Model," Clin. Cancer Res., Apr. 1, 2001, 7:1061-1072.
Taki, "National Haemophilia Foundation (NHF) Medical and Scientific Advisory Council (MASAC) Recommendations Concerning Prophylaxis," The Journal of Japanese Society on Thrombosis and Hemostasis, Feb. 2, 2002;13:109-113 (with partial English translation).
Tamura et al., "Structural correlates of an anticarcinoma antibody: identification of specificity-determining residues (SDRs) and development of a minimally immunogenic antibody variant by retention of SDRs only," J Immunol., Feb. 1, 2000;164(3):1432-41.
Tan et al., "Contributions of a highly conserved $V_H/V_L$ hydrogen bonding interaction to scFv folding stability and refolding efficiency," Biophys J., Sep. 1998; 75(3):1473-82.
Tan et al., "Engineering the isoelectric point of a renal cell carcinoma targeting antibody greatly enhances scFv solubility," Immunotechnology, Oct. 31, 1998, 4(2):107-114.
Tang et al., "Selection of linkers for a catalytic single-chain antibody using phage display technology", The Journal of Biological Chemistry, Jun. 28, 1996, 271(26):15682-15686.
Tarditi et al., "Selective high-performance liquid chromatographic purification of bispecific monoclonal antibodies," J. Chromatogr., May 2, 1992, 599:13-20.
Tedder et al., "CD22, a B Lymphocyte-Specific Adhesion Molecule That Regulates Antigen Receptor Signaling," Annu. Rev. Immunol., Apr. 15, 1997, 15:481-504.
Teeling et al., "The biological activity of human CD20 monoclonal antibodies is linked to unique epitopes on CD20," J. Immunol., Jul. 1, 2006, 177(1):362-71.

Teerinen et al., "Structure-based stability engineering of the mouse IgG1 Fab fragment by modifying constant domains," J Mol Biol., Aug. 25, 2006, 361(4):687-97.
Ten Kate et al., "Effect of isoelectric point on biodistribution and inflammation. imaging with indium-111-labelled IgG," Eur. J. Nucl. Med., Jun. 1, 1990, 17:305-309.
Thies et al., "The alternatively folded state of the antibody C(H)3 domain," J Mol Biol., Jun. 22, 2001;309(5):1077-85.
Thilenius et al., "Agonist antibody and Fas ligand mediate different sensitivity to death in the signaling pathways of Fas and cytoplasmic mutants," Eur. J. Immunol., May 1, 1997, 27:1108-1114.
Tsubaki et al., "C-terminal modification of monoclonal antibody drugs: amidated species as a general product-related substance," Int J Biol Macromol., 52:139-47. doi: 10.1016/j.ijbiomac.2012.09.016. Epub Sep. 25, 2012.
Tsuchiya, Credit Suisse Seminar, "Therapeutic Antibody," at Fuji-Gotemba Laboratories, p. 21 (Sep. 22, 2006) (with English translation).
Tsurushita et al., "Design of humanized antibodies: From anti-Tac to Zenapax," Methods, May 31, 2005, 36:69-83.
Turner et al., "Importance of the linker in expression of single-chain Fv antibody fragments: optimization of peptide sequence using phage display technology," Journal of Immunological Methods, Jun. 23, 1997, 205:43-54.
Unkeless et al., "Structure and Function of Human and Murine Receptors for IgG," Annu Rev Immunol., Apr. 1988, 6:251-81.
Vaccaro et al., "Divergent activities of an engineered antibody in murine and human systems have implications for therapeutic antibodies," Proc Natl Acad Sci U S A. Dec. 5, 2006;103(49):18709-14. Epub Nov. 20, 2006.
Vaisitti et al., "Cationization of monoclonal antibodies: another step towards the "magic bullet"?," J. Biol. Regul. Homeost. Agents., Jul. 1, 2005, 19(3-4):105-12.
Vajdos et al., "Comprehensive functional maps of the antigen-binding site of an anti-ErbB2 antibody obtained with shotgun scanning mutagenesis," J. Mol. Biol., Jul. 5, 2002, 320(2):415-28.
Van Den Burg et al., "Selection of mutations for increased protein stability," Curr. Opin. Biotechnol., Aug. 1, 2002, 13(4):333-337.
Van Der Neut Kolfschoten et al., "Anti-inflammatory activity of human IgG4 antibodies by dynamic Fab arm exchange," Science, Sep. 14, 2007;317(5844):1554-7.
Van Loghem et al., "Staphylococcal protein A and human IgG subclasses and allotypes," Scand. J. Immunol., Mar. 1, 1982, 15(3):275-8.
Van Walle et al., "Immunogenicity screening in protein drug development," Expert Opin. Biol. Ther., Mar. 1, 2007, 7(3):405-18.
Vargas-Madrazo et al., "An improved model of association for VH-VL immunoglobulin domains: asymmetries between VH and VL in the packing of some interface residues," J Mol. Recognit., May-Jun. 2003;16(3):113-20.
Vaughan et al., "Human antibodies with sub-nanomolar affinities isolated from a large non-immunized phage display library," Nat Biotechnol., Mar. 1996;14(3):309-14.
Vehar et al., "Structure of human factor VIII," Nature, Nov. 22, 1984, 312(5992):337-42.
Verhoeyen et al., "Construction of a reshaped HMFG1 antibody and comparison of its fine specificity with that of the parent mouse antibody," Immunology, Mar. 1993;78(3):364-70.
Verhoeyen et al., "Monoclonal Antibodies in Clinical Oncology," 1991, Edited by AA Epenetos, Chapter 5, pp. 37-43, Chapman and Hall.
Vieille et al., "Hyperthermophilic enzymes: sources, uses, and molecular mechanisms for thermostability," Microbiology and Molecular Biology Reviews, Mar. 1, 2001, 65(1):1-43.
Volkel et al., "Optimized linker sequences for the expression of monomeric and dimeric bispecific single-chain diabodies," Protein Engineering, Oct. 1, 2001, 14(10):815-823.
Wally et al., "Identification of a novel substitution in the constant region of a gene coding for an amyloidogenic kappal light chain," Biochim Biophys Acta., May 31, 1999;1454(1):49-56.
Wang et al., "Conserved amino acid networks involved in antibody variable domain interactions," Proteins, Jul. 2009;76(1):99-114. doi: 10.1002/prot.22319.

(56) References Cited

OTHER PUBLICATIONS

Wang et al., "Polyethylene Glycol-modified Chimeric Toxin Composed of Transforming Growth Factor alpha and Pseudomonas Exotoxin," Cancer. Res., Oct. 1, 1993, 53:4588-4594.
Ward et al., "Binding activities of a repertoire of single immunoglobulin variable domains secreted from *Escherichia coli*," Nature, Oct. 12, 1989;341:544-546.
Ward et al., "Effects of engineering complementary charged residues into the hydrophobic subunit interface of tyrosyl-tRNA synthetase. Appendix: Kinetic analysis of dimeric enzymes that reversibly dissociate into inactive subunits," Biochemistry, Jun. 30, 1987;26(13):4131-8.
Warnaar et al., "Purification of bispecific F(ab')2 from murine trinoma OC/TR with specificity for CD3 and ovarian cancer," Hybridoma, Dec. 13, 1994, 13:519-526.
Weiner et al., "A Human Tumor Xenograft Model of Therapy with a Bispecific Monoclonal Antibody Targeting c-erbB-2 and CD16," Cancer Res., Jan. 1, 1993;53:94-100.
Weiner et al., "The Role of T Cell Activation in Anti-CD3 x Antitumor Bispecific Antibody Therapy," J. Immunol., Mar. 1, 1994;152:2385-92.
Wells, "Perspectives in Biochemistry," Biochemistry, Sep. 1990, 29(37):8509-8517.
Whitlow et al., "An improved linker for single-chain Fv with reduced aggregation and enhanced proteolytic stability," Protein Engineering, Nov. 1, 1993, 6(8):989-995.
Wiens et al., "Mutation of a single conserved residue in VH complementarity-determining region 2 results in a severe Ig secretion defect," J. Immunol., Aug. 15, 2001, 167(4):2179-86.
Wiens et al., "Somatic mutation in VH complementarity-determining region 2 and framework region 2: differential effects on antigen binding and Ig secretion," J. Immunol., Aug. 1, 1997, 159(3):1293-302.
Wood et al., "Expression of active human factor VIII from recombinant DNA clones," Nature, Nov. 22, 1984, 312(5992):330-7.
Woodle et al., "Anti-Human Class I MHC Antibodies Induce Apoptosis by a Pathway That Is Distinct from the Fas Antigen-Mediated Pathway," J. Immunol., Mar. 1, 1997, 158:2156-2164.
Woodle et al., "Anti-Human Class I α3 Domain-Specific Monoclonal Antibody Induces Programmed Cell Death in Murine Cells Expressing Human Class I MHC Transgenes," Transplant. Proc., Jun. 30, 1998, 30:1059-1060.
Woodle et al., "Class I MHC Mediates Programmed Cell Death in Human Lymphoid Cells," Transplantation, Jul. 15, 1997, 64:140-146.
Worn et al., "Stability engineering of antibody single-chain Fv fragments," J Mol Biol., Feb. 2, 2001;305(5):989-1010.
Wozniak-Knopp et al., "Introducing antigen-binding sites in structural loops of immunoglobulin constant domains: Fc fragments with engineered HER2/neu-binding sites and antibody properties," Protein Eng Des Sel. Apr. 2010; 23(4):289-97.doi:10.1093/protein/gzq005. Epub Feb. 11, 2010.
Wu et al., "Development of motavizumab, an ultra-potent antibody for the prevention of respiratory syncytial virus infection in the upper and lower respiratory tract," J. Mol. Biol., May 4, 2007, 368(3):652-65.
Wu et al., "Multimerization of a chimeric anti-CD20 single-chain Fv-Fc fusion protein is mediated through variable domain exchange," Protein Eng., Dec. 2001;14(12):1025-33.
Wu et al., "Tumor localization of anti-CEA single-chain Fvs: improved targeting by non-covalent chillers," Immunotechnology, Feb. 1, 1996, 2:21-36.
Wypych et al., "Human IgG2 antibodies display disulfide-mediated structural isoforms," J. Biol. Chem., Jun. 6, 2008, 283(23):16194-16205.
Xiang et al., "Production of murine V-human Crl chimeric anti-TAG72 antibody using V region cDNA amplified by PCR," Mol Immunol., Aug. 1990;27(8):809-817.

Xiang et al., "Study of B72.3 combining sites by molecular modeling and site-directed mutagenesis," Protein Eng., May 1, 2000, 13(5):339-44.
Xiong et al., "Efficient inhibition of human B-cell lymphoma xenografts with an anti-CD20 X anti-CD3 bispecific diabody," Cancer Lett., Mar. 8, 2002, 177:29-39.
Xu et al., "Insight into hepatocellular carcinogenesis at transcriptome level by comparing gene expression profiles of hepatocellular carcinoma with those of corresponding noncancerous liver," Proc. Natl. Acad. Sci. USA, Dec. 18, 2001, 98:15089-15094.
Yamasaki et al., "Pharmacokinetic analysis of in vivo disposition of succinylated proteins targeted to liver nonparenchymal cells via scavenger receptors: importance of molecular size and negative charge density for in vivo recognition by receptors," J. Pharmacol. Exp. Ther., May 1, 2002, 301:467-477.
Yang et al., "CDR Walking Mutagenesis for the Affinity Maturation of a Potent Human Anti-HIV-1 Anitbody into the Picomolar Range," J Mol. Biol., 254(3):392-403 (Dec. 1995).
Yang et al., "Tailoring structure-function and pharmacokinetic properties of single-chain Fv proteins by site-specific PEGylation," Protein Eng., Oct. 1, 2003, 16:761-770.
Yasukawa et al., "Structure and expression of human B cell stimulatory factor-2 (BSF-2/IL-6) gene," EMBO J., Oct. 1987;6(10):2939-45.
Zeidler et al., "Simultaneous Activation of T Cells and Accessory Cells by a New Class of Intact Bispecific Antibody Results in Efficient Tumor Cell Killing," J Immuno I. Aug. 1, 1999;163(3):1246-52.
Zhu et al., "An efficient route to the production of an IgG-like bispecific antibody", Protein Eng., May 1, 2000, 13:361-367.
Zhu et al., "MHC class I-related neonatal Fc receptor for IgG is functionally expressed in monocytes, intestinal macrophages, and dendritic cells," J. Immunol., Mar. 1, 2001, 166(5):3266-76.
Zhu et al., "Remodeling domain interfaces to enhance heterodimer formation," Protein Sci., Apr. 1997;6(4):781-8.
Zuckier et al., "Chimeric human-mouse IgG antibodies with shuffled constant region exons demonstrate that multiple domains contribute to in vivo half-life," Cancer Res., Sep. 1, 1998, 58:3905-08.
Zuo et al., "An efficient route to the production of an IgG-like bispecific antibody," Protein Eng., May 1, 2000, 13(5):361-7.
Zwick et al., "The long third complementarity-determining region of the heavy chain is important in the activity of the broadly neutralizing anti-human immunodeficiency virus type 1 antibody 2F5," J. Virol., 78(6):3155-61 (Mar. 15, 2004).
Fish & Richardson P.C., Reply to Restriction Requirement dated Jun. 1, 2016 in U.S. Appl. No. 14/127,576, filed Aug. 24, 2016, 2 pages.
USPTO Non-Final Office Action in U.S. Appl. No. 14/127,576, dated Sep. 20, 2016, 17 pages.
International Search Report for App. Ser. No. PCT/JP2014/075728, dated Dec. 22, 2014, 4 pages.
International Preliminary Report on Patentability for App. Ser. No. PCT/JP2014/075728, dated Mar. 29, 2016, 15 pages.
USPTO Restriction Requirement in U.S. Appl. No. 12/295,075, dated Feb. 22, 2011, 9 pages.
Fish & Richardson P.C., Response to Restriction Requirement dated Feb. 22, 2011 in U.S. Appl. No. 12/295,075, filed Aug. 18, 2011, 2 pages.
USPTO Non-Final Office Action in U.S. Appl. No. 12/295,075, dated Nov. 4, 2011, 14 pages.
Fish & Richardson P.C., Amendment in Reply to Action dated Nov. 4, 2011 in U.S. Appl. No. 12/295,075, filed May 3, 2012, 12 pages.
USPTO Final Office Action in U.S. Appl. No. 12/295,075, dated Jul. 19, 2012, 12 pages.
Fish & Richardson P.C., Amendment in Reply to Action dated Jul. 19, 2012 in U.S. Appl. No. 12/295,075, filed Jan. 17, 2013, 113 pages.
USPTO Non-Final Office Action in U.S. Appl. No. 12/295,075, dated Jun. 7, 2013, 17 pages.
International Preliminary Report on Patentability for App. Ser. No. PCT/JP2007/057058, dated Oct. 21, 2008, 11 pages.
International Preliminary Report on Patentability for App. Ser. No. PCT/JP2010/073361, dated Aug. 14, 2012, 7 pages.

(56) References Cited

OTHER PUBLICATIONS

USPTO Restriction Requirement in U.S. Appl. Ser. No. 10/560,098, dated Jul. 13, 2007, 9 pages.
Fish & Richardson P.C., Response to Restriction Requirement dated Jul. 13, 2007 in U.S. Appl. No. 10/560,098, filed Aug. 10, 2007, 6 pages.
USPTO Non-Final Office Action in U.S. Appl. No. 10/560,098, dated Oct. 23, 2007, 17 pages.
USPTO Final Office Action in U.S. Appl. No. 10/560,098, dated Sep. 11, 2008, 20 pages.
USPTO Interview Summary for U.S. Appl. No. 10/560,098, dated Jun. 5, 2009, 8 pages.
Fish & Richardson P.C., Amendment in Reply to Office Action dated Sep. 11, 2008 in U.S. Appl. No. 10/560,098, filed Jun. 10, 2009, 12 pages.
USPTO Office Action in U.S. Appl. No. 10/560,098, dated Aug. 13, 2009, 21 pages.
Fish & Richardson P.C., Amendment in Reply to Office Action dated Aug. 13, 2009 in U.S. Appl. No. 10/560,098, filed Feb. 16, 2010, 14 pages.
USPTO Final Office Action in U.S. Appl. No. 10/560,098, dated Jun. 3, 2010, 16 pages.
Fish & Richardson P.C., Amendment in Reply to Final Office Action dated Jun. 3, 2010 in U.S. Appl. No. 10/560,098, filed Jul. 5, 2011, 17 pages.
USPTO Non-Final Office Action in U.S. Appl. No. 10/560,098, dated Dec. 8, 2011, 11 pages.
Fish & Richardson P.C., Amendment in Reply to Non-Final Office Action dated Dec. 8, 2011 in U.S. Appl. No. 10/560,098, filed Jun. 5, 2012, 11 pages.
USPTO Final Office Action in U.S. Appl. No. 10/560,098, dated Aug. 15, 2012, 10 pages.
Fish & Richardson P.C., Amendment in Reply to Final Office Action dated Aug. 15, 2012 in U.S. Appl. No. 10/560,098, filed Sep. 5, 2012, 8 pages.
USPTO Interview Summary in U.S. Appl. No. 10/560,098, dated Sep. 7, 2012, 3 pages.
USPTO Notice of Allowance in U.S. Appl. No. 10/560,098, dated Apr. 25, 2013, 12 pages.
USPTO Notice of Allowance in U.S. Appl. No. 10/560,098, dated Jul. 9, 2013, 6 pages.
International Preliminary Report on Patentability for App. Ser. No. PCT/JP2004/008585, dated Apr. 15, 2005, 16 pages.
International Preliminary Report on Patentability for App. Ser. No. PCT/JP2007/057036, dated Oct. 21, 2008, 6 pages.
International Preliminary Report on Patentability for App. Ser. No. PCT/JP2008/067534, dated Apr. 7, 2010, 7 pages.
International Preliminary Report on Patentability for App. Ser. No. PCT/JP2009/057309, dated Nov. 30, 2010, 7 pages.
USPTO Restriction Requirement in U.S. Appl. No. 12/295,039, dated Oct. 12, 2010, 9 pages.
Fish & Richardson P.C., Response to Restriction Requirement dated Oct. 12, 2010 in U.S. Appl. No. 12/295,039, filed Apr. 11, 2011, 9 pages.
USPTO Non-Final Office Action in U.S. Appl. No. 12/295,039, dated Jun. 28, 2011, 9 pages.
Fish & Richardson P.C., Amendment in Reply to Office Action dated Jun. 28, 2011 in U.S. Appl. No. 12/295,039, filed Dec. 27, 2011, 14 pages.
USPTO Final Office Action in U.S. Appl. No. 12/295,039, dated Apr. 12, 2012, 8 pages.
Fish & Richardson P.C., Amendment in Reply to Action dated Apr. 12, 2012 in U.S. Appl. No. 12/295,039, filed Sep. 11, 2012, 12 pages.
Fish & Richardson P.C., Amendment and Response to Restriction Requirement dated Nov. 18, 2009 in U.S. Appl. No. 10/575,905, filed Apr. 16, 2010, 12 pages.
Fish & Richardson P.C., Amendment in Reply to Action dated Jun. 23, 2010 in U.S. Appl. No. 10/575,905, filed Dec. 22, 2010, 10 pages.
USPTO Final Office Action in U.S. Appl. No. 10/575,905, dated Feb. 24, 2011, 7 pages.
Fish & Richardson P.C., Amendment in Reply to Action dated Jun. 23, 2010 in U.S. Appl. No. 10/575,193, filed Dec. 22, 2010, 13 pages.
USPTO Notice of Allowance in U.S. Appl. No. 10/575,193, dated Mar. 18, 2011, 11 pages.
Fish & Richardson P.C., Amendment in U.S. Appl. No. 10/575,193, filed Jun. 17, 2011, 15 pages.
USPTO Notice of Allowance in U.S. Appl. No. 10/575,193, dated Jul. 13, 2011, 8 pages.
USPTO Restriction Requirement in U.S. Appl. No. 11/910,836, dated Mar. 18, 2011, 7 pages.
Fish & Richardson P.C., Response to Restriction Requirement dated Mar. 18, 2011 in U.S. Appl. No. 11/910,836, filed Sep. 6, 2011, 1 page.
USPTO Non-Final Office Action in U.S. Appl. No. 11/910,836, dated Sep. 30, 2011, 21 pages.
USPTO Restriction Requirement in U.S. Appl. No. 12/936,587, dated Dec. 6, 2011, 7 pages.
Fish & Richardson P.C., Third Preliminary Amendment and Response to Restriction Requirement dated Dec. 6, 2011 in U.S. Appl. No. 12/936,587, filed Jun. 5, 2012, 7 pages.
USPTO Restriction Requirement in U.S. Appl. No. 12/936,587, dated Jun. 25, 2012, 5 pages.
Fish & Richardson P.C., Response to Species Election Requirement dated Jun. 25, 2012 in U.S. Appl. No. 12/936,587, filed Jul. 25, 2012, 1 page.
USPTO Non-Final Office Action in U.S. Appl. No. 12/936,587, dated Nov. 7, 2012, 13 pages.
USPTO Restriction Requirement in U.S. Appl. No. 12/680,082, dated Jun. 6, 2012, 12 pages.
Fish & Richardson P.C., Fourth Preliminary Amendment and Response to Restriction Requirement dated Jun. 6, 2012 in U.S. Appl. No. 12/680,082, filed Jun. 29, 2012, 13 pages.
USPTO Restriction Requirement in U.S. Appl. No. 12/680,082, dated Sep. 14, 2012, 6 pages.
Fish & Richardson P.C., Amendment and Response to Election Requirement dated Sep. 14, 2012 in U.S. Appl. No. 12/680,082, filed Nov. 8, 2012, 14 pages.
USPTO Non-Final Office Action U.S. Appl. No. 12/680,082, dated Feb. 14, 2013, 12 pages.
Fish & Richardson P.C., Amendment in Reply to Non-Final Office Action dated Feb. 14, 2013 in U.S. Appl. No. 12/680,082, filed Aug. 12, 2013, 17 pages.
International Preliminary Report on Patentability for App. Ser. No. PCT/JP2010/066490, dated Apr. 2012, 6 pages.
USPTO Restriction Requirement in U.S. Appl. No. 13/434,643, dated Jul. 27, 2012, 6 pages.
Fish & Richardson P.C., Response to Restriction Requirement dated Jul. 27, 2012 and Preliminary Amendment in U.S. Appl. No. 13/434,643, filed Jan. 24, 2013, 12 pages.
USPTO Non-Final Office Action in U.S. Appl. No. 13/434,643, dated Feb. 12, 2013, 17 pages.
Fish & Richardson P.C., Amendment in Reply to Office Action dated Feb. 12, 2013 in U.S. Appl. No. 13/434,643, filed May 13, 2013, 18 pages.
USPTO Final Office Action in U.S. Appl. No. 13/434,643, dated Jul. 11, 2013, 19 pages.
USPTO Restriction Requirement in U.S. Appl. No. 12/679,922, dated Oct. 2, 2012, 9 pages.
Fish & Richardson P.C., Response to Restriction Requirement dated Oct. 2, 2012 in U.S. Appl. No. 12/679,922, filed Nov. 1, 2012, 2 pages.
USPTO Non-Final Office Action in U.S. Appl. No. 12/679,922, dated Jan. 3, 2013, 25 pages.
Fish & Richardson P.C., Amendment in Reply to Action dated Jan. 3, 2013 in U.S. Appl. No. 12/679,922, filed Jul. 2, 2013, 18 pages.
USPTO Final Office Action in U.S. Appl. No. 12/679,922, dated Aug. 2, 2013, 12 pages.
USPTO Non-Final Office Action in U.S. Appl. No. 13/595,139, dated Nov. 14, 2012, 10 pages.

(56) References Cited

OTHER PUBLICATIONS

International Preliminary Report on Patentability for App. Ser. No. PCT/JP2011/055101, dated Oct. 2, 2012, 6 pages.
USPTO Restriction Requirement in U.S. Appl. No. 13/497,269, dated Dec. 6, 2012, 9 pages.
Fish & Richardson P.C., Response to Restriction Requirement dated Dec. 6, 2012 in U.S. Appl. No. 13/497,269, filed May 1, 2013, 2 pages.
USPTO Non-Final Office Action in U.S. Appl. No. 13/497,269, dated Aug. 15, 2013, 13 pages.
USPTO Restriction Requirement in U.S. Appl. No. 13/257,145, dated Mar. 20, 2013, 11 pages.
Fish & Richardson P.C., Preliminary Amendment and Response to Restriction Requirement dated Mar. 20, 2013 in U.S. Appl. No. 13/257,145, filed Apr. 22, 2013, 7 pages.
USPTO Non-Final Office Action in U.S. Appl. No. 13/257,145, dated Jul. 2, 2013, 20 pages.
International Preliminary Report on Patentability for App. Ser. No. PCT/JP2011/076486, dated Jun. 12, 2013, 9 pages.
International Search Report for App. Ser. No. PCT/JP2011/076486, dated Dec. 27, 2011, 4 pages.
International Search Report for App. Ser. No. PCT/JP2012/078103, dated Jan. 22, 2013, 6 pages.
International Preliminary Report on Patentability for App. Ser. No. PCT/JP2012/078103, dated May 6, 2014, 6 pages.
Notice of Opposition against EP 1 876 236, dated May 20, 2015, in the name of Chugai Seiyaku Kabushiki Kaisha brought by Novo Nordisk A/S, 23 pages.
Notice of Opposition against EP 1 876 236, dated May 22, 2015, in the name of Chugai Seiyaku Kabushiki Kaisha brought by Baxalta Innovations GmbH, 37 pages.
Chugai Seiyaku Kabushiki Kaisha's letter dated Jun. 12, 2013, regarding oral proceedings scheduled on Jun. 26, 2013, in App. Ser. No. EP 06 73 0769.4-1412.

\* cited by examiner

FIG. 22
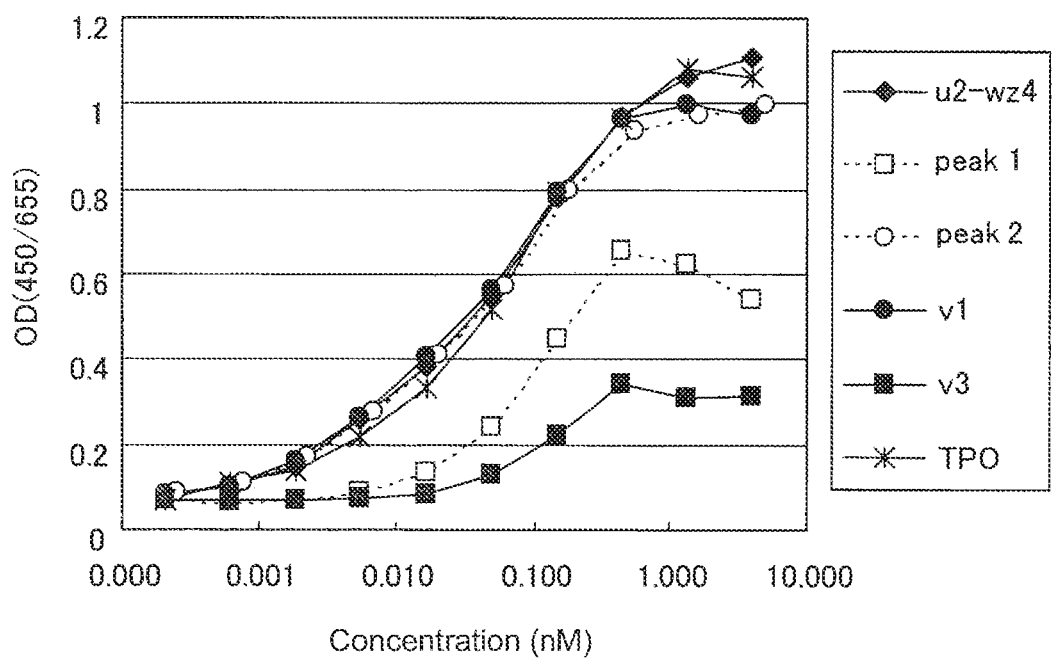
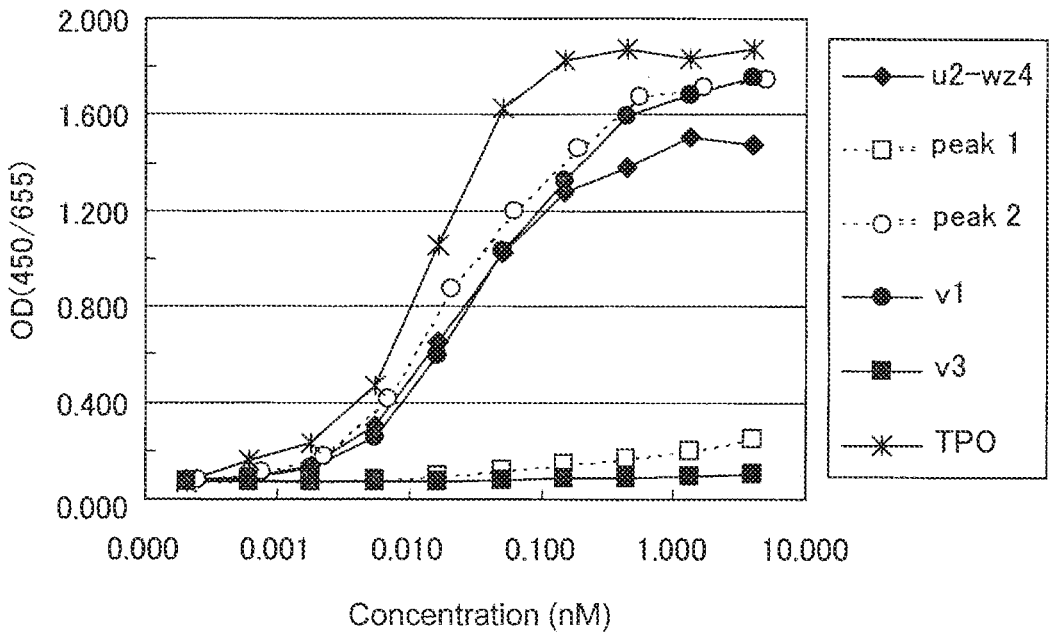

FIG. 23
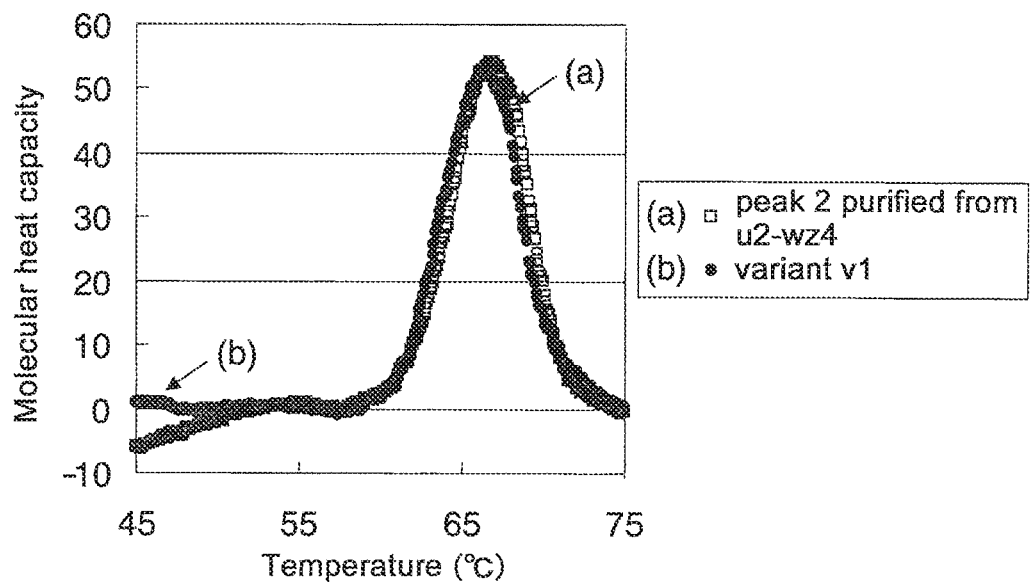
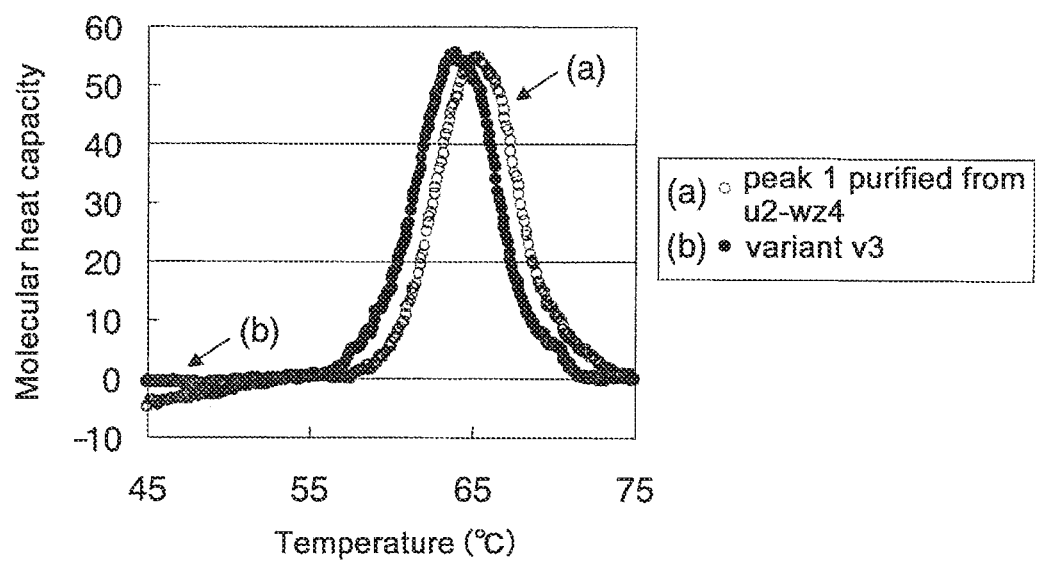

FIG. 29

| Name | A-Homo | BiAb | B-Homo |
|---|---|---|---|
| wild type | 20 | 48 | 32 |
| KiH | 0 | 97 | 3 |
| s1 | 8 | 87 | 5 |
| s2 | 5 | 92 | 3 |
| s3 | 3 | 92 | 6 |
| w1 | 1 | 97 | 2 |
| w2 | 0 | 94 | 6 |
| w3 | 4 | 93 | 3 |

| Name | A-Homo | BiAb | B-Homo |
|---|---|---|---|
| wild type | 21 | 49 | 30 |
| KiH | 0 | 99 | 1 |
| s1C | 5 | 94 | 1 |
| s2C | 11 | 87 | 2 |
| s3C | 3 | 88 | 10 |
| w3C | 3 | 95 | 2 |
| w3C2 | 6 | 93 | 1 |

FIG. 30

| Name | Monomer recovery rate (%) |
|---|---|
| wild type | 66 |
| KiH | 36 |
| s2 | 39 |
| s3 | 72 |
| w3 | 47 |
| s2C | 81 |
| s3C | 79 |
| w3C | 83 |
| w3C2 | 74 |

FIG. 32

| Name | A-Homo | BiAb | B-Homo |
|---|---|---|---|
| wild type | 24 | 50 | 27 |
| KiH | 0 | 99 | 1 |
| w1 | 0 | 98 | 2 |
| w2 | 0 | 98 | 2 |
| w3 | 4 | 94 | 2 |

100

SEQUENCE LISTING

```
<160> NUMBER OF SEQ ID NOS: 60

<210> SEQ ID NO 1
<211> LENGTH: 423
<212> TYPE: DNA
<213> ORGANISM: Artificial Sequence
<220> FEATURE:
<223> OTHER INFORMATION: an artificially synthesized sequence

<400> SEQUENCE: 1
atgaaacacc tgtggttctt cctcctcctg gtggcagctc ccagatgggt cctgtctcag      60
gtgcagctgc agcagtcagg acctggcctc gtgaaacctt ctgagactct gtctctcacc     120
tgcactgtct ctggctactc catctccagt ggttattact ggacctggat ccggcagcct     180
ccaggaaagg gtctggaatg gattggctac atatccttcg acggtaccaa tgactacaac     240
ccatctctca aaaatcgagt caccatctct cgtgacacat ctaagaacaa ttttccctg     300 aagttgaact ctgtaactgc tgcagacaca gctgtatatt actgtgcaag aggccccccc     360
gctacttact ggggccaagg gactctggtc actgtctctt caggtaagtc ggcctcgggg     420
gcc                                                                  423

<210> SEQ ID NO 2
<211> LENGTH: 115
<212> TYPE: PRT
<213> ORGANISM: Artificial Sequence
<220> FEATURE:
```

<223> OTHER INFORMATION: an artificially synthesized sequence

<400> SEQUENCE: 2

```
Gln Val Gln Leu Gln Gln Ser Gly Pro Gly Leu Val Lys Pro Ser Glu
1               5                   10                  15
Thr Leu Ser Leu Thr Cys Thr Val Ser Gly Tyr Ser Ile Ser Ser Gly
            20                  25                  30
Tyr Tyr Trp Thr Trp Ile Arg Gln Pro Pro Gly Lys Gly Leu Glu Trp
        35                  40                  45
Ile Gly Tyr Ile Ser Phe Asp Gly Thr Asn Asp Tyr Asn Pro Ser Leu
    50                  55                  60
Lys Asn Arg Val Thr Ile Ser Arg Asp Thr Ser Lys Asn Asn Phe Ser
65                  70                  75                  80
Leu Lys Leu Asn Ser Val Thr Ala Ala Asp Thr Ala Val Tyr Tyr Cys
                85                  90                  95
Ala Arg Gly Pro Pro Ala Thr Tyr Trp Gly Gln Gly Thr Leu Val Thr
            100                 105                 110
Val Ser Ser
        115
```

<210> SEQ ID NO 3
<211> LENGTH: 384
<212> TYPE: DNA
<213> ORGANISM: Artificial Sequence
<220> FEATURE:
<223> OTHER INFORMATION: an artificially synthesized sequence

<400> SEQUENCE: 3

```
atggacatga gggtgcccgc tcagctcctg gggctcctgc tactctggct ccgaggtgcc    60
agatgtgaaa ttgtgttgac gcagtctcca tcctccctgt ctgcatctgt aggagacaga   120
gtcaccatca cttgcagggc cacctcaagt gtaaattaca tttactggta tcagcagaaa   180
ccagggaaag cccctaagct cctgatctat tatacatcca acctggctcc tggggtccca   240
tcaaggttca gcggcagtgg atctgggaca gatttcactc tcaccatcaa cagcctgcag   300
cctgaagatt ttgcaactta ctattgccag cagttttcta gttccccatg gacgttcggc   360
ggagggacca agctggagat caaa                                          384
```

<210> SEQ ID NO 4
<211> LENGTH: 106
<212> TYPE: PRT
<213> ORGANISM: Artificial Sequence
<220> FEATURE:
<223> OTHER INFORMATION: an artificially synthesized sequence

<400> SEQUENCE: 4

```
Glu Ile Val Leu Thr Gln Ser Pro Ser Ser Leu Ser Ala Ser Val Gly
1               5                   10                  15
Asp Arg Val Thr Ile Thr Cys Arg Ala Thr Ser Ser Val Asn Tyr Ile
            20                  25                  30
Tyr Trp Tyr Gln Gln Lys Pro Gly Lys Ala Pro Lys Leu Leu Ile Tyr
        35                  40                  45
Tyr Thr Ser Asn Leu Ala Pro Gly Val Pro Ser Arg Phe Ser Gly Ser
    50                  55                  60
Gly Ser Gly Thr Asp Phe Thr Leu Thr Ile Asn Ser Leu Gln Pro Glu
65                  70                  75                  80
Asp Phe Ala Thr Tyr Tyr Cys Gln Gln Phe Ser Ser Ser Pro Trp Thr
                85                  90                  95
```

Phe Gly Gly Gly Thr Lys Leu Glu Ile Lys
            100                 105

<210> SEQ ID NO 5
<211> LENGTH: 443
<212> TYPE: DNA
<213> ORGANISM: Artificial Sequence
<220> FEATURE:
<223> OTHER INFORMATION: an artificially synthesized sequence

<400> SEQUENCE: 5
atggactgga cctggagggt cttctgcttg ctggctgtag ctccaggtgc tcactcccag      60
gtgcagctgg tgcagtctgg ggctgaggtg aagaagcctg ggcctcagt gaaggtttcc     120 tgcaaggcat ctggatacac cttcacccac tttgttttgc actgggtgcg acaggccct     180 ggacaagggc ttgagtggat gggatatatt attccttaca atgatggtac taagtacaat     240
gagaagttca aaggcagagt caccatgacc agtgacacgt ccacgagcac agtctacatg     300
gagctgagca tcctgaaatc tgaggacacg gccgtgtatt tctgtgcgag agggaatagg     360
tacgacgtag gttcctatgc tatggactac tggggccaag gaccacggt caccgtctca     420 tcaggtaagt ggcctcgggg gcc                                             443

<210> SEQ ID NO 6
<211> LENGTH: 123
<212> TYPE: PRT
<213> ORGANISM: Artificial Sequence
<220> FEATURE:
<223> OTHER INFORMATION: an artificially synthesized sequence

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr His Phe
            20                  25                  30

Val Leu His Trp Val Arg Gln Ala Pro Gly Gln Gly Leu Glu Trp Met
        35                  40                  45

Gly Tyr Ile Ile Pro Tyr Asn Asp Gly Thr Lys Tyr Asn Glu Lys Phe
    50                  55                  60

Lys Gly Arg Val Thr Met Thr Ser Asp Thr Ser Thr Ser Thr Val Tyr
65                  70                  75                  80

Met Glu Leu Ser Ile Leu Arg Ser Glu Asp Thr Ala Val Tyr Phe Cys
                85                  90                  95

Ala Arg Gly Asn Arg Tyr Asp Val Gly Ser Tyr Ala Met Asp Tyr Trp
            100                 105                 110

Gly Gln Gly Thr Thr Val Thr Ser Val Ser Ser
        115                 120

<210> SEQ ID NO 7
<211> LENGTH: 399
<212> TYPE: DNA
<213> ORGANISM: Artificial Sequence
<220> FEATURE:
<223> OTHER INFORMATION: an artificially synthesized sequence

<400> SEQUENCE: 7
atggtgttgc agacccaggt cttcatttct ctgttgctct ggatctctgg tgcctacggg      60
gacatcgtga tgacccagtc tccagactcc ctggctgtgt ctctgggcga gagggccacc     120
atcaactgca gtccagtca gagcctttta tatagtagca atcaaaagaa ctacttggcc     180

```
tggtaccagc agaaaccagg acagcctcct aagctgctca tttactgggc atccactagg    240
gaatctgggg tccctgaccg attcagtggc agcgggtctg ggacagattt cactctcaag    300
atcagccgcg tgcaggctga agatgtggga gtttattact gtcagcaata ttataggttt    360
ccgtacacgt tcggcggagg gaccaaggtg gagatcaaa                           399
```

```
<210> SEQ ID NO 8
<211> LENGTH: 113
<212> TYPE: PRT
<213> ORGANISM: Artificial Sequence
<220> FEATURE:
<223> OTHER INFORMATION: an artificially synthesized sequence

<400> SEQUENCE: 8
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Gln Ala Glu Asp Val Gly Val Tyr Tyr Cys Gln Gln
                85                  90                  95

Tyr Tyr Arg Phe Pro Tyr Thr Phe Gly Gly Gly Thr Lys Val Glu Ile
            100                 105                 110

Lys

```
<210> SEQ ID NO 9
<211> LENGTH: 327
<212> TYPE: PRT
<213> ORGANISM: Homo sapiens

<400> SEQUENCE: 9
```

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
210                 215                 220

Glu Pro Gln Val Cys Thr Leu Pro Pro Ser Gln Glu Glu Met Thr Lys
225                 230                 235                 240

Asn Gln Val Ser Leu Trp Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 10
<211> LENGTH: 107
<212> TYPE: PRT
<213> ORGANISM: Homo sapiens

<400> SEQUENCE: 10

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
                35                  40                  45

Ser Gly Asn Ser Gln Glu Ser Val Thr Glu Gln Asp Ser Lys Asp Ser
            50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 11
<211> LENGTH: 327
<212> TYPE: PRT
<213> ORGANISM: Homo sapiens

<400> SEQUENCE: 11

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
             100                 105                 110

Glu Phe Leu Gly Gly Pro Ser Val Phe Leu Phe Pro Pro Lys Pro Lys
         115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Cys Glu Met Thr Lys
225                 230                 235                 240

Asn Gln Val Ser Leu Ser Cys Ala Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Val Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 12
<211> LENGTH: 1572
<212> TYPE: DNA
<213> ORGANISM: Homo sapiens

<400> SEQUENCE: 12
atggactgga cctggaggtt cctctttgtg gtggcagcag ctacaggtgt ccagtcccag    60
gtgcagctgg tgcagtctgg acctgaggtg aagaagcctg ggcctcagt gaaggtctcc    120 tgcaaggctt ctggatacac cttcaccaac tcctggatga actgggtgag cagaggcct    180 ggaaagggtc ttgagtggat tggacggatt tatcctggag atggagaaac tatctacaat    240
gggaaattca gggtcagagt cacgattacc gcggacgaat ccacgagcac agcctacatg    300
caactgagca gcctgagatc tgaggacacg gccgtgtatt actgtgcgag aggctatgat    360
gattactcgt ttgcttactg gggccaggga accacggtca ccgtctcttc aggtggtggt    420
ggatccggag gtggtggatc gggtggtgga ggatcggata ttgtgatgac tcagtctcca    480

```
ctctccctgc ccgtcacccc tggagagccg gcctccatct cctgcaggtc tagtaagagt    540
ctcctgcata gtaatggcaa cacttacttg tattggttcc tgcagaagcc agggcagtct    600
ccacagctcc tgatctatcg gatgtccaac cttgcctcag ggtccctga caggttcagt    660
ggcagtggat caggcacaga ttttacactg aaaatcagca gagtggaggc tgaggatgtt    720
ggggtttatt actgcatgca acatatagaa tatccttta cgttcggcca agggaccaaa    780
ctggaaatca aggaggtgg tggatcgggt ggtggtggtt cgggaggcgg tggatcgcag    840
gtgcagctgg tgcagtctgg acctgaggtg aagaagcctg ggcctcagt gaaggtctcc    900
tgcaaggctt ctggatacac cttcaccaac tcctggatga actgggtgag gcagaggcct    960
ggaaagggtc ttgagtggat tggacggatt tatcctggag atggagaaac tatctacaat   1020
gggaaattca gggtcagagt cacgattacc gcggacgaat ccacgagcac agcctacatg   1080
caactgagca gcctgagatc tgaggacacg gccgtgtatt actgtgcgag aggctatgat   1140
gattactcgt ttgcttactg gggccaggga accacggtca ccgtctcttc aggtggtggt   1200
ggatccggag gtggtggatc gggtggtgga ggatcggata ttgtgatgac tcagtctcca   1260
ctctccctgc ccgtcacccc tggagagccg gcctccatct cctgcaggtc tagtaagagt   1320
ctcctgcata gtaatggcaa cacttacttg tattggttcc tgcagaagcc agggcagtct   1380
ccacagctcc tgatctatcg gatgtccaac cttgcctcag ggtccctga caggttcagt   1440
ggcagtggat caggcacaga ttttacactg aaaatcagca gagtggaggc tgaggatgtt   1500
ggggtttatt actgcatgca acatatagaa tatccttta cgttcggcca agggaccaaa   1560
ctggaaatca aa                                                       1572

<210> SEQ ID NO 13
<211> LENGTH: 118
<212> TYPE: PRT
<213> ORGANISM: Homo sapiens

<400> SEQUENCE: 13

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Asn Ser
            20                  25                  30

Trp Met Asn Trp Val Arg Gln Arg Pro Gly Lys Gly Leu Glu Trp Ile
        35                  40                  45

Gly Arg Ile Tyr Pro Gly Asp Gly Glu Thr Ile Tyr Asn Gly Lys Phe
    50                  55                  60

Arg Val Arg Val Thr Ile Thr Ala Asp Glu Ser Thr Ser Thr Ala Tyr
65                  70                  75                  80

Met Gln Leu Ser Ser Leu Arg Ser Glu Asp Thr Ala Val Tyr Tyr Cys
                85                  90                  95

Ala Arg Gly Tyr Asp Asp Tyr Ser Phe Ala Tyr Trp Gly Gln Gly Thr
            100                 105                 110

Thr Val Thr Val Ser Ser
        115

<210> SEQ ID NO 14
<211> LENGTH: 112
<212> TYPE: PRT
<213> ORGANISM: Homo sapiens

<400> SEQUENCE: 14

Asp Ile Val Met Thr Gln Ser Pro Leu Ser Leu Pro Val Thr Pro Gly
```

```
1               5                  10                 15
Glu Pro Ala Ser Ile Ser Cys Arg Ser Ser Lys Ser Leu Leu His Ser
                20                  25                  30

Asn Gly Asn Thr Tyr Leu Tyr Trp Phe Leu Gln Lys Pro Gly Gln Ser
                35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Ile Glu Tyr Pro Phe Thr Phe Gly Gln Gly Thr Lys Leu Glu Ile Lys
                100                 105                 110
```

<210> SEQ ID NO 15
<211> LENGTH: 1572
<212> TYPE: DNA
<213> ORGANISM: Artificial Sequence
<220> FEATURE:
<223> OTHER INFORMATION: an artificially synthesized sequence

<400> SEQUENCE: 15

```
atggactgga cctggaggtt cctctttgtg gtggcagcag ctacaggtgt ccagtcccag     60
gtgcagctgg tgcagtctgg acctgaggtg aagaagcctg ggcctcagt gaaggtctcc    120
tgcaaggctt ctggatacac cttcaccaac tcctggatga actgggtgag ggagaggcct    180
ggaaagggtc ttgagtggat tggacggatt tatcctggag atggagaaac tatctacaat    240
gggaaattca gggtcagagt cacgattacc gcggacgaat ccacgagcac agcctacatg    300
caactgagca gcctgagatc tgaggacacg gccgtgtatt actgtgcgag aggctatgat    360
gattactcgt ttgcttactg gggccaggga accacggtca ccgtctcttc aggtggtggt    420
ggatccggag gtggtggatc gggtggtgga ggatcggata ttgtgatgac tcagtctcca    480
ctctccctgc ccgtcacccc tggagagccg gcctccatct cctgcaggtc tagtaagagt    540
ctcctgcata gtaatggcaa cacttacttg tattggttcc tgaagaagcc agggcagtct    600
ccacagctcc tgatctatcg gatgtccaac cttgcctcag ggtccctga caggttcagt    660
ggcagtggat caggcacaga ttttacactg aaaatcagca gagtggaggc tgaggatgtt    720
ggggtttatt actgcatgca acatatagaa tatccttttta cgttcggcca agggaccaaa    780
ctggaaatca aggagggtgg tggatcgggt ggtggtggtt cggagggcgg tggatcgcag    840
gtgcagctgg tgcagtctgg acctgaggtg aagaagcctg ggcctcagt gaaggtctcc    900
tgcaaggctt ctggatacac cttcaccaac tcctggatga actgggtgag gaagaggcct    960
ggaaagggtc ttgagtggat tggacggatt tatcctggag atggagaaac tatctacaat   1020
gggaaattca gggtcagagt cacgattacc gcggacgaat ccacgagcac agcctacatg   1080
caactgagca gcctgagatc tgaggacacg gccgtgtatt actgtgcgag aggctatgat   1140
gattactcgt ttgcttactg gggccaggga accacggtca ccgtctcttc aggtggtggt   1200
ggatccggag gtggtggatc gggtggtgga ggatcggata ttgtgatgac tcagtctcca   1260
ctctccctgc ccgtcacccc tggagagccg gcctccatct cctgcaggtc tagtaagagt   1320
ctcctgcata gtaatggcaa cacttacttg tattggttcc tgaagaagcc agggcagtct   1380
ccacagctcc tgatctatcg gatgtccaac cttgcctcag ggtccctga caggttcagt   1440
ggcagtggat caggcacaga ttttacactg aaaatcagca gagtggaggc tgaggatgtt   1500
```

```
ggggtttatt actgcatgca acatatagaa tatccttta cgttcggcca agggaccaaa    1560
ctggaaatca aa                                                       1572
```

<210> SEQ ID NO 16
<211> LENGTH: 524
<212> TYPE: PRT
<213> ORGANISM: Artificial Sequence
<220> FEATURE:
<223> OTHER INFORMATION: an artificially synthesized sequence

<400> SEQUENCE: 16

| | | | | | | | | | | | | | | |
|---|---|---|---|---|---|---|---|---|---|---|---|---|---|---|
| Met | Asp | Trp | Thr | Trp | Arg | Phe | Leu | Phe | Val | Val | Ala | Ala | Ala | Thr | Gly |
| 1 | | | | 5 | | | | | 10 | | | | | 15 | |
| Val | Gln | Ser | Gln | Val | Gln | Leu | Val | Gln | Ser | Gly | Pro | Glu | Val | Lys | Lys |
| | | | 20 | | | | | 25 | | | | | 30 | | |
| Pro | Gly | Ala | Ser | Val | Lys | Val | Ser | Cys | Lys | Ala | Ser | Gly | Tyr | Thr | Phe |
| | | 35 | | | | | 40 | | | | | 45 | | | |
| Thr | Asn | Ser | Trp | Met | Asn | Trp | Val | Arg | Glu | Arg | Pro | Gly | Lys | Gly | Leu |
| | 50 | | | | | 55 | | | | | 60 | | | | |
| Glu | Trp | Ile | Gly | Arg | Ile | Tyr | Pro | Gly | Asp | Gly | Glu | Thr | Ile | Tyr | Asn |
| 65 | | | | | 70 | | | | | 75 | | | | | 80 |
| Gly | Lys | Phe | Arg | Val | Arg | Val | Thr | Ile | Thr | Ala | Asp | Glu | Ser | Thr | Ser |
| | | | | 85 | | | | | 90 | | | | | 95 | |
| Thr | Ala | Tyr | Met | Gln | Leu | Ser | Ser | Leu | Arg | Ser | Glu | Asp | Thr | Ala | Val |
| | | | 100 | | | | | 105 | | | | | 110 | | |
| Tyr | Tyr | Cys | Ala | Arg | Gly | Tyr | Asp | Asp | Tyr | Ser | Phe | Ala | Tyr | Trp | Gly |
| | | 115 | | | | | 120 | | | | | 125 | | | |
| Gln | Gly | Thr | Thr | Val | Thr | Val | Ser | Ser | Gly | Gly | Gly | Ser | Gly | Gly |
| | 130 | | | | | 135 | | | | | 140 | | | | |
| Gly | Gly | Ser | Gly | Gly | Gly | Ser | Asp | Ile | Val | Met | Thr | Gln | Ser | Pro |
| 145 | | | | | 150 | | | | | 155 | | | | | 160 |
| Leu | Ser | Leu | Pro | Val | Thr | Pro | Gly | Glu | Pro | Ala | Ser | Ile | Ser | Cys | Arg |
| | | | | 165 | | | | | 170 | | | | | 175 | |
| Ser | Ser | Lys | Ser | Leu | Leu | His | Ser | Asn | Gly | Asn | Thr | Tyr | Leu | Tyr | Trp |
| | | | 180 | | | | | 185 | | | | | 190 | | |
| Phe | Leu | Glu | Lys | Pro | Gly | Gln | Ser | Pro | Gln | Leu | Leu | Ile | Tyr | Arg | Met |
| | | 195 | | | | | 200 | | | | | 205 | | | |
| Ser | Asn | Leu | Ala | Ser | Gly | Val | Pro | Asp | Arg | Phe | Ser | Gly | Ser | Gly | Ser |
| | 210 | | | | | 215 | | | | | 220 | | | | |
| Gly | Thr | Asp | Phe | Thr | Leu | Lys | Ile | Ser | Arg | Val | Glu | Ala | Glu | Asp | Val |
| 225 | | | | | 230 | | | | | 235 | | | | | 240 |
| Gly | Val | Tyr | Tyr | Cys | Met | Gln | His | Ile | Glu | Tyr | Pro | Phe | Thr | Phe | Gly |
| | | | | 245 | | | | | 250 | | | | | 255 | |
| Gln | Gly | Thr | Lys | Leu | Glu | Ile | Lys | Gly | Gly | Gly | Gly | Ser | Gly | Gly | Gly |
| | | | 260 | | | | | 265 | | | | | 270 | | |
| Gly | Ser | Gly | Gly | Gly | Gly | Ser | Gln | Val | Gln | Leu | Val | Gln | Ser | Gly | Pro |
| | | 275 | | | | | 280 | | | | | 285 | | | |
| Glu | Val | Lys | Lys | Pro | Gly | Ala | Ser | Val | Lys | Val | Ser | Cys | Lys | Ala | Ser |
| | 290 | | | | | 295 | | | | | 300 | | | | |
| Gly | Tyr | Thr | Phe | Thr | Asn | Ser | Trp | Met | Asn | Trp | Val | Arg | Lys | Arg | Pro |
| 305 | | | | | 310 | | | | | 315 | | | | | 320 |
| Gly | Lys | Gly | Leu | Glu | Trp | Ile | Gly | Arg | Ile | Tyr | Pro | Gly | Asp | Gly | Glu |
| | | | | 325 | | | | | 330 | | | | | 335 | |
| Thr | Ile | Tyr | Asn | Gly | Lys | Phe | Arg | Val | Arg | Val | Thr | Ile | Thr | Ala | Asp |

```
                340             345             350
Glu Ser Thr Ser Thr Ala Tyr Met Gln Leu Ser Ser Leu Arg Ser Glu
                355             360             365
Asp Thr Ala Val Tyr Tyr Cys Ala Arg Gly Tyr Asp Asp Tyr Ser Phe
            370             375             380
Ala Tyr Trp Gly Gln Gly Thr Thr Val Thr Val Ser Ser Gly Gly Gly
385             390             395                 400
Gly Ser Gly Gly Gly Gly Ser Gly Gly Gly Gly Ser Asp Ile Val Met
                405             410             415
Thr Gln Ser Pro Leu Ser Leu Pro Val Thr Pro Gly Glu Pro Ala Ser
                420             425             430
Ile Ser Cys Arg Ser Ser Lys Ser Leu Leu His Ser Asn Gly Asn Thr
            435             440             445
Tyr Leu Tyr Trp Phe Leu Lys Lys Pro Gly Gln Ser Pro Gln Leu Leu
        450             455             460
Ile Tyr Arg Met Ser Asn Leu Ala Ser Gly Val Pro Asp Arg Phe Ser
465             470             475                 480
Gly Ser Gly Ser Gly Thr Asp Phe Thr Leu Lys Ile Ser Arg Val Glu
                485             490             495
Ala Glu Asp Val Gly Val Tyr Tyr Cys Met Gln His Ile Glu Tyr Pro
                500             505             510
Phe Thr Phe Gly Gln Gly Thr Lys Leu Glu Ile Lys
            515             520

<210> SEQ ID NO 17
<211> LENGTH: 1572
<212> TYPE: DNA
<213> ORGANISM: Artificial Sequence
<220> FEATURE:
<223> OTHER INFORMATION: an artificially synthesized sequence

<400> SEQUENCE: 17
atggactgga cctggaggtt cctctttgtg gtggcagcag ctacaggtgt ccagtcccag      60
gtgcagctgg tgcagtctgg acctgaggtg aagaagcctg ggcctcagt gaaggtctcc     120 tgcaaggctt ctggatacac cttcaccaac tcctggatga actgggtgag ggagaggcct     180
ggaaagggtc ttgagtggat tggacggatt tatcctggag atggagaaac tatctacaat     240
gggaaattca gggtcagagt cacgattacc gcggacgaat ccacgagcac agcctacatg     300
caactgagca gcctgagatc tgaggacacg gccgtgtatt actgtgcgag aggctatgat     360
gattactcgt ttgcttactg gggccaggga accacggtca ccgtctcttc aggtggtggt     420
ggatccggag gtggtggatc gggtggtgga ggatcggata ttgtgatgac tcagtctcca     480 ctctcccctgc ccgtcacccc tggagagccg gcctccatct cctgcaggtc tagtaagagt     540
ctcctgcata gtaatggcaa cacttacttg tattggttcc tgaagaagcc agggcagtct     600
ccacagctcc tgatctatcg gatgtccaac cttgcctcag ggtccctga caggttcagt     660 ggcagtggat caggcacaga ttttacactg aaaatcagca gagtggaggc tgaggatgtt     720
ggggtttatt actgcatgca acatatagaa tatccttttta cgttcggcca agggaccaaa     780
ctggaaatca aggaggtgg tggatcgggt ggtggtggtt cggaggcgg tggatcgcag     840 gtgcagctgg tgcagtctgg acctgaggtg aagaagcctg ggcctcagt gaaggtctcc     900 tgcaaggctt ctggatacac cttcaccaac tcctggatga actgggtgag gagaggcct     960 ggaaagggtc ttgagtggat tggacggatt tatcctggag atggagaaac tatctacaat    1020
```

```
gggaaattca gggtcagagt cacgattacc gcggacgaat ccacgagcac agcctacatg    1080
caactgagca gcctgagatc tgaggacacg gccgtgtatt actgtgcgag aggctatgat    1140
gattactcgt ttgcttactg gggccaggga accacggtca ccgtctcttc aggtggtggt    1200
ggatccggag gtggtggatc gggtggtgga ggatcggata ttgtgatgac tcagtctcca    1260
ctctccctgc ccgtcacccc tggagagccg gcctccatct cctgcaggtc tagtaagagt    1320
ctcctgcata gtaatggcaa cacttacttg tattggttcc tggagaagcc agggcagtct    1380
ccacagctcc tgatctatcg gatgtccaac cttgcctcag gggtccctga caggttcagt    1440
ggcagtggat caggcacaga ttttacactg aaaatcagca gagtggaggc tgaggatgtt    1500
ggggtttatt actgcatgca acatatagaa tatcctttta cgttcggcca agggaccaaa    1560
ctggaaatca aa                                                       1572
```

<210> SEQ ID NO 18
<211> LENGTH: 524
<212> TYPE: PRT
<213> ORGANISM: Artificial Sequence
<220> FEATURE:
<223> OTHER INFORMATION: an artificially synthesized sequence

<400> SEQUENCE: 18

```
Met Asp Trp Thr Trp Arg Phe Leu Phe Val Val Ala Ala Ala Thr Gly
1               5                   10                  15

Val Gln Ser Gln Val Gln Leu Val Gln Ser Gly Pro Glu Val Lys Lys
            20                  25                  30

Pro Gly Ala Ser Val Lys Val Ser Cys Lys Ala Ser Gly Tyr Thr Phe
        35                  40                  45

Thr Asn Ser Trp Met Asn Trp Val Arg Glu Arg Pro Gly Lys Gly Leu
    50                  55                  60

Glu Trp Ile Gly Arg Ile Tyr Pro Gly Asp Gly Glu Thr Ile Tyr Asn
65                  70                  75                  80

Gly Lys Phe Arg Val Arg Val Thr Ile Thr Ala Asp Glu Ser Thr Ser
                85                  90                  95

Thr Ala Tyr Met Gln Leu Ser Ser Leu Arg Ser Glu Asp Thr Ala Val
            100                 105                 110

Tyr Tyr Cys Ala Arg Gly Tyr Asp Asp Tyr Ser Phe Ala Tyr Trp Gly
        115                 120                 125

Gln Gly Thr Thr Val Thr Val Ser Ser Gly Gly Gly Gly Ser Gly Gly
    130                 135                 140

Gly Gly Ser Gly Gly Gly Ser Asp Ile Val Met Thr Gln Ser Pro
145                 150                 155                 160

Leu Ser Leu Pro Val Thr Pro Gly Glu Pro Ala Ser Ile Ser Cys Arg
                165                 170                 175

Ser Ser Lys Ser Leu Leu His Ser Asn Gly Asn Thr Tyr Leu Tyr Trp
            180                 185                 190

Phe Leu Lys Lys Pro Gly Gln Ser Pro Gln Leu Leu Ile Tyr Arg Met
        195                 200                 205

Ser Asn Leu Ala Ser Gly Val Pro Asp Arg Phe Ser Gly Ser Gly Ser
    210                 215                 220

Gly Thr Asp Phe Thr Leu Lys Ile Ser Arg Val Glu Ala Glu Asp Val
225                 230                 235                 240

Gly Val Tyr Tyr Cys Met Gln His Ile Glu Tyr Pro Phe Thr Phe Gly
                245                 250                 255

Gln Gly Thr Lys Leu Glu Ile Lys Gly Gly Gly Gly Ser Gly Gly Gly
```

```
            260                 265                 270
Gly Ser Gly Gly Gly Ser Gln Val Gln Leu Val Gln Ser Gly Pro
        275                 280                 285
Glu Val Lys Lys Pro Gly Ala Ser Val Lys Val Ser Cys Lys Ala Ser
    290                 295                 300
Gly Tyr Thr Phe Thr Asn Ser Trp Met Asn Trp Val Arg Lys Arg Pro
305                 310                 315                 320
Gly Lys Gly Leu Glu Trp Ile Gly Arg Ile Tyr Pro Gly Asp Gly Glu
                325                 330                 335
Thr Ile Tyr Asn Gly Lys Phe Arg Val Arg Val Thr Ile Thr Ala Asp
            340                 345                 350
Glu Ser Thr Ser Thr Ala Tyr Met Gln Leu Ser Ser Leu Arg Ser Glu
        355                 360                 365
Asp Thr Ala Val Tyr Tyr Cys Ala Arg Gly Tyr Asp Asp Tyr Ser Phe
    370                 375                 380
Ala Tyr Trp Gly Gln Gly Thr Thr Val Thr Val Ser Ser Gly Gly Gly
385                 390                 395                 400
Gly Ser Gly Gly Gly Gly Ser Gly Gly Gly Gly Ser Asp Ile Val Met
                405                 410                 415
Thr Gln Ser Pro Leu Ser Leu Pro Val Thr Pro Gly Glu Pro Ala Ser
            420                 425                 430
Ile Ser Cys Arg Ser Ser Lys Ser Leu Leu His Ser Asn Gly Asn Thr
        435                 440                 445
Tyr Leu Tyr Trp Phe Leu Glu Lys Pro Gly Gln Ser Pro Gln Leu Leu
    450                 455                 460
Ile Tyr Arg Met Ser Asn Leu Ala Ser Gly Val Pro Asp Arg Phe Ser
465                 470                 475                 480
Gly Ser Gly Ser Gly Thr Asp Phe Thr Leu Lys Ile Ser Arg Val Glu
                485                 490                 495
Ala Glu Asp Val Gly Val Tyr Tyr Cys Met Gln His Ile Glu Tyr Pro
            500                 505                 510
Phe Thr Phe Gly Gln Gly Thr Lys Leu Glu Ile Lys
        515                 520

<210> SEQ ID NO 19
<211> LENGTH: 411
<212> TYPE: DNA
<213> ORGANISM: Homo sapiens

<400> SEQUENCE: 19
atggactgga cctggagaat cctcttttg gtggcagcag ccaaaggtgc ccactccgag      60
gtccagcttg tgcagtctgg ggctgaggtg gtgaagcctg gtcctcagt gaaggtttcc     120 tgcacggcct ctggatacac cttcagtgac tactatatgc actgggtgcg ccaggccccc    180
ggagaagggc ttgagtggat gggatacatt aatcctagca gtggttatac taagtacaat    240
cggaagttca gggacagagt caccattacc gcggacaaat ccacgagcac agcctacatg    300
gagctgagca gcctgagatc tgaagacacg gctgtgtatt actgtgcgag agggggtctc    360
ggttactacc ttgactactg gggcgagggc accacggtca ccgtctcctc a             411

<210> SEQ ID NO 20
<211> LENGTH: 137
<212> TYPE: PRT
<213> ORGANISM: Homo sapiens

<400> SEQUENCE: 20
```

Met Asp Trp Thr Trp Arg Ile Leu Phe Leu Val Ala Ala Lys Gly
1               5                   10                  15

Ala His Ser Glu Val Gln Leu Val Gln Ser Gly Ala Glu Val Val Lys
            20                  25                  30

Pro Gly Ser Ser Val Lys Val Ser Cys Thr Ala Ser Gly Tyr Thr Phe
            35                  40                  45

Ser Asp Tyr Tyr Met His Trp Val Arg Gln Ala Pro Gly Glu Gly Leu
50                      55                  60

Glu Trp Met Gly Tyr Ile Asn Pro Ser Ser Gly Tyr Thr Lys Tyr Asn
65                  70                  75                  80

Arg Lys Phe Arg Asp Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
                100                 105                 110

Tyr Tyr Cys Ala Arg Gly Gly Leu Gly Tyr Tyr Leu Asp Tyr Trp Gly
            115                 120                 125

Glu Gly Thr Thr Val Thr Val Ser Ser
        130                 135

<210> SEQ ID NO 21
<211> LENGTH: 414
<212> TYPE: DNA
<213> ORGANISM: Homo sapiens

<400> SEQUENCE: 21
atggactgga cctggagcat ccttttcttg gtggcagcag caacaggtgc ccactccgag    60
gtgcagctgg tgcagtctgg agctcaggtg aagaagccgg ggcctcagt gaaggtctcc    120 tgcaaggcct ctggctacac gttttccgac aacaacatgg actgggtgcg acaggcccct   180 ggaaaaggc ttgagtggat gggagatatt aatactaaaa gtggtggttc tatctacaac    240
cagaagttca gggcagagt catcatgacc atagacaaat ccacgggcac agcctacatg    300
gaattgagga gcctgagatc agacgacacg gccatatatt actgtgcgag gaggaggagc   360
tacggctact actttgacta ctggggccgg ggaaccctgg tcaccgtctc ctca         414

<210> SEQ ID NO 22
<211> LENGTH: 138
<212> TYPE: PRT
<213> ORGANISM: Homo sapiens

<400> SEQUENCE: 22

Met Asp Trp Thr Trp Ser Ile Leu Phe Leu Val Ala Ala Ala Thr Gly
1               5                   10                  15

Ala His Ser Glu Val Gln Leu Val Gln Ser Gly Ala Gln Val Lys Lys
            20                  25                  30

Pro Gly Ala Ser Val Lys Val Ser Cys Lys Ala Ser Gly Tyr Thr Phe
            35                  40                  45

Ser Asp Asn Asn Met Asp Trp Val Arg Gln Ala Pro Gly Lys Gly Leu
50                      55                  60

Glu Trp Met Gly Asp Ile Asn Thr Lys Ser Gly Gly Ser Ile Tyr Asn
65                  70                  75                  80

Gln Lys Phe Lys Gly Arg Val Ile Met Thr Ile Asp Lys Ser Thr Gly
                85                  90                  95

Thr Ala Tyr Met Glu Leu Arg Ser Leu Arg Ser Asp Asp Thr Ala Ile
                100                 105                 110

Tyr Tyr Cys Ala Arg Arg Ser Tyr Gly Tyr Tyr Phe Asp Tyr Trp
            115                 120                 125

Gly Arg Gly Thr Leu Val Thr Val Ser Ser
    130                 135

<210> SEQ ID NO 23
<211> LENGTH: 384
<212> TYPE: DNA
<213> ORGANISM: Homo sapiens

<400> SEQUENCE: 23
atggacatga gggtccccgc tcagctcctg gggctcctgc tactctggct ccgaggtgcc      60
agatgtgaca tcgtgatgac ccagtctcca tcctccctgt ctgcatctgt aggagacaga     120
gtcaccatca cttgcaaggc cagtcagaat gtggggactg ctgtagcctg gtatcagcag     180
aaaccaggga agcccctaa gctcctgatc tattcggcat cctaccgggc cagtggggtc      240
ccatcaaggt tcagtggcag tcgatatggg acagatttca ctctcaccat ctcaagcttg     300
caacctgaag atttagcaac ttactactgt cagcaatata gcaactatat cacgttcggc     360
caagggacca aggtggagat caaa                                            384

<210> SEQ ID NO 24
<211> LENGTH: 128
<212> TYPE: PRT
<213> ORGANISM: Homo sapiens

<400> SEQUENCE: 24

Met Asp Met Arg Val Pro Ala Gln Leu Leu Gly Leu Leu Leu Leu Trp
1               5                   10                  15

Leu Arg Gly Ala Arg Cys Asp Ile Val Met Thr Gln Ser Pro Ser Ser
            20                  25                  30

Leu Ser Ala Ser Val Gly Asp Arg Val Thr Ile Thr Cys Lys Ala Ser
        35                  40                  45

Gln Asn Val Gly Thr Ala Val Ala Trp Tyr Gln Lys Pro Gly Lys
    50                  55                  60

Ala Pro Lys Leu Leu Ile Tyr Ser Ala Ser Tyr Arg Ala Ser Gly Val
65                  70                  75                  80

Pro Ser Arg Phe Ser Gly Ser Arg Tyr Gly Thr Asp Phe Thr Leu Thr
                85                  90                  95

Ile Ser Ser Leu Gln Pro Glu Asp Leu Ala Thr Tyr Tyr Cys Gln Gln
            100                 105                 110

Tyr Ser Asn Tyr Ile Thr Phe Gly Gln Gly Thr Lys Val Glu Ile Lys
        115                 120                 125

<210> SEQ ID NO 25
<211> LENGTH: 327
<212> TYPE: PRT
<213> ORGANISM: Homo sapiens

<400> SEQUENCE: 25

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

```
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 26
<211> LENGTH: 327
<212> TYPE: PRT
<213> ORGANISM: Homo sapiens

<400> SEQUENCE: 26

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110
```

```
            100                 105                 110
Glu Phe Leu Gly Gly Pro Ser Val Phe Leu Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Asp Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 27
<211> LENGTH: 327
<212> TYPE: PRT
<213> ORGANISM: Homo sapiens

<400> SEQUENCE: 27

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140
```

```
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Lys Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 28
<211> LENGTH: 327
<212> TYPE: PRT
<213> ORGANISM: Homo sapiens

<400> SEQUENCE: 28

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190
```

-continued

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Glu Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 29
<211> LENGTH: 327
<212> TYPE: PRT
<213> ORGANISM: Homo sapiens

<400> SEQUENCE: 29

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Pro Cys Pro Ala Pro
        100                 105                 110

Glu Phe Leu Gly Gly Pro Ser Val Phe Leu Phe Pro Pro Lys Pro Lys
    115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
        180                 185                 190

Trp Leu Asn Gly Lys Glu Tyr Lys Cys Lys Val Ser Asn Lys Gly Leu
    195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Lys Met Thr Lys

```
                225                 230                 235                 240
Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 30
<211> LENGTH: 327
<212> TYPE: PRT
<213> ORGANISM: Homo sapiens

<400> SEQUENCE: 30

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270
```

```
Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Glu Ser
305                 310                 315                 320

Leu Ser Leu Ser Leu Gly Lys
            325

<210> SEQ ID NO 31
<211> LENGTH: 327
<212> TYPE: PRT
<213> ORGANISM: Homo sapiens

<400> SEQUENCE: 31

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320
```

Leu Ser Leu Ser Leu Gly Lys
            325

<210> SEQ ID NO 32
<211> LENGTH: 327
<212> TYPE: PRT
<213> ORGANISM: Homo sapiens

<400> SEQUENCE: 32

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Glu Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Asp Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 33
<211> LENGTH: 327
<212> TYPE: PRT

<213> ORGANISM: Homo sapiens

<400> SEQUENCE: 33

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Lys Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Lys Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 34
<211> LENGTH: 327
<212> TYPE: PRT
<213> ORGANISM: Homo sapiens

<400> SEQUENCE: 34

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr

```
                20                  25                  30
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Asp Leu Thr Val Asp Lys Ser Arg Trp Gln Glu Gly Asn Val Phe Ser
    290                 295                 300

Cys Ser Val Met His Glu Ala Leu His Asn His Tyr Thr Gln Glu Ser
305                 310                 315                 320

Leu Ser Leu Ser Leu Gly Lys
                325

<210> SEQ ID NO 35
<211> LENGTH: 327
<212> TYPE: PRT
<213> ORGANISM: Homo sapiens

<400> SEQUENCE: 35

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Lys Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Lys Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 36
<211> LENGTH: 327
<212> TYPE: PRT
<213> ORGANISM: Homo sapiens

<400> SEQUENCE: 36

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
                 35                  40                  45

Gly Val His Thr Phe Pro Ala Val Leu Gln Ser Ser Gly Leu Tyr Ser
             50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
                100                 105                 110
```

```
Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Glu Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Glu Ser
305                 310                 315                 320

Leu Ser Leu Ser Leu Gly Lys
                325

<210> SEQ ID NO 37
<211> LENGTH: 327
<212> TYPE: PRT
<213> ORGANISM: Homo sapiens

<400> SEQUENCE: 37

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
```

```
              145                 150                 155                 160
     Gly Val Glu Val His Asn Ala Lys Thr Lys Pro Arg Glu Glu Gln Phe
                     165                 170                 175

Asn Ser Thr Tyr Arg Val Val Ser Val Leu Thr Val Leu His Gln Asp
                     180                 185                 190

Trp Leu Asn Gly Lys Glu Tyr Lys Cys Lys Val Ser Asn Lys Gly Leu
                     195                 200                 205

Pro Ser Ser Ile Glu Lys Thr Ile Ser Lys Ala Lys Gly Gln Pro Arg
                     210                 215                 220

Glu Pro Gln Val Tyr Thr Leu Pro Pro Ser Gln Lys Lys Met Thr Lys
     225                 230                 235                 240

Asn Gln Val Ser Leu Thr Cys Leu Val Lys Gly Phe Tyr Pro Ser Asp
                     245                 250                 255

Ile Ala Val Glu Trp Glu Ser Asn Gly Gln Pro Glu Asn Asn Tyr Lys
                     260                 265                 270

Thr Thr Pro Pro Val Leu Asp Ser Asp Gly Ser Phe Phe Leu Tyr Ser
                     275                 280                 285

Arg Leu Thr Val Asp Lys Ser Arg Trp Gln Glu Gly Asn Val Phe Ser
                     290                 295                 300

Cys Ser Val Met His Glu Ala Leu His Asn His Tyr Thr Gln Lys Ser
     305                 310                 315                 320

Leu Ser Leu Ser Leu Gly Lys
                     325

<210> SEQ ID NO 38
<211> LENGTH: 327
<212> TYPE: PRT
<213> ORGANISM: Homo sapiens

<400> SEQUENCE: 38

Ala Ser Thr Lys Gly Pro Ser Val Phe Pro Leu Ala Pro Cys Ser Arg
     1               5                   10                  15

Ser Thr Ser Glu Ser Thr Ala Ala Leu Gly Cys Leu Val Lys Asp Tyr
                     20                  25                  30

Phe Pro Glu Pro Val Thr Val Ser Trp Asn Ser Gly Ala Leu Thr Ser
                     35                  40                  45

Gly Val His Thr Phe Pro Ala Val Leu Gln Ser Ser Gly Leu Tyr Ser
                     50                  55                  60

Leu Ser Ser Val Val Thr Val Pro Ser Ser Ser Leu Gly Thr Lys Thr
     65                  70                  75                  80

Tyr Thr Cys Asn Val Asp His Lys Pro Ser Asn Thr Lys Val Asp Lys
                     85                  90                  95

Arg Val Glu Ser Lys Tyr Gly Pro Pro Cys Pro Pro Cys Pro Ala Pro
                     100                 105                 110

Glu Phe Leu Gly Gly Pro Ser Val Phe Leu Phe Pro Pro Lys Pro Lys
                     115                 120                 125

Asp Thr Leu Met Ile Ser Arg Thr Pro Glu Val Thr Cys Val Val Val
     130                 135                 140

Asp Val Ser Gln Glu Asp Pro Glu Val Gln Phe Asn Trp Tyr Val Asp
     145                 150                 155                 160

Gly Val Glu Val His Asn Ala Lys Thr Lys Pro Arg Glu Glu Gln Phe
                     165                 170                 175

Asn Ser Thr Tyr Arg Val Val Ser Val Leu Thr Val Leu His Gln Asp
                     180                 185                 190
```

-continued

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Cys Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Asp Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 39
<211> LENGTH: 327
<212> TYPE: PRT
<213> ORGANISM: Homo sapiens

<400> SEQUENCE: 39

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Cys Gln Glu Glu Met Thr Lys
225                 230                 235                 240

```
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Lys Ser Asp Gly Ser Phe Phe Leu Tyr Ser
            275                 280                 285
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 40
<211> LENGTH: 327
<212> TYPE: PRT
<213> ORGANISM: Homo sapiens

<400> SEQUENCE: 40

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
Glu Pro Gln Val Cys Thr Leu Pro Pro Ser Gln Glu Glu Met Thr Lys
225                 230                 235                 240
Asn Gln Val Ser Leu Thr Cys Leu Val Glu Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
```

```
            275                 280                 285
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 41
<211> LENGTH: 327
<212> TYPE: PRT
<213> ORGANISM: Homo sapiens

<400> SEQUENCE: 41

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
                100                 105                 110
Glu Phe Leu Gly Gly Pro Ser Val Phe Leu Phe Pro Pro Lys Pro Lys
            115                 120                 125
Asp Thr Leu Met Ile Ser Arg Thr Pro Glu Val Thr Cys Val Val Val
        130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
Glu Pro Gln Val Tyr Thr Leu Pro Pro Cys Gln Glu Lys Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
```

```
Leu Ser Leu Ser Leu Gly Lys
            325

<210> SEQ ID NO 42
<211> LENGTH: 327
<212> TYPE: PRT
<213> ORGANISM: Homo sapiens

<400> SEQUENCE: 42

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Cys Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Glu Ser
305                 310                 315                 320

Leu Ser Leu Ser Leu Gly Lys
            325

<210> SEQ ID NO 43
<211> LENGTH: 327
<212> TYPE: PRT
<213> ORGANISM: Homo sapiens
```

<400> SEQUENCE: 43

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Cys Gln Lys Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 44
<211> LENGTH: 327
<212> TYPE: PRT
<213> ORGANISM: Homo sapiens

<400> SEQUENCE: 44

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Cys Thr Leu Pro Pro Ser Gln Glu Glu Met Thr Lys
225                 230                 235                 240

Asn Gln Val Ser Leu Thr Cys Leu Val Glu Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Glu Ser
305                 310                 315                 320

Leu Ser Leu Ser Leu Gly Lys
                325

<210> SEQ ID NO 45
<211> LENGTH: 327
<212> TYPE: PRT
<213> ORGANISM: Homo sapiens

<400> SEQUENCE: 45

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr

```
                65                  70                  75                  80
Tyr Thr Cys Asn Val Asp His Lys Pro Ser Asn Thr Lys Val Asp Lys
                    85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Cys Gln Lys Lys Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 46
<211> LENGTH: 327
<212> TYPE: PRT
<213> ORGANISM: Homo sapiens

<400> SEQUENCE: 46

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110
```

```
Glu Phe Leu Gly Gly Pro Ser Val Phe Leu Phe Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Cys Gln Glu Glu Met Thr Lys
225                 230                 235                 240

Asn Gln Val Ser Leu Thr Cys Leu Val Glu Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Glu Ser
305                 310                 315                 320

Leu Ser Leu Ser Leu Gly Lys
                325

<210> SEQ ID NO 47
<211> LENGTH: 327
<212> TYPE: PRT
<213> ORGANISM: Homo sapiens

<400> SEQUENCE: 47

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Cys Thr Leu Pro Pro Ser Gln Lys Lys Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 48
<211> LENGTH: 330
<212> TYPE: PRT
<213> ORGANISM: Homo sapiens

<400> SEQUENCE: 48

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

```
            195                 200                 205
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                    325                 330

<210> SEQ ID NO 49
<211> LENGTH: 330
<212> TYPE: PRT
<213> ORGANISM: Homo sapiens

<400> SEQUENCE: 49

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Cys Thr Leu Pro Pro Ser Arg Asp Glu
225                 230                 235                 240
```

Leu Thr Lys Asn Gln Val Ser Leu Trp Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 50
<211> LENGTH: 330
<212> TYPE: PRT
<213> ORGANISM: Homo sapiens

<400> SEQUENCE: 50

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Cys Glu
225                 230                 235                 240

Leu Thr Lys Asn Gln Val Ser Leu Ser Cys Ala Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
            275                 280                 285

```
Leu Val Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 51
<211> LENGTH: 330
<212> TYPE: PRT
<213> ORGANISM: Homo sapiens

<400> SEQUENCE: 51

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Glu Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Asp Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 52
<211> LENGTH: 330
<212> TYPE: PRT
<213> ORGANISM: Homo sapiens

<400> SEQUENCE: 52

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Lys
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Lys Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 53
<211> LENGTH: 330
<212> TYPE: PRT
<213> ORGANISM: Homo sapiens

<400> SEQUENCE: 53

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Asp Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Glu Ser Leu Ser Leu Ser Pro Gly Lys
                325                 330

<210> SEQ ID NO 54
<211> LENGTH: 330
<212> TYPE: PRT
<213> ORGANISM: Homo sapiens

<400> SEQUENCE: 54

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Lys Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Lys Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 55
<211> LENGTH: 330
<212> TYPE: PRT
<213> ORGANISM: Homo sapiens

<400> SEQUENCE: 55

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Glu Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Glu Ser Leu Ser Leu Ser Pro Gly Lys
                325                 330

<210> SEQ ID NO 56
<211> LENGTH: 330
<212> TYPE: PRT
<213> ORGANISM: Homo sapiens

<400> SEQUENCE: 56

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
```

```
            115                 120                 125
Lys Pro Lys Asp Thr Leu Met Ile Ser Arg Thr Pro Glu Val Thr Cys
130                 135                 140

Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Lys Lys
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 57
<211> LENGTH: 119
<212> TYPE: PRT
<213> ORGANISM: Mus musculus

<400> SEQUENCE: 57

Met Glu Val Gln Leu Gln Gln Ser Gly Ala Glu Leu Val Lys Pro Gly
1               5                   10                  15

Ala Ser Val Lys Leu Ser Cys Thr Ala Ser Gly Phe Asn Ile Lys Asp
            20                  25                  30

Tyr Tyr Met His Trp Ile Lys Gln Arg Pro Gly Gln Gly Leu Glu Trp
        35                  40                  45

Leu Gly Tyr Ile Asn Pro Ser Ser Gly Tyr Thr Lys Tyr Asn Arg Lys
    50                  55                  60

Phe Arg Asp Lys Ala Thr Leu Thr Ala Asp Lys Ser Ser Ser Thr Ala
65                  70                  75                  80

Tyr Met Gln Leu Thr Ser Leu Thr Tyr Glu Asp Ser Ala Val Tyr Tyr
                85                  90                  95

Cys Ala Arg Gly Gly Asn Gly Tyr Tyr Leu Asp Tyr Trp Gly Gln Gly
            100                 105                 110

Thr Thr Leu Thr Val Ser Ser
        115

<210> SEQ ID NO 58
<211> LENGTH: 120
<212> TYPE: PRT
<213> ORGANISM: Mus musculus
```

```
<400> SEQUENCE: 58

Met Gln Val Gln Leu Gln Gln Ser Gly Pro Glu Leu Val Lys Pro Gly
1               5                   10                  15

Ala Ser Val Lys Ile Ser Cys Lys Ala Ser Gly Tyr Thr Phe Thr Asp
                20                  25                  30

Asn Asn Met Asp Trp Val Lys Gln Ser His Gly Lys Gly Leu Glu Trp
            35                  40                  45

Ile Gly Asp Ile Asn Thr Lys Ser Gly Gly Ser Ile Tyr Asn Gln Lys
        50                  55                  60

Phe Lys Gly Lys Ala Thr Leu Thr Ile Asp Lys Ser Ser Ser Thr Ala
65                  70                  75                  80

Tyr Met Glu Leu Arg Ser Leu Thr Ser Glu Asp Thr Ala Val Tyr Tyr
                85                  90                  95

Cys Ala Arg Arg Arg Ser Tyr Gly Tyr Tyr Phe Asp Tyr Trp Gly Gln
            100                 105                 110

Gly Thr Thr Leu Thr Val Ser Ser
            115                 120

<210> SEQ ID NO 59
<211> LENGTH: 107
<212> TYPE: PRT
<213> ORGANISM: Homo sapiens

<400> SEQUENCE: 59

Asp Ile Val Met Thr Gln Ser His Lys Phe Met Ser Thr Ser Val Gly
1               5                   10                  15

Asp Arg Val Ser Ile Thr Cys Lys Ala Ser Gln Asn Val Gly Thr Ala
                20                  25                  30

Val Ala Trp Tyr Gln Gln Lys Pro Gly Gln Ser Pro Lys Leu Leu Ile
            35                  40                  45

Tyr Ser Ala Ser Tyr Arg Tyr Ser Gly Val Pro Asp Arg Phe Thr Gly
        50                  55                  60

Ser Arg Tyr Gly Thr Asp Phe Thr Leu Thr Ile Ser Asn Val Gln Ser
65                  70                  75                  80

Glu Asp Leu Ala Asp Tyr Leu Cys Gln Gln Tyr Ser Asn Tyr Ile Thr
                85                  90                  95

Phe Gly Gly Gly Thr Lys Leu Glu Leu Lys Arg
            100                 105

<210> SEQ ID NO 60
<211> LENGTH: 15
<212> TYPE: PRT
<213> ORGANISM: Artificial Sequence
<220> FEATURE:
<223> OTHER INFORMATION: synthetic

<400> SEQUENCE: 60

Gly Gly Gly Gly Ser Gly Gly Gly Gly Ser Gly Gly Gly Gly Ser
1               5                   10                  15
```

METHODS FOR PRODUCING POLYPEPTIDES BY REGULATING POLYPEPTIDE ASSOCIATION

This application is a continuation of U.S. application Ser. No. 11/910,128, filed Oct. 7, 2008, now U.S. Pat. No. 10,011,858, which is the National Stage of International Application No. PCT/JP2006/306803, filed on Mar. 31, 2006, which claims the benefit of Japanese Patent Applications Serial No. 2005/101105, filed on Mar. 31, 2005, and Serial No. 2005/378266, filed on Dec. 28, 2005. The contents of all of the foregoing applications are hereby incorporated by reference in their entireties.

TECHNICAL FIELD

The present invention relates to methods for producing polypeptides by regulating the intramolecular or intermolecular association of each molecule, polypeptides whose intramolecular or intermolecular association is regulated, and pharmaceutical compositions and the like containing such polypeptides as an active ingredient.

BACKGROUND ART

Due to their highly stable nature in blood and relatively few side effects, antibodies have been receiving much attention as pharmaceuticals. Of particular note are bispecific antibodies that can simultaneously recognize two types of antigens. MDX-210, which is currently under clinical trial investigation, is an IgG-type bispecific antibody that retargets FcγRI-expressing monocytes and such to HER-2/neu-expressing cancer cells (see Non-Patent Document 1). In general, antibodies are produced using genetic recombination techniques. One specific technique involves the cloning of a DNA encoding an antibody protein from antibody-producing cells, such as hybridomas or sensitized lymphocytes that produce antibodies or a phage library presenting antibody genes, and the insertion of such into a suitable vector, which is then transfected into host cells for antibody production. Production of IgG type bispecific antibodies using genetic recombination techniques involves the introduction of a total of four types of genes into cells, in which these genes of H chains and L chains constitute two types of IgGs of interest, and the secretion of the antibodies by coexpression. In this type of system, expression of the wild type H chains and L chains constituting genes leads to random covalent bonding between two types of H chains and non-covalent bonding between H and L chains, and thus, the proportion of the bispecific antibody of interest becomes very small. More particularly, only one out of ten types produced is the bispecific antibody of interest, rendering the production efficiency quite low. Decreased efficiency in the production of the antibody of interest is not only an obstacle for purifying the antibody of interest, but also increases the nonuniformity, such as the lot-to-lot differences, which, in turn, leads to swelling production costs.

Preferential secretion of IgGs with a heterologous combination of H chains by introducing amino acid substitutions into the IgG H chain CH3 region has been reported as a means to improve the efficiency of bispecific antibody production (see Patent Document 1 and Non-Patent Documents 2 and 3). This method involves induction of promotion of heterologous H chain formation and inhibition of homogeneous H chain formation by substituting an amino acid side chain present in the CH3 region of one of the H chains to a larger side chain (knob), and substituting the amino acid side chain present in the CH3 region of the other H chain to a smaller side chain (hole), such that the knob is placed into the hole. A finding that uses a similar "knob" and "hole" at the interface where the H chain variable region (hereinafter referred to as VH) associates with the L chain variable region (hereinafter referred to as VL) has also been reported (see Non-Patent Document 4). According to the report by Zhe et al., substitution of two types of amino acids present at the VH-VL interface (four types for both chains) promotes the formation of the heterologous molecule 1.28 times more efficiently (wild type: 72%, and modified type: 92%). Meanwhile, substitution of one type of amino acid (two types for both chains) results in the same level of efficiency as the wild type. However, the method of setting a knob and a hole in VH and VL does not sufficiently promote the formation of heterologous molecules.

[Patent Document 1] International publication WO 96/27011
[Non-Patent Document 1] Segal D M et al., Current Opinion in Immunology, 1999, Vol. 11, p. 558-562.
[Non-Patent Document 2] Ridgway J B et al., Protein Engineering, 1996, Vol. 9, p. 617-621.
[Non-Patent Document 3] Merchant A M et al., Nature Biotechnology, 1998, Vol. 16, p. 677-681.
[Non-Patent Document 4] Zhe Z et al., Protein Science, 1997, Vol. 6, p. 781-788.

DISCLOSURE OF THE INVENTION

Problems to be Solved by the Present Invention

The present invention was achieved in view of the above circumstances. An objective of the present invention is to provide a method for regulating polypeptide association, polypeptides whose association is regulated, and methods for producing such polypeptides. In one embodiment, it is an objective of the present invention to provide methods for efficiently producing bispecific antibodies by regulating association at the VH-VL interface. Another objective is to provide methods for efficiently producing one of the conformational isomers of sc(Fv)2.

Means for Solving the Problems

The present inventors selected VH and VL of the antibodies as peptides to be subjected for the regulation of association, and carried out dedicated research on methods that allow the association between these VH and VL to be regulated.

As a result, the inventors discovered that the association between VH and VL can be regulated by substituting amino acids present at the VH-VL interface with charged amino acids. This, in turn, leads to a more efficient formation of the heterologous molecules than the above-mentioned methods that utilize the knob and hole techniques.

Surprisingly, according to the methods of the present invention, substitution with only one type of amino acid present at each side of the VH-VL interface (a total of two amino acids for VH and VL) allows for the efficient production of a heterologous molecule. From the viewpoint of antigenicity, fewer amino acid substitutions are preferred. In an embodiment of the present invention, a mere substitution of one amino acid present at the VH-VL interface enables the efficient formation of heterologous molecules.

Accordingly, associations between VH and VL can be regulated by the findings discovered by the present inventors. The present invention can be applied not only to the regulation of association between VH and VL, but can also be applied to the regulation of associations among arbitrary polypeptides.

Furthermore, the present inventors confirmed that function is actually retained in bispecific antibodies obtained by the methods for regulating association of the present invention.

As described above, the present inventors succeeded in developing methods that can regulate the association between arbitrary polypeptides, and thus completed the present invention.

The present invention relates to methods for regulating polypeptide association, polypeptides whose association is regulated, and methods for producing such polypeptides, and more specifically the invention provides:

[1] a method for producing a polypeptide comprising a mutation in an amino acid residue forming a polypeptide interface such that polypeptide association will be regulated, wherein the method comprises:
(a) modifying a nucleic acid encoding an amino acid residue forming the polypeptide interface from the original nucleic acid, such that polypeptide association will be inhibited;
(b) culturing host cells such that said nucleic acid is expressed; and
(c) recovering said polypeptide from the host cell culture;
[2] a method for producing a heteromultimer comprising a mutation in an amino acid residue forming an interface between polypeptides such that heteromultimer association will be regulated, wherein the method comprises:
(a) modifying a nucleic acid encoding an amino acid residue forming the interface between polypeptides from the original nucleic acid, such that the association between polypeptides will be inhibited;
(b) culturing host cells such that said nucleic acid is expressed; and
(c) recovering said heteromultimer from the host cell culture;
[3] the method of [1], wherein a nucleic acid encoding an amino acid residue forming a polypeptide interface is modified from the original nucleic acid, so that the polypeptide association forming one or more types of conformational isomers will be inhibited in a polypeptide that may form two or more types of conformational isomers;
[4] the method of [2], wherein a nucleic acid encoding an amino acid residue forming an interface between polypeptides is modified from the original nucleic acid, so that the association between polypeptides forming one or more types of multimers will be inhibited in a heteromultimer that may form two or more types of multimers;
[5] the method of [1] or [2], wherein the modification of step (a) is modifying the original nucleic acid so that an amino acid residue mutation is introduced to the interface such that two or more amino acid residues forming the interface will carry the same type of charge;
[6] the method of [5], wherein the introduced amino acid residue is glutamic acid (E);
[7] the method of [5], wherein the introduced amino acid residue is aspartic acid (D);
[8] the method of [5], wherein the introduced amino acid residue is lysine (K);
[9] the method of [5], wherein the introduced amino acid residue is arginine (R);
[10] the method of [5], wherein the introduced amino acid residue is histidine (H);
[11] the method of [1] or [2], wherein the modification of step (a) is modifying the original nucleic acid so that an amino acid residue mutation is introduced to the interface such that an amino acid residue forming a hydrophobic core present in the interface will become charged amino acid residues;
[12] the method of [11], wherein the introduced amino acid residue is glutamic acid (E);
[13] the method of [11], wherein the introduced amino acid residue is aspartic acid (D);
[14] the method of [11], wherein the introduced amino acid residue is lysine (K);
[15] the method of [11], wherein the introduced amino acid residue is arginine (R);
[16] the method of [11], wherein the introduced amino acid residue is histidine (H);
[17] the method of [1] or [2], wherein the interface of the polypeptide is formed by an antibody heavy chain variable region and light chain variable region;
[18] the method of [1] or [2], wherein the polypeptide interface is formed by two or more types of heavy chain variable regions;
[19] the method of [1] or [2], wherein the polypeptide interface is formed by an antibody heavy chain constant region and light chain constant region;
[20] the method of [1] or [2], wherein the polypeptide interface is formed by two or more types of heavy chain constant regions;
[21] the method of [1] wherein the polypeptide is a single chain polypeptide in which two or more heavy chain variable regions and two or more light chain variable regions are linked by linkers;
[22] the method of [2], wherein the heteromultimer is a multi-specific antibody comprising two or more types of heavy chain variable regions and two or more types of light chain variable regions;
[23] the method of [22], wherein the heteromultimer is a bispecific antibody;
[24] a mutant polypeptide or heteromultimer produced by the method of [1] or [2];
[25] a mutant polypeptide, comprising a modification made to an amino acid residue forming an interface in the original polypeptide such that the association within said polypeptide is inhibited;
[26] a heteromultimer, comprising a modification made to an amino acid residue forming an interface between the original polypeptides such that the association between said polypeptides is inhibited;
[27] the mutant polypeptide of [25], wherein the original polypeptide may form two or more types of conformational isomers;
[28] the heteromultimer of [26], wherein the original polypeptides may form two or more types of multimers;
[29] the mutant polypeptide of [25] or the heteromultimer of [26], wherein said modification of the amino acid residues forming a polypeptide interface is introducing an amino acid residue mutation to the interface such that two or more amino acid residues forming the interface will carry the same type of charge;
[30] the mutant polypeptide or heteromultimer of [29], wherein the introduced amino acid residue is glutamic acid (E);
[31] the mutant polypeptide or heteromultimer of [29], wherein the introduced amino acid residue is aspartic acid (D);
[32] the mutant polypeptide or heteromultimer of [29], wherein the introduced amino acid residue is lysine (K);
[33] the mutant polypeptide or heteromultimer of [29], wherein the introduced amino acid residue is arginine (R);

[34] the mutant polypeptide or heteromultimer of [29], wherein the introduced amino acid residue is histidine (H);
[35] the mutant polypeptide of [25] or the heteromultimer of [26], wherein the modification of amino acid residues forming the polypeptide interface is introducing an amino acid residue mutation to the interface such that an amino acid residue forming a hydrophobic core present in the interface will become charged amino acid residues;
[36] the mutant polypeptide or heteromultimer of [35], wherein the introduced amino acid residue is glutamic acid (E);
[37] the mutant polypeptide or heteromultimer of [35], wherein the introduced amino acid residue is aspartic acid (D);
[38] the mutant polypeptide or heteromultimer of [35], wherein the introduced amino acid residue is lysine (K);
[39] the mutant polypeptide or heteromultimer of [35], wherein the introduced amino acid residue is arginine (R);
[40] the mutant polypeptide or heteromultimer of [35], wherein the introduced amino acid residue is histidine (H);
[41] the mutant polypeptide of [25] or the heteromultimer of [26], wherein the polypeptide interface is formed by an antibody heavy chain variable region and light chain variable region;
[42] the mutant polypeptide of [25] or the heteromultimer of [26], wherein the polypeptide interface is formed by two or more types of heavy chain variable regions;
[43] the mutant polypeptide of [25] or the heteromultimer of [26], wherein the polypeptide interface is formed by an antibody heavy chain constant region and light chain constant region;
[44] the mutant polypeptide of [25] or the heteromultimer of [26], wherein the polypeptide interface is formed by two of more types of heavy chain constant regions;
[45] the mutant polypeptide of [25], wherein the polypeptide is a single chain polypeptide in which two or more heavy chain variable regions and two or more light chain variable regions are linked by linkers;
[46] the heteromultimer of [26], wherein the heteromultimer is a multispecific antibody comprising two or more types of heavy chain variable regions and two or more types of light chain variable regions;
[47] the heteromultimer of [46], wherein the heteromultimer is a bispecific antibody;
[48] a composition comprising the mutant polypeptide of [25] or the heteromultimer of [26], and a pharmaceutically acceptable carrier;
[49] a nucleic acid encoding the mutant polypeptide of [25] or the heteromultimer of [26];
[50] a host cell comprising the nucleic acid of [49];
[51] a method for producing the mutant polypeptide of [25] or the heteromultimer of [26], which comprises the steps of culturing the host cell of [50], and recovering the polypeptide from the cell culture;
[52] a method for regulating polypeptide association, which comprises modifying an amino acid residue forming an interface in the original polypeptide such that the association within the polypeptide is inhibited;
[53] a method for regulating heteromultimer association, which comprises modifying amino acid residues forming an interface between the original polypeptides such that the association between the polypeptides is inhibited;
[54] the method of [52], which comprises modifying an amino acid residue forming an interface in a polypeptide, such that the association of a polypeptide forming one or more types of conformational isomers will be inhibited in a polypeptide that may form two or more types of conformational isomers;
[55] the method of [53], which comprises modifying amino acid residues forming an interface between polypeptides, such that the association between polypeptides that form one or more types of conformational isomers will be inhibited in a heteromultimer that may form two or more types of multimers;
[56] the method of [52] or [53], wherein said modification of an amino acid residue forming a polypeptide interface is introducing an amino acid residue mutation to the interface such that two or more amino acid residues forming the interface will have the same type of charge;
[57] the method of [56], wherein the introduced amino acid residue is glutamic acid (E);
[58] the method of [56], wherein the introduced amino acid residue is aspartic acid (D);
[59] the method of [56], wherein the introduced amino acid residue is lysine (K);
[60] the method of [56], wherein the introduced amino acid residue is arginine (R);
[61] the method of [56], wherein the introduced amino acid residue is histidine (H);
[62] the method of [52] or [53], wherein said modification of amino acid residues forming a polypeptide interface is introducing an amino acid residue mutation to the interface such that an amino acid residue forming a hydrophobic core present in the interface will become charged amino acid residues;
[63] the method of [62], wherein the introduced amino acid residue is glutamic acid (E);
[64] the method of [62], wherein the introduced amino acid residue is aspartic acid (D);
[65] the method of [62], wherein the introduced amino acid residue is lysine (K);
[66] the method of [62], wherein the introduced amino acid residue is arginine (R;
[67] the method of [62], wherein the introduced amino acid residue is histidine (H);
[68] the method of [52] or [53], wherein the polypeptide interface is formed by an antibody heavy chain variable region and light chain variable region;
[69] the method of [52] or [53], wherein the polypeptide interface is formed by two or more types of heavy chain variable regions;
[70] the method of [52] or [53], wherein the polypeptide interface is formed by an antibody heavy chain constant region and light chain constant region;
[71] the method of [52] or [53], wherein the polypeptide interface is formed by two or more types of heavy chain constant regions;
[72] the method of [52], wherein the polypeptide is a single chain polypeptide in which two or more heavy chain variable regions and two or more light chain variable regions are linked by linkers;
[73] the method of [53], wherein the heteromultimer is a multispecific antibody comprising two types or more of heavy chain variable regions and two types or more of light chain variable regions;
[74] the method of [73], wherein the heteromultimer is a bispecific antibody;
[75] an antibody comprising a heavy chain variable region and a light chain variable region, wherein the following amino acid residues of (1) and (2) carry the same type of charge:

(1) an amino acid residue which is included in the heavy chain variable region and corresponds to position 39 (glutamine) in the amino acid sequence of SEQ ID NO: 6; and
(2) an amino acid residue which is included in the light chain variable region and corresponds to position 44 (glutamine) in the amino acid sequence of SEQ ID NO: 8;
[76] an antibody comprising a heavy chain variable region and a light chain variable region, wherein the following amino acid residues of (1) and (2) carry the same type of charge:
(1) an amino acid residue which is included in the heavy chain variable region and corresponds to position 45 (leucine) in the amino acid sequence of SEQ ID NO: 6; and
(2) an amino acid residue which is included in the light chain variable region and corresponds to position 50 (proline) in the amino acid sequence of SEQ ID NO: 8;
[77] an antibody comprising a heavy chain variable region and a light chain variable region, wherein either one of the following amino acid residues of (1) or (2) is a charged amino acid residue:
(1) an amino acid residue which is included in the heavy chain variable region and corresponds to position 45 (leucine) in the amino acid sequence of SEQ ID NO: 6; and
(2) an amino acid residue which is included in the light chain variable region and corresponds to position 50 (proline) in the amino acid sequence of SEQ ID NO: 8;
[78] the antibody of [75] or [76], wherein amino acid residues carrying the same type of charge are selected from amino acid residues included in the group of either (a) or (b):
(a) glutamic acid (E) and aspartic acid (D); or
(b) lysine (K), arginine (R), and histidine (H);
[79] the antibody of [77], wherein said charged amino acid residue is glutamic acid (E), aspartic acid (D), lysine (K), arginine (R), or histidine (H);
[80] the antibody of any one of [75] to [77], wherein the polypeptide is a single chain polypeptide in which two or more heavy chain variable regions and two or more light chain variable regions are linked by linkers;
[81] the antibody of any one of [75] to [77], wherein the polypeptide is a multispecific antibody comprising two or more types of heavy chain variable regions and two or more types of light chain variable regions;
[82] the antibody of [81], wherein the polypeptide is a bispecific antibody;
[83] a composition comprising the antibody of any one of [75] to [77] and a pharmaceutically acceptable carrier;
[84] a nucleic acid encoding a polypeptide constituting the antibody of any one of [75] to [77];
[85] a host cell comprising the nucleic acid of [84];
[86] the method for producing the antibodies of any one of [75] to [77], which comprises the steps of culturing the host cell of [85] and recovering the polypeptides from the cell culture;
[87] an antibody comprising two or more types of heavy chain CH3 regions, wherein one to three pair(s) of amino acid residues in the first heavy chain CH3 region is/are selected from the pair(s) of amino acid residues indicated in (1) to (3) that carry the same type of charge:
(1) amino acid residues included in the heavy chain CH3 region at positions 356 and 439 according to the EU numbering system;
(2) amino acid residues included in the heavy chain CH3 region at positions 357 and 370 according to the EU numbering system; and
(3) amino acid residues included in the heavy chain CH3 region at positions 399 and 409 according to the EU numbering system;

[88] the antibody of [87], in which pairs of the amino acid residues in the second heavy chain CH3 region are selected from the pairs of amino acid residues of (1) to (3), wherein the one to three pairs of amino acid residues corresponding to the pairs of amino acid residues of (1) to (3) carrying the same type of charge in said first heavy chain CH3 region, carry opposite charges from the corresponding amino acid residues in said first heavy chain CH3 region;
[89] the antibody of [87], wherein said amino acid residues carrying the same type of charge are selected from the amino acid residues included in the group of either (a) or (b):
(a) glutamic acid (E) and aspartic acid (D); or
(b) lysine (K), arginine (R), and histidine (H);
[90] the antibody of [87], wherein said first heavy chain CH3 region and the second heavy chain CH3 region are cross-linked by a disulfide bond;
[91] the antibody of [87], wherein the antibody comprises two or more types of heavy chain constant regions;
[92] the antibody of [87], wherein the multispecific antibody comprises two or more types of heavy chain variable regions and two or more types of light chain variable regions;
[93] the antibody of [92], which is a bispecific antibody;
[94] a composition comprising the antibody of [87] and a pharmaceutically acceptable carrier;
[95] a nucleic acid encoding a polypeptide constituting the antibody of [87];
[96] a host cell comprising the nucleic acid of [95]; and
[97] a method for producing the antibody of [87], which comprises the steps of culturing the host cell of [96], and recovering the polypeptides from the cell culture.

BRIEF DESCRIPTION OF THE DRAWINGS

FIG. 22 depicts the results of an assay evaluating the TPO-like agonist activity of peak 1 purified from u2-wz4, peak 2 purified from u2-wz4, variant v1, and variant v3.

FIG. 23 depicts the results of DSC analyses of peak 1 purified from u2-wz4, peak 2 purified from u2-wz4, variant v1, and variant v3.

FIG. 29 depicts the formation ratio of A-Homo, BiAb, and B-Homo obtained by IEX analysis of humanized bispecific antibodies (IgG4-type) whose CH3 interface has been modified.

FIG. 30 depicts the percentage of monomer recovered after thermal acceleration tests at 60° C.-1 W on BiAb purified from humanized bispecific antibodies (IgG4-type) whose CH3 interface has been modified.

FIG. 32 depicts the formation ratio obtained through IEX analysis for A-Homo, BiAb, and B-Homo, which are humanized bispecific antibodies (IgG1-type) whose CH3 interface has been modified.

BEST MODE FOR CARRYING OUT THE INVENTION

Figure 1:
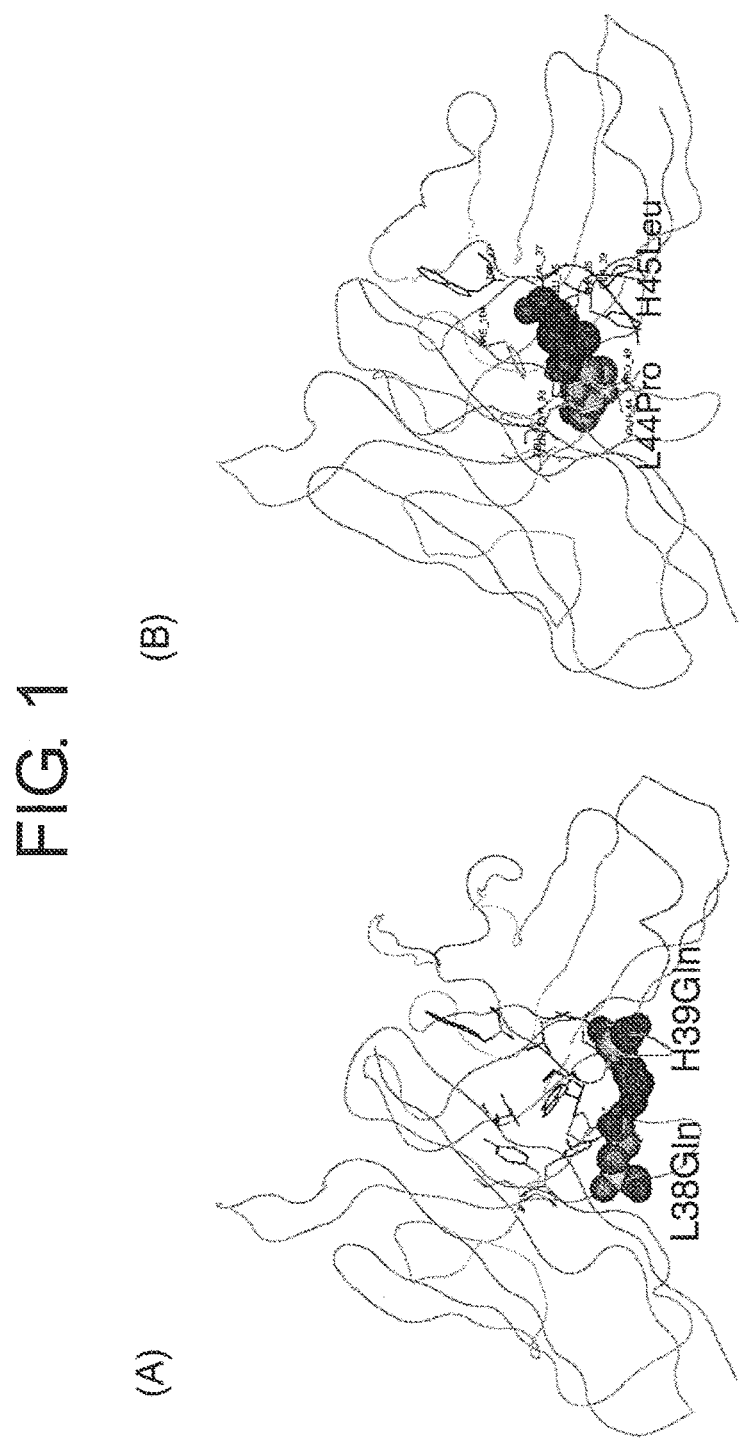
FIG. 1 depicts models of the Fv region of humanized SB04. Part (A) depicts H39 and L38, which are amino acid residues at the VH-VL interface, and part (B) depicts H45 and L44, which are amino acid residues at the VH-VL interface.

The present invention relates to methods for regulating the association of polypeptides or association of heteromultimers composed of polypeptides.

First, the present invention provides methods for regulating polypeptide association, such methods including the step of modifying amino acid residues in an original peptide forming an interface so as to inhibit the association within the polypeptide.

In the present invention, the term "polypeptides" ordinarily refers to peptides and proteins whose length is about ten amino acids or longer. Polypeptides are ordinarily derived from organisms but are not particularly limited thereto, and for example, they may be composed of an artificially designed sequence. They may also be any of naturally derived polypeptides, synthetic polypeptides, recombinant polypeptides, or such. Additionally, fragments of the above-mentioned polypeptides are also included in the polypeptides of the present invention.

In the present invention, the phrase "polypeptide association" refers to, for example, a condition in which two or more polypeptide regions interact.

In the present invention, the phrase "regulating association" refers to regulating to achieve a desired association condition, and more specifically refers to regulating so that undesirable associations are not formed in the polypeptides.

In the present invention, the term "interface" ordinarily refers to the association surface that results from association (interaction), and amino acid residues that form the interface are ordinarily one or more amino acid residues included in the polypeptide regions which participate in the association, and are more preferably amino acid residues that approach each other during association and are involved in the interaction. More specifically, this interaction includes, for example, instances where the amino acid residues come close during the association to form hydrogen bonds, electrostatic interactions, or salt bridges with each other.

In the present invention, the phrase, "amino acid residues forming an interface" more specifically refers to amino acid residues included in the polypeptide region that constitutes the interface. For example, polypeptide regions constituting the interface refer to polypeptide regions responsible for selective binding within or between molecules such as in antibodies, ligands, receptors, or substrates. More specifically, in antibodies, such examples include heavy chain variable regions and light chain variable regions.

"Modification" of amino acid residues in the methods of the present invention specifically refers to substituting original amino acid residue(s) for other amino acid residue(s), deleting original amino acid residue(s), adding new amino acid residue(s), and such, but preferably refers to substituting one or more original amino acid residues for other amino acid residues.

In the present invention, the term "polypeptides" preferably refers to polypeptides that form two or more types of conformational isomers. Conformational isomers are proteins whose amino acid sequences are identical but their three-dimensional (tertiary) structures are different. Ordinarily, among conformational isomers, at least either one of chemical or physical properties is also different.

A preferred embodiment of the present invention relates to methods for preferentially (efficiently) obtaining desirable conformational isomers from among two or more types of potential conformational isomers. More specifically, an embodiment relates to methods for modifying the one or more amino acid residues that form an interface between the polypeptides so as to inhibit an association between polypeptides forming one or more types of conformational isomers from among those polypeptides that may form two or more types of conformational isomers.

For example, when the first to fourth peptide regions exist in a polypeptide, and any two of these regions can associate, the following cases are conceivable where mainly three types of conformational isomers can exist: (1) the first and second polypeptide regions associate and the third and fourth polypeptide regions associate, (2) the first and third polypeptide regions associate, and the second and fourth polypeptide regions associate, and (3) the first and fourth polypeptide regions associate, and the second and third polypeptide regions associate.

Under the above-mentioned circumstance, when one wishes to preferentially obtain a polypeptide (conformational isomer) associated with the interaction of (1), for example, amino acid residues forming the interfaces present in the first, third, or fourth polypeptide regions are modified so that association of the first polypeptide region with the third and fourth polypeptide regions is inhibited.

The methods of the present invention also relates to methods for regulating heteromultimer association, such methods including the step of modifying amino acid residues that form the interface between the original polypeptides, such that the association between the polypeptides is inhibited.

In the present invention, the term "heteromultimer" refers to a protein multimer composed of more than one type of polypeptide, in which the polypeptides can associate with each other. More specifically, a "heteromultimer" includes at least a first polypeptide and a second polypeptide; in this context, the second polypeptide is a molecule which differs from the first polypeptide by at least one amino acid residue. Furthermore, without particular limitation, the heteromultimers preferably have binding specificity toward at least two different types of ligands, antigens, receptors, substrates, or such. In addition to a "heterodimer" formed by a first and second polypeptide, another different type of polypeptide may exist in the heteromultimer. More specifically, "heteromultimers" of the present invention are not limited to heterodimers and include for example heterotrimers and heterotetramers.

Preferred embodiments of the above-mentioned methods are methods of modifying amino acid residues that form the interface between polypeptides in heteromultimers that may form two or more types of multimers, such that association between polypeptides forming one or more types of multimers is inhibited.

For example, when any two of the polypeptides can associate in the protein multimers composed of the first to fourth polypeptides, the following multimers can mainly exist: (1) multimers in which the first and second polypeptides are associated and the third and fourth polypeptides are associated, (2) multimers in which the first and third polypeptides are associated and the second and fourth polypeptides are associated, or (3) multimers in which the first and fourth polypeptides are associated and the second and third polypeptides are associated.

Under the above-mentioned circumstance, when one wishes to preferentially obtain multimers associated with the interaction of (1), for example, amino acid residues included in the first, third, or fourth polypeptide can be modified so that association of the first polypeptide with the third and fourth polypeptides is inhibited.

Preferred embodiments of the methods of the present invention for regulating polypeptide association include, for example, methods in which modification of amino acid residues forming the interface of polypeptides include introducing amino acid residue mutations to the interface so that two or more amino acid residues forming an interface will have the same type of charge.

In the methods mentioned above, by modifying two or more amino acid residues involved in an association at the interface such that they carry the same kind of charge, repulsive forces among those charges will inhibit association among these amino acid residues.

Therefore, in the method mentioned above, the amino acid residues that are to be modified are preferably two or more amino acid residues that come close to each other during association in the region between the polypeptide regions that form the interface.

Amino acid residues that come close to each other during association can be identified, for example, by analyzing the three dimensional structures of the polypeptides, and investigating the amino acid sequences of the polypeptide regions forming the interface when these polypeptides associate. Amino acid residues that come close to each other at the interface will be preferred targets for "modifications" in the methods of the present invention.

Some amino acids are known to be charged amino acids. Generally, lysine (K), arginine (R), and histidine (H) are known as positively charged amino acids (cationic amino acids) whereas aspartate (D), glutamate (E), and such are known as negatively charged amino acids (anionic amino acids). Therefore, in the context of the present invention, amino acids carrying the same type of charge preferably refer to amino acids that are either positively charged or negatively charged.

In the methods of the present invention, all of the mutated amino acid residues are preferably modified to have the same type of charges, but the methods are not necessarily limited to such cases. For example, when a number of amino acid residues are introduced by the modification, there may be a few uncharged amino acid residues among these amino acid residues.

The number of amino acid residues that undergo modification in the methods of the present invention is not particularly limited. However, when modifying the variable region(s) of an antibody, it is preferable that only a few amino acid residues are modified so as not to decrease the antigen binding activity or increase the antigenicity of the resulting antibody. The methods of the present invention can regulate association by modifying one or both of the two amino acid residues that come close to each other at the interface, as indicated in the Examples described below. The term "few" as used in the above-mentioned context refers to about one to ten for example, preferably about one to five, more preferably about one to three, and even more preferably about one to two.

In a preferred embodiment, the amino acid residues that are introduced by modification (i.e., subjected to modification) are preferably all selected from among the above-mentioned positively charged amino acids, or, alternatively, are all selected from among the above-mentioned negatively charged amino acids.

Furthermore, in the present invention, preferred amino acid residues to be introduced include glutamic acid (E), asparagine (D), lysine (K), arginine (R), or histidine (H).

In another preferred embodiment of the present invention, when an interface-forming amino acid residue (X) in an original polypeptide (before modification) is already charged, it is preferable that the amino acid residue that comes close to and faces this amino acid residue (X) during association is modified to be the same amino acid residue (or an amino acid residue with the same type of charge) as the amino acid residue (X). In this embodiment, it is only necessary to modify one of the amino acid residues that form the interface.

Preferred embodiments of the methods of the present invention for regulating association include methods in which modification of amino acid residues forming the interface of the polypeptides that feature the introduction of amino acid residue mutations to the interface such that the amino acid residues forming a hydrophobic core present at the interface are transformed into charged amino acid residues.

In general, the term "hydrophobic core" refers to a part of a polypeptide that is formed by an assembly of hydrophobic amino acid side chains at the interior of the associated polypeptides. Examples of hydrophobic amino acids include alanine, isoleucine, leucine, methionine, phenylalanine, proline, tryptophan, and valine. Furthermore, amino acid residues other than hydrophobic amino acids (for example tyrosine) may be involved in the formation of a hydrophobic core. This hydrophobic core together with a hydrophilic surface, in which hydrophilic amino acid side chains are exposed to the exterior, becomes a driving force for promoting association of water-soluble polypeptides. When hydrophobic amino acids of two different domains are present on a molecular surface and are exposed to water molecules, the entropy will increase and the free energy will increase. Accordingly, the two domains will associate with each other to decrease the free energy and become stable, and hydrophobic amino acids at the interface will be buried into the interior of the molecule to form a hydrophobic core.

When polypeptide associations take place, modification of hydrophobic amino acids forming the hydrophobic core to charged polar amino acids inhibits the formation of the hydrophobic core, and as a result, inhibits the polypeptide association.

Those skilled in the art can identify the organized sites (regions) and such, as well as the presence of the hydrophobic core, by analyzing the amino acid sequence of the desired polypeptides. Thus, the present invention relates to methods for regulating association that feature the step of modifying amino acid residues involved with the formation of the hydrophobic core at the interface into charged amino acid residues.

Examples of charged amino acid residues suitable for use in the methods described above preferably include glutamic acid (E), aspartic acid (D), lysine (K), arginine (R), and histidine (H).

The methods of the present invention for regulating association can be used as methods for preferentially obtaining (producing) antibodies (polypeptides) of interest and in the production of antibodies, antibody fragments, polypeptides having antibody-like activity, and the like.

Herein, the term "antibody" is used in the broadest sense, and includes monoclonal antibodies, polyclonal antibodies, and mutant antibodies (chimeric antibodies, humanized antibodies, minibodies (including antibody fragments), and multispecific antibodies), so long as they exhibit a desired biological activity. Furthermore, in the context of the present invention, the "antibody" can be a polypeptide or heteromultimer. Preferred antibodies include monoclonal antibodies, chimeric antibodies, humanized antibodies, and minibodies, such as antibody fragments.

In the context of the present invention, the term "multispecific antibody" (used in the present description to have the same meaning as "polyspecific antibody") refers to an antibody that may bind specifically to different types of epitopes. More specifically, multispecific antibodies are antibodies having specificity to at least two different types of epitopes, and, in addition to antibodies recognizing different antigens, antibodies recognizing different epitopes on the same antigen are also included. For example, when the antigens are heterologous receptors, multispecific antibodies can recognize different domains constituting the heterologous receptors; alternatively, when the antigens are monomers, multispecific antibodies recognize multiple sites on the monomer antigens. Ordinarily, such molecules bind to two antigens (bispecific antibodies; used in the present description to have the same meaning as "dual-specific antibodies"), but they may even have specificity toward more antigens (for example three types).

In addition to the antibodies described above, the antibodies of the present invention include antibodies whose amino acid sequences have been modified by amino acid substitutions, deletions, additions, and/or insertions, or chimerization, humanization, and such. Such amino acid sequence modifications, such as amino acid substitutions, deletions, additions, and/or insertions, and humanization and chimerization, can be achieved by methods known to those skilled in the art. When the antibodies of the present invention are prepared as recombinant antibodies, likewise, the amino acid sequences of the antibody variable and constant regions may also be modified by amino acid substitutions, deletions, additions, and/or insertions, or chimerization, humanization and the like.

The antibodies of the present invention may be derived from any animal, such as a mouse, human, rat, rabbit, goat, or camel. Furthermore, the antibodies may be modified, for example, chimeric antibodies, and in particular, modified antibodies that include amino acid substitutions in their sequence, such as humanized antibodies. The antibodies may be any type of antibody, such as antibody modification products linked with various molecules, antibody fragments, and minibodies.

"Chimeric antibodies" are antibodies prepared by combining sequences derived from different animals. An example is an antibody having heavy and light chain variable (V) regions from a mouse antibody and heavy and light chain constant (C) regions from a human antibody. Chimeric antibodies can be prepared by known methods. To obtain such chimeric antibodies, for example, a DNA encoding an antibody V region may be ligated with a DNA encoding a human antibody C region; the resulting ligation product can be inserted into an expression vector; and the construct can be introduced into a host to produce the chimeric antibody.

"Humanized antibodies" are also referred to as reshaped human antibodies, and can be obtained by substituting the complementarity determining region (CDR) of a human antibody for the CDR of an antibody derived from a non-human mammal, for example, a mouse. Methods for identifying CDRs are known in the art (Kabat et al., Sequence of Proteins of Immunological Interest (1987), National Institute of Health, Bethesda, Md.; Chothia et al., Nature (1989) 342:877). General genetic recombination techniques suitable for this purpose are also known (see European Patent Application EP 125023; and WO 96/02576). For example, the CDR of a mouse antibody can be determined by known methods, and a DNA can be prepared such that it encodes an antibody in which the CDR is ligated with the framework region (FR) of a human antibody. A humanized antibody can then be produced using a system that uses conventional expression vectors. Such DNAs can be synthesized by PCR, using as primers several oligonucleotides designed to include portions that overlap the ends of both the CDR and FR regions (see the method described in WO 98/13388). Human antibody FRs linked via CDRs are selected such that the CDRs form a suitable antigen binding site. If required, amino acids in the FRs of an antibody variable region may be substituted so that the CDRs of the reshaped human antibody can form a suitable antigen binding site (Sato, K. et al., Cancer Res. (1993) 53:851-856). Modifiable amino acid residues in the FRs include portions that directly bind to an antigen via non-covalent bonds (Amit et al., Science (1986) 233: 747-53), portions that have some impact or effect on the CDR structure (Chothia et al., J. Mol. Biol. (1987) 196: 901-17), and portions involved in the interaction between VH and VL (EP 239400).

When the antibodies of the present invention are chimeric antibodies or humanized antibodies, the C regions of these antibodies are preferably derived from human antibodies. For example, Cγ1, Cγ2, Cγ3, and Cγ4 can be used for the H chain, while Cκ and Cλ can be used for the L chain. Meanwhile, the human antibody C region may be modified as required to improve antibody or production stability. A chimeric antibody of the present invention preferably includes a variable region of an antibody derived from a nonhuman mammal and a constant region of a human antibody. A humanized antibody preferably includes CDRs of an antibody derived from a nonhuman mammal and FRs and C regions of a human antibody. The variable regions are described in detail in (3)-3. The constant regions of the human antibodies include specific amino acid sequences, which vary depending on the isotype of the antibody, for example, IgG (IgG1, IgG2, IgG3, and IgG4), IgM, IgA, IgD, and IgE. The constant regions used to prepare the humanized antibodies of the present invention may be the constant regions of antibodies of any isotype. A constant region of human IgG is preferably used, though the invention is not limited thereto. The FRs derived from a human antibody, which are used to prepare the humanized antibodies, are not particularly limited, and thus may be derived from an antibody of any isotype.

The variable and constant regions of chimeric or humanized antibodies of the present invention may be modified by deletion, substitution, insertion, and/or addition, so long as the antibodies exhibit the same binding specificity as that of the original antibodies.

Since their antigenicity in the human body has been attenuated, chimeric and humanized antibodies using human-derived sequences are expected to find utility when administered to humans for therapeutic purposes or such.

In addition, minibodies are useful as the antibodies because of their in vivo kinetic characteristics and low-cost production using E. coli, plant cells, or such.

Antibody fragments are one type of minibody. The term "minibodies" includes antibodies that include an antibody fragment as a partial structural unit. The minibodies of the present invention are not particularly limited by their structure nor their method of production, so long as they have antigen binding activity. Some minibodies have an activity greater than that of a whole antibody (Orita et al., Blood (2005) 105:562-566). Herein, the "antibody fragments" are not particularly limited, so long as they are a portion of a whole antibody (for example, whole IgG). However, the antibody fragments preferably include a heavy chain variable region (VH) or a light chain variable region (VL). Examples of preferred antibody fragments are: Fab, F(ab')$_2$, Fab', and Fv. The amino acid sequence of a VH or VL in an antibody fragment may be modified by substitution, deletion, addition, and/or insertion. Furthermore, some portions of a VH and VL may be deleted, so long as the resulting fragments retain their antigen binding ability. For example, of the antibody fragments described above, "Fv" is a minimal antibody fragment composed of the complete antigen recognition and binding sites. "Fv" is a dimer (VH-VL dimer) composed of one unit of VH and one unit of VL bound very strongly by non-covalent bonding. An antigen binding site is formed on the surface of the VH-VL dimer by the three complementarity determining regions (CDRs) of each variable region. Six CDRs confer an antigen binding site to the antibody. However, even one variable region (or half of an Fv composed of only three antigen-specific CDRs) has the ability to recognize and bind to an antigen, although its affinity is lower than that of the complete binding site. Thus, molecules smaller than Fv are also included in the context of antibody fragments of the present invention. The variable regions of an antibody fragment may also be chimerized or humanized.

The minibodies preferably include both VH and VL. Examples of suitable minibodies include antibody fragments such as Fab, Fab', F(ab')2, and Fv, and scFv (single-chain Fv), which can be prepared using antibody fragments, (Huston et al., Proc. Natl. Acad. Sci. USA (1988) 85: 5879-83; Plickthun "The Pharmacology of Monoclonal Antibodies" Vol. 113, Resenburg and Moore (eds.), Springer Verlag, New York, pp. 269-315, (1994)); diabodies (Holliger et al., Proc. Natl. Acad. Sci. USA (1993) 90:6444-8; EP 404097; WO93/11161; Johnson et al., Method in Enzymology (1991) 203: 88-98; Holliger et al., Protein Engineering (1996) 9:299-305; Perisic et al., Structure (1994) 2:1217-26; John et al., Protein Engineering (1999) 12(7):597-604; Atwell et al., Mol. Immunol. (1996) 33:1301-12; sc(Fv)2 (Hudson et al, J Immunol. Methods (1999) 231:177-89; Orita et al., Blood (2005) 105:562-566); triabodies (Journal of Immunological Methods (1999) 231: 177-89); and tandem diabodies (Cancer Research (2000) 60:4336-41).

An antibody fragment can be prepared by treating an antibody with an enzyme, for example, a protease such as papain or pepsin (see Morimoto et al., J. Biochem. Biophys. Methods (1992) 24: 107-17; Brennan et al., Science (1985) 229:81). Alternatively, antibody fragments can also be produced by genetic recombination based on its amino acid sequence.

A minibody having a structure that results from modification of an antibody fragment can be prepared using antibody fragments obtained by enzyme treatment or genetic recombination. Alternatively, after constructing a gene which encodes a whole minibody, and introducing the construct into an expression vector, the minibody may be expressed in appropriate host cells (see, for example, Co et al., J. Immunol. (1994) 152: 2968-76; Better and Horwitz, Methods Enzymol. (1989) 178: 476-96; Pluckthun and Skerra, Methods Enzymol. (1989) 178: 497-515; Lamoyi, Methods Enzymol. (1986) 121: 652-63; Rousseaux et al., Methods Enzymol. (1986) 121: 663-9; Bird and Walker, Trends Biotechnol. (1991) 9: 132-7).

The above described scFVs are single-chain polypeptides that include two variable regions linked together via a linker or such, as required. The two variable regions in an scFv are typically one VH and one VL, but an scFv may include two VH or two VL. In general, scFv polypeptides include a linker between the VH and VL domains, thereby forming a paired portion of VH and VL required for antigen binding. A peptide linker composed of ten or more amino acids is typically used as the linker between VH and VL when forming an intramolecular paired portion between VH and VL. However, the linkers of the scFv of the present invention are not limited to such peptide linkers, so long as they do not inhibit the formation of an scFv. To review scFv, see Pluckthun "The Pharmacology of Monoclonal Antibody", Vol. 113 (Rosenburg and Moore ed., Springer Verlag, NY, pp. 269-315 (1994)).

The term, "diabodies (Db)" refers to bivalent antibody fragments constructed by gene fusion (P. Holliger et al., Proc. Natl. Acad. Sci. USA 90: 6444-6448 (1993); EP 404,097; WO93/11161 and such). Diabodies are dimers composed of two polypeptide chains, wherein each polypeptide chain includes within the same chain a light chain variable region (VL) and a heavy chain variable region (VH) connected with a linker short enough to disable interaction of these two regions, for example a linker of about five amino acid residues. VL and VH encoded on the same polypeptide chain will form a dimer because the linker between VL and VH is too short to form a single chain V region fragment. Therefore, the resulting diabody has two antigen-binding sites. Herein, when VL and VH directed against two different epitopes (a and b) are expressed simultaneously as combinations of VLa-VHb and VLb-VHa connected with a linker of about five residues, they are secreted as bispecific Db. In this case, the two different epitopes may be epitopes at two different sites on the same antigen, or epitopes at two different sites, each on two different antigens.

Since diabodies include two molecules of scFvs, they thus composed of four variable regions, and as a result have two antigen binding sites. When the objective is to form a diabody, unlike as in the case with scFvs that do not form dimers, ordinarily, linkers forming a connection between VH and VL in each scFv molecules are linkers of about five amino acids when used as peptide linkers. However, scFv linkers for diabody formation are not limited to such peptide linkers so long as they do not interfere with scFv expression and diabody formation.

Examples of preferred polypeptides or heteromultimers subjected to the methods of the present invention include polypeptides or heteromultimers composed of antibody heavy chain variable regions and light chain variable regions. More preferably, preferred embodiments of the present invention are methods for regulating association when polypeptides or heteromultimers of the present invention include two or more types of heavy chain variable regions and two or more types of light chain variable regions. Such polypeptides or heteromultimers are preferably those that recognize two or more types of epitopes, and examples include multispecific antibodies.

More preferably, examples of multispecific antibodies in the present invention include bispecific antibodies.

More specifically, preferred embodiments of the present invention relate to, for example, methods for regulating association of bispecific antibodies composed of two types of heavy chain variable regions (first heavy chain and second heavy chain) and two types of light chain variable regions (first light chain and second light chain).

Describing the "bispecific antibodies" of the preferred embodiments of the present invention more precisely, the above-mentioned "first heavy chain" refers to one of the two H chains forming the antibody, and the second H chain refers to the other H chain that is different from the first H chain. That is, of the two H chains, one of them can be arbitrarily defined as the first H chain and the other can be defined as the second H chain. Similarly, the "first light chain" refers to one of the two L chains forming the bispecific antibody, and the "second L chain" refers to the other L chain that is different from the first L chain. Of the two L chains, one of them can be arbitrarily defined as the first L chain and the other can be defined as the second L chain. Ordinarily, the first L chain and the first H chain are derived from the same antibody that recognizes a certain antigen (or epitope), and the second L chain and the second H chain are also derived from the same antibody that recognizes a certain antigen (or epitope). Herein, the L chain-H chain pair formed by the first H chain and L chain is called as the first pair, and the L chain-H chain pair formed by the second H chain and L chain is called as the second pair. An antigen (or epitope) used to produce the antibody from which the second pair derives is preferably different from the antigen used to produce the antibody from which the first pair is derives. More specifically, antigens recognized by the first pair and the second pair may be the same but different antigens (or epitopes) are preferred to be recognized. Herein, the H chains and L chains of the first pair and second pair preferably have amino acid sequences that differ from each other. When the first pair and the second pair recognize different epitopes, the first and the second pair may recognize a completely different antigen, or they may recognize different sites (different epitopes) on the same antigen. Furthermore, one of them may recognize an antigen such as a protein, peptide, gene, or sugar, and the other may recognize cytotoxic substances such as radioactive substances, chemotherapeutic agents, or cell-derived toxins. However, when one wishes to produce an antibody having pairs formed by specific combinations of H chains and L chains, those specific H chains and L chains may be arbitrary determined to be the first pair and second pair.

The above-mentioned "bispecific antibodies" are not necessarily limited to antibodies composed of two types of heavy chains and two types of light chains, and for example, they may be antibodies (for example, sc(Fv)2) having a structure in which two types of heavy chain variable regions and two types of light chain variable regions are linked to form a single chain.

As for the genes encoding the H chain or L chain of antibodies before introduction of mutations by methods of the present invention (herein, it may be simply referred to as "an antibody of the present invention"), known sequences can be used, or they can be obtained by methods known to those skilled in the art. For example, they may be obtained from an antibody library, or they may be obtained by cloning genes encoding the antibody from hybridomas producing monoclonal antibodies.

Regarding antibody libraries, many antibody libraries are already well known, and since methods for producing antibody libraries are known, those skilled in the art can appropriately obtain antibody libraries. For example, regarding antibody phage libraries, one can refer to the literature such as Clackson et al., Nature 1991, 352: 624-8; Marks et al., J. Mol. Biol. 1991, 222: 581-97; Waterhouses et al., Nucleic Acids Res. 1993, 21: 2265-6; Griffiths et al., EMBO J. 1994, 13: 3245-60; Vaughan et al., Nature Biotechnology 1996, 14: 309-14; and Japanese Patent Kohyo Publication No. (JP-A) H20-504970 (unexamined Japanese national phase publication corresponding to a non-Japanese international publication). In addition, known methods, such as methods that use eukaryotic cells as libraries (WO95/15393) and ribosome display methods, may be used. Furthermore, techniques to obtain human antibodies by panning using human antibody libraries are also known. For example, variable regions of human antibodies can be expressed on the surface of phages as single chain antibodies (scFvs) using phage display methods, and phages that bind to antigens can be selected. Genetic analysis of the selected phages can determine the DNA sequences encoding the variable regions of human antibodies that bind to the antigens. Once the DNA sequences of scFvs that bind to the antigens is revealed, suitable expression vectors can be produced based on these sequences to obtain human antibodies. These methods are already well known, and one can refer to WO92/01047, WO92/20791, WO93/06213, WO93/11236, WO93/19172, WO95/01438, and WO95/15388.

As for methods for obtaining genes encoding antibodies from hybridomas, known techniques may be used, involving the use of desired antigens or cells expressing the desired antigens as sensitizing antigens, using these to perform immunizations according to conventional immunization methods, fusing the immune cells thus obtained with known parent cells by ordinary cell fusion methods, screening monoclonal antibody producing cells (hybridomas) by ordinary screening methods, synthesizing cDNAs of antibody variable regions (V regions) from mRNAs of the obtained hybridomas using reverse transcriptase, and linking them with DNAs encoding the desired antibody constant regions (C regions).

More specifically, without being particular limited to the following examples, sensitizing antigens for obtaining the above-mentioned antibody genes encoding the H chains and L chains include both complete antigens with immunogenicity and incomplete antigens composed of haptens and such that do not show antigenicity. For example, full length proteins and partial peptides of proteins of interest can be used. In addition, it is known that substances composed of polysaccharides, nucleic acids, lipids, and such may become antigens. Thus, there are no particular limitations on antigens of the antibodies of the present invention. Antigens can be prepared by methods known to those skilled in the art, and they can be prepared, for example, by the following methods using baculoviruses (for example, WO98/46777). Hybridomas can be produced, for example, the following methods of Milstein et al. (G. Kohler and C. Milstein, Methods Enzymol. 1981, 73: 3-46), and such. When the immunogenicity of an antigen is low, it can be linked to a macromolecule that has immunogenicity, such as albumin, and then used for immunization. Furthermore, by linking antigens with other molecules if necessary, they can be converted into soluble antigens. When transmembrane molecules such as receptors are used as antigens, portions of the extracellular regions of the receptors can be used as a fragment, or cells expressing transmembrane molecules on their cell surface may be used as immunogens.

Antibody-producing cells can be obtained by immunizing animals using suitable sensitizing antigens described above. Alternatively, antibody-producing cells can be prepared by in vitro immunization of lymphocytes that can produce antibodies. Various mammals can be used as the animals for immunization, where rodents, lagomorphas and primates are generally used. Examples of such animals include mice, rats, and hamsters for rodents, rabbits for lagomorphas, and monkeys including the cynomolgus monkey, rhesus monkey, hamadryas, and chimpanzees for primates. In addition, transgenic animals carrying human antibody gene repertoires are also known, and human antibodies can be obtained by using these animals (see WO96/34096; Mendez et al., Nat. Genet. 1997, 15: 146-56). Instead of using such transgenic animals, for example, desired human antibodies having binding activity against antigens can be obtained by in vitro sensitization of human lymphocytes with desired antigens or cells expressing the desired antigens, and then fusing the sensitized lymphocytes with human myeloma cells such as U266 (see Japanese Patent Application Kokoku Publication No. (JP-B) H1-59878 (examined, approved Japanese patent application published for opposition)). Furthermore, desired human antibodies can be obtained by immunizing transgenic animals carrying a complete repertoire of human antibody genes, with desired antigens (see WO93/12227, WO92/03918, WO94/02602, WO96/34096, and WO96/33735).

Animal immunization can be carried out by appropriately diluting and suspending a sensitizing antigen in Phosphate-Buffered Saline (PBS), physiological saline, or such, and forming an emulsion by mixing an adjuvant if necessary, followed by an intraperitoneal or subcutaneous injection into animals. After that, the sensitizing antigen mixed with Freund's incomplete adjuvant is preferably administered several times every four to 21 days. Antibody production can be confirmed by measuring the target antibody titer in animal sera using conventional methods.

Antibody-producing cells obtained from lymphocytes or animals immunized with a desired antigen can be fused with myeloma cells to generate hybridomas using conventional fusing agents (for example, polyethylene glycol) (Goding, Monoclonal Antibodies: Principles and Practice, Academic Press, 1986, 59-103). When required, hybridoma cells can be cultured and grown, and the binding specificity of the antibody produced from these hybridomas can be measured using known analysis methods, such as immunoprecipitation, radioimmunoassay (RIA), and enzyme-linked immunosorbent assay (ELISA). Thereafter, hybridomas that produce antibodies of interest whose specificity, affinity, or activity has been determined can be subcloned by methods such as limiting dilution.

Next, genes encoding the selected antibodies can be cloned from hybridomas or antibody-producing cells (sensitized lymphocytes, and such) using probes that may specifically bind to the antibodies (for example, oligonucleotides complementary to sequences encoding the antibody constant regions). Cloning from mRNA using RT-PCR is also possible. Immunoglobulins are classified into five different classes, IgA, IgD, IgE, IgG and IgM. These classes are further divided into several subclasses (isotypes) (for example, IgG-1, IgG-2, IgG-3, and IgG-4; IgA-1 and IgA-2; and such). H chains and L chains used in the present invention to produce antibodies are not particularly limited and may derive from antibodies belonging to any of these classes or subclasses; however, IgG is particularly preferred.

Herein, it is possible to modify H-chain-encoding genes and L-chain-encoding genes using genetic engineering techniques. Genetically modified antibodies, such as chimeric antibodies, humanized antibodies that have been artificially modified for the purpose of decreasing heterologous antigenicity and such against humans, can be appropriately produced if necessary for antibodies such as mouse antibodies, rat antibodies, rabbit antibodies, hamster antibodies, sheep antibodies, and camel antibodies. Chimeric antibodies are antibodies composed of a nonhuman mammal antibody H chain and L chain variable regions, such as mouse antibody, and the H chain and L chain constant regions of human antibody. They can be obtained by ligating the DNA encoding a variable region of a mouse antibody to the DNA encoding a constant region of a human antibody, incorporating them into an expression vector, and introducing the vector into a host for production of the antibody. A humanized antibody, which is also called a reshaped human antibody, can be synthesized by PCR from a number of oligonucleotides produced so that they have overlapping portions at the ends of DNA sequences designed to link the complementarity determining regions (CDRs) of an antibody of a nonhuman mammal such as a mouse. The obtained DNA can be ligated to a DNA encoding a human antibody constant region. The ligated DNA can be incorporated into an expression vector, and the vector can be introduced into a host to produce the antibody (see EP239400 and WO96/02576). Human antibody FRs that are ligated via the CDR are selected when the CDR forms a favorable antigen-binding site. If necessary, amino acids in the framework region of an antibody variable region may be substituted such that the CDR of the reshaped human antibody forms an appropriate antigen-binding site (K. Sato et al., Cancer Res. 1993, 53: 851-856).

In addition to the humanization techniques described above, antibodies may be modified to improve their biological properties, for example, antigenic affinity. Such modifications can be carried out using methods such as site-directed mutagenesis (see for example, Kunkel (1985) Proc. Natl. Acad. Sci. USA 82: 488), PCR mutagenesis, and cassette mutagenesis. In general, mutant antibodies whose biological properties have been improved show amino acid sequence homology and/or similarity of 70% or higher, more preferably 80% or higher, and even more preferably 90% or higher (for example, 95% or higher, 97%, 98%, 99%, etc.), when compared to the amino acid sequence of the original antibody variable region. Herein, sequence homology and/or similarity is defined as the ratio of amino acid residues that are homologous (same residue) or similar (amino acid residues classified into the same group based on the general properties of amino acid side chains) to the original antibody residues, after the sequence homology value has been maximized by sequence alignment and gap introduction, if necessary. Generally, naturally-occurring amino acid residues are classified into groups based on the characteristics of their side chains: (1) hydrophobic: alanine, isoleucine, norleucine, valine, methionine, and leucine; (2) neutral hydrophilic: asparagine, glutamine, cysteine, threonine, and serine; (3) acidic: aspartic acid, and glutamic acid; (4) basic: arginine, histidine, and lysine; (5) residues that affect the orientation of the chain: glycine, and proline; and (6) aromatic: tyrosine, tryptophan, and phenylalanine.

Ordinarily, a total of six complementarity determining regions (CDRs; hypervariable regions) present in the H chain and L chain variable regions interact to form the antigen binding site(s) of an antibody. Even one of these variable regions is known to have the ability to recognize and bind to the antigen, although the affinity will be lower than when all binding sites are included. Therefore, antibody genes of the present invention encoding the H chain and L chain only have to encode fragment portions having each of the antigen binding sites of H chain and L chain, and polypeptides encoded by these genes only have to maintain affinity with the desired antigens.

The methods of the present invention for regulating association, allow one to preferentially (efficiently) obtain, for example, the desired bispecific antibodies as described above. More specifically, desired bispecific antibodies which are heteromultimers can be efficiently formed from a mixture of monomers.

Herein below, the case of IgG-type bispecific antibodies composed of two types of heavy chain variable regions (VH1 and VH2) and two types of light chain variable regions (VL1 and VL2) are described in detail; however, the methods of the present invention can be applied similarly to other heteromultimers.

When one wishes to obtain a bispecific antibody that recognizes one of the epitopes with a first heavy chain variable region (VH1) and a first light chain variable region (VL1) and the other epitope with a second heavy chain variable region (VH2) and a second light chain variable region (VL2), expressing each of the four types of chains to produce this antibody may theoretically produce 10 types of antibody molecules.

In this case, the desired antibody molecule can be preferentially obtained if the regulation is carried out in a manner to inhibit the association between polypeptides, for example, VH1 and VL2 and/or VH2 and VL1.

An example includes modifying amino acid residues forming the interfaces between the polypeptide of VH1 and the polypeptide of VL2, and/or the polypeptide of VH2 and the polypeptide of VL1 as described above so as to inhibit the associations between these polypeptides.

Furthermore, associations between the heavy chains (VH1 and VH2) or between the light chains (VL1 and VL2) can also be suppressed using the methods of the present invention for regulating association.

Heavy chain variable regions are ordinarily composed of three CDR regions and FR regions as described above. In a preferred embodiment of the present invention, amino acid residues subjected to "modification" can be appropriately selected from among amino acid residues positioned in the CDR regions or FR regions. Generally, modification of the amino acid residues in the CDR regions can decrease affinity towards antigens. Therefore, in the present invention, amino acid residues subjected to "modification" are not particularly limited but are preferred to be appropriately selected from among amino acid residues positioned in the FR regions.

As for the desired polypeptides whose association is to be regulated by the methods of the present invention, those skilled in the art can appropriately find out the types of amino acid residues that come close to each other at the interface of FRs during association.

Furthermore, sequences that can be used as variable region FRs of the antibodies of organisms, such as humans or mice, can be appropriately obtained by those skilled in the art using public databases. More specifically, amino acid sequence information of the FR regions can be obtained by means described later in the Examples.

Specific examples of amino acid residues that come close to each other at the interface of FRs during association in the bispecific antibodies indicated in the following Examples include glutamine (Q) at position 39 in the heavy chain variable region (FR2 region) (for example, at position 39 in the amino acid sequence of SEQ ID NO: 6), and the opposing (contacting) glutamine (Q) at position 38 on the light chain variable region (FR2 region) (for example, at position 44 in the amino acid sequence of SEQ ID NO: 8). Furthermore, favorable examples include leucine (L) at position 45 in the heavy chain variable region (FR2) (for example, at position 45 in the amino acid sequence of SEQ ID NO: 6), and the opposing proline (P) at position 44 in the light chain variable region (FR2) (for example, at position 50 in the amino acid sequence of SEQ ID NO: 8). These positions are numbered according to the document by Kabat et al. (Kabat E A et al. 1991. Sequence of Proteins of Immunological Interest. NIH).

As indicated in the following Examples, desired antibodies can be preferentially obtained by modifying these amino acid residues and performing the methods of the present invention.

Since these amino acid residues are known to be highly conserved in humans and mice (J. Mol. Recognit. 2003; 16: 113-120), association of antibody variable regions can be regulated for VH-VL association of antibodies other than those indicated in the Examples by modifying amino acid residues corresponding to the above-mentioned amino acid residues.

More specifically, in a preferred embodiment, the present invention provides antibodies (polypeptides (for example, sc(Fv)2), heteromultimers (for example IgG-type antibodies or such) composed of heavy chain variable regions and light chain variable regions, which are antibodies whose amino acid residues of (1) and (2), or (3) and (4) described below carry the same kind of charges:

(1) an amino acid residue which is included in the heavy chain variable region and corresponds to position 39 in the amino acid sequence of SEQ ID NO: 6;

(2) an amino acid residue which is included in the light chain variable region and corresponds to position 44 in the amino acid sequence of SEQ ID NO: 8;

(3) an amino acid residue which is included in the heavy chain variable region and corresponds to position 45 in the amino acid sequence of SEQ ID NO: 6; and (4) an amino acid residue which is included in the light chain variable region and corresponds to position 50 in the amino acid sequence of SEQ ID NO: 8.

The amino acid sequences of SEQ ID NOs: 6 and 8 are mentioned above to exemplify a more specific example of the positions of the amino acid residues that are subjected to modification in the present invention. Accordingly, the present invention is not limited to cases where the heavy chain variable regions or light chain variable regions have these amino acid sequences.

Each of the amino acid residues of (1) and (2), and (3) and (4) mentioned above come close to each other during association as indicated in FIG. 1 and in the following Examples. Those skilled in the art can identify the positions corresponding to the above-mentioned amino acid residues of (1) to (4) in the desired heavy chain variable regions or light chain variable regions using homology modeling and such, using commercially available softwares. Once identified, the amino acid residues of these positions can be appropriately subjected to modification.

In the antibodies mentioned above, "charged amino acid residues" are preferably selected, for example, from amino acid residues included in either one of the following groups:
(a) glutamic acid (E) and aspartic acid (D); and
(b) lysine (K), arginine (R), and histidine (H).

Furthermore the present invention provides antibodies (polypeptides, heteromultimers, and such) having heavy chain variable regions and light chain variable regions, in which either one of the amino acid residues of the following (3) or (4) is a charged amino acid residue. The side chains of the amino acid residues indicated in (3) and (4) shown below may come close to each other to form a hydrophobic core:
(3) an amino acid residue which is included in the heavy chain variable region and corresponds to position 45 in the amino acid sequence of SEQ ID NO: 6; and
(4) an amino acid residue which is included in the light chain variable region and corresponds to position 50 in the amino acid sequence of SEQ ID NO: 8.

In the above-mentioned antibodies, "charged amino acid residues" are preferably, for example, glutamic acid (E), aspartic acid (D), lysine (K), arginine (R), or histidine (H).

Ordinarily, the above-mentioned amino acid residues of (1) to (4) are (1) glutamine (Q), (2) glutamine (Q), (3) leucine (L), and (4) proline (P), respectively, in humans and mice. Therefore, in preferred embodiments of the present invention, these amino acid residues are subjected to modification (for example, substitution to charged amino acids). The types of the above-mentioned amino acid residues of (1) to (4) are not necessarily limited to the above-mentioned amino acid residues, and may be other amino acids that correspond to these amino acids. For example, in the case of humans, an amino acid on the light chain variable region corresponding to position 44 in the amino acid sequence of SEQ ID NO: 8 may be, for example, histidine (H). Those skilled in the art can find out the type of amino acid residue corresponding to any position on SEQ ID NO: 8 by referring to disclosed publications and such (for example, J. Mol. Recognit. 2003; 16:113-120), and can appropriately modify these amino acid residues (for example, substitution to charged amino acids).

Methods for producing the above-mentioned antibodies, and methods of the present invention for regulating association which feature modifying the amino acid residues of (1) to (4) mentioned above are also preferred embodiments of the present invention.

In another embodiment, the present invention provides methods for suppressing association between heavy chains or between a heavy chain and a light chain by introducing electrostatic repulsion to the interface of the heavy chain or light chain constant region. Examples of amino acid residues contacting each other at the interface of heavy chain constant regions include regions corresponding to positions 377 (356) and 470 (439), positions 378 (357) and 393 (370), and positions 427 (399) and 440 (409) in the CH3 region. Examples of amino acid residues that contact each other at the interface between a heavy chain constant region and a light chain constant region include regions corresponding to position 221 (position 213) of the CH1 region and position 123 of the CL region. Numbering in the antibody constant regions is based on the document by Kabat et al. (Kabat E A et al. 1991. Sequences of Proteins of Immunological Interest. NIH), and the EU numbering is shown in parenthesis for the heavy chain constant regions.

As indicated in the following Examples, association of antibody heavy chains will be regulated and desired antibodies can be preferentially obtained by modifying these amino acid residues and performing the methods of the present invention.

More specifically, in a preferred embodiment, the present invention provides antibodies having two or more types of heavy chain CH3 regions and Fc region-binding proteins (for example, IgG-type antibodies, minibodies (Alt M et al. FEBS Letters 1999; 454: 90-94), immunoadhesin (Non-Patent Document 2), and such), in which one to three pairs of amino acid residues in the first heavy chain CH3 region, selected from the pairs of amino acid residues indicated in (1) to (3) below, carry the same type of charge:
(1) amino acid residues included in the heavy chain CH3 region at positions 356 and 439 according to the EU numbering system;
(2) amino acid residues included in the heavy chain CH3 region at positions 357 and 370 according to the EU numbering system; and
(3) amino acid residues included in the heavy chain CH3 region at positions 399 and 409 according to the EU numbering system.

In a more preferred embodiment, the present invention provides an antibody in which pairs of the amino acid residues in the second heavy chain CH3 region that are different from the first heavy chain CH3 region mentioned above, are selected from the aforementioned pairs of amino acid residues of (1) to (3) wherein the one to three pairs of amino acid residues corresponding to the aforementioned pairs of amino acid residues of (1) to (3) carrying the same type of charge in the first heavy chain CH3 region mentioned above, carry opposite charges from the corresponding amino acid residues in the first heavy chain CH3 region mentioned above.

Figure 27:
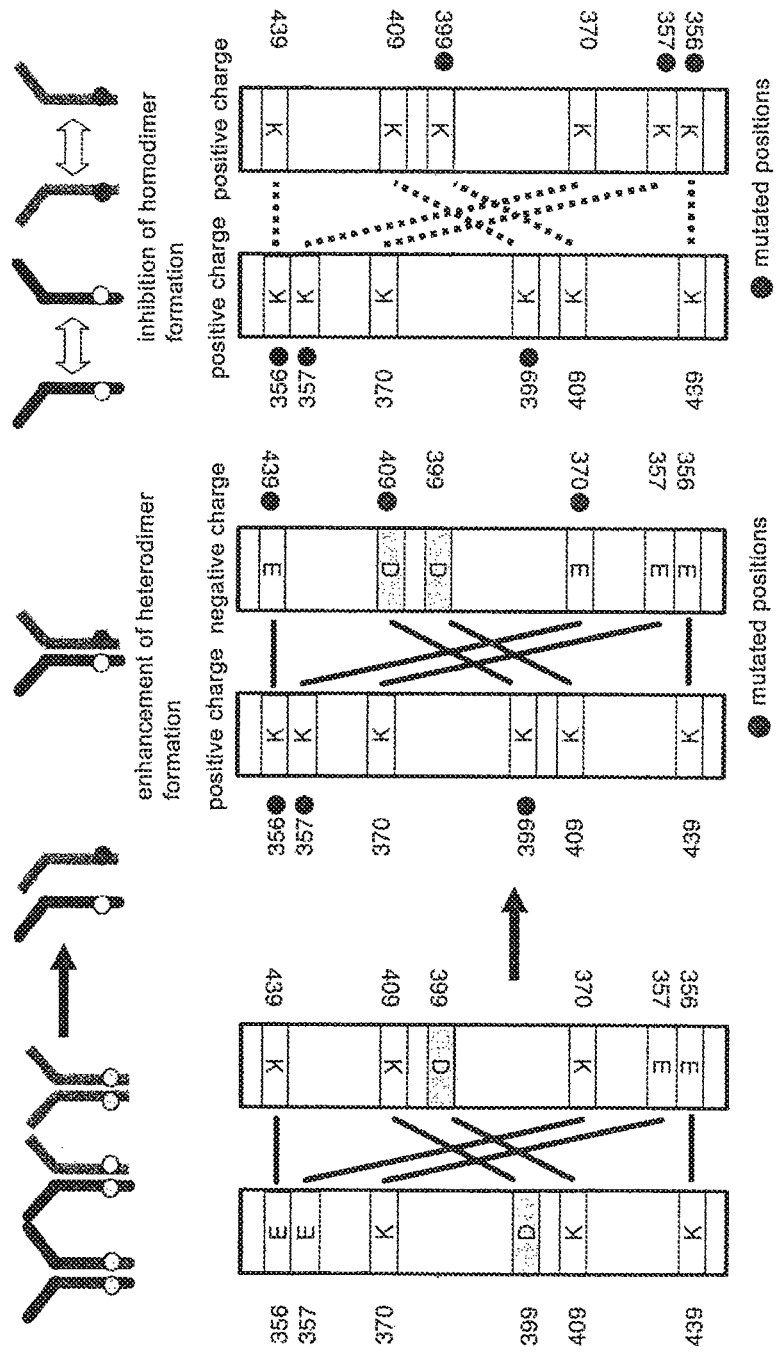
FIG. 27 presents a schematic diagram describing the method for improving the efficiency of the formation of bispecific antibody by modifying the H-chain constant region. The numbers indicating the positions of modification are based on the EU numbering system (Kabat E A et al. 1991. Sequences of Proteins of Immunological Interest. NIH).

Each of the amino acid residues indicated above in (1) to (3) come close to each other during association, as shown in FIG. 27 and in the Examples described below. Those skilled in the art can find out the positions corresponding to the above-mentioned amino acid residues of (1) to (3) in a desired heavy chain CH3 region or heavy chain constant region by homology modeling and such using commercially available software, and amino acid residues of these positions can be appropriately subjected to modification.

In the antibodies mentioned above, "charged amino acid residues" are preferably selected, for example, from amino acid residues included in either one of the following groups:
(a) glutamic acid (E) and aspartic acid (D); and
(b) lysine (K), arginine (R), and histidine (H).

In the above-mentioned antibodies, the phrase "carrying the same charge" means, for example, that all of the two or more amino acid residues composed of the amino acid residues included in either one of (a) or (b) mentioned above. The phrase "carrying opposite charges" means, for example, that when at least one of the amino acid residues among two or more amino acid residues is composed of amino acid residues included in either one of the above-mentioned groups of (a) or (b), and the remaining amino acid residues are composed of the amino acid residues included in the other group.

In a preferred embodiment, the antibodies mentioned above may have their first heavy chain CH3 region and second heavy chain CH3 region crosslinked by disulfide bonds.

In the present invention, amino acid residues subjected to "modification" are not limited to the above-mentioned amino acid residues of the antibody variable regions or the antibody constant regions. Those skilled in the art can identify the amino acid residues that form the interface in mutant polypeptides or heteromultimers using homology modeling and such, using commercially available software; amino acid residues of these positions can then be subjected to modification so as to regulate the association.

The methods of the present invention, although not mandatory, can be carried out in combination with known techniques. For example, in addition to "modifications" of the present invention to promote association between VH1 and VL1, and/or VH2 and VL2, substitution of an amino acid side chain present in one of the H chain variable regions to a larger side chain (knob) and substitution of the opposing amino acid side chain present in the variable region of the other H chain to a smaller side chain (hole) promotes association between VH1 and VL1, and/or VH2 and VL2 such that the knob is placed into the hole. As a result, the association between polypeptides VH1 and VL2, and/or VH2 and VL1 can be further suppressed.

The methods of the present invention for regulating association can be carried out suitably when preferentially (efficiently) obtaining desired sc(Fv)2s. Hereinafter, the case of sc(Fv)2 composed of two types of heavy chain variable regions (H1 and H2) and two types of light chain variable regions (L1 and L2) will be described more precisely as an example.

Generally, sc(Fv)2 is a single chain polypeptide in which two heavy chain variable regions (VH1 and VH2) and two light chain variable regions (VL1 and VL2) are linked by linkers. More specifically, sc(Fv)2 is a minibody in which four antibody variable regions are linked with a linker and such to produce a single chain. Ordinarily, sc(Fv)2 is an antibody in which four variable regions, two light chain variable regions and two heavy chain variable regions, are linked by linkers to produce a single chain (Hudson et al., J. Immunol. Methods 1999; 231:177-189).

sc(Fv)2 can be produced by methods known to those skilled in the art, for example, by linking scFvs with linkers. scFv includes antibody VH and VL, and these regions are present in a single polypeptide chain (for a review on scFv, see Pluckthun "The Pharmacology of Monoclonal Antibodies" Vol. 113 (Rosenburg and Moore ed. (Springer Verlag, New York) pp. 269-315, 1994).

An antibody in which two VHs and two VLs are arranged in the order of VH, VL, VH, VL ([VH] linker [VL] linker [VH] linker [VL]) starting from the N-terminal side of a single chain polypeptide is preferred.

The order of the two VHs and the two VLs is not particularly limited to the above-mentioned arrangement and may be in any order, including for example, the following arrangements.

[VL] linker [VH] linker [VH] linker [VL]
[VH] linker [VL] linker [VL] linker [VH]
[VH] linker [VH] linker [VL] linker [VL]
[VL] linker [VL] linker [VH] linker [VH]
[VL] linker [VH] linker [VL] linker [VH]

sc(Fv)2 may also include amino acid sequences other than those of the antibody variable regions and linkers.

The variable regions of the above-mentioned antibodies may be full-length variable regions or partial sequences of the variable regions, so long as the affinity to antigens is maintained. Furthermore, the amino acid sequences in the variable regions may contain substitutions, deletions, additions, insertions, or such. For example, they may be converted to chimeric or humanized antibodies to decrease antigenicity.

Arbitrary peptide linkers or synthetic linker compounds that can be introduced by genetic engineering (for example, see disclosed in Protein Engineering, 9(3), 299-305, 1996) can be used as linkers that link the variable regions of an antibody, but peptide linkers are preferred in the present invention. The length of the peptide linkers is not particularly limited, and can be suitably selected according to the purpose by those skilled in the art. The length is preferably twelve amino acids or more (with no particular upper limit, normally 30 amino acids or less, and preferably 20 amino acids or less), and particularly preferably 15 amino acids. When three peptide linkers are included in sc(Fv)2, all of the peptide linkers used may have the same length, or peptide linkers of different lengths may be used.

Examples of peptide linkers include:
Ser
Gly•Ser
Gly•Gly•Ser
Ser•Gly•Gly
Gly•Gly•Gly•Ser
Ser•Gly•Gly•Gly
Gly•Gly•Gly•Gly•Ser
Ser•Gly •Gly •Gly •Gly
Gly •Gly •Gly •Gly •Gly •Ser
Ser•Gly •Gly •Gly •Gly •Gly
Gly•Gly•Gly•Gly•Gly•Gly•Ser
Ser•Gly•Gly•Gly•Gly•Gly•Gly
(Gly•Gly•Gly•Gly•Ser)n
(Ser•Gly •Gly •Gly •Gly)n
[where n is an integer of 1 or more]. However, the length and sequence of the peptide linkers can be suitably selected according to the purpose by those skilled in the art.

Preferred embodiments of sc(Fv)2 include for example the following sc(Fv)2: [VH] peptide linker (15 amino acids) [VL] peptide linkers (15 amino acids) [VH] peptide linkers (15 amino acids) [VL].

Synthetic linkers (chemical crosslinking agents) that can be used include crosslinking agents that are routinely used to crosslink peptides, for example, N-hydroxy succinimide (NHS), disuccinimidyl suberate (DSS), bis(succinimidyl) suberate ($BS^3$), dithiobis(succinimidyl propionate) (DSP), dithiobis(succinimidyl propionate) (DTSSP), ethylene glycol bis(succinimidyl succinate) (EGS), ethylene glycol bis (sulfosuccinimidyl succinate) (sulfo-EGS), disuccinimidyl tartrate (DST), disulfosuccinimidyl tartrate (sulfo-DST), bis [2-(succinimidoxycarbonyloxy)ethyl] sulfone (BSOCOES), and bis[2-(succinimidoxycarbonyloxy)ethyl] sulfone (sulfo-BSOCOES). These crosslinking agents are commercially available.

Ordinarily, three linkers are required to link four antibody variable regions together and the linkers to be used may all be of the same type or different types.

Furthermore, for example, single chain diabody-type and bivalent scFv-type exist as conformational isomers of sc(Fv)2.

When the arrangement in sc(Fv)2 is in the order [variable region 1] (linker 1) [variable region 2] (linker 2) [variable region 3] (linker 3) [variable region 4], bivalent scFv-type in the present invention refers to sc(Fv)2 having a structure in which variable region 1 and variable region 2 are associated, as well as variable region 3 and variable region 4 are associated. In the present invention, single chain diabody-type refers to sc(Fv)2 having a structure in which variable region 1 and variable region 4 are associated, as well as variable region 2 and variable region 3 are associated.

Figure 12:
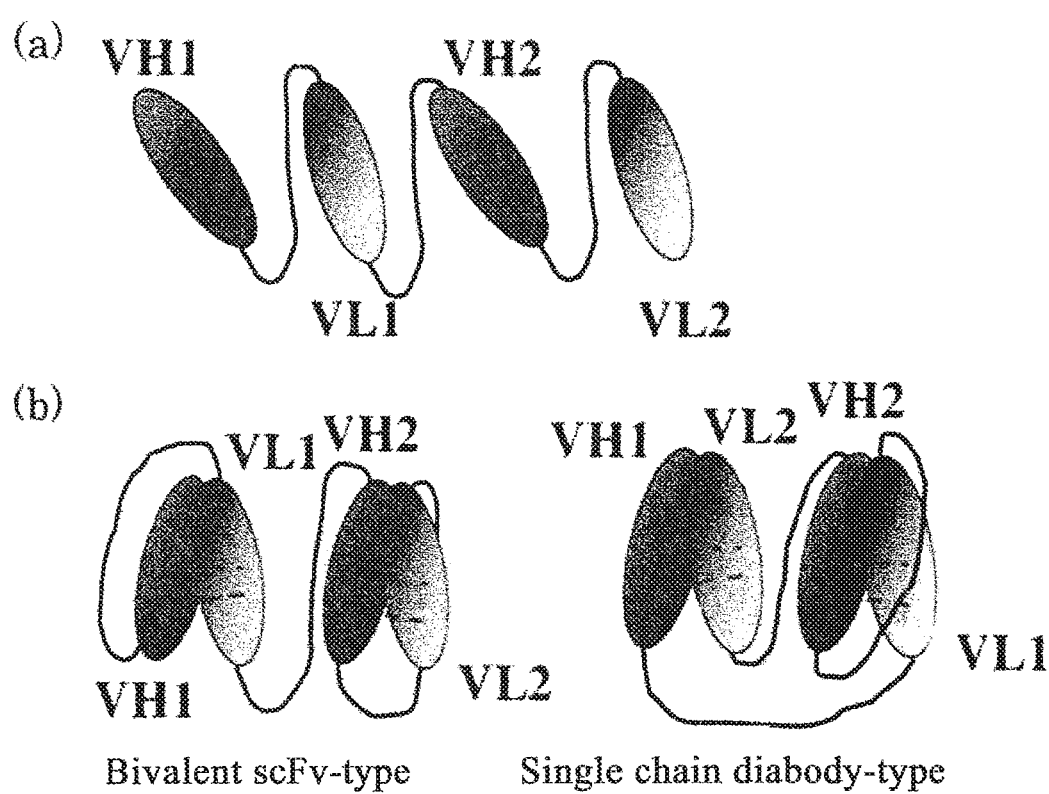
FIG. 12 presents a schematic diagram of examples of the conformations of an sc(Fv)2 having two types of heavy chain variable regions (VH1 and VH2) and two types of light chain variable regions (VL1 and VL2). An sc(Fv)2 having the structure of (a) is mainly present as two types of conformational isomers shown in (b).

An example of a single chain diabody-type is an sc(Fv)2 having the structure shown on the right in FIG. 12(*b*), and an example of a bivalent scFv-type is an sc(Fv)2 having the structure shown on the left in FIG. 12(*b*).

Whether an sc(Fv)2 has a single chain diabody-type structure or a bivalent scFv-type structure can be analyzed, for example, by protease-limited proteolysis. For example, the analysis can be carried out by a method such as the following.

Limited proteolysis of a test sc(Fv)2 is carried out using subtilisin A, a type of protease that can partially and restrictively degrade the linker portions of an sc(Fv)2.

When the sc(Fv)2 is the single chain diabody-type, no matter which linker among the three linkers possessed by the sc(Fv)2 is cleaved, the apparent molecular weight will not change due to interaction between the VH and VL.

On the other hand, when the sc(Fv)2 is a bivalent scFv-type, molecular species having half of the original molecular weight will be produced when the central linker is cleaved.

Therefore, the bivalent scFv-type and single chain diabody-type can be differentiated by analyzing the reaction products.

The reaction products can be analyzed, for example, by gel filtration chromatography. Furthermore, using chromatography, the proportions of bivalent sc(Fv)2 and single chain diabody conformations present in sc(Fv)2 can be evaluated quantitatively based on peak areas.

The methods of the present invention for regulating association can be suitably used for the above-mentioned sc(Fv)2 when one wishes to preferentially obtain the desired form, that is either one the single chain diabody-form or bivalent scFv-form.

More specifically, when sc(Fv)2 has the structure VH1-(linker)-VL1-(linker)-VH2-(linker)-VL2, and one wishes to preferentially obtain bivalent scFv-type sc(Fv)2 using the methods of the present invention for regulating association, it is necessary to only suppress the association, for example, between VH1 and VL2, and/or VH2 and VL1 (For example, mutations are introduced so that amino acid residues forming the interface between VH1 and VL2 will carry the same type of charge).

Alternatively, when one wishes to preferentially obtain single-chain diabody type sc(Fv)2, it is necessary to only inhibit the association, for example, between VH1 and VL1, and/or VH2 and VL2 (For example, mutations are introduced so that amino acid residues forming the interface between VH1 and VL1 will carry the same type of charges).

The present invention can also be carried out similarly when sc(Fv)2 is a monospecific antibody.

In addition to these techniques, each of the VH and VL domains can be cross linked by disulfide bonds (Clin. Cancer Res. 1996 February; 2(2):245-52).

The methods of the present invention for regulating association allow, for example, for the efficient production of antibodies or polypeptides that are active. Examples of such activities include binding activity, neutralizing activity, cytotoxic activity, agonist activity, antagonist activity, and enzyme activity and such. Agonist activity is an activity that induces some kind of changes in physiological activity through binding of an antibody to an antigen, such as a receptor, which causes signal transduction or such in cells. Examples of the physiological activity include growth activity, survival activity, differentiation activity, transcriptional activity, membrane transport activity, binding activity, proteolytic activity, phosphorylation/dephosphorylation activity, redox activity, transfer activity, nucleolytic activity, dehydration activity, cell death-inducing activity, and apoptosis-inducing activity and such, but are not limited thereto.

Antibodies or polypeptides that recognize the desired antigens or bind to the desired receptors can be produced efficiently by the methods of the present invention.

The antigens are not particularly limited, and any type of antigen can be used. Examples of antigens include receptors or their fragments, cancer antigens, MHC antigens, and differentiation antigens and the like, but are not particularly limited thereto.

Examples of the receptors include receptors belonging to the hematopoietic factor receptor family, cytokine receptor family, tyrosine kinase-type receptor family, serine/threonine kinase-type receptor family, TNF receptor family, G protein-coupled receptor family, GPI-anchored receptor family, tyrosine phosphatase-type receptor family, adhesion factor family, hormone receptor family, and such. Reports on the receptors belonging to these receptor families and their characteristics can be found in various sources of documents, for example, in Cooke B A., King R J B., van der Molen H J. ed. New Comprehensive Biochemistry Vol. 18B "Hormones and their Actions Part II" pp. 1-46 (1988) Elsevier Science Publishers BV., New York, USA; Patthy L. (1990) Cell, 61: 13-14; Ullrich A., et al. (1990) Cell, 61: 203-212; Massagul J. (1992) Cell, 69: 1067-1070; Miyajima A., et al. (1992) Annu. Rev. Immunol., 10: 295-331; Taga T. and Kishimoto T. (1992) FASEB J., 7: 3387-3396; Fantl W I., et al. (1993) Annu. Rev. Biochem., 62: 453-481; Smith C A., et al. (1994) Cell, 76: 959-962; Flower D R. (1999) Biochim. Biophys. Acta, 1422: 207-234; Miyasaka M. ed. Cell Technology, Handbook Series "Handbook for adhesion factors" (1994) Shujunsha, Tokyo, Japan; and such. Examples of specific receptors belonging to the above-mentioned receptor families include human or mouse erythropoietin (EPO) receptor, human or mouse granulocyte-colony stimulating factor (G-CSF) receptor, human or mouse thrombopoietin (TPO) receptor, human or mouse insulin receptor, human or mouse Flt-3 ligand receptor, human or mouse platelet-derived growth factor (PDGF) receptor, human or mouse interferon (IFN)-$\alpha$ or -$\beta$ receptor, human or mouse leptin receptor, human or mouse growth hormone (GH) receptor, human or mouse interleukin (IL)-10 receptor, human or mouse insulin-like growth factor (IGF)-I receptor, human or mouse leukemia inhibitory factor (LIF) receptor, and human or mouse ciliary neurotrophic factor (CNTF) receptor (hEPOR: Simon, S. et al. (1990) Blood 76, 31-35; mEPOR: D'Andrea, A D. et al. (1989) Cell 57, 277-285; hG-CSFR: Fukunaga, R. et al. (1990) Proc. Natl. Acad. Sci. USA. 87, 8702-8706; mG-CSFR: Fukunaga, R. et al. (1990) Cell 61, 341-350; hTPOR: Vigon, I. et al. (1992) 89, 5640-5644; mTPOR: Skoda, R C. et al. (1993) 12, 2645-2653; hInsR: Ullrich, A. et al. (1985) Nature 313, 756-761; hFlt-3: Small, D. et al. (1994) Proc. Natl. Acad. Sci. USA. 91, 459-463; hPDGFR: Gronwald, R G K. et al. (1988) Proc. Natl. Acad. Sci. USA. 85, 3435-3439; hIFN $\alpha/\beta$ R: Uze, G. et al. (1990) Cell 60, 225-234; and Novick, D. et al. (1994) Cell 77, 391-400).

Cancer antigens are antigens that are expressed as cells become malignant, and are also called tumor-specific antigens. Furthermore, abnormal sugar chains that appear on cell surfaces and protein molecules when the cells become cancerous are also cancer antigens and are specifically called as carcinoma associated carbohydrate antigen. Examples of cancer antigens include CA19-9, CA15-3, and sialyl SSEA-1 (SLX).

MHC antigens can be classified broadly into MHC class I antigens and MHC class II antigens: MHC class I antigens include HLA-A, -B, -C, -E, -F, -G, and -H; and MHC class II antigens include HLA-DR, -DQ, and -DP.

Differentiation antigens include CD1, CD2, CD3, CD4, CD5, CD6, CD7, CD8, CD10, CD11a, CD11b, CD11c, CD13, CD14, CD15s, CD16, CD18, CD19, CD20, CD21, CD23, CD25, CD28, CD29, CD30, CD32, CD33, CD34, CD35, CD38, CD40, CD41a, CD41b, CD42a, CD42b, CD43, CD44, CD45, CD45RO, CD48, CD49a, CD49b, CD49c, CD49d, CD49e, CD49f, CD51, CD54, CD55, CD56, CD57, CD58, CD61, CD62E, CD62L, CD62P, CD64, CD69, CD71, CD73, CD95, CD102, CD106, CD122, CD126, and CDw130.

The present invention also provides for mutant polypeptides or heteromultimers whose association is regulated by the methods of the present invention. More specifically, the present invention relates to polypeptides or heteromultimers that are obtained by methods of the present invention for regulating associations.

Preferred embodiments of the present invention provide mutant polypeptides that have modifications made to the amino acid residues that form the interface in the original polypeptides so as to inhibit the association within the polypeptides.

Other embodiments of the present invention provide heteromultimers that have modifications made to amino acid residues forming the interface between the original polypeptides such that the association between the polypeptides is inhibited.

In the present invention, the phrase "original polypeptides" refer to polypeptides in the condition before modification by the methods of the present invention where association is regulated.

An example of the above-mentioned mutant polypeptides of the present invention is a mutant in which the original polypeptide can form two types of conformational isomers.

Furthermore, an example of the above-mentioned heteromultimers is a multimer in which the original polypeptide can form two or more types of multimers.

Mutant polypeptides or heteromultimers whose association is regulated by the above-mentioned methods of the present invention for regulating association are also included in the present invention. More specifically, in preferred embodiments of the above-described methods for regulating association, a polypeptide or heteromultimer whose association is regulated is also a preferred embodiment of the present invention.

The present invention also provides methods for producing polypeptides or heteromultimers in which association of polypeptides or heteromultimers is regulated.

Preferred embodiments of the production methods of the present invention provides methods for producing polypeptides having mutations in the amino acid residues forming the interface in the polypeptides so that polypeptide association is regulated, wherein the methods for producing the mutant polypeptides include the steps of:
(a) modifying nucleic acids encoding the amino acid residues that form an interface in the polypeptides from the original nucleic acids, so as to inhibit the association in the polypeptides;
(b) culturing host cells so that these nucleic acids are expressed; and
(c) recovering the polypeptides from the host cell culture.

In other embodiments, the present invention provides methods for producing heteromultimers whose amino acid residues that form the interface between polypeptides have mutations that allow for the regulation of the heteromultimer association, wherein the methods for producing heteromultimers include the steps of:
(a) modifying nucleic acids encoding the amino acid residues forming an interface between polypeptides from the original nucleic acids, so as to inhibit the association between the polypeptides;
(b) culturing host cells so that these nucleic acids are expressed; and
(c) recovering the heteromultimers from the host cell culture.

A method including the step of using the above-described methods of the present invention for regulating association to modify nucleic acids encoding amino acid residues forming the interface in (between) polypeptides from the original nucleic acids so that polypeptide association will be inhibited is also a preferred embodiment of the above-mentioned production methods of the present invention.

The phrase "modify nucleic acids" in the above-mentioned methods of the present invention refers to modifying nucleic acids so that they correspond to amino acid residues introduced by the "modifications" of the present invention. More specifically, it refers to modifying the nucleic acids encoding the original (pre-modified) amino acid residues to the nucleic acids encoding the amino acid residues that are to be introduced by the modification. Ordinarily, it means performing gene manipulations or mutation treatment that would result in at least one nucleotide insertion, deletion, or substitution to the original nucleic acid so that codons encoding amino acid residues of interest is formed. More specifically, codons encoding the original amino acid residues are substituted with codons encoding the amino acid residues that are to be introduced by the modification. Such nucleic acid modification can be performed suitably by those skilled in the art using known techniques such as site-specific mutagenesis and PCR mutagenesis.

Furthermore, nucleic acids of the present invention are ordinarily carried by (inserted into) suitable vectors and then introduced into host cells. These vectors are not particularly limited so long as the inserted nucleic acid is stably maintained. For example, when using $E.$ $coli$ as the host, the cloning vector is preferably a pBluescript vector (Stratagene) and such, but various commercially available vectors may be used. Expression vectors are particularly useful as vectors for producing the polypeptides of the present invention. Expression vectors are not particularly limited so long as they can express polypeptides in test tubes, $E.$ $coli$, cultured cells, or individual organisms. For example, preferred vectors include pBEST vector (Promega) for expression in test tubes, pET vector (Invitrogen) for $E.$ $coli$, pME18S-FL3 vector (GenBank Accession No. AB009864) for cultured cells, and pME18S vector (Mol. Cell Biol. 8:466-472 (1998)) for individual organisms. Insertion of a DNA of the present invention into vectors can be performed by standard methods such as ligase reactions using restriction enzyme sites (Current protocols in Molecular Biology edit. Ausubel et al. (1987) Publish. John Wiley & Sons. Section 11.4-11.11).

The above-mentioned host cells are not particularly limited, and various host cells can be used, depending on the purpose. Cells used for expressing the polypeptides include bacterial cells (for example, *Streptococcus, Staphylococcus, E. coli, Streptomyces,* and *Bacillus subtilis*), fungal cells (for example, yeast and *Aspergillus*), insect cells (for example, *Drosophila* S2 and *Spodoptera* SF9), animal cells (for example, CHO, COS, HeLa, C127, 3T3, BHK, HEK293, Bowes melanoma cell), and plant cells. Vectors can be introduced into host cells using known methods, such as the calcium phosphate precipitation method, electroporation method (Current protocols in Molecular Biology edit. Ausubel et al. (1987) Publish. John Wiley & Sons. Section 9.1-9.9), lipofectamine method (GIBCO-BRL), and microinjection method.

For secreting host cell-expressed polypeptides into the lumen of the endoplasmic reticulum, periplasmic space, or extracellular environment, suitable secretion signals can be incorporated into the polypeptides of interest. These signals may be intrinsic or foreign to the polypeptides of interest.

When the polypeptides of the present invention are secreted into the culture media, the polypeptides produced by the above-mentioned method can be harvested by collecting the media. When the polypeptides of the present invention are produced inside cells, first, the cells are lysed, and then these polypeptides are collected.

The polypeptides of the present invention can be collected and purified from recombinant cell cultures by using known methods, including ammonium sulfate or ethanol precipitation, acidic extraction, anion or cation exchange chromatography, phosphocellulose chromatography, hydrophobic interaction chromatography, affinity chromatography, hydroxyapatite chromatography, and lectin chromatography.

The present invention relates to compositions (pharmaceutical agents) composed of a mutant polypeptide or heteromultimer of the present invention and a pharmaceutically acceptable carrier.

In the present invention, pharmaceutical compositions ordinarily refer to pharmaceutical agents for treating or preventing, or testing and diagnosing diseases.

The pharmaceutical compositions of the present invention can be formulated by methods known to those skilled in the art. For example, such pharmaceutical compositions can be used parenterally, as injections which are sterile solutions or suspensions including an antibody along with water or another pharmaceutically acceptable liquid. For example, such compositions may be formulated as unit doses that meet the requirements for the preparation of pharmaceuticals by appropriately combining the antibody with pharmaceutically acceptable carriers or media, specifically with sterile water, physiological saline, a vegetable oil, emulsifier, suspension, detergent, stabilizer, flavoring agent, excipient, vehicle, preservative, binder, or such. In such preparations, the amount of active ingredient is adjusted such that the dose falls within an appropriately pre-determined range.

Sterile compositions for injection can be formulated using vehicles such as distilled water for injection, according to standard protocols for formulation.

Aqueous solutions for injection include, for example, physiological saline and isotonic solutions containing dextrose or other adjuvants (for example, D-sorbitol, D-mannose, D-mannitol, and sodium chloride). Appropriate solubilizers, for example, alcohols (ethanol and such), polyalcohols (propylene glycol, polyethylene glycol, and such), non-ionic detergents (polysorbate 80™, HCO-50, and such), may be used in combination.

Oils include sesame and soybean oils. Benzyl benzoate and/or benzyl alcohol can be used in combination as solubilizers. Buffers (for example, phosphate buffer and sodium acetate buffer), soothing agents (for example, procaine hydrochloride), stabilizers (for example, benzyl alcohol and phenol), and/or antioxidants can also be combined. Prepared injectables are generally filled into appropriate ampules.

The pharmaceutical compositions of the present invention are preferably administered parenterally. For example, the compositions may be injections, transnasal compositions, transpulmonary compositions or transdermal compositions. For example, such compositions can be administered systemically or locally by intravenous injection, intramuscular injection, intraperitoneal injection, subcutaneous injection, or such.

The administration methods can be appropriately selected in consideration of a patient's age and symptoms. The dose of a pharmaceutical composition composed of an antibody or a polynucleotide encoding an antibody may be, for example, from 0.0001 to 1000 mg/kg for each administration. Alternatively, the dose may be, for example, from 0.001 to 100,000 mg per patient. However, the doses are not limited to the ranges described above. The doses and administration methods vary depending on a patient's weight, age, symptoms, and such. Those skilled in the art can select appropriate doses and administration methods in consideration of the factors described above.

The polypeptides or heteromultimers of the present invention can be formulated by combining with other pharmaceutical components as necessary.

The present invention also provides nucleic acids that encode the mutant polypeptides of the present invention or the heteromultimers of the present invention. Further, vectors that carry these nucleic acids are also included in the present invention.

The present invention provides host cells carrying the above described nucleic acids. The host cells are not particularly limited and include, for example, *E. coli* and various animal cells. The host cells may be used, for example, as a production system to produce and express the antibodies or the polypeptides of the present invention. In vitro and in vivo production systems are available for polypeptide production systems. Production systems that use eukaryotic cells or prokaryotic cells are examples of in vitro production systems.

Eukaryotic cells that can be used as a host cell include, for example, animal cells, plant cells, and fungal cells. Animal cells include: mammalian cells, for example, CHO (J. Exp. Med. (1995)108, 945), COS, 3T3, myeloma, BHK (baby hamster kidney), HeLa, and Vero; amphibian cells such as *Xenopus laevis* oocytes (Valle, et al. (1981) Nature 291, 338-340); and insect cells (e.g., Sf9, Sf21, and Tn5). In the expression of the antibodies of the present invention, CHO-DG44, CHO-DX11B, COST cells, and BHK cells can be suitably used. Among animal cells, CHO cells are particularly preferable for large-scale expression. Vectors can be introduced into a host cell by, for example, calcium phosphate methods, the DEAE-dextran methods, methods using cationic liposome DOTAP (Boehringer-Mannheim), electroporation methods, or lipofection methods.

Plant cells include, for example, *Nicotiana tabacum*-derived cells known as a protein production system. Calluses can be cultured from these cells to produce the antibodies of the present invention. Known protein production systems are those using fungal cells including yeast cells, for example, cells of genus *Saccharomyces* such as *Saccharomyces cerevisiae* and *Saccharomyces pombe*; and cells of filamentous fungi, for example, genus *Aspergillus* such as *Aspergillus niger*. These cells can be used as a host to produce the antibodies of the present invention.

Bacterial cells can be used in the prokaryotic production systems. Examples of bacterial cells include *Bacillus subtilis* as well as *E. coli* described above. Such cells can be used to produce the antibodies of the present invention.

When producing an antibody using a host cell of the present invention, the polynucleotide encoding an antibody of the present invention may be expressed by culturing the host cells transformed with the expression vector containing the polynucleotide. The culture can be performed using known methods. For example, when using animal cells as a host, DMEM, MEM, RPMI 1640, or IMDM may be used as the culture medium, and may be used with or without serum supplements such as FBS or fetal calf serum (FCS). Serum-free cultures are also acceptable. The preferred pH is about 6 to 8 during the course of culturing. Incubation is carried out typically at a temperature of about 30 to 40° C. for about 15 to 200 hours. Medium is exchanged, aerated, or agitated, as necessary.

On the other hand, production systems using animal or plant hosts may be used as systems for producing polypeptides in vivo. For example, a polynucleotide of interest is introduced into an animal or plant and the polypeptide is produced in the body of the animal or plant and then collected. The "hosts" of the present invention includes such animals and plants.

Animals to be used for the production system include mammals or insects. Mammals such as goats, pigs, sheep, mice, and cattle may be used (Vicki Glaser SPECTRUM Biotechnology Applications (1993)). Alternatively, the mammals may be transgenic animals.

For example, a polynucleotide encoding an antibody of the present invention may be prepared as a fusion gene with a gene encoding a polypeptide specifically produced in milk, such as the goat β-casein gene. Polynucleotide fragments containing the fusion gene are injected into goat embryos, which are then introduced back to female goats. The desired antibody can be obtained from milk produced by the transgenic goats, which are born from the goats that received the embryos, or from their offspring. Appropriate hormones may be administered to increase the volume of milk containing the antibody produced by the transgenic goats (Ebert et al., Bio/Technology 12: 699-702 (1994)).

Insects such as silkworms, may also be used for producing the antibodies of the present invention. Baculoviruses carrying a polynucleotide encoding an antibody of interest can be used to infect silkworms, and the antibody of interest can be obtained from the body fluids (Susumu et al., Nature 315: 592-594 (1985)).

Plants used for producing the antibodies of the present invention include, for example, tobacco. When tobacco is used, a polynucleotide encoding an antibody of interest is inserted into a plant expression vector, for example, pMON 530, and then the vector is introduced into a bacterium, such as *Agrobacterium tumefaciens*. The bacteria are then used to infect tobacco such as *Nicotiana tabacum*, and the desired antibodies can be recovered from the leaves (Ma et al., Eur. J. Immunol. 24: 131-138 (1994)).

The resulting antibody may be isolated from the inside or outside (such as the medium and milk) of host cells, and purified as a substantially pure and homogenous antibody. Methods are not limited to any specific method and any standard method for isolating and purifying antibodies may be used. Antibodies may be isolated and purified, by selecting an appropriate combination of, for example, chromatographic columns, filtration, ultrafiltration, salting out, solvent precipitation, solvent extraction, distillation, immunoprecipitation, SDS-polyacrylamide gel electrophoresis, isoelectric focusing, dialysis, recrystallization, and others.

Chromatographies include, for example, affinity chromatographies, ion exchange chromatographies, hydrophobic chromatographies, gel filtrations, reverse-phase chromatographies, and adsorption chromatographies (Strategies for Protein Purification and Characterization: A Laboratory Course Manual. Ed Daniel R. Marshak et al., Cold Spring Harbor Laboratory Press, 1996). These chromatographies can be carried out using liquid phase chromatographies such as HPLC and FPLC. Examples of the affinity chromatography columns include protein A columns and protein G columns. Examples of the proteins A columns include Hyper D, POROS, and Sepharose F. F. (Pharmacia).

An antibody can be modified freely and peptide portions can be deleted from it by treating the antibody with an appropriate protein modifying enzyme before or after antibody purification, as necessary. Such protein modifying enzymes include, for example, trypsins, chymotrypsins, lysyl endopeptidases, protein kinases, and glucosidases.

In another preferred embodiment, the present invention also includes methods for producing the mutant polypeptides or heteromultimers of the present invention, such methods including the steps of culturing the host cells of the present invention as described above and recovering the polypeptides from such cell culture.

All prior art references cited herein are incorporated by reference into the present specification.

EXAMPLES

Herein below, the present invention will be specifically described with reference to Examples; however, the invention should not be construed as being limited thereto.

[Example 1] Production of Non-Neutralizing Antibodies Against Factor IXa (F.IXa)

1-1. Immunization and Hybridoma Production

Eight BALB/c mice (male, starting immunization at 6 weeks of age, Japan Charles River) and 5 MRL/lpr mice (male, starting immunization at 6 weeks of age, Japan Charles River) were immunized as described below with Factor IXαβ (Enzyme Research Laboratories, Inc.). Factor IXαβ emulsified in FCA (Freund's complete adjuvant H37 Ra (Difco laboratories)) was administered subcutaneously at 40 μg/head as primary immunization. Two weeks later, Factor IXαβ emulsified in FIA (Freund's incomplete adjuvant (Difco laboratories)) was administered subcutaneously at 40 μg/head. Thereafter, boosters were given at one week intervals, a total of 3 to 7 times. After the elevation in serum antibody titer against factor IXαβ was confirmed by ELISA (enzyme linked immunosorbent assay) shown in 1-2, factor IXαβ diluted in PBS(-) (phosphate buffered saline that does not contain calcium ions and magnesium ions) was administered intravenously at 40 μg/head. Three days after the final immunization, mouse spleen cells and mouse myeloma cells P3X63Ag8U.1 (referred to as P3U1, ATCC CRL-1597) were fused, following conventional procedures using PEG1500 (Roche Diagnostics). Selective culturing of hybridomas was performed by plating fused cells suspended in RPMI1640 medium (Invitrogen) containing 10% FBS (Invitrogen) (hereinafter referred to as 10% FBS/RPMI1640) onto a 96-well culture plate and substituting the medium with HAT selection medium (10% FBS/RPMI1640/2% HAT 50× concentrate (Dainippon Pharmaceutical)/5% BM-Condimed H1 (Roche Diagnostics)) at 1, 2, 3, and 5 days after fusion. Hybridomas having a binding activity to Factor IXa were selected using the culture supernatant collected on day 8 or day 9 after fusion, and measuring binding activity against Factor IXa by ELISA shown in 1-2. Then hybridomas that did not have neutralizing activity against Factor IXa were selected by measuring the ability of hybridoma to neutralize the enzyme activity of Factor IXa, according to the method shown in 5-3. Hybridomas were cloned with two rounds of limiting dilution by plating cells into a 96-well culture plate at one cell per well to establish hybridoma XB12 that produced anti-Factor IXa antibodies.

1-2. Factor IXa ELISA

Factor IXαβ diluted to 1 μg/mL with coating buffer (100 mM sodium bicarbonate, pH9.6, 0.02% sodium azide) was dispensed into Nunc-Immuno plate (Nunc-Immuno™ 96 MicroWell™ plates MaxiSorp™ (Nalge Nunc International)) at 100 μL/well, and then incubated overnight at 4° C. After three washes with PBS(−) containing Tween® 20, the plate was blocked with diluent buffer (50 mM Tris-HCl, pH8.1, 1% bovine serum albumin, 1 mM $MgCl_2$, 0.15 M NaCl, 0.05% Tween® 20, 0.02% sodium azide) at room temperature for two hours. After buffer removal, mouse anti-serum or hybridoma culture supernatant diluted in the diluent buffer was added to the plate at 100 μL/well and incubated at room temperature for one hour. The plate was washed three times, then alkaline phosphatase-labeled goat anti-mouse IgG (H+L) (Zymed Laboratories) diluted at 1/2000 with the diluent buffer was added at 100 μL/well. This was incubated at room temperature for one hour. The plate was washed six times, chromogenic substrate Blue-Phosυ Phosphate Substrate (Kirkegaard & Perry Laboratories) was added at 100 μL/well, and was then incubated at room temperature for 20 minutes. After adding Blue-Phos™ Stop Solution (Kirkegaard & Perry Laboratories) at 100 μL/well, the absorbance at 595 nm was measured with a Microplate Reader Model 3550 (Bio-Rad Laboratories).

1-3. Factor IXa Neutralizing Activity Measurements

Phospholipid (Sigma-Aldrich) was dissolved in distilled water for injection, and then sonicated to prepare a 400 μg/mL phospholipid solution. 40 μL of tris buffer saline solution containing 0.1% bovine serum albumin (herein after referred to as TBSB), 10 μL of 30 ng/mL Factor IXαβ (Enzyme Research Laboratories), 5 μL of 400 μg/mL phospholipid solution, 5 μL of TBSB containing 100 mM $CaCl_2$ and 20 mM $MgCl_2$, and 10 μL of hybridoma culture supernatant were mixed in a 96-well plate, and then incubated at room temperature for one hour. 20 μL of 50 mg/mL Factor X (Enzyme Research Laboratories) and 10 μL of 3 U/mL Factor VIIIa (American diagnostica) were added to this mixed solution, and then were reacted at room temperature for 30 minutes. 10 μL of 0.5 M EDTA was added to stop the reaction. Fifty μL of S-2222 solution (Chromogenix) was added to the reaction solution, which was then incubated at room temperature for 30 minutes, followed by measuring the absorbance at measurement wavelength of 405 nm and control wavelength of 655 nm on a Microplate Reader Model 3550 (Bio-Rad Laboratories, Inc.).

[Example 2] Preparation of Non-Neutralizing Antibodies Against Factor X (F.X)

2-1. Immunization and Hybridoma Preparation

Eight BALB/c mice (male, starting immunization at 6 weeks of age, Japan Charles River) and 5 MRL/lpr mice (male, starting immunization at 6 weeks of age, Japan Charles River) were immunized with factor X (Enzyme Research Laboratories) as described below. For the initial immunization, factor X emulsified with FCA was subcutaneously administered at 40 μg/head. Two weeks later, factor X emulsified with FIA was subcutaneously administered at 20 or 40 μg/head. Thereafter, a total of 3 to 6 boosters were given at one week intervals. After the elevation of the titer of a serum antibody against Factor X was confirmed by ELISA as described in 2-2, Factor X diluted in PBS(−) was administered intravenously at 20 or 40 μg/head as a final immunization. Three days after the final immunization, mouse spleen cells were fused with mouse myeloma P3U1 cells according to a standard method using PEG1500. Fused cells suspended in 10% FBS/RPMI1640 medium were seeded in a 96-well culture plate, and hybridomas were selectively cultured by replacing the medium with a HAT selection medium at 1, 2, 3, and 5 days after the fusion. Binding activity against Factor X was measured by ELISA described in 2-2, using the culture supernatant collected on the eighth day after fusion. Hybridomas having Factor X-binding activity were selected, and their activities to neutralize Factor Xa enzymatic activity were measured according to the method described in 2-3. Hybridomas that were incapable of neutralizing the enzyme activity of Factor Xa were cloned using two rounds of limiting dilution to establish hybridoma SB04 that produced anti-Factor X antibodies.

2-2. Factor X ELISA

Factor X diluted to 1 μg/mL with a coating buffer was dispensed into Nunc-Immuno plate at 100 μL/well, and then incubated overnight at 4° C. After three washes with PBS(−) containing Tween® 20, the plate was blocked with the diluent buffer at room temperature for 2 hours. After removal of the buffer, mouse antiserum or hybridoma culture supernatant diluted with the diluent buffer was added to the plate, and incubated at room temperature for 1 hour. The plate was washed three times, then alkaline phosphatase-labeled goat anti-mouse IgG (H+L) diluted to 1/2000 with the diluent buffer was added, and incubated at room temperature for 1 hour. The plate was washed six times, after which a colorimetric substrate Blue-Phos™ Phosphate Substrate (Kirkegaard & Perry Laboratories) was added at 100 μL/well. The plate was then incubated at room temperature for 20 minutes. After adding Blue-Phos™ Stop Solution (Kirkegaard & Perry Laboratories) at 100 μL/well, the absorbance at 595 nm was measured on a Microplate Reader Model 3550 (Bio-Rad Laboratories).

2-3. Measurement of Factor Xa Neutralizing Activity

Ten μL of hybridoma culture supernatant diluted to 1/5 with TBSB was mixed with 40 μL of TBCP (TBSB containing 2.78 mM $CaCl_2$, 22.2 μM phospholipids (phosphatidylcholine:phosphatidylserine=75:25, Sigma-Aldrich)) containing 250 pg/mL of Factor Xa (Enzyme Research Laboratories) and incubated at room temperature for 1 hour. To this mixed solution, 50 μL of TBCP containing 20 μg/mL prothrombin (Enzyme Research Laboratories) and 100 ng/mL activated coagulation factor V (Factor Va (Haematologic Technologies)) were added, and reacted at room temperature for 10 minutes. The reaction was stopped with the addition of 10 μL of 0.5 M EDTA. To this reaction solution, 50 μL of 1 mM S-2238 solution (Chromogenix) was added, followed by incubation at room temperature for 30 minutes, at which point absorbance was measured at 405 nm on a Microplate Reader Model 3550 (Bio-Rad Laboratories, Inc.).

[Example 3] Construction of Chimeric Bispecific Antibody Expression Vectors 3-1. Preparation of Antibody Variable Region-Encoding DNA Fragments from Hybridomas Total RNA was extracted from hybridoma XB12 that produced anti-F.IXa antibody or hybridoma SB304 that produced anti-F.X antibody using QIAGEN® RNeasy® Mini Kit (QIAGEN) according to the method described in the instruction manual. The total RNA was dissolved in 40 μL of sterile water. Single-stranded cDNA was synthesized by RT-PCR using the SuperScript cDNA synthesis system (Invitrogen) with 1-2 μg of the purified RNA as template according to the method described in the instruction manual.

3-2. PCR Amplification of Antibody H-Chain Variable Region and Sequence Analysis HB primer mixture and HF primer mixture described in the report by Krebber et al. (J. Immunol. Methods 1997; 201:35-55) were prepared as amplification primers for the mouse antibody H chain variable region (VH) cDNA. Using 0.5 µL each of 100 µM HB primer mixture and 100 µM HF primer mixture, 25 µL of the reaction solution (2.5 µL of cDNA solution prepared in 3-1, KOD plus buffer (Toyobo), 0.2 mM dNTPs, 1.5 mM $MgCl_2$, 0.75 units DNA polymerase KOD plus (Toyobo)) was prepared. PCR was performed using a thermal cycler GeneAmp PCR system 9700 (Perkin Elmer) under either with condition A (heating at 98° C. for 3 minutes, followed by 32 cycles of reacting at 98° C. for 20 seconds, 58° C. for 20 seconds, and 72° C. for 30 seconds per cycle) or condition B (heating at 94° C. for 3 minutes, followed by 5 cycles of reacting at 94° C. for 20 seconds, 46° C. for 20 seconds, and 68° C. for 30 seconds per cycle, and 30 cycles of reacting at 94° C. for 20 seconds, 58° C. for 20 seconds, and 72° C. for 30 seconds per cycle), depending on the amplification efficiency of the cDNA fragment. After PCR, the reaction solution was subjected to 1% agarose gel electrophoresis. Amplified fragments having the size of interest (approximately 400 bp) were purified using QIAquick Gel Extraction Kit (QIAGEN) according to the method described in the instruction manual, and eluted with 30 µL at of sterile water. The nucleotide sequence of each DNA fragment was determined by a DNA sequencer ABI PRISM 3100 Genetic Analyzer (Applied Biosystems) using a BigDye Terminator Cycle Sequencing Kit (Applied Biosystems) according to the method described in the instruction manual. The group of sequences determined by this method was analyzed comparatively using an analysis software GENETYX-SV/RC Version 6.1 (Genetyx), and those having a different sequence were selected.

3-3. Preparations of Antibody Variable Region DNA Fragments for Cloning

The following procedure was performed to add restriction enzyme Sfi I cleavage sites for cloning to both ends of the fragments of antibody variable region that were amplified.

To amplify the Sfi I cleavage site added to the VH fragments (Sfi I-VH), a primer (primer VH-5' end) in which the (Gly4Ser)2-linker sequence of primer HB was modified to a sequence having Sfi I cleavage sites was prepared. Using 0.5 µL at each of the 10 µM sequence-specific primer VH-5' end and 10 µM primer sc for (J. Immunol. Methods 1997; 201: 35-55), a reaction solution (20 µL) (1 µL at of purified solution of amplified VH cDNA fragment prepared in 3-2, KOD plus buffer (TOYOBO), 0.2 mM dNTPs, 1.5 mM $MgCl_2$, 0.5 units DNA polymerase KOD plus (TOYOBO)) was prepared. Using a thermal cycler GeneAmp PCR system 9700 (Perkin Elmer), PCR was performed either with condition A (heating at 98° C. for 3 minutes, followed by 32 cycles of reacting at 98° C. for 20 seconds, 58° C. for 20 seconds, and 72° C. for 30 seconds per cycle) or condition B (heating at 94° C. for 3 min followed by 5 cycles of reacting at 94° C. for 20 seconds, 46° C. for 20 seconds, and 68° C. for 30 seconds per cycle, and 30 cycles of reacting at 94° C. for 20 seconds, 58° C. for 20 seconds, and 72° C. for 30 seconds per cycle), depending on the amplification efficiency for the fragments. After PCR, the reaction solution was subjected to 1% agarose gel electrophoresis. Amplified fragments of the desired size (about 400 bp) were purified using QIAquick Gel Extraction Kit (QIAGEN) according to the method described in the instruction manual, and eluted with 30 µL of sterile water.

To amplify the mouse antibody L chain variable region (VL) cDNA fragments, 0.5 µL each of the 100 µM LB primer mixture and 100 µM LF primer mixture described in the report by Krebber et al. (J. Immunol. Methods 1997; 201: 35-55) was used first, and a reaction solution (25 µL) (2.5 µL of cDNA solution prepared in 3-1, KOD plus buffer (TOYOBO), 0.2 mM dNTPs, 1.5 mM $MgCl_2$, 0.75 units DNA polymerase KOD plus (TOYOBO)) was prepared. Using a thermal cycler GeneAmp PCR system 9700 (Perkin Elmer), PCR was performed according to the amplification efficiency of the fragments, under conditions of heating at 94° C. for 3 min followed by 5 cycles of reaction (reacting at 94° C. for 20 seconds, 46° C. for 20 seconds, and 68° C. for 30 seconds per cycle, and 30 cycles of reacting at 94° C. for 20 seconds, 58° C. for 20 seconds, and 72° C. for 30 seconds per cycle. After the PCR, the reaction solution was subjected to 1% agarose gel electrophoresis. Amplified fragments of the desired size (about 400 bp) were purified using the QIAquick Gel Extraction Kit (QIAGEN) according to the method described in the instruction manual, and were eluted with 30 µL of sterile water. The fragments are in a state in which the primer LF-derived (Gly4Ser)3-linker sequence is added to their C termini. In order to add an Sfi I cleavage site to the C termini of the fragments, a primer (primer VL-3' end) where the primer LF (Gly4Ser)3-linker sequence was modified to a sequence having Sfi I cleavage site was prepared. To amplify the Sfi I cleavage site-added VL fragments (Sfi I-VL), 0.5 µL each of the 10 µM VL-3' end primer mixture and 10 µM sc back primer was used, and 20 µL of a reaction solution (1 µL of a solution of purified VL cDNA amplification fragment, KOD plus buffer (TOYOBO), 0.2 mM dNTPs, 1.5 mM $MgCl_2$, 0.5 units DNA polymerase KOD plus (TOYOBO)) was prepared. PCR was performed using a thermal cycler GeneAmp PCR system 9700 (Perkin Elmer) under conditions of heating at 94° C. for 3 min followed by 5 cycles of reaction (reacting at 94° C. for 20 seconds, 46° C. for 20 seconds, and 68° C. for 30 seconds per cycle, and 30 cycles of reacting at 94° C. for 20 seconds, 58° C. for 20 seconds, and 72° C. for 30 seconds per cycle. After the PCR, the reaction solution was subjected to 1% agarose gel electrophoresis. Amplified fragments of the desired size (about 400 bp) were purified using the QIAquick Gel Extraction Kit (QIAGEN) according to the method described in the instruction manual, and were eluted with 30 µL of sterile water.

Purified Sfi I-VH and Sfi I-VL fragments were digested with Sfi I (Takara Bio) at 50° C. for overnight in a reaction solution prepared according to the method described in the instruction manual. Subsequently, the reaction solution was purified using a QIAquick PCR Purification Kit (QIAGEN) according to the method described in the instruction manual, and eluted with 30 µL of Buffer EB included in the kit.

3-4. Human IgG4-Mouse Chimeric Bispecific IgG Antibody Expression Plasmid

The knobs-into-holes technique of IgG1 (Non-Patent Document 3) was utilized to produce the bispecific IgG antibody of interest, to allow heteromolecule formation in each H chain, and an amino acid substituent in which the CH3 portion of the IgG4 is substituted was prepared. Type a (IgG4γa) is an IgG4 substituted at Y349C and T366W, and type b (IgG4γb) is an IgG4 substituted at E356C, T366S, L368A, and Y407V. Furthermore, a substitution (-ppcp-Scp-->-ppcpPcp-) was also introduced at the hinge regions of both substituted IgG4s. Most become heteromolecules using this technique; however, this does not necessarily apply to L chains, and the generation of unnecessary antibody molecules may affect subsequent activity measurements. Therefore, in this method those that are inducible by different pharmaceuticals were used as the expression vectors for each HL molecule to separately express the arms of each antibody molecule (called as HL molecule) which have various specificities, and to efficiently produce the bispecific IgG antibody of interest within cells.

As an expression vector for one arm of the antibody molecule (referred to as right arm HL molecule for convenience), a respective H chain or L chain region incorporated to a tetracycline-induced type vector pcDNA4 (Invitrogen) (pcDNA4-g4H or pcDNA4-g4L) was prepared, i.e. a suitable mouse antibody variable region (VH or VL) and a human IgG4γa constant region (SEQ ID NO: 9) or κ (constant region (SEQ ID NO: 10) incorporated into the downstream of the signal sequence (IL3ss) used for animal cells (Proc. Natl. Acad. Sci. USA. 1984; 81: 1075). First, Eco RV and Not I (Takara Bio) were used to digest pcDNA4 at the restriction enzyme cleavage sites that are present in the multi-cloning site. The right arm H chain- or L chain-expression unit (about 1.6 kb or about 1.0 kb respectively) of a chimeric bispecific antibody having suitable antibody variable regions was digested with Xho I (Takara Bio). The antibody was then purified with the QIAquick PCR Purification Kit (QIAGEN) according to the method described in the instruction manual, and reacted with DNA polymerase KOD (TOYOBO) at 72° C. for 10 minutes in a reaction solution composition described in the instruction manual to blunt the ends. The blunt-ended fragments were purified with QIAquick PCR Purification Kit (QIAGEN) according to the method described in the instruction manual, and digested with Not I (Takara Bio). The Not I/blunt ended fragments (about 1.6 kb or 1.0 kb respectively) and the Eco RV/Not I-digested pcDNA4 were subjected to ligation reaction using Ligation High (TOYOBO), according to the method described in the instruction manual. An *E. coli* DH5a strain (Competent high DH5a (TOYOBO)) was transformed with the above-described reaction solution. >From the ampicillin-resistant clones thus obtained, respective plasmid DNAs were isolated using QIAprep Spin Miniprep Kit (QIAGEN).

According to the above-described method, as for the other arm (referred to herein as left arm HL molecule for convenience) of the antibody molecule, the respective H chain or L chain region incorporated to the ecdysone analogue inducible type vector pIND (Invitrogen) (pIND-g4H or pIND-g4L) was prepared, i.e. a suitable mouse antibody variable region (VH or VL) and a human IgG4γb constant region (SEQ ID NO: 11) or κ constant region incorporated into the downstream of the signal sequence (IL3ss) used for animal cells (EMBO. J. 1987; 6: 2939). Respective plasmid DNAs were then isolated.

3-5. Construction of Bispecific Antibody Expression Vectors

The tetracycline-induced type expression plasmid prepared in 3-4 (pcDNA4-g4H or pcDNA4-g4L) was digested with Sfi I, and the reaction solution was subjected to 1% agarose gel electrophoresis. Fragments (approximately 5 kb) lacking the original antibody variable region part (VH or VL) were purified using the QIAquick Gel Extraction Kit (QIAGEN) according to the method described in the instruction manual, and eluted with 30 μL of sterile water. The fragments, and the corresponding Sfi I-VH or Sfi-VL fragment derived from the Sfi I-digested anti-F.IXa antibody XB12 prepared in 3-3, were subjected to ligation reaction using the Quick Ligation Kit (New England Biolabs) according to the method described in the instruction manual. An *E. coli* DH5α strain (Competent high DH5α (TOYOBO)) was transformed with the above-described reaction solution. Next, fragments obtained by removing the antibody variable region part (VH or VL), using a technique similar to that described above from the Sfi I-digested ecdysone analogue-induced type expression plasmid (pIND-g4H or pIND-g4L) prepared in 3-4, and the corresponding Sfi I-digested anti-F.X antibody SB304-derived Sfi I-VH or Sfi I-VL fragment prepared in 3-3 were incorporated by a similar method.

Nucleotide sequences for each DNA fragment were determined using a BigDye Terminator Cycle Sequencing Kit (Applied Biosystems) and DNA sequencer ABI PRISM 3100 Genetic Analyzer (Applied Biosystems), according to the method described in the instruction manual. A group of sequences determined by the present method were analyzed using an analysis software, GENETYX-SV/RC Version 6.1 (Genetyx).

From the clones of interest, the respective plasmid DNAs were isolated using a QIAprep Spin Miniprep Kit (QIAGEN), and then dissolved in 100 μL of sterile water. Anti-F.IXa antibody chimeric H chain expression vector, anti-F.IXa antibody chimeric L chain expression vector, anti-F.X antibody chimeric H chain expression vector, and anti-F.X antibody chimeric L chain expression vector were named pcDNA4-g4 XB12H, pcDNA4-g4 XB12L, pIND-g4 SB04H, and pIND-g4 SB04L, respectively.

[Example 4] Production of Chimeric Bispecific Antibodies 4-1. Preparation of DNA Solutions Expression of the right arm antibody HL molecule expression vectors (pcDNA4-g4 XB12H and pcDNA4-g4 XB12L) is induced by tetracycline. In the absence of tetracycline, Tet repressor-encoding plasmid pcDNA6/TR (Invitrogen) is required to completely suppress their expressions. Furthermore, expression of the left arm antibody HL molecule expression vectors (pINE-g4 SB04H and pIND-g4 SB04L) was induced by an insect hormone ecdysone analogue (ponasterone A). Thus, plasmid pVgRXR (Invitrogen), which encodes the ecdysone receptor and retinoid X receptor that react with ponasterone A, was required to induce expression. Therefore, for the transfection of animal cells, a mixture of six types of plasmid DNAs in total was prepared. For 10 mL of cell culture, 3 μg each of pcDNA4-g4 XB12H, pcDNA4-g4 XB12L, pIND-g4 SB04H and pIND-g4 SB04L, as well as 18 μg each of pcDNA6/TR and pVgRXR were used.

4-2. Transfection of Animal Cells

Human fetal renal carcinoma cell-derived HEK293H strain (Invitrogen) was suspended in a DMEM medium (Invitrogen) containing 10% FCS (MOREGATE), and 10 mL of this was seeded at a cell density of $5\times10^5$ cells/mL in each dish used for adhesive cells (10-cm diameter, CORNING) and cultured for a day and night in a $CO_2$ incubator (37° C., 5% $CO_2$). The plasmid DNA mixture prepared in 4-1 was added to a mixture of transfection reagents, 75.8 μL of Lipofectaine 2000 (Invitrogen) and 2708 μL of Opti-MEM I medium (Invitrogen), and left to stand at room temperature for 20 minutes. The resulting mixture was added to the cells in each well and incubated for 4 to 5 hours in a $CO_2$ incubator (37° C., 5% $CO_2$).

4-3. Induction of Bispecific IgG Antibody Expression

Culture medium was removed by suction from the transfected cell culture as described above, and then 10 mL of a CHO-S-SFM-II (Invitrogen) medium containing 1 μg/mL tetracycline (Wako Pure Chemical Industries) was added. This mixture was incubated for one day in a $CO_2$ incubator (37° C., 5% $CO_2$) to induce primary expression of the right arm antibody HL molecule. Subsequently, after removing the medium by suction and washing with 10 mL of CHO-S-SFM-II medium, and adding 10 mL of a CHO-S-SFM-II medium containing 5 µM of ponasterone A (Invitrogen), this was incubated in a $CO_2$ incubator (37° C., 5% $CO_2$) for 3 days, and secondary expression of the left arm antibody HL molecule was induced so that the bispecific IgG antibody was secreted into the medium. The culture supernatant was recovered and centrifuged (approximately 2000 g for 5 min at room temperature) to remove the cells, and then sterilized by passing through a 0.22 µm filter MILLEX®-GV (Millipore). The sample was stored at 4° C. until use.

4-4. Antibody Purification

One hundred µL of rProtein A Sepharose™ Fast Flow (Amersham Biosciences) was added to 10 mL of the culture supernatant obtained according to the method described in Example 4-3, and the solution was mixed by overturning at 4° C. for 4 hours. The solution was transferred to an Ultrafree®.-MC 0.22 µm filter cup (Millipore) and after washing 3 times with 500 µL of TBS containing 0.01% Tween® 20, the rProtein A Sepharose™ resin was suspended in 100 µL of 10 mM HCl containing 0.01% Tween® 20 at pH 2.0 and left to stand for 2 minutes. Then, the antibody was eluted, and the eluate was immediately neutralized by adding 5 µL of 1 M Tris-HCl, pH 8.0.

4-5. Quantification of Human IgG Concentration

Goat anti-human IgG (Biosource International) was adjusted to 1 µg/mL with a coating buffer, and immobilized to a Nunc-Immuno plate (Nunc). After blocking with a diluent buffer (D.B.), a sample of the culture supernatant suitably diluted with D.B. was added. Furthermore, as a standard for calculating the antibody concentration, human IgG4 (humanized anti-TF antibody, see WO 99/51743) diluted with D.B. in a three-fold dilution series up to eleven stages starting from 2000 ng/mL was added similarly. After 3 washes, goat anti-human IgG alkaline phosphatase (Biosource International) was reacted. After 5 washes, the color was developed using Sigma 104® phosphatase substrate (Sigma-Aldrich) as a substrate, and the absorbance at 405 nm was measured on an absorbance reader Model 3550 (Bio-Rad Laboratories) with a reference wavelength of 655 nm. Using the Microplate Manager III (Bio-Rad Laboratories) software, human IgG concentration in the culture supernatant was calculated from the standard curve.

[Example 5] Plasma Coagulation Assay

To elucidate whether a bispecific antibody corrects the coagulation ability of hemophilia A blood, effects of the bispecific antibody on activated partial thromboplastin time (APTT) were examined using Factor VIII-deficient plasma. A mixed solution comprising 50 µL of an antibody solution at various concentrations, 50 µL of Factor VIII-deficient plasma (Biomerieux), and 50 µL of APTT reagent (Dade Behring) was heated at 37° C. for 3 minutes. Coagulation reaction was initiated by adding 50 µL of 20 mM $CaCl_2$ (Dade Behring) to this mixed solution. The time required for coagulation was measured with CR-A (Amelung)-connected KC10A (Amelung).

Using a calibration curve produced by defining the coagulation time for Factor VIII-deficient plasma as 0% and the coagulation for normal plasma as 100%, Factor VIII-like activity (%) of a bispecific antibody was calculated from the coagulation time measured when bispecific antibody was added.

[Example 6] Humanization of Bispecific Antibody

Anti-factor IXa antibody XB12 and anti-factor X antibody SB04, which were the most effective in shortening blood coagulation time, were subjected to humanization as follows.

6-1. Homology Search of Human Antibodies

Using a database constructed using amino acid sequence data of human antibodies from publicly disclosed Kabat Database (ftp://ftp.ebi.ac.uk/pub/databases/kabat/) and IMGT Database (http://imgt.cines.fr/), a homology search was carried out separately for the mouse XB12-H chain variable region, mouse XB12-L chain variable region, mouse SB04-H chain variable region, and mouse SB04-L chain variable region. The results confirmed that they have high homologies to the human antibody sequences shown below, and it was thus decided that the framework region (hereinafter abbreviated as FR) of humanized antibodies would be used.

(1) XB12-H chain variable region: KABATID-020619 (Kabat Database) (Mariette et al., Arthritis Rheum. 1993; 36: 1315-1324)

(2) XB12-L chain variable region: EMBL Accession No. X61642 (IMGT Database) (Mark et al., J. Mol. Biol. 1991; 222: 581-597.)

(3) SB04-H chain variable region: KABATID-025255 (Kabat Database) (Demaison et al., Immunogetetics 1995; 42: 342-352)

(4) SB04-L chain variable region: EMBL Accession No. AB064111 (IMGT Database) (Unpublished data)

Humanized antibodies in which complementarity determining regions (hereinafter abbreviated as CDR) of each mouse antibody were grafted into the FRs of human antibodies (1)-(4) were prepared.

Also, the web homology search site publicly disclosed by NCBI (http://www.ncbi.nln.nih.gov/BLAST/) was used to search for secretory signal sequences of human antibodies that are highly homologous to the human antibodies of (1)-(4). The following secretory signal sequences obtained by the search were used.

(1) XB12-H chain variable region: GenBank Accession No. AF062120

(2) XB12-L chain variable region: GenBank Accession No. M74019

(3) SB04-H chain variable region: GenBank Accession No. BC019337

(4) SB04-L chain variable region: GenBank Accession No. AY204756.

6-2. Construction of Humanized Antibody Gene Expression Vector

Twelve synthetic oligoDNAs of about 50 bases were prepared from a nucleotide sequence encoding the amino acid sequence from the secretory signal sequence to the antibody variable region, such that about 20 bases of their 3'-end anneal with each other. Furthermore, a primer annealing to the 5'-end of an antibody variable region gene and having the XhoI cleavage sequence, and a primer annealing to the 3'-end of an antibody variable region gene and having the SfiI cleavage sequence were prepared.

One µL each of the synthetic oligoDNAs prepared at 2.5 µM were mixed, and 1× TaKaRa Ex Taq Buffer, 0.4 mM dNTPs, and 0.5 units TaKaRa Ex Taq (all from Takara Shuzo) were added to prepare a 48 µL reaction solution. After keeping this at 94° C. for 5 minutes, 2 cycles of reacting at 94° C. for 2 minutes, 55° C. for 2 minutes, and 72° C. for 2 minutes were performed to assemble and elongate each of the synthetic oligoDNAs. Next, 1 µL each of a primer annealing to the 5'-end and a primer annealing to the 3'-end of the antibody gene were added at 10 µM, and the antibody variable region genes were amplified by 35 cycles of reacting at 94° C. for 30 seconds, 55° C. for 30 seconds, and 72° C. for 1 min and then reacting at 72° C. for 5 minutes. After PCR, the entire reaction solution was subjected to 1% agarose gel electrophoresis. Amplified fragments having the size of interest (approximately 400 bp) were purified using QIAquick Gel Extraction Kit (QIAGEN) according to the method described in the instruction manual, and eluted with 30 µL of sterile water. These fragments were cloned using the pGEM-T Easy Vector System (Promega) according to the method described in the instruction manual. Nucleotide sequences for each of the DNA fragments were determined using the BigDye Terminator Cycle Sequencing Kit (Applied Biosystems) and an ABI PRISM 3700 DNA Sequencer (Applied Biosystems) according to the method described in the instruction manual.

A plasmid confirmed to have the correct humanized antibody variable region gene sequence was then digested with EcoRI and SfiI and the reaction solution was subjected to 1% agarose gel electrophoresis. DNA fragments having the size of interest (approximately 400 bp) were purified using QIAquick Gel Extraction Kit (QIAGEN) according to the method described in the instruction manual, and eluted with 30 µL of sterile water. Furthermore, after the EcoRI and SfiI digestion of the tetracycline-induced type expression plasmids (pcDNA4-g4H, pcDNA4-g4L) and the ecdysone analogue induced type expression plasmids (pIND-g4H, pIND-g4L) prepared in Example 3-3, fragments comprising the antibody constant region (approximately 5 kb) were purified using the QIAquick Gel Extraction Kit (QIAGEN) according to the method described in the instruction manual, and eluted with 30 µL of sterile water. The humanized XB12 antibody gene fragment (H chain variable region or L chain variable region) digested with EcoRI and SfiI, and the tetracycline-induced type expression plasmid (pcDNA4-g4H, pcDNA4-g4L) digested with EcoRI and SfiI were subjected to ligation reaction using Rapid DNA Ligation Kit (Roche Diagnostics) according to the method described in the instruction manual. In addition, the humanized SB04 antibody gene fragment digested with EcoRI and SfiI (H chain variable region or L chain variable region), and the ecdysone analogue induced type expression plasmid (pIND-g4H, pIND-g4L) digested with EcoRI and SfiI were subjected to ligation reaction using the Rapid DNA Ligation Kit (Roche Diagnostics) according to the method described in the instruction manual. A portion of each of the reaction mixture was used to transform DH5a strain $E.$ $coli$ (TOYOBO).

Furthermore, an expression vector was prepared as follows for expression as an ordinary humanized antibody, but not as a bispecific antibody. Plasmids (pCAG-g4H, pCAG-gκ) with an insert of wild type antibody constant regions to pCAGGS having a chicken β-actin promoter (Niwa et al. 1991 Gene, 108: 193-199) were digested with XhoI and SfiI to prepare expression plasmids that carry humanized XB12 antibody gene fragment (H chain variable region or L chain variable region) or humanized SB04 antibody gene fragment (H chain variable region or L chain variable region) collected after digesting the bispecific antibody expression vector mentioned above with XhoI and SfiI. DNA ligation reaction was performed using the Rapid DNA Ligation Kit (Roche Diagnostics), and $E.$ $coli$ DH5a strain (TOYOBO) was transformed.

6-3. Preparation of humanized bispecific antibody

The genes were transfected and expression was induced in HEK293H according to the methods described in Examples 4-2 and 4-3, using 4 types of humanized bispecific antibody expression vectors as well as pcDNA6/TR and pVgRXR. Further, antibody purification and quantification of antibody concentration were conducted according to the methods shown in Examples 4-4 and 4-5.

6-4. Preparation of Humanized Antibodies

Expression of an ordinary humanized antibody, which is not a bispecific antibody, was accomplished by transfecting genes to HEK293H according to the method shown in Example 4-2, using humanized H chain antibody expression vector and humanized L chain antibody expression vector prepared in Example 6-3. After gene transfection, cells were washed by addition and removal of 10 mL of CHO-S-SFM-II medium (Invitrogen), then 10 mL of CHO-S-SFM-II was added, and then the cells were cultured for 3 days in a $CO_2$ incubator (37° C., 5% $CO_2$) for secretion of the humanized antibodies.

6-5. Activity Assessment of Humanized Bispecific Antibody and Modification of Antibody Sequence To assess the plasma coagulation ability of the prepared humanized bispecific antibody and chimeric bispecific antibody XB12/SB04, effects of the antibodies on APTT were examined using F. VIII-deficient plasma according to the method of Example 5. Amino acids of the human antibody FR were modified to increase activities of humanized bispecific antibodies whose blood coagulation capability has been reduced. In addition, the cysteine residues in the CDR3 of XB12 antibody VH, whose possible drop in thermostability is a concern, were modified to alanine. Specifically, mutations were introduced into the humanized antibody variable region using the QuikChange Site-Directed Mutagenesis Kit (Stratagene) according to the method described in the instruction manual. By repeating amino acid modifications to the FR sequence and assessment of blood coagulation ability, a humanized bispecific antibody (humanized XB12 antibody (VH:hXB12f-A, VL:hXBVL)/humanized SB04 antibody (VH:hSB04e, VL:hSBVL-F3f)) having the same activity as XB12/SB04 was obtained. Each antibody variable regions sequences is shown in the following SEQ ID NOs.

(1) humanized XB12 antibody VH (hXB12f-A) SEQ ID NO: 1 (nucleotide sequence), SEQ ID NO: 2 (amino acid sequence)
(2) humanized XB12 antibody VL (hXBVL) SEQ ID NO: 3 (nucleotide sequence), SEQ ID NO: 4 (amino acid sequence)
(3) humanized SB04 antibody VH (hSB04e) SEQ ID NO: 5 (nucleotide sequence), SEQ ID NO: 6 (amino acid sequence)
(4) humanized SB04 antibody VL (hSBVL-F3f) SEQ ID NO: 7 (nucleotide sequence), SEQ ID NO: 8 (amino acid sequence)

[Example 7] Modeling of Humanized Antibody

An antibody Fv region model was prepared by homology modeling using MOE software (Chemical Computing Group Inc.) to confirm the amino acid residues at the VH-VL interface of the humanized SB04 antibody. The amino acids of H39 and L38 at the VH-VL interface are both glutamine (Gln) and formation of hydrogen bonds by the side chains of both residues was confirmed (FIG. 1A). The amino acids of H45 and L44 were leucine (Leu) and proline (Pro), respectively, the side chains of both residues were very close to each other and were found to form a hydrophobic core (FIG. 1B). The amino acid residues at these two positions have been reported to be highly conserved in human antibodies (Vargas-Madrazo E et al. J. Mol. Recognit. 2003, 16: 113-120). Numbering of these antibodies such as H39, L38, H45, and L44 were based on the literature of Kabat et al. (Kabat E A et al. 1991. Sequences of Proteins of Immunological Interest. NIH).

[Example 8] Preparation and Assessment of H39 and L38 Amino Acid-Modified Humanized Antibody 8-1. Construction of an Expression Vector of H39 and L38-Modified Antibody To inhibit the association between humanized XB12 H chain and humanized SB04 L chain, H39 glutamine of humanized XB12H chain and L38 glutamine of humanized SB04 L chain were substituted based on the findings in Example 7. Specifically, to inhibit hydrogen bonding of the glutamine side chains and to allow electrostatic repulsion, both amino acids (H39 and L38) were substituted with lysine (Lys) or arginine (Arg) carrying a positive charge on their side chain, or to glutamic acid (Glu) or aspartic acid (Asp) which carry a negative charge on their side chain. Substitution of the humanized antibody gene was performed using QuickChange Site-Directed Mutagenesis Kit (Stratagene), and mutations were introduced according to the method described in the instruction manual. Each humanized antibody gene fragment carrying amino acid substitutions was inserted into a bispecific antibody expression vector used in Example 6-2 or into an ordinary antibody expression vector.

8-2. Preparation of Antibodies for Association Regulation Assessment and Association Regulation Assessment of the Antibodies To assess the regulation of H chain and L chain association, gene transfection into HEK293H was performed according to the method shown in Example 4-2 using 3 types of prepared antibody expression vectors: humanized XB12H chain (H39-modified), humanized SB04 L chain (L38-modified), and wild-type humanized XB12 L chain. The antibodies were then secreted into the culture supernatant. Next, antibody purification and quantification of antibody concentration were carried out according to the methods of Examples 4-4 and 4-5.

Two-hundred ng of purified antibodies were reduced in a sample buffer (TEFCO), applied to a 14% SDS-PAGE mini gel (TEFCO), and then subjected to electrophoresis. After electrophoresis, the gels were subjected to immobilization treatment by soaking in 7% acetic acid solution containing 10% methanol for 30 minutes, and then stained by soaking in SYPRO® Ruby protein gel stain solution (BIO-RAD) for one day and night. Subsequently, the gels were subjected to decolorization treatment by soaking in 7% acetic acid solution containing 10% methanol for 1 hour and the image was analyzed using a fluorescence imager FluorImager SI (Amersham Biosciences) and the image was obtained. The obtained image was used to calculate the fluorescence intensities of the H chain and L chain bands using ImageQuant ver. 4.2 (Amersham Biosciences).

Figure 2:
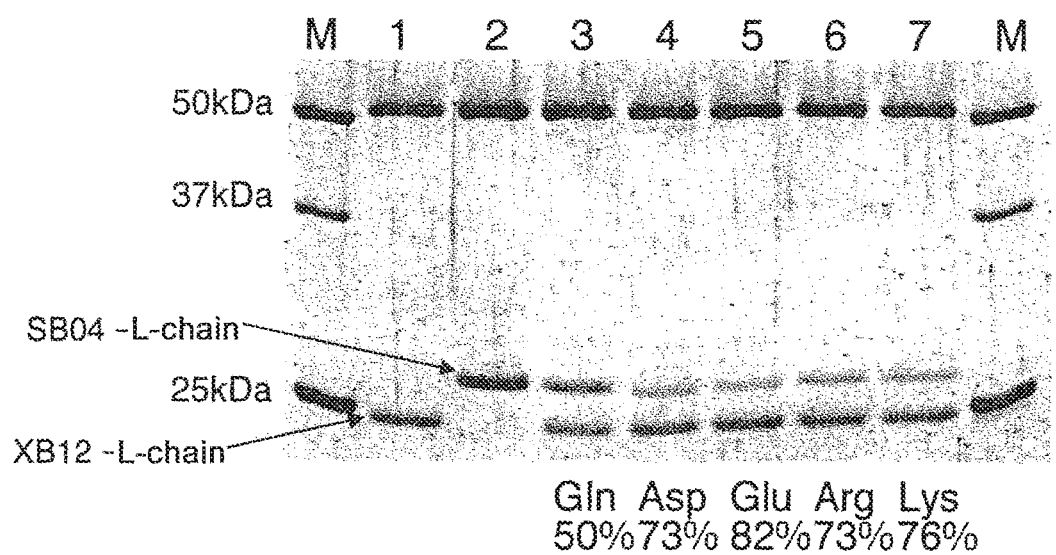
FIG. 2 is a photograph depicting the results of an assay evaluating the associations between H and L chains in H39 and L38-modified antibodies. These results demonstrate that for all modified antibodies, the associated proportion of the antibody of interest is increased when compared to the wild type.
Description of the Lanes:
M: molecular marker;
1: humanized XB12 H chain (Q)+humanized XB12 L chain (Q);
2: humanized XB12 H chain (Q)+humanized SB04 L chain (Q);
3: wild type: humanized XB12 H chain (Q)+humanized XB12 L chain (Q)+humanized SB04 L chain (Q);
4: D variant: humanized XB12 H chain (D)+humanized XB12 L chain (Q)+humanized SB04 L chain (D);
5: E variant: humanized XB12 H chain (E)+humanized XB12 L chain (Q)+humanized SB04 L chain (E);
6: R variant: humanized XB12 H chain (R)+humanized XB12 L chain (Q)+humanized SB04 L chain (R); and
7: K variant: humanized XB12 H chain (K)+humanized XB12 L chain (Q)+humanized SB04 L chain (K)

The results are shown in FIG. 2. The proportion (%) of the XB12-L chain of interest was calculated according to the formula "XB12-L chain/total amount of L chain (XB12-L chain+SB04-L chain)×100" using the calculated fluorescence intensity values. The proportion was 50% when the amino acids of the humanized XB12 H chain (H39) and humanized SB04 L chain (L38) were glutamine (Gln) as in the wild type, whereas the proportion of the humanized XB12L chain increased when H39 and L38 were substituted. In the case of substitution to glutamic acid (Glu), this proportion was found to increase 1.6 times to 82%.

8-3. Preparation of Bispecific Antibodies for Coagulation Activity Assessment and Coagulation Activity Assessment of the Antibodies To assess the coagulation activity, gene transfection into HEK293H and induction of expression were carried out according to the methods described in Examples 4-2 and 4-3, using the prepared humanized XB12 H chain (H39-modified) and humanized SB04 L chain (L38-modified) bispecific antibody expression vector and wild-type humanized XB12 L chain and humanized SB04 H chain bispecific antibody expression vector, pcDNA6/TR and pVgRXR. Furthermore, antibody purification and quantification of antibody concentration were carried out according to the methods of Examples 4-4 and 4-5.

Figure 3:
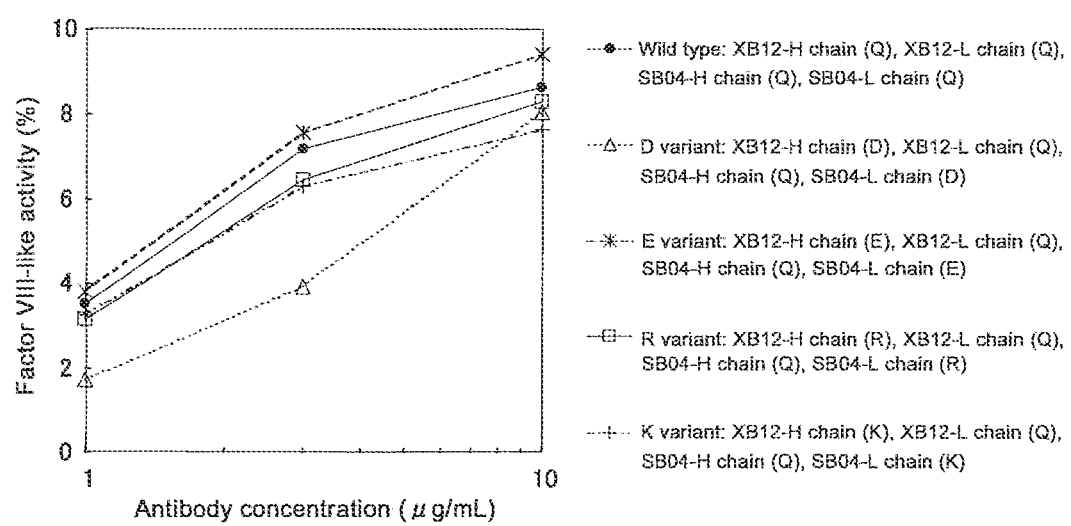
FIG. 3 depicts the results of an assay evaluating coagulation activity in H39 and L38-modified antibodies. The results demonstrate that the bispecific antibody whose XB12 H chain (H39) and SB04 L chain (L38) have been modified to Glu has a coagulation activity equal to or greater than that of the wild-type.

Assessment of coagulation activity was performed according to the method shown in Example 5, and the results are shown in FIG. 3. Glutamic acid (Glu: E)-modified antibody whose proportion increased up to 82% in the association regulation assessment was found to show a coagulation activity greater than or equal to that of the wild type.

8-4. Preparation of Antibodies for Binding Activity Assessment

To assess the binding activity to Factor IXa and Factor X, gene transfection into HEK293H and secretion of antibodies into the culture supernatant was performed according to the method described in Example 4-2, using humanized XB12 H chain (H39-modified) and wild-type humanized XB12L chain antibody expression vector, or wild-type humanized SB04 H chain and humanized SB04 L chain (L38-modified) antibody expression vector. Furthermore, antibody purification and quantification of antibody concentration were carried out according to the methods of Examples 4-4 and 4-5.

Figure 4:
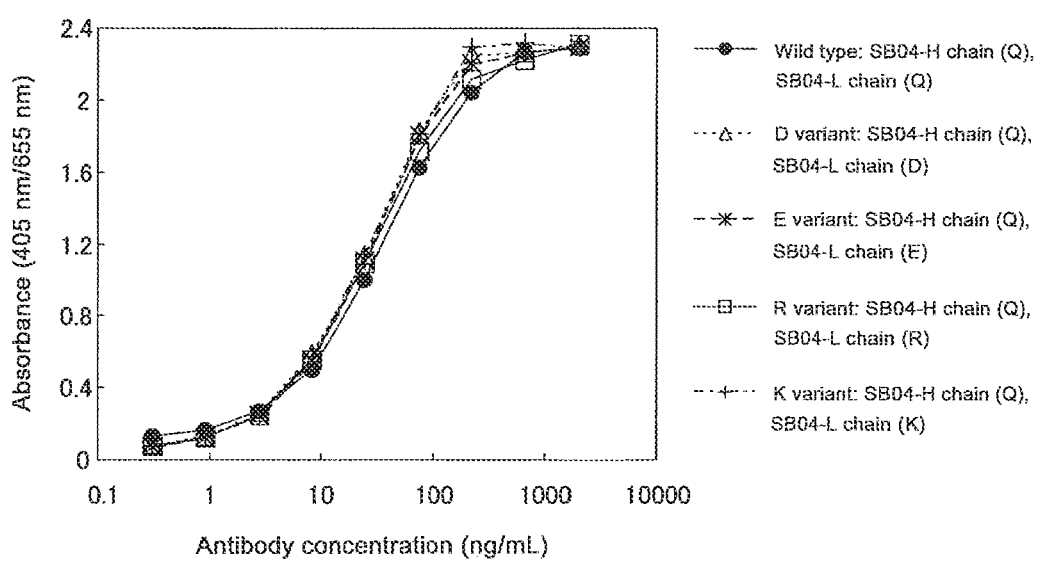
FIG. 4 depicts the results of an assay evaluating Factor IXa binding activity in H39 and L38-modified antibodies. The results demonstrate that all modified antibodies have a binding activity equivalent to that of the wild-type.
Figure 5:
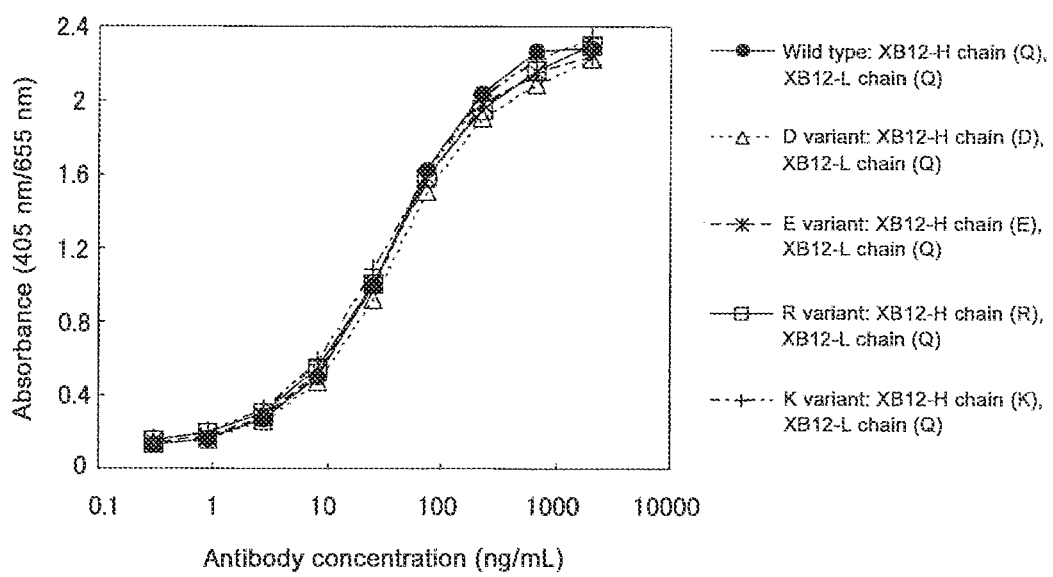
FIG. 5 shows the results of an assay evaluating Factor X binding activity in H39 and L38-modified antibodies. The results show that all modified antibodies have a binding activity equivalent to that of the wild-type.

Assessment of binding activity against Factor IXa and Factor X were performed according to the methods described in Examples 1-2 and 2-2. The results are shown in FIG. 4 and FIG. 5. It was confirmed that substitution of amino acids at H39 and L38 did not alter the binding activity.

These results suggested that by modifying H39 of XB12 H chain and L38 of SB04 L chain, the proportion of bispecific antibodies of interest could be increased without decreasing biological activities, including binding activity to antigens and coagulation activity that substitute for Factor VIII. So far, including the methods using knob and hole, there are no reported cases where the association was regulated by introducing only a single amino acid mutation in a polypeptide without decreasing the function. Accordingly, the findings of the present invention are considered to be the first of such kind.

[Example 9] Preparation and Assessment of L44 Amino Acid-Modified Humanized Antibody 9-1. Construction of an Expression Vector L44-Modified Antibody To inhibit the association between humanized XB12 H chain and humanized SB04 L chain, based on the findings in Example 7, L44 proline of humanized SB04 L chain was substituted to an amino acid carrying a charge on its side chain. Specifically, proline present in the hydrophobic core of the VH-VL interface was substituted to lysine (Lys) or arginine (Arg) carrying positive charge on their side chain, and glutamic acid (Glu) carrying a negative charge on its side chain was substituted to aspartic acid (Asp). Substitution of the humanized antibody gene was performed using QuickChange Site-Directed Mutagenesis Kit (Stratagene), and mutations were introduced according to the method described in the instruction manual. Each humanized antibody gene fragment having amino acid substitutions were inserted into a bispecific antibody expression vector used in Example 6-2 or into an ordinary antibody expression vector.

9-2. Preparation of Antibodies for Association Regulation Assessment and Association Regulation Assessment of the Antibodies To assess the regulation of H chain and L chain association, gene transfection into HEK293H was performed according to the method of Example 4-2, using 3 types of prepared antibody expression vectors, humanized SB04 L chain (L44-modified), wild-type humanized XB12H chain, and wild-type humanized XB12 L chain, and the antibodies were secreted into the culture supernatant. Furthermore, antibody purification and quantification of antibody concentration were carried out according to the methods of Examples 4-4 and 4-5.

Two-hundred ng of purified antibodies were reduced in a sample buffer (TEFCO), applied to a 14% SDS-PAGE mini gel (TEFCO), and then subjected to electrophoresis. After electrophoresis, the gels were subjected to immobilization treatment by soaking in 7% acetic acid solution containing 10% methanol for 30 minutes, and then stained by soaking in SYPRO® Ruby protein gel stain solution (BIO-RAD) for one day and night. Subsequently, the gels were subjected to decolorization treatment by soaking in 7% acetic acid solution containing 10% methanol for 1 hour and the image was analyzed using a fluorescence imager FluorImager SI (Amersham Biosciences) and the images were obtained. The obtained images were used to calculate the fluorescence intensities of the H chain and L chain bands using ImageQuant ver. 4.2 (Amersham Biosciences).

Figure 6:
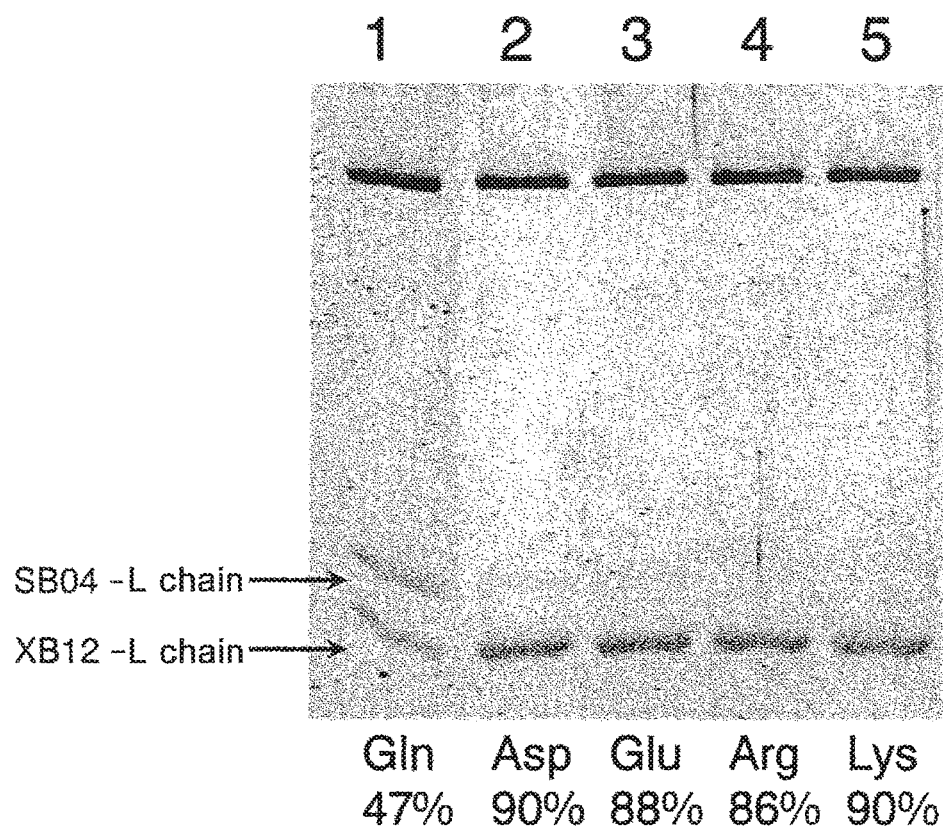
FIG. 6 is a photograph depicting the results of an assay evaluating the association between the H and L chains in the L44-modified antibodies. The results demonstrate that for all modified antibodies, the associated proportion of the antibody of interest is increased when compared to that of the wild type.
Description of the Lanes:
1: wild type: humanized XB12 H chain+humanized XB12 L chain (P)+humanized SB04 L chain (P);
2: D variant: humanized XB12 H chain+humanized XB12 L chain (P)+humanized SB04 L chain (D);
3: E variant: humanized XB12 H chain+humanized XB12 L chain (P)+humanized SB04 L chain (E);
4: R variant: humanized XB12 H chain+humanized XB12 L chain (P)+humanized SB04 L chain (R); and
5: K variant: humanized XB12 H chain+humanized XB12 L chain (P)+humanized SB04 L chain (K)

The results are shown in FIG. 6. The proportion (%) of the XB12-L chain of interest was calculated according to the formula "XB12-L chain/total amount of L chain (XB12-L chain+SB04-L chain)×100" using the calculated fluorescence intensity values. The proportion was 47% when the amino acid of the humanized SB04 L chain (L44) was proline (Pro) as in the wild type, whereas the proportion of the humanized XB12L chain increased when L44 was substituted, and this proportion was found to increase 1.8-1.9 times to 86-90%.

9-3. Preparation of Bispecific Antibodies for Coagulation Activity Assessment and Coagulation Activity Assessment of the Antibodies To assess the coagulation activity, gene transfection into HEK293H and induction of expression were carried out according to the methods described in Examples 4-2 and 4-3, using the prepared humanized SB04 L chain (L44-modified) bispecific antibody expression vector and wild-type humanized XB12 H chain, humanized XB12 L chain, and humanized SB04 H chain bispecific antibody expression vector, pcDNA6/TR and pVgRXR. Furthermore, antibody purification and quantification of antibody concentration were carried out according to the methods of Examples 4-4 and 4-5.

Figure 7:
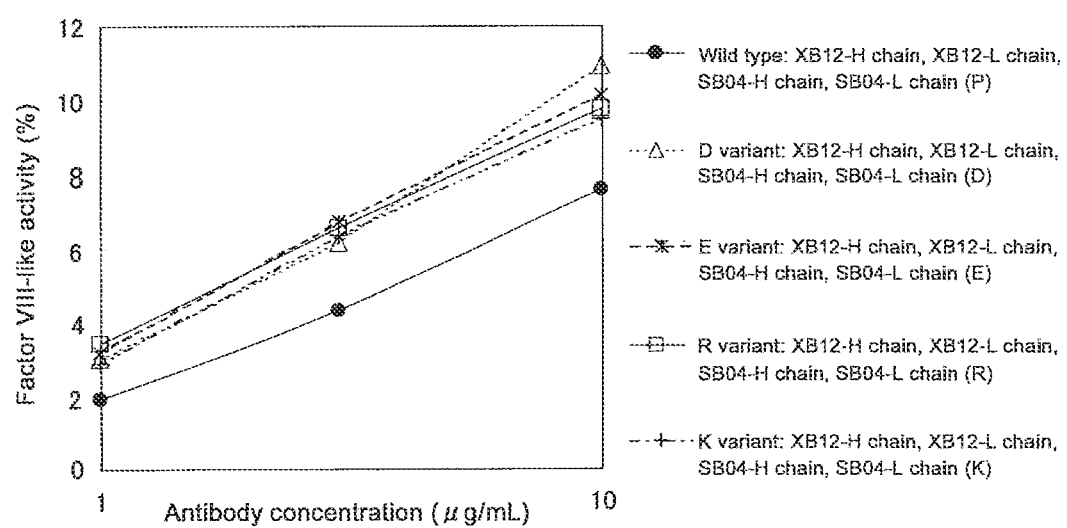
FIG. 7 depicts the results of an assay evaluating coagulation activity in L44-modified antibodies. The results demonstrate that all modified antibodies have coagulation activity greater than that of the wild-type.

Assessment of coagulation activity was performed according to the method shown in Example 5, and the results are shown in FIG. 7. All modified antibodies whose proportion had increased in the association regulation assessment were found to show a coagulation activity greater than that of the wild type.

9-4. Preparation of Antibodies for Binding Activity Assessment

To assess the binding activity against Factor X, gene transfection into HEK293H and secretion of antibodies into the culture supernatant was performed according to the method described in Example 4-2, using wild-type humanized SB04 H chain and humanized SB04 L chain (L44-modified) antibody expression vector. Furthermore, quantification of antibody concentration in the culture supernatant was carried out according to the method of Example 4-5.

Figure 8:
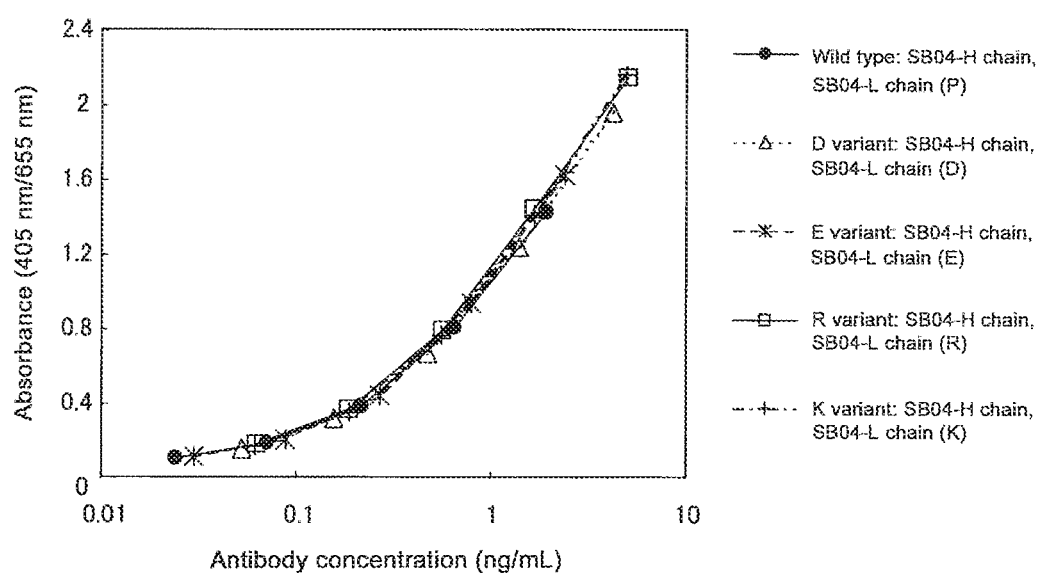
FIG. 8 depicts the results of an assay evaluating Factor X binding activity in L44-modified antibodies. The results demonstrate that all modified antibodies have a binding activity equivalent to that of the wild type.

Assessment of binding activity against Factor X was performed using the culture supernatant according to the method described in Example 2-2. The results are shown in FIG. 8. It was confirmed that substitution of amino acid at L44 does not change the binding activity.

These results suggested that by modifying the amino acid at one position, L44, in the SB04 L chain, the proportion of bispecific antibodies of interest could be increased without decreasing biological activities, including binding activity to the antigens and coagulation activity that substitute for Factor VIII. So far, including the methods using knob and hole, there are no reported cases where the association was regulated by introducing only a single amino acid in a polypeptide without decreasing the function. Thus, the findings of the instant invention are considered to be the first of such kind.

[Example 10] Preparation and Assessment of H39 and L38, and L44 Amino Acid-Modified Humanized Antibody 10-1. Construction of an Expression Vector of H39 and L38, and L44-Modified Antibody To inhibit the association between humanized XB12 H chain and humanized SB04 L chain, H39 of humanized XB12 H chain and L38 and L44 of humanized SB04 L chain were substituted with amino acids carrying a charge on their side chain based on the findings of Examples 8 and 9. Specifically, both amino acids at H39 of humanized XB12 H chain and L38 of humanized SB04 L chain were substituted with glutamic acid (Glu), which was found to be most effective in Example 8, and proline present at L44 of humanized SB04 L chain was substituted to lysine (Lys) or arginine (Arg) carrying a positive charge in their side chain, or to glutamic acid (Glu) or aspartic acid (Asp) carrying a negative charge in their side chain. Substitution of the humanized antibody gene was performed using QuickChange Site-Directed Mutagenesis Kit (Stratagene), and mutations were introduced according to the method described in the instruction manual. Each humanized antibody gene fragment carrying amino acid substitutions was inserted into the bispecific antibody expression vector used in Example 6-2 or an ordinary antibody expression vector.

10-2. Preparation of Antibodies for Association Regulation Assessment and Association Regulation Assessment of the Antibodies To assess the regulation of H chain and L chain association, gene transfection into HEK293H was performed according to the method of Example 4-2, using 3 types of antibody expression vectors: modified humanized SB04 L chain, modified humanized XB12 H chain, and wild-type humanized XB12 L chain. The antibodies were then secreted into the culture supernatant. Furthermore, antibody purification and quantification of antibody concentration were carried out according to the methods of Examples 4-4 and 4-5.

Two-hundred ng of purified antibodies were reduced in a sample buffer (TEFCO), applied to a 14% SDS-PAGE mini gel (TEFCO), and then subjected to electrophoresis. After electrophoresis, the gels were subjected to immobilization treatment by soaking in 7% acetic acid solution containing 10% methanol for 30 minutes, and then stained by soaking in SYPRO® Ruby protein gel stain solution (BIO-RAD) for one day and night. Subsequently, the gels were subjected to decolorization treatment by soaking in 7% acetic acid solution containing 10% methanol for one hour and the image was analyzed using a fluorescence imager FluorImager SI (Amersham Biosciences) and the images were obtained. The obtained images were used to calculate the fluorescence intensities of the H chain and L chain bands using ImageQuant ver. 4.2 (Amersham Biosciences).

Figure 9:
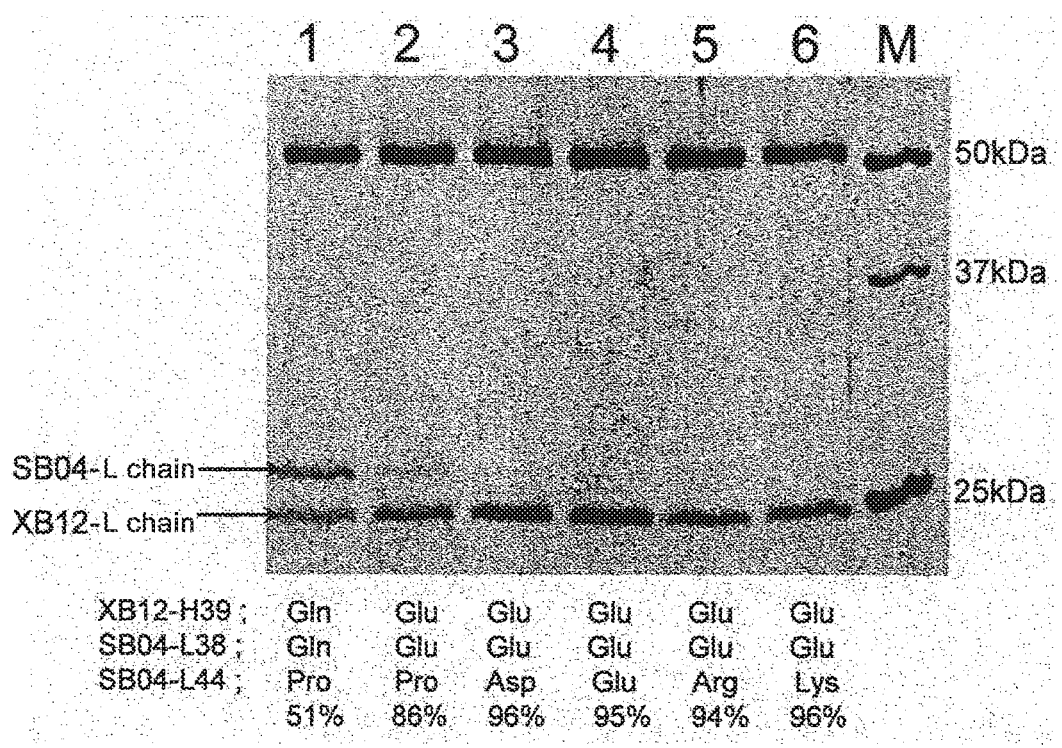
FIG. 9 is a photograph depicting the results of an assay evaluating the association between the H and L chains in H39, L38, and L44-modified antibodies. The results demonstrate that for all modified antibodies, associated proportion of the antibody of interest is increased when compared to that of the wild type.
Description of the Lanes:
1: wild type: humanized XB12 H chain (H39: Q)+humanized XB12 L chain (L38: Q)+humanized SB04 L chain (L38: Q, L44: P);
2: E+D variant: humanized XB12 H chain (H39: E)+humanized XB12 L chain (L38: Q)+humanized SB04 L chain (L38: E, L44: D);
3: E+E variant: humanized XB12 H chain (H39: E)+humanized XB12 L chain (L38: Q)+humanized SB04 L chain (L38: E, L44: E);
4: E+R variant: humanized XB12 H chain (H39: E)+humanized XB12 L chain (L38: Q)+humanized SB04 L chain (L38: E, L44: R);
5: E+K variant: humanized XB12 H chain (H39: E)+humanized XB12 L chain (L38: Q)+humanized SB04 L chain (L38: E, L44: K); and
M: molecular marker

The results are shown in FIG. 9. The proportion (%) of the XB12-L chain of interest was calculated according to the formula "XB12-L chain/total amount of L chain (XB12-L chain+SB04-L chain)×100" using the calculated fluorescence intensity values. The proportion was 82% when both amino acids of the humanized XB12 H chain (H39) and humanized SB04 L chain (L38) was modified to glutamic acid (Glu) and the humanized SB04 L chain (L44) was proline (Pro) as in the wild type, whereas the proportion of the humanized XB12L chain increased to 94-96% when L44 was substituted in addition to the substitution of both amino acids of the humanized XB12 H chain (H39) and humanized SB04 L chain (L38) to glutamic acid (Glu). This increase in proportion was greater than the 86-90% observed when L44 alone was substituted in Example 9.

10-3. Preparation of Bispecific Antibodies for Coagulation Activity Assessment and Coagulation Activity Assessment of the Antibodies To assess the coagulation activity, gene transfection into HEK293H and induction of expression were carried out according to the methods described in Examples 4-2 and 4-3, using the prepared modified humanized XB12 H chain, humanized XB12 L chain, and humanized SB04 H chain bispecific antibody expression vector and wild-type humanized XB12 H chain, humanized XB12 L chain, and humanized SB04 H chain bispecific antibody expression vector, pcDNA6/TR and pVgRXR. Furthermore, antibody purification and quantification of antibody concentration were carried out according to the methods of Examples 4-4 and 4-5.

Figure 10:
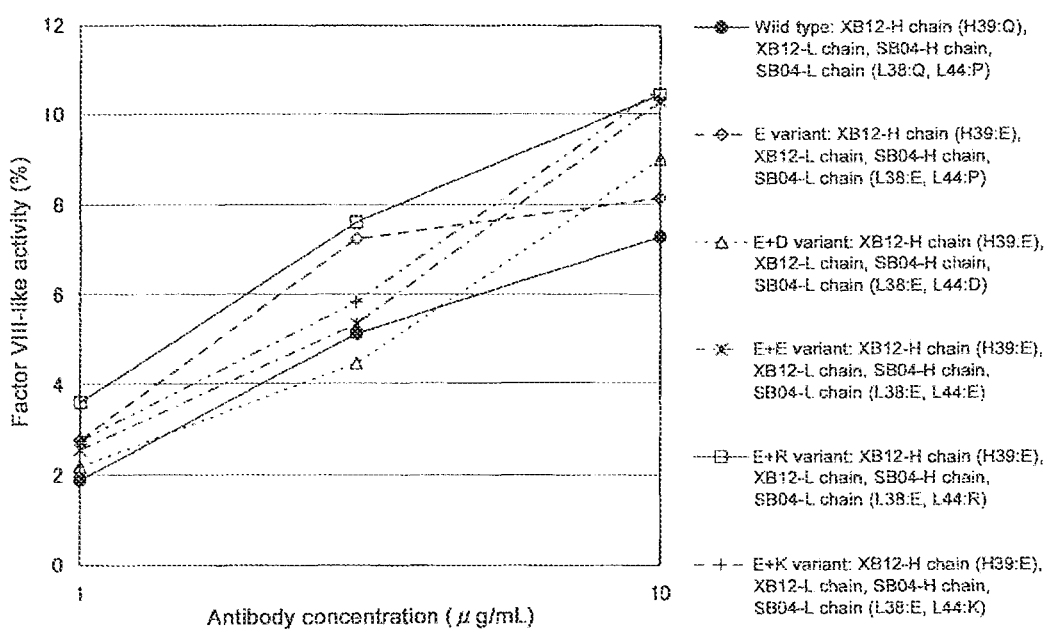
FIG. 10 depicts the results of an assay evaluating coagulation activity in H39, L38, and L44-modified antibodies. The results demonstrate that bispecific antibodies whose XB12 H chain (H39) and SB04 L chain (L38, L44) have been modified have a coagulation activity equal to or greater than that of the wild type.

Assessment of coagulation activity was performed according to the method shown in Example 5, and the results are shown in FIG. 10. All modified antibodies whose proportion had increased in the association regulation assessment were found to show a coagulation activity equivalent to that of the wild type.

10-4. Preparation of Antibodies for Binding Activity Assessment

To assess the binding activity against Factor X, gene transfection into HEK293H and secretion of antibodies into the culture supernatant was performed according to the method described in Example 4-2 using wild-type humanized SB04 H chain and modified humanized SB04 L chain antibody expression vector. Furthermore, quantification of antibody concentration in the culture supernatant was carried out according to the method of Example 4-5.

Figure 11:
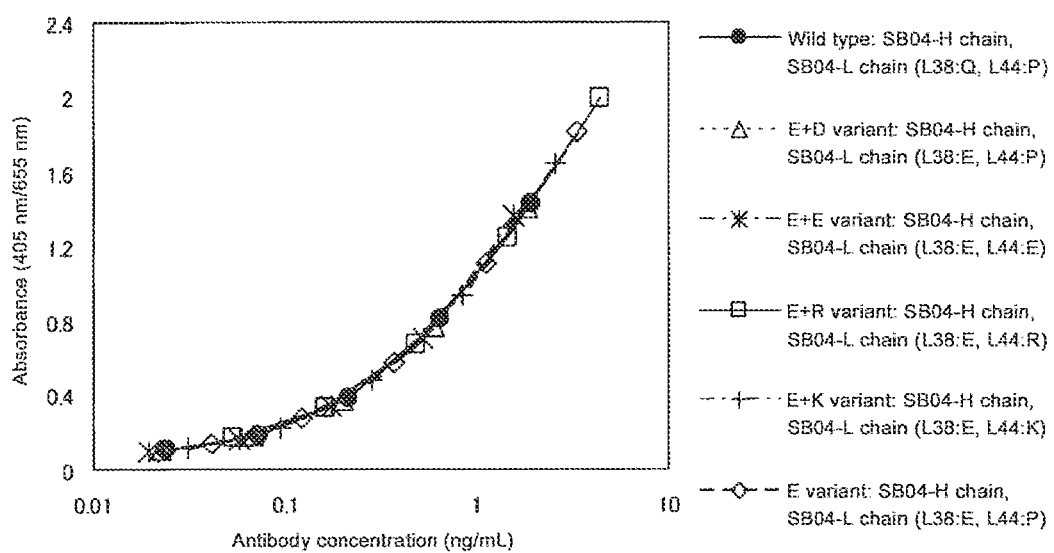
FIG. 11 depicts the results of an assay evaluating Factor IXa binding activity in H39, L38, and L44-modified antibodies. The results demonstrate that all modified antibodies have a binding activity equivalent to that of the wild type.

Assessment of binding activity against Factor X was performed using the culture supernatant according to the method described in Example 2-2. The results are shown in FIG. 11. It was confirmed that substitution of both amino acids at L38 and L44 did not alter the binding activity.

These results suggested that by modifying the amino acids at H39 of the XB12 H chain and L38 and L44 in the SB04 L chain, the proportion of bispecific antibodies of interest can be increased without decreasing biological activities which are binding activity to antigens and coagulation activity that substitute for Factor VIII. The proportion of the bispecific antibody was found to increase as the number of amino acids modified at the interface increased.

[Example 11] Separation and Structure Determination of Structural Isomers of hVB22B u2-Wz4 sc(Fv)2

11-1. Preparation of Humanized Anti-Human MpI Antibody hVB22B u2-Wz4 sc(Fv)2

Methods for producing hVB22B u2-wz4 sc(Fv)2 (hereinafter referred to as u2-wz4) which is a humanized anti-MpI antibody is described in WO2005/56604. This gene was prepared by PCR using a nucleotide sequence encoding the linker sequence (GlyGlyGlyGlySer)×3 so that it will comprise a nucleotide sequence composed of VH-linker sequence-VL-linker sequence-VH-linker sequence-VL (see SEQ ID NO: 12; and SEQ ID NO: 286 of WO2005/56604). After the nucleotide sequence of the gene was confirmed, cell lines with stable expression was prepared by constructing an expression vector by cloning a DNA fragment into expression vector pCXND3, and introducing the gene into CHO-DG44 cells. More specifically, 0.75 mL of a mixture of the expression vector (20 µg) and CHO-DG44 cells ($1\times10^7$ cells/mL) suspended in PBS was placed on ice for 10 minutes and transferred to a cuvette, and then a pulse was applied at 1.5 kV and 25 µFD using a Gene Pulser Xcell (BioRad). After a recovery period of 10 minutes at room temperature, cells subjected to electroporation treatment were selected by placing them into CHO-S-SFMII medium (Invitrogen) containing 500 µg/mL Geneticin (Invitrogen), and an u2-wz4-producing CHO cell line was established.

Since the humanized antibody, hVB22B u2-wz4 sc(Fv)2, does not have a Flag tag added, the purification from the culture supernatant was carried out using a fusion protein of GST and MG10 (Gln213 to Ala231 in the amino acid sequence of human MpI) which is an epitope recognized by the antibody. The MG10-GST fusion protein was purified using Glutathione Sepharose 4B (Amersham Biosciences) according to the supplier's protocol. Then, the purified MG10-GST fusion protein was immobilized onto HiTrap NHS-activated HP (Amersham Biosciences) to prepare an affinity column, according to the supplier's protocol. The culture supernatant of CHO cells expressing the humanized antibody, hVB22B u2-wz4 sc(Fv)2, was loaded onto the MG10-GST fusion protein-immobilized column, humanized antibody hVB22B u2-wz4 sc(Fv)2 was adsorbed to the column, and then was eluted with 100 mM Glycine-HCl (pH 3.5), 0.01% Tween80. The eluted fractions were immediately neutralized with 1 M Tris-HCl (pH7.4), and the monomer was purified by gel filtration chromatography using HiLoad 16/60 Superdex200pg (Amersham Biosciences). 20 mM citrate buffer (pH7.5) containing 300 mM NaCl and 0.01% Tween 80 was used in the gel filtration chromatography.

11-2. Separation and Purification of Conformational Isomers of hVB22B u2-Wz4 sc(Fv)2

Since hVB22B u2-wz4 sc(Fv)2 is an sc(Fv)2 composed of the sequence $VH_1$-linker-VL2-linker-$VH_3$-linker-VL4, as shown in FIG. 12, depending on the combination of Fvs (molecules having non-covalent bonds between VH and VL), 2 kinds of conformational isomers can exist, as in VB22B sc(Fv)2, which are the bivalent scFv-type in which each pairs of $VH_1$ and $VL_2$, and $VH_3$ and $VL_4$ forms a Fv, and the single chain diabody-type in which each pairs of $VH_1$ and $VL_4$, and $VH_2$ and $VL_3$ form a Fv.

Result of examination of the separation of conformational isomers of hVB22B u2-wz4 sc(Fv)2 suggested that each component of hVB22B u2-wz4 sc(Fv)2 can be separated by cation exchange chromatography using Bio Assist S (TOSOH) under the following elution conditions.

Mobile phase A: 20 mM sodium phosphate, pH7.5
Mobile phase B: 20 mM sodium phosphate, 500 mM NaCl, pH 7.5
Flow rate: 0.8 mL/min
Gradient: B 0% to B 35% (30 minutes)

Figure 13:
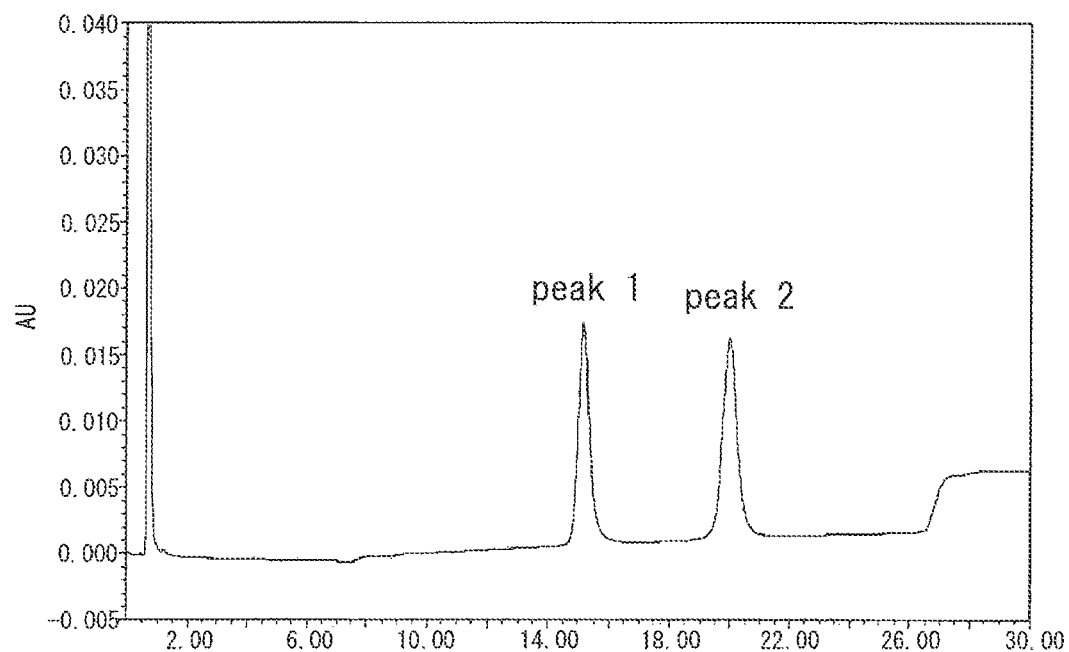
FIG. 13 depicts the results of separating peak 1 and peak 2 corresponding to the conformational isomers of u2-wz4, by cation exchange chromatography.

Under the above-mentioned conditions, hVB22B u2-wz4 sc(Fv)2 was separated into two peaks. The chromatogram shown in FIG. 13 was obtained, and starting from the shorter retention time, the peaks were named peak 1 and peak 2.

The molecular weight of peak 1 and peak 2 were measured using a Q-TOF-type mass spectrometer (Q T of Ultima, Micro Mass). Sample solutions were infused into Q-TOF, and deconvolution of the obtained polyvalent ion spectra (+) using the included software (MassLynx) gave results showing that the molecular weight of peak 1 and peak 2 are 53768 Da and 53769 Da, respectively. This showed that peak 1 and peak 2 have the same molecular weight.

Figure 14:
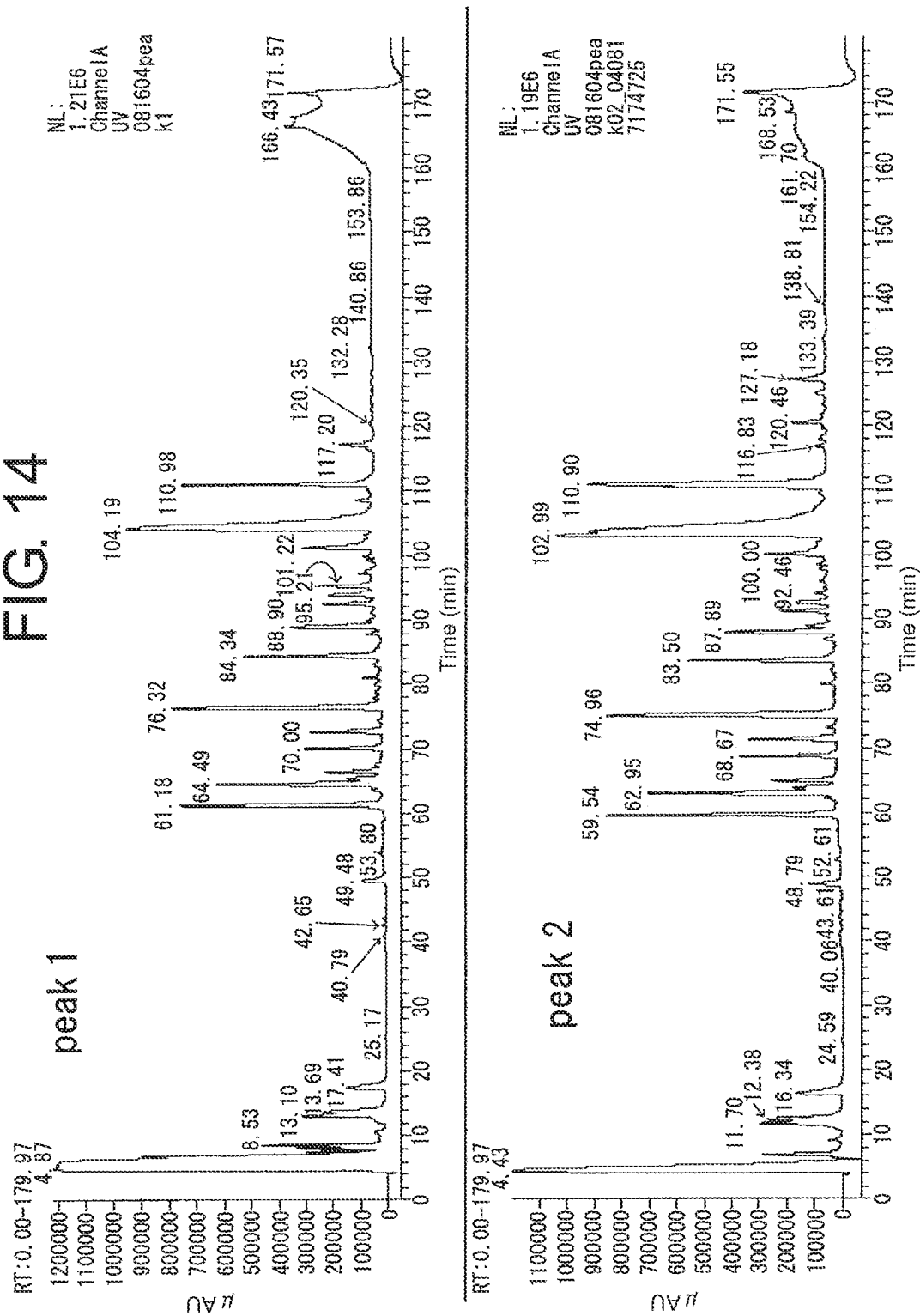
FIG. 14 depicts the results of peptide mapping of peak 1 and peak 2 separated by cation exchange chromatography.

Peptide mapping was performed on peak 1 and peak 2. After reductive denaturation and carboxymethylation, peptide fragments were obtained by digestion using trypsin, and peptide maps were obtained by reverse-phase chromatography (YMC-Pack-ODS). Comparing the peptide maps of peak 1 and peak 2, the mapping patterns of peak 1 and peak 2 were the same as shown in FIG. 14, therefore, the amino acid primary structure was found to be the same.

Since hVB22B u2-wz4 sc(Fv)2 is not glycosylated, peak 1 and peak 2 have the same molecular weight according to TOF-MASS measurements, and peak 1 and peak2 have the same mapping patterns, peak 1 and peak 2 were found to be conformational isomers having different three dimensional structures.

Since hVB22B u2-wz4 sc(Fv)2 is an sc(Fv)2 comprising the sequence, $VH_1$-linker-$VL_2$-linker-$VH_3$-linker-$VL_4$, as shown in FIG. 12, depending on the combination of Fvs (molecules comprising non-covalent bonds between VH and VL), 2 kinds of conformational isomers can exist. Namely, the isomers are the bivalent scFv-type in which each pairs of $VH_1$ and $VL_2$, and $VH_3$ and $VL_4$ forms a Fv, and the single chain diabody-type in which each pairs of $VH_1$ and $VL_4$, and $VH_2$ and $VL_3$ forms a Fv. Peak 1 and peak 2 were considered to have either one of the conformations; the bivalent scFv-type or the single chain diabody-type.

Figure 15:
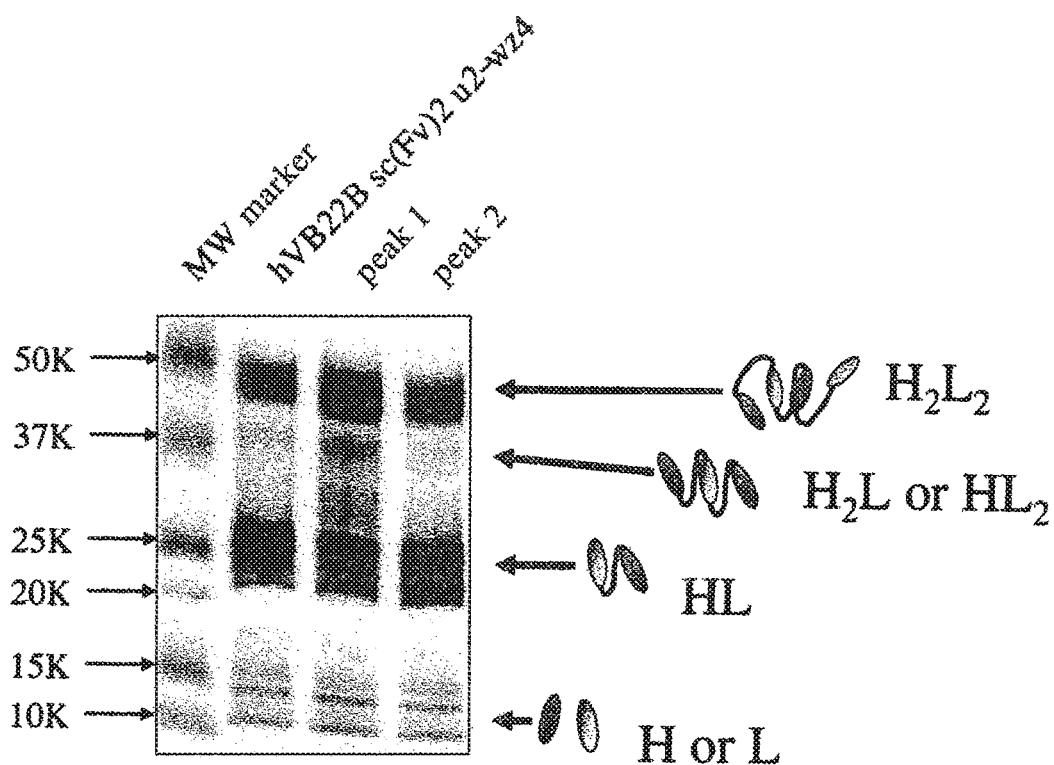
FIG. 15 is a photograph depicting the results of a reduced SDS-PAGE assay performed after subtilisin treatment of u2-wz4 before separation of peak 1 and peak 2, which are conformational isomers of u2-wz4. The conformations corresponding to the obtained bands are shown on the right.

Protease-limited proteolysis was developed as an analysis method for identifying the two types of conformational isomers. Since the linker portion of sc(Fv)2 has a relatively free structure, it is considered to have low resistance to proteases, and peak 1, peak 2, and hVB22B u2-wz4 sc(Fv)2 (The ratio of peak 1:peak 2 is approximately 1:4) were reacted with subtilisin A, a type of protease, under the following conditions:

20 mM sodium citrate, 150 mM NaCl, pH7.5
hVB22B u2-wz4 sc(Fv)2 peak 1 or peak 2: 0.15 mg/mL
Subtilisin A: 10 µg/mL
37° C., 30 minutes After the reaction, reductive SDS-PAGE was performed using Phastgel Homogeneous 12.5%. As a result, as shown in FIG. 15, hVB22B u2-wz4 sc(Fv)2 bulk, peak 1, and peak 2 all showed the same band patterns. The use of the above-mentioned reaction conditions was found to enable partial and limited digestion of the linker portions of hVB22B u2-wz4 sc(Fv)2, since specific bands for each of the fragments that appeared to be produced by the digestion of the three linker portions of hVB22B u2-wz4 sc(Fv)2 were obtained.

Figure 16:
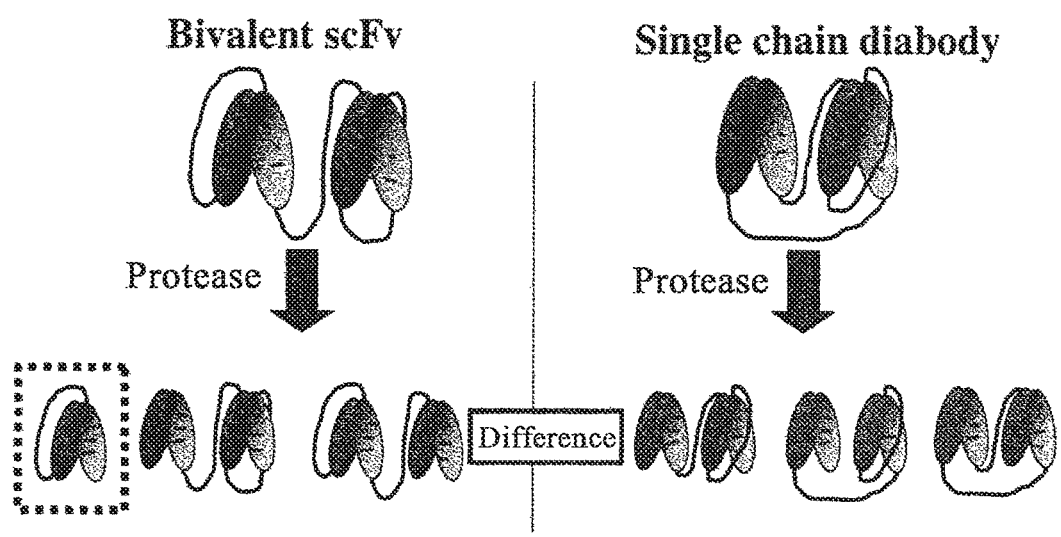
FIG. 16 depicts the difference in degradation patterns after limited proteolysis by subtilisin, which is caused by differences in the conformation of a bivalent scFv and single chain antibody. In the case of the bivalent ScFv structure, the minibody fragment in the dotted frame is formed.

When one of the three linkers is cleaved in the bivalent scFv-type and single chain diabody-type conformations, as shown in FIG. 16, under native conditions, the apparent molecular weight will not change no matter which linker among the three is cleaved in the single chain diabody-type conformation due to non-covalent bonding between VH and VL. However, in the bivalent scFv-type when the central linker is cleaved, molecular species having half the molecular weight will be produced. Therefore, hVB22B u2-wz4 sc(Fv)2 bulk, peak 1, and peak 2 whose linkers were partially cleaved by the above-mentioned reaction conditions were analyzed by gel filtration chromatography using TSK Super SW2000 (TOSOH). Gel filtration chromatography was performed under the following conditions:

Mobile phase: DPBS(−) pH7.4
Flow rate: 0.2 mL/min

Figure 17:
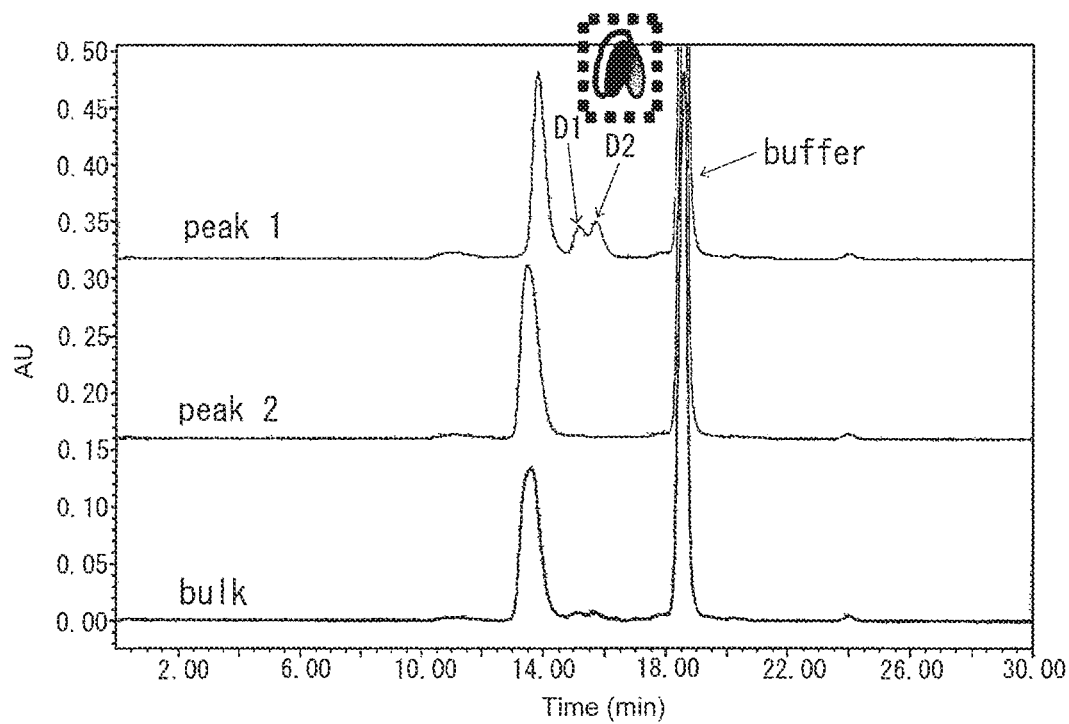
FIG. 17 depicts the results of a gel filtration chromatography assay after limited proteolysis by subtilisin on u2-wz4 before separation and on peak 1 and peak 2, which are conformational isomers of u2-wz4. The elution positions of the minibody peaks are shown by arrows.

As a result, as shown in FIG. 17, minibody peaks was not observed at all in peak 2, whereas, minibody peaks (approximately half the molecular weight) were observed for peak 1. hVB22B u2-wz4 sc(Fv)2 bulk which is a mixture of peak 1 and peak 2 showed low-molecular weight peaks whose amount correspond to the abundance ratio of peak 1. Therefore, these results identified peak 1 as a bivalent scFv-type and peak 2 as a single chain diabody-type.

[Example 12] Preparation, Conformational Isomer Analysis, and Identification of VH/VL Interface-Modified Sc(Fv)2

12-1. Preparation of VH/VL Interface-Modified Sc(Fv)2

VH/VL interface-modified sc(Fv)2 was prepared by the following method to confirm whether the formation of conformational isomers of sc(Fv)2 could be regulated through regulation of the association by the VH/VL interface modification to sc(Fv)2, which is a minibody.

Gln at position 39 of VH (position 39 in the amino acid sequence of SEQ ID NO: 13; see SEQ ID NO: 289 of WO2005/56604), and Gln at position 38 of VL (position 43 in the amino acid sequence of SEQ ID NO: 14; see SEQ ID NO: 289 of WO2005/56604) which are amino acids that form the VH/VL interface of u2-wz4 were modified as follows. First, the hVB22B u2-wz4(v1) sc(Fv)2 gene (hereinafter referred to as v1; the nucleotide sequence is shown in SEQ ID NO: 15, and the amino acid sequence encoded by the nucleotide sequence is shown in SEQ ID NO: 16), in which Gln at position 39 of VH1 (genetic codon: CAG) was modified to Glu (genetic codon: GAG), Gln at position 38 of VL2 (genetic codon: CAG) was modified to Glu (genetic codon: GAG), Gln at position 39 of $VH_3$ (genetic codon: CAG) was modified to Lys (genetic codon: AAG), and Gln at position 38 of VL4 (genetic codon: CAG) was modified to Lys (genetic codon: AAG), was produced. Furthermore, the hVB22B u2-wz4(v3) sc(Fv)2 gene (hereinafter referred to as v3; the nucleotide sequence is shown in SEQ ID NO: 17, and the amino acid sequence encoded by the nucleotide sequence is shown in SEQ ID NO: 18), in which Gln at position 39 of VH1 (genetic codon: CAG) was modified to Glu (genetic codon: GAG), Gln at position 38 of VL2 (genetic codon: CAG) was modified to Lys (genetic codon: AAG), Gln at position 39 of VH3 (genetic codon: CAG) was modified to Lys (genetic codon: AAG), and Gln at position 38 of VL4 (genetic codon: CAG) was modified to Glu (genetic codon: GAG), was produced. Gene modification was carried out by introducing point mutations using QuikChange Site-Directed Mutagenesis Kit (STRATA-GENE) according to the manufacturer's protocol. After confirming the nucleotide sequences of each genes, stable cell lines were prepared by constructing expression vectors by cloning DNA fragments into expression vector pCXND3, and introducing the gene into CHO-DG44 cells. The v1-producing CHO cell line and v3-producing CHO cell line were established according to the method shown in Example 11.

Figure 18:
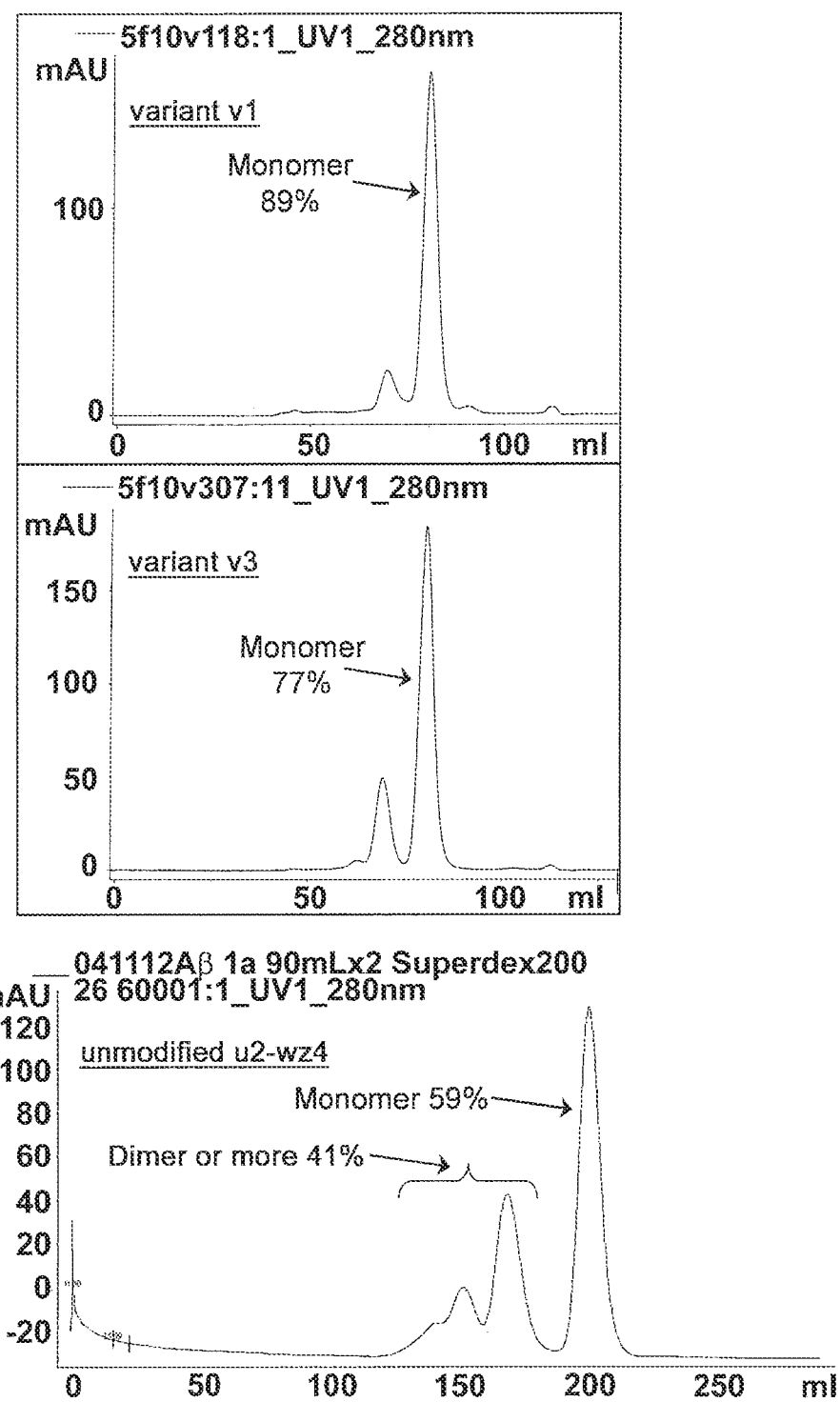
FIG. 18 depicts the results of a gel filtration chromatography assay on u2-wz4, variant v1, and variant v3 after purification through an MG10-GST fusion protein-immobilized column.

Monomeric molecules of variants v1 and v3 were purified according to the method of Example 11 using the MG10-GST fusion protein immobilized column. The results of gel filtration chromatography shown in FIG. 18 showed that for variants v1 and v3, the dimers and larger aggregates decreased in the culture supernatant and the proportion of monomers increased from 59% (u2-wz4 before modification) to 89% for v1 and 77% for v3. It seems that modification of amino acids at the VH/VL interface inhibits unfavorable associations by charge repulsion and promotes favorable association in variants v1 and v3. Accordingly, efficient expression of the monomeric molecules was successfully accomplished by this regulation of the association.

12-2. Conformational isomer analysis and identification of VH/VL interface-modified sc(Fv)2

The ratios of conformational isomers present in the obtained VH/VL interface-modified v1 and v3, and in the unmodified u2-wz4 were analyzed by cation exchange chromatography and isoelectric focusing. The conformations were identified by the protease-limited proteolysis method.

Cation exchange chromatography was performed as follows:
Column: TSK-gel Bioassist S, 4.6 mm$\phi$×50 mm (TOSOH)
Flow rate: 0.8 mL/min
Detection wavelength: 220 nm
Elution condition:
Eluent A: 20 mmol/L Phosphate buffer (pH 7.0)
Eluent B: 20 mmol/L Phosphate buffer/500 mmol/L NaCl (pH7.0)
Gradient:

| Time (minutes) | B % |
| --- | --- |
| 0 | 0 |
| 5 | 0 |
| 25 | 30 |
| 25.1 | 100 |
| 35 | 100 |
| 35.1 | 0 |

Isoelectric focusing was performed as follows. PhastGel Dry IEF gel (Amersham Biosciences) was swollen for 30 minutes in the gel swelling solution described below. First, the samples were applied to the swollen gel, and subjected to electrophoresis using the PhastSystem under the following conditions. After electrophoresis, the gel was soaked for 30 minutes in a 20% TCA solution, then subjected to a five-minute wash for three times or more in milliQ water, and then to Coomassie stained or silver stained depending on the protein concentration of the samples. In Coomassie staining, 0.02% CBB containing 0.1% $CuSO_4$ (w/v) was used as the solution for staining, and 30% methanol containing 10% acetic acid was used for decolorization. In silver staining, Silver stain kit, Protein (Amersham Biosciences) was used and staining was performed according to the standard protocol attached to the kit.

| <gel swelling solution> | |
| --- | --- |
| Pharmalyte 8.5-10 | 80 µL |
| Biolyte 7-9 | 10 µL |
| Biolyte 3-9 | 10 µL |
| 20% Glycerol | 2.0 mL |

| <electrophoresis program> | |
| --- | --- |
| SAMPLE APPLICATION DOWN AT step 2 | 0 Vh |
| SAMPLE APPLICATION UP AT step 3 | 0 Vh |
| Step 1 2000 V 2.5 mA 3.5 W 15° C. | 75 Vh |
| Step 2 200 V 2.5 mA 3.5 W 15° C. | 15 Vh |
| Step 3 2000 V 2.5 mA 3.5 W 15° C. | 410 Vh |

Figure 19:
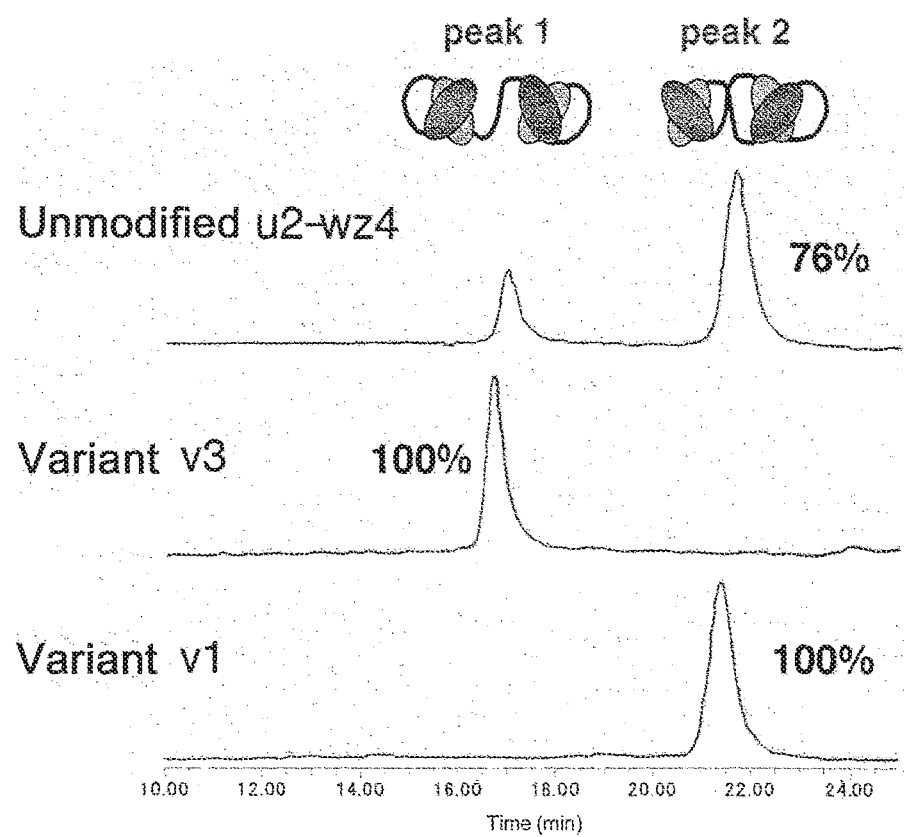
FIG. 19 depicts the results of a cation exchange chromatography assay on u2-wz4, variant v1, and variant v3.
Figure 20:
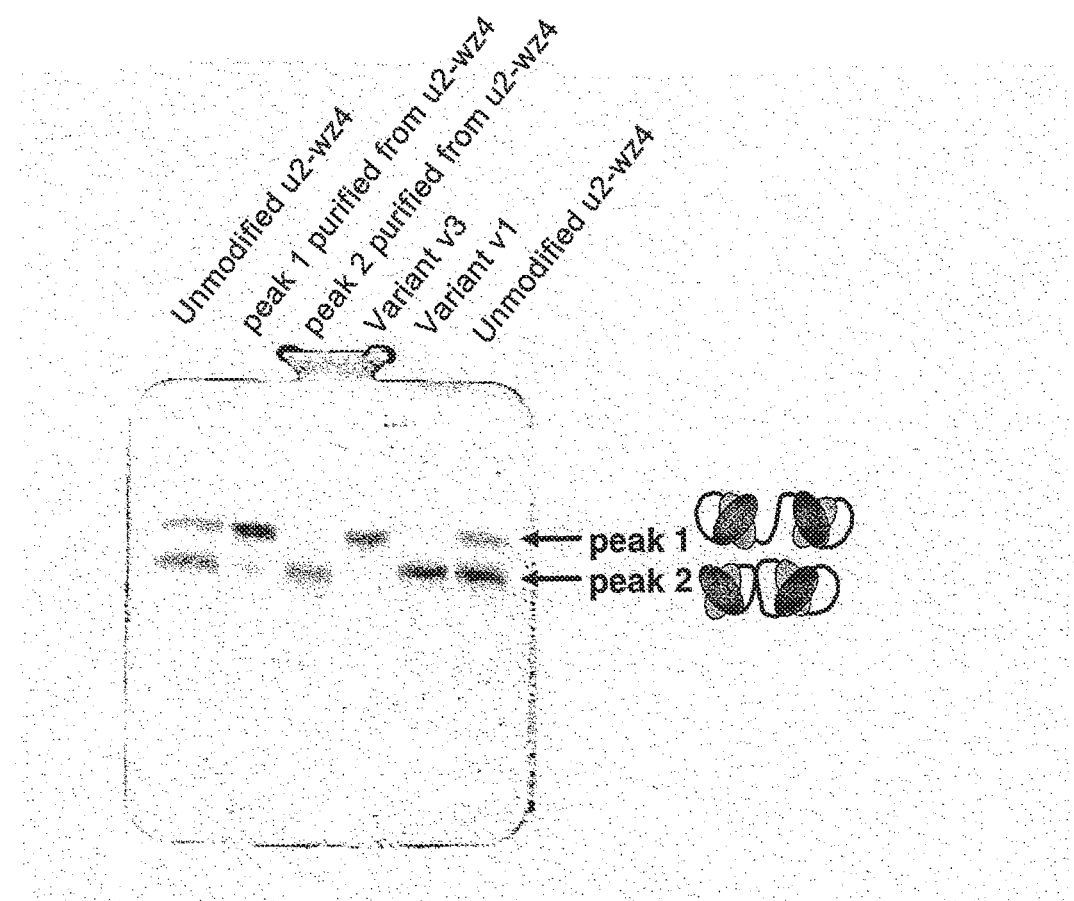
FIG. 20 is a photograph depicting the results of isoelectric focusing of u2-wz4, peak 1 purified from u2-wz4, peak 2 purified from u2-wz4, variant v1, and variant v3.
Figure 21:
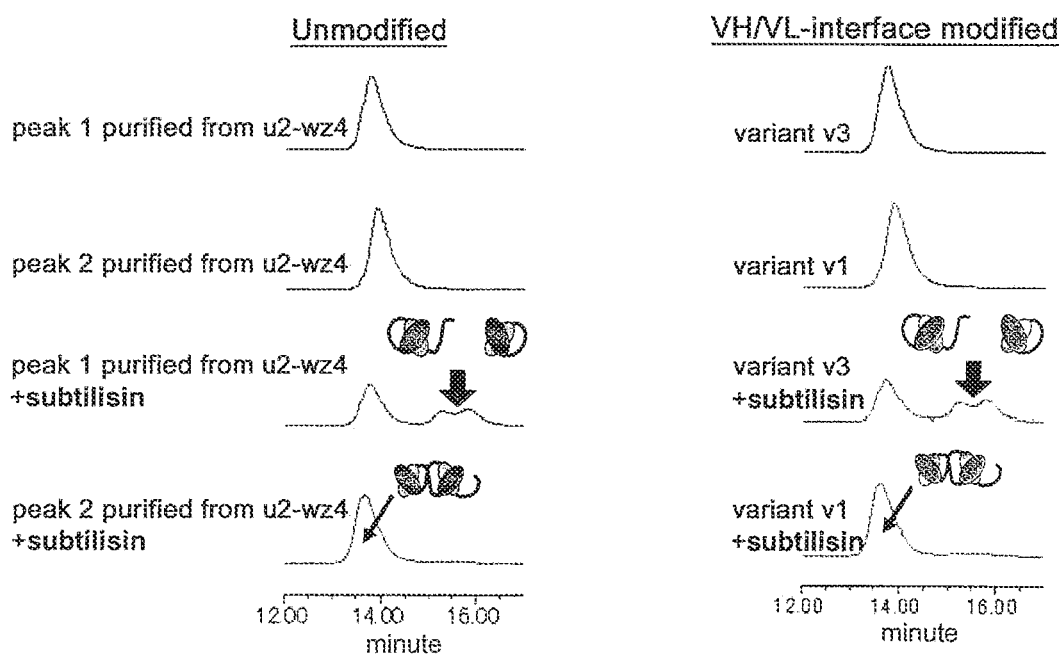
FIG. 21 depicts the results of gel filtration analyses performed after protease-limited proteolysis of peak 1 purified from u2-wz4, peak 2 purified from u2-wz4, variant v1, and variant v3.

Conformations were identified under the following conditions by the protease-limited proteolysis method. Peak 1 purified from u2-wz4, peak 2 purified from u2-wz4, and variant v1 and variant v3 were allowed to react using subtilisin A under the following conditions:
20 mM sodium citrate, 150 mM NaCl, pH7.5
hVB22B u2-wz4 sc(Fv)2 peak 1 or peak 2: 0.15 mg/mL
Subtilisin A: 10 µg/mL
37° C., 30 minutes The obtained reaction solution was analyzed by gel filtration chromatography under the following conditions:
Column: TSKgel Super2000sw (TOSOH)
Eluent: 50 mM sodium phosphate, 300 mM KCl, pH7.0
Flow rate: 0.2 mL/min
Detection: 220 nm From the results of conformational isomer analysis by cation exchange chromatography and isoelectric focusing shown in FIGS. 19 and 20, u2-wz4 was found to be expressed as a mixture of both conformational isomers in which 24% is the bivalent scFv-type and 76% is the single chain diabody-type, whereas 100% of variant v1 was expressed as the single chain diabody-type conformational isomer, and 100% of variant v3 was expressed as the bivalent scFv-type conformational isomer. Furthermore, as shown in FIG. 21, the results of protease-limited proteolysis showed that the minibody peaks are found in variant v3 as in peak 1 purified from u2-wz4 and that the minibody peaks are absent in variant v1 as in peak 2 purified from u2-wz4. This data confirms that variant v1 is expressed as a single chain diabody-type conformational isomer and variant v3 is expressed as a bivalent scFv-type conformational isomer.

[Example 13] Activity Assessment and Stability Assessment of VH/VL Interface-Modified Sc(Fv)2

13-1. Assessment of Biological Activity of VH/VL Interface-Modified Sc(Fv)2

It has been reported in literature (Blood 2005; 105:562-566) that anti-human MpI antibody VB22B sc(Fv)2 shows TPO-like agonist activity. Accordingly, the TPO-like agonist activity of the separated conformational isomers was assessed using BaF3-human MpI or BaF3-monkey MpI that indicates TPO-dependent growth.

Each cell was washed twice with RPMI1640 (Invitrogen) containing 1% Fetal Bovine Serum (Invitrogen), then suspended in RPMI1640 containing 10% Fetal Bovine Serum to $4 \times 10^5$ cells/mL, and then dispensed into a 96-well plate at 60 μL/well. 404 of rhTPO (R&D) or the conformational isomer sample was added to each well at various concentrations and, and the cells were cultured at 37° C. under 5% $CO_2$ for 24 hours. Immediately after adding WST-8 reagent (Cell Count Reagent SF, Nakalai Tesque) at 10 μL/well, the absorbance at 450 nm (control: 655 nm) was measured on Benchmark Plus, and the absorbance at 450 nm (control: 655 nm) was measured again after culturing for 2 hours. Since WST-8 reagent exhibits a chromogenic reaction at 450 nm depending on the number of viable cells, TPO-like agonist activity was assessed using the change in absorption during the 2 hours as an indicator.

The results of assessing TPO-like agonist activity in BaF3-human MpI and BaF3-monkey MpI using the purified VB22B sc(Fv)2 conformational isomer are shown individually in FIG. 17. Comparison of agonist activity of the conformational isomers of peak 1 and peak 2 indicated that peak 2 possessed a significantly higher activity. This suggested that in order for anti-MpI antibody sc(Fv)2 to exert TPO-like agonist activity, it has to form a single chain diabody conformation.

According to the method indicated in Example 1, agonist activity of VH/VL interface-modified v1 and v3 were evaluated. Agonist activity differs greatly between the conformational isomers, and as shown in FIG. 12, peak 2 having a single chain diabody conformation showed a very high agonist activity, whereas the activity of peak 1 having a bivalent scFv conformation was decreased significantly. As shown in FIG. 22, variant v1 showed the same activity as peak 2, and variant v3 showed nearly the same activity as peak 1. Accordingly, biological activities also confirmed that variant v1 formed a single chain diabody conformation, and variant v3 forms a bivalent scFv conformation.

13-2. Assessment of Stability of VH/VL Interface-Modified Sc(Fv)2

To assess the stability of peak 1 purified from u2-wz4, peak 2 purified from u2-wz4, variant v1, and variant v3, the denaturation transition temperature (Tm value) was measured using differential scanning calorimetry under the following conditions.

DSC: N-DSCII (Applied Thermodynamics)
Elution conditions: 20 mM sodium citrate, 300 mM NaCl, pH7.0
Protein concentration: 0.1 mg/mL
Scanning speed: 1° C./minute The results of the respective DSC measurements are shown in FIG. 23. The Tm values for peak 2 purified from uw-wz4 and variant v1 had nearly the same Tm values as the unmodified form, and their stabilities were found to be the same. Between peak 1 purified from u2-wz4 and variant v3, variant v3 showed slightly lower stability. As an example of interface regulation performed according to methods that utilize the knob-into-hole technique, there is a report (Acta. Pharmacol. Sin. 2005 26(6): 649-58) that in the heterologous association of IgG CH3 domains, the Tm value for the unmodified CH3 domain is 80.4° C., whereas the Tm value for the modified CH3 domain is 69.4° C., and the Tm value decreases by a large amount and the stability decreases. In contrast, it was confirmed in the present invention that association can be regulated without decreasing the stability.

Next, stability assessment was performed by thermal acceleration tests under the following conditions on peak 1 purified from u2-wz4 and peak 2 purified from u2-wz4, and on VH/VL interface-modified variants v1 and v3.

<Thermal Acceleration Conditions>
Solution conditions: 20 mM sodium citrate, pH 6.0
Protein concentration: 0.25 mg/mL
Acceleration conditions: 40° C.—6 days, 12 days The accelerated samples were analyzed by gel filtration chromatography and cation exchange chromatography under the following conditions.

Figure 24:
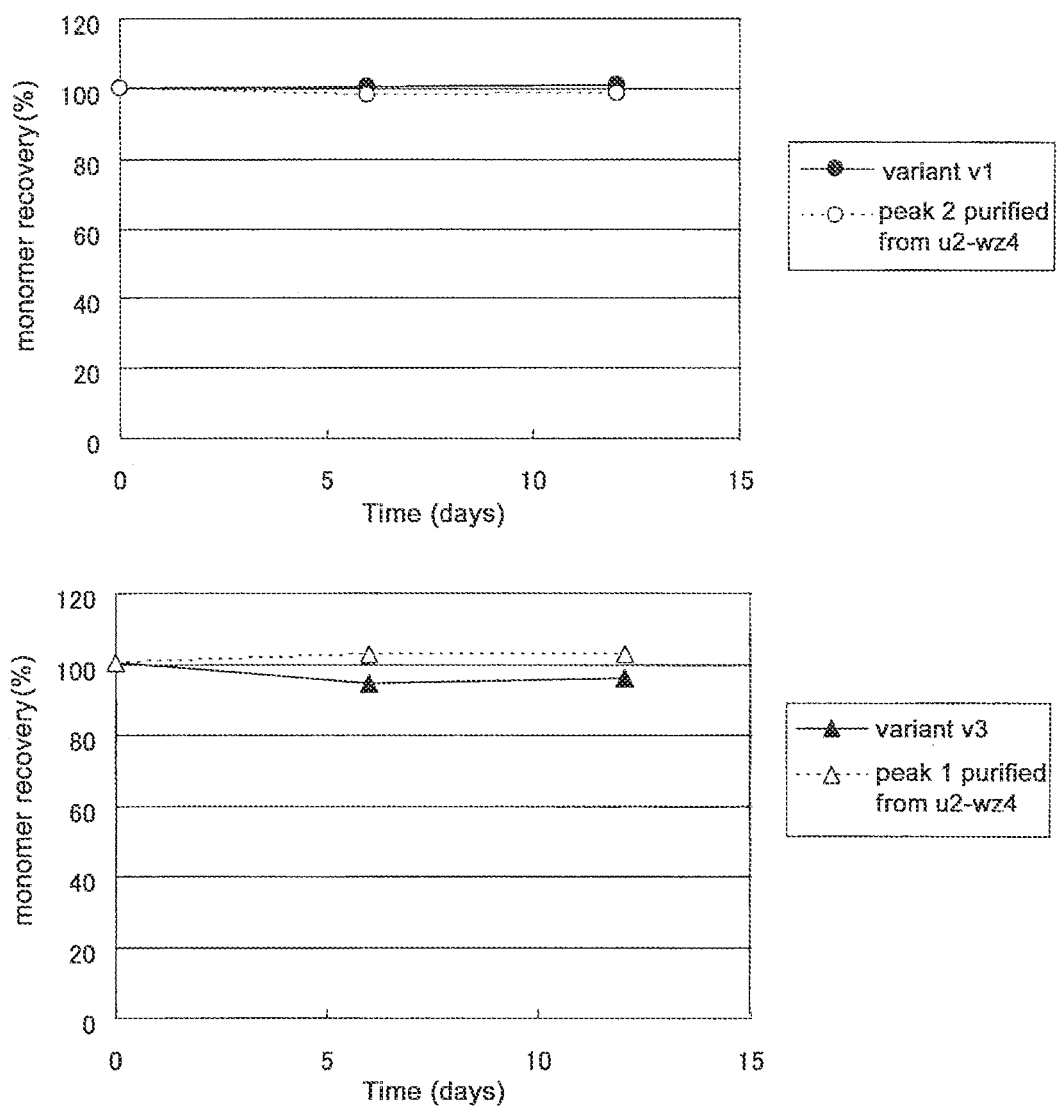
FIG. 24 depicts the percentage of monomers recovered by gel filtration chromatographic analysis in thermal acceleration tests of peak 1 purified from u2-wz4, peak 2 purified from u2-wz4, variant v1, and variant v3.

As shown in FIG. 24, the results of gel filtration chromatography analysis confirmed that the monomer recovery rate is nearly the same for peak 2 purified from u2-wz4 and variant v1, and the stability of association was nearly the same. The monomer recovery rate was also nearly the same for peak 1 purified from u2-wz4 and variant v3, and the stability of association was nearly the same in both conformational isomers.

Figure 25:
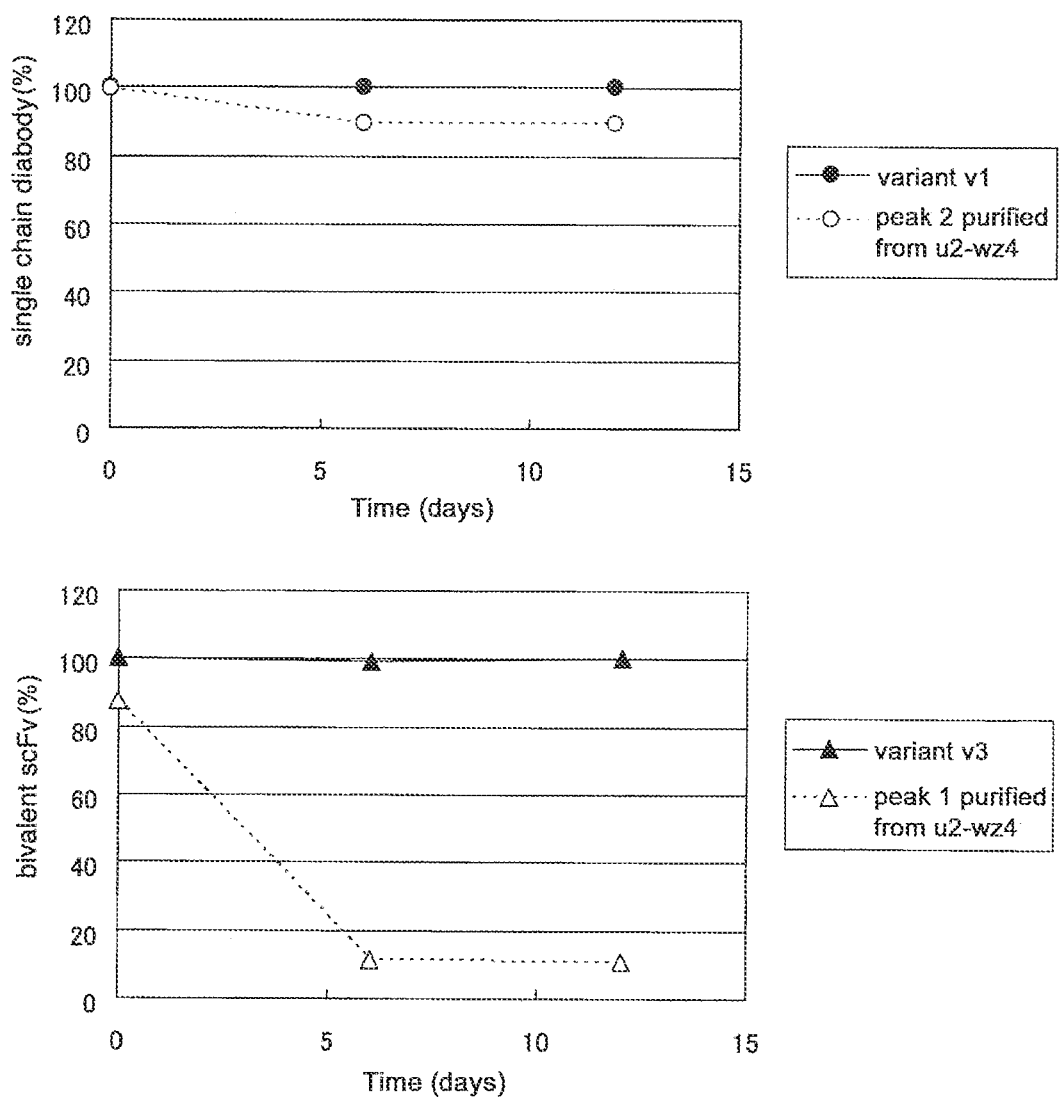
FIG. 25 depicts the conformational isomer content percentage obtained by cation exchange chromatographic analysis in thermal acceleration tests of peak 1 purified from u2-wz4, peak 2 purified from u2-wz4, variant v1, and variant v3.

As indicated in FIG. 25, as a result of cation exchange chromatography analysis, purified peak 1 in the unmodified form isomerized to peak 2 by an isomerization reaction, and purified peak 2 in the unmodified form isomerized to peak 1 by an isomerization reaction, whereas the VH/VL interface-modified v1 and v2 did not undergo an isomerization reaction even after the thermal acceleration. It was found out that applying modifications to the VH/VL interface allow one of the two types of conformational isomers alone to be expressed at 100%, and in addition, the respective conformational isomers obtained do not undergo an isomerization reaction and can be stably stored.

The present Example demonstrated that one of the two types of conformational isomers alone can be expressed at 100% by using the VH/VL interface modifications applied to v1 and v3. A known method for VH/VL-interface regulation for obtaining a single chain antibody having the conformation of interest is a method of regulating the conformations of bispecific diabodies using the knobs-into-holes technique (Protein Sci. 1997 April; 6(4):781-8, Remodeling domain interfaces to enhance heterodimer formation, Zhu Z, Presta L G; Zapata G, Carter P). It is reported that this method increases the percentage of formation of the heterodimer conformation of interest from 72% to 92% by modifying amino acids at a total of four positions per VH/VL interface. In contrast, the present invention succeeded in obtaining the conformation of interest at 100% and without decreasing the thermal stability and the stability of the conformational isomer by modifying amino acids at four positions.

[Example 14] Humanization of Bispecific Antibody Carrying a Hybrid L Chain

The bispecific antibody (Japanese Patent Application No. 2005-112514) composed of a combination of anti-Factor IXa antibody A69-VH, anti-Factor X antibody B26-VH, and hybrid L chain (BBA), which was the most effective in shortening blood coagulation time, was subjected to humanization as follows.

14-1. Homology Search of Humanized Antibodies

Using database constructed by obtaining amino acid sequence data of human antibodies from publicly disclosed Kabat Database (ftp://ftp.ebi.ac.uk/pub/databases/kabat/) and IMGT Database (http://imgt.cines.fr/), homology search was carried out separately for the mouse A69-H chain variable region (amino acid sequence: SEQ ID NO: 57), mouse B26-H chain variable region (amino acid sequence: SEQ ID NO: 58), and mouse BBA-L chain variable region (amino acid sequence: SEQ ID NO: 59). The results confirmed that they have high homologies to the human antibody sequences shown below, and it was thus decided that they would be used as the framework region (hereinafter abbreviated as FR) of humanized antibodies.

(1) A69-H chain variable region: KABATID-000064 (Kabat Database) (Kipps et al., J. Clin. Invest. 1991; 87:2087-2096)
(2) B26-H chain variable region: EMBL Accession No. AB063872 (IMGT Database) (Unpublished data)
(3) BBA-L chain variable region: KABATID-024300 (Kabat Database) (Welschof et al., J. Immunol. Method 1995; 179:203-214)
Humanized antibodies in which complementarity determining regions (hereinafter abbreviated as CDR) of each mouse antibody were grafted into the FRs of human antibodies (1)-(3) were prepared.

Also, the web homology search site publicly disclosed by NCBI (http://www.ncbi.nlm.nih.gov/BLAST/) was used to search secretory signal sequences of human antibodies that are highly homologous to the human antibodies of (1)-(3). The following secretory signal sequences obtained by the search were used.
(1) A69-H chain variable region: GenBank Accession No. AF062257
(2) B26-H chain variable region: GenBank Accession No. AAC18248
(3) BBA-L chain variable region: GenBank Accession No. AAA59100

14-2. Construction of Humanized Antibody Gene Expression Vector

Twelve synthetic oligoDNAs of about 50 bases were prepared from a nucleotide sequence encoding the amino acid sequence from the secretory signal sequence to the antibody variable region, such that about 20 bases of their 3'-end anneal with each other. Furthermore, a primer annealing to the 5'-end of an antibody variable region gene and having the XhoI cleavage sequence, and a primer annealing to the 3'-end of an antibody variable region gene, having the SfiI cleavage sequence and also encoding the 5'-end sequence of the intron sequence were prepared.

1 µL each of the synthetic oligoDNAs prepared at 2.5 µM were mixed, and 1× TaKaRa Ex Taq Buffer, 0.4 mM dNTPs, and 0.5 units TaKaRa Ex Taq (all from Takara Shuzo) were added to prepare 48 µL of a reaction solution. After heating this at 94° C. for 5 minutes, 2 cycles of reacting at 94° C. for 2 minutes, 55° C. for 2 minutes, and 72° C. for 2 minutes were performed to assemble and elongate each of the synthetic oligoDNAs. Next, 1 µL (10 µM each) of primers annealing to the 5'-end and to the 3'-end of the antibody gene were added, and the antibody variable region genes were amplified by 35 cycles of reacting at 94° C. for 30 seconds, 55° C. for 30 seconds, and 72° C. for 1 min and then reacting at 75° C. for 5 minutes. After PCR, the whole amount of the reaction solution was subjected to 1% agarose gel electrophoresis. Amplified fragments having the size of interest (approximately 400 bp) were purified using the QIAquick Gel Extraction Kit (QIAGEN) according to the method described in the instruction manual, and were eluted with 30 µL of sterile water. These fragments were cloned using the pGEM-T Easy Vector System (Promega) according to the method described in the instruction manual. Nucleotide sequence of each of the DNA fragments was determined using the BigDye Terminator Cycle Sequencing Kit (Applied Biosystems) and ABI PRISM 3730xL DNA Sequencer (Applied Biosystems) according to the method described in the instruction manual.

The H-chain variable region fragment-inserted plasmid and the L-chain variable region fragment-inserted plasmid, each of which were confirmed to have the correct humanized antibody variable region gene sequence, were digested with XhoI and SfiI, and EcoRI respectively. Then, the reaction solution was subjected to 1% agarose gel electrophoresis. DNA fragments having the size of interest (approximately 400 bp) were purified using QIAquick Gel Extraction Kit (QIAGEN) according to the method described in the instruction manual, and eluted with 30 µL of sterile water. Then, expression vectors for animal cells were prepared as follows. To preferentially express IgG4 whose H chains are of a heterologous combination, a CH3 portion amino acid-substituted IgG4 was used by referring to the knobs-into-holes technique of IgG1 (Non-Patent Document 3). Furthermore, to promote H chain dimer formation, amino acid substitution (-ppcpScp-->-ppcpPcp-) was also introduced to the hinge. Humanized A69 H chain expression vector was prepared by inserting humanized A69 H chain variable region antibody gene fragment into an expression vector prepared by inserting Y349C and T366W-substituted constant region gene to pCAGGS comprising a chicken β-actin promoter (Niwa et al. 1991 Gene, 108: 193-199). Humanized B26 H chain expression vector was prepared by inserting humanized B26 H chain variable region antibody gene fragment into an expression vector prepared by inserting E356C, T366S, L368A, and Y407V-substituted constant region gene to pCAGGS. Plasmid (pCAG-gκDNA) prepared by inserting a wild type antibody L chain constant region to pCAGGS was digested with EcoRI to prepare expression vectors inserted with humanized BBA L chain variable region antibody gene fragment. Ligation reaction was performed using Rapid DNA Ligation Kit (Roche Diagnostics), and DH5α strain *E. coli* (TOYOBO) was transformed.

14-3. Preparation of Humanized Bispecific Antibodies

Humanized bispecific antibodies were expressed according to the method described in Example 4-2 or according to the following method. Human fetal renal carcinoma cell-derived HEK293H strain (Invitrogen) was suspended in a DMEM medium (Invitrogen) containing 10% FCS (Invitrogen), and 10 mL of this was seeded at a cell density of 5-6×10$^5$ cells/mL in each dish used for adhesive cells (10-cm diameter, CORNING) and cultured for one day and night in a $CO_2$ incubator (37° C., 5% $CO_2$). Then, the medium was removed by suction, and 6.9 mL of CHO-S-SFM-II (Invitrogen) medium was added. The plasmid DNA mixture solution prepared in 14-2 (total of 13.8 µg) was mixed with 20.7 µL of 1 µg/mL Polyethylenimine (Polysciences Inc.) and 690 µL of CHO-S-SFMII medium, left to stand at room temperature for 10 minutes, then the cells were seeded into each dish and incubated in a $CO_2$ incubator (37° C., 5% $CO_2$) for 4-5 hours. Thereafter, 6.9 mL of CHO-S-SFM-II medium was added and then the cells were incubated in a $CO_2$ incubator for 3 days. The culture supernatant was recovered, then cells were removed by centrifugation (at approximately 2000 g for 5 minutes at room temperature), and the solution was sterilized by passing it through a 0.22 µm filter MILLEX®-GV (Millipore). The sample was stored at 4° C. until use.

Next, antibodies were purified according to the method described in Example 4-4, and the antibody concentration was quantified according to the method described in Example 4-5 or according to the following method. Protein A was immobilized on Sensor Chip CM5 (BIACORE) using BIAcore3000 (BIACORE). More specifically, Protein A-immobilized sensor chip was prepared according to the manufacturer's protocol by reacting an activated sensor chip with a Protein A solution diluted to 50 µg/mL with 10 mM aqueous sodium acetate solution (pH 4.0, BIACORE) at 5 µL/min for 30 minutes, and then performing a blocking operation. This sensor chip was used to measure the concentration of the culture supernatant and the purified product using BIAcore Q. HBS-EP Buffer (BIACORE) was used for the immobilization of the sensor chip and for the measurements of concentration. As a standard for concentration measurements, human IgG4 (humanized anti-TF antibody, see WO 99/51743) diluted with HBS-EP Buffer in a two-fold dilution series up to six stages beginning at 2000 ng/mL was used.

14-4. Activity Assessment of Humanized Bispecific Antibodies and Modification of Antibody Sequence To assess the plasma coagulation abilities of the prepared humanized bispecific antibody and the chimeric bispecific antibody (A69/B26/BBA), the effects of the antibodies on APTT were examined using F. VIII-deficient plasma according to the method of Example 5. A humanized bispecific antibody whose blood coagulation ability had decreased was subjected to amino acid modifications in the human antibody FR in order to increase its activity. During expression and secretion 3 types of antibodies, humanized A69/humanized BBA antibody, humanized B26/humanized BBA antibody, and humanized A69/humanized B26/humanized BBA bispecific antibody were expressed, these 3 types of antibodies were separated, and amino acid modifications that decrease the isoelectric point of the humanized A69 H chain variable region and increase the isoelectric point of the humanized B26 H chain variable region were carried out in order to purify the bispecific antibody alone. Specifically, mutations were introduced to the humanized antibody variable region using a QuikChange Site-Directed Mutagenesis Kit (Stratagene) according to the method described in the instruction manual. The H-chain variable region fragment-inserted plasmid and L-chain variable region fragment-inserted plasmid were confirmed to have the humanized antibody variable region gene sequence of interest were digested with XhoI and SfiI, and EcoRI respectively. The reaction solution was subjected to 1% agarose gel electrophoresis. DNA fragments having the size of interest (approximately 400 bp) were purified using QIAquick Gel Extraction Kit (QIAGEN) according to the method described in the instruction manual, and eluted with 30 µL of sterile water. Then, expression vectors for animal cells were prepared according to the method described in Example 14-2. Humanized bispecific antibody was prepared according to the method described in Example 14-3, and blood coagulation activity was evaluated according to the method described in Example 5.

Figure 26:
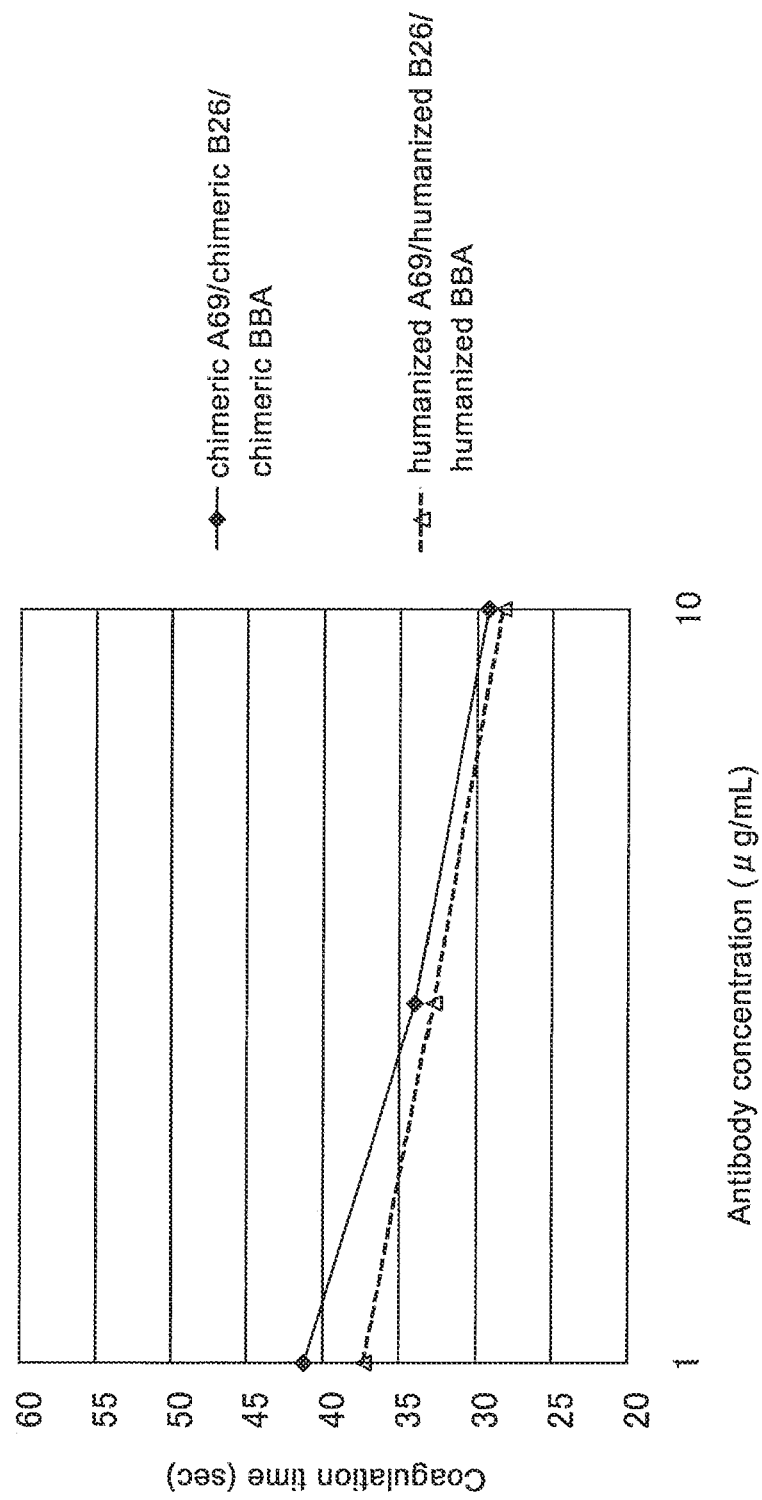
FIG. 26 depicts the results of an assay evaluating the coagulation activities of humanized bispecific antibodies (humanized A69 (hA69-PFL)/humanized B26 (hB26-PF)/humanized BBA (hAL-AQ)). The results demonstrate that the coagulation activities are equivalent to or greater than those of chimeric bispecific antibodies.

By repeated amino acid modifications of the FR sequence and assessment of blood coagulation ability, humanized bispecific antibody (humanized A69 (hA69-PFL)/humanized B26 (hB26-PF)/humanized BBA (hAL-AQ)) having the same level of activity as the chimeric bispecific antibody (A69/B26/BBA) was obtained (FIG. 26). Each of the antibody variable region sequences are indicated in the following SEQ ID NOs.
(1) humanized A69 antibody VH (hA69-PFL) SEQ ID NO: 19 (nucleotide sequence), SEQ ID NO: 20 (amino acid sequence)
(2) humanized B26 antibody VH (hB26-PF) SEQ ID NO: 21 (nucleotide sequence), SEQ ID NO: 22 (amino acid sequence)
(3) humanized BBA antibody VL (hAL-AQ) SEQ ID NO: 23 (nucleotide sequence), SEQ ID NO: 24 (amino acid sequence)

[Example 15] Selection of Amino Acid Modification Positions in the Constant Region to Improve the Formation Efficiency of a Bispecific Antibody Aiming for the increase in the formation efficiency of a bispecific antibody, a heterodimer, by using charge repulsion, examinations were carried out by modifying amino acids present at the constant region CH3 interface. First, from the crystal structure of the CH3 region (Protein Data bank, PDB code 1OQX), pairs of amino acids that interact electrostatically during CH3 homodimer formation were searched. As a result, at the interface during CH3 homodimer formation, 3 pairs, H-chain positions 356 and 439, positions 357 and 370, and positions 399 and 409 (the numbers are based on the EU numbering system (Kabat E A et al. 1991. Sequences of Proteins of Immunological Interest. NIH)), were found to be interacting electrostatically where each of the amino acids carry a positive charge and a negative charge, and these were selected as the positions for modification. It was postulated that heterodimer formation would be promoted by a modification method that carries out a modification by switching the charge of pairs of positively and negatively charged amino acids. The principle of this regulation is described in FIG. 27. Experiments were also performed with modifications that simultaneously introduce disulfide bonds to the CH3 interface. The positions of the modified amino acids are summarized in Table 1.

[Example 16] Amino Acid Modifications at the Interface of Humanized Bispecific Antibody Constant Region CH3

To modify the amino acids at the H-chain constant region CH3 interface selected in Example 15, the following operation was performed. Each H-chain constant region was amplified by PCR using the human IgG1 and human IgG4 H-chain constant region genes as templates and using a 5'-end primer designed so that the nucleotide sequence encoding two amino acids (Ala-Ser) in the N-terminal side of the H-chain constant region will be an NheI recognition sequence (GCTAGC) and a primer that anneals to the 3'-end and that carries a NotI recognizing site. Then, pBCH (comprising an IgG1 constant region gene) and pBCH4 (IgG4 comprising a constant region gene) linked to a vector prepared by digesting pBluescriptKS+ vector (TOYOBO) with NheI and Not I (both from TaKaRa) were prepared. PCR was performed using a primer that is complementary to the 5'-end nucleotide sequence of the H-chain variable region of the humanized A69 antibody and humanized B26 antibody and that has a Kozak sequence (CCACC) and an EcoRI recognition sequence, and a primer on the 3'-end nucleotide sequence having an NheI recognition sequence, and the obtained PCR products were inserted into pBCH or pBCH4 digested with EcoRI and NheI (both from TaKaRa) and the variable regions and the constant regions were linked. Next, to modify amino acids present at the H-chain constant region CH3 interface, mutations were introduced to the H-chain constant regions using QuikChange Site-Directed Mutagenesis Kit (Stratagene) according to the method described in the instruction manual. The H-chain gene fragment-inserted plasmid was confirmed to have the H-chain constant region gene sequence of interest and then was digested with EcoRI and NotI (both from TaKaRa). The reaction solution was subjected to 1% agarose gel electrophoresis. H-chain gene fragments having the size of interest (approximately 1400 bp) were purified using QIAquick Gel Extraction Kit (QIAGEN) according to the method described in the instruction manual, and eluted with 30 µL of sterile water. Then, the fragments were inserted into pCAGGS digested with EcoRI and NotI to prepare expression plasmids. Preparation of humanized bispecific antibodies was performed following the method described in Example 14-3. The positions of modified amino acids are summarized in Table 1. The EU numbering system (Kabat E A et al. 1991. Sequences of Proteins of Immunological Interest. NIH) was employed for the numbers of the modified positions shown in Table 1. The alphabet in front of the number of the modified position is the one-letter code representation for the amino acid before modification, and the alphabet after the number indicates the one letter code representation of the amino acid after modification.

TABLE 1

| | Name | Humanized A69 antibody H-chain constant region | | Humanized A26 antibody H-chain constant region | |
|---|---|---|---|---|---|
| | | Modified position | SEQ ID NO of the amino acid | Modified position | SEQ ID NO of the amino acid |
| IgG4 | wild type | — | 25 | — | 25 |
| | KiH | Y349C, T366W | 9 | E356C, T366S, L368A, Y407V | 11 |
| | s1 | R409D | 26 | D399K | 27 |
| | s2 | K370E | 28 | E357K | 29 |
| | s3 | K439E | 30 | E356K | 31 |
| | w1 | R409D, K370E | 32 | D399K, E357K | 33 |
| | w2 | R409D, K439E | 34 | D399K, E356K | 35 |
| | w3 | K370E, K439E | 36 | E357K, E356K | 37 |
| | s1C | R409D, Y349C | 38 | D399K, S354C | 39 |
| | s2C | K370E, Y349C | 40 | E357K, S354C | 41 |
| | s3C | K439E, Y349C | 42 | E356K, S354C | 43 |
| | w3C | K370E, K439E, Y349C | 44 | E357K, E356K, S354C | 45 |
| | w3C2 | K370E, K439E, S354C | 46 | E357K, E356K, Y349C | 47 |
| IgG4 | wild type | — | 48 | — | 48 |
| | KiH | Y349C, T366W | 49 | D356C, T366S, L368A, Y407V | 50 |
| | w1 | R409D, K370E | 51 | D399K, E357K | 52 |
| | w2 | R409D, K439E | 53 | D399K, E356K | 54 |
| | w3 | K370E, K439E | 55 | E357K, E356K | 56 |

In the Table shown above, KiH indicates the variant described in Non-Patent Document 3 prepared using the Knobs-into-holes technique.

[Example 17] Assessment of Formation Efficiency and Stability of the CH3 Interface-Modified Bispecific Antibodies (IgG4-Type)

Figure 28:
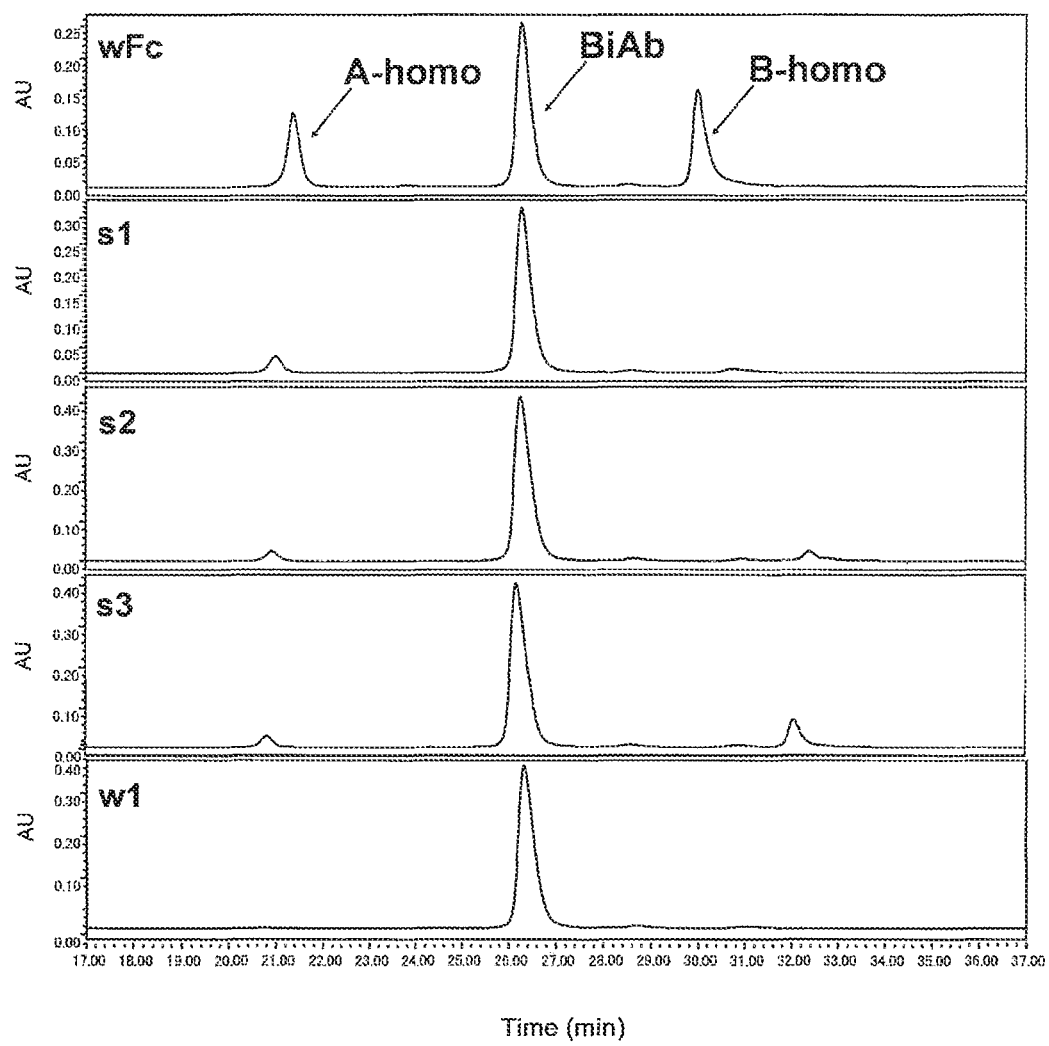
FIG. 28 depicts chromatograms of IEX analysis of humanized bispecific antibodies (IgG4-type) whose CH3 interface has been modified.

IgG4-type wild type, KiH, s1, s2, s3, w1, w2, w3, s1C, s2C, s3C, w3C, and w3C2 were analyzed by cation exchange chromatography (IEX), and the formation efficiency of bispecific antibody (hereinafter referred to as BiAb) was evaluated. The conditions for the cation exchange chromatographic analysis were as follows, and the ratio of the peak areas of A-Homo, a homodimer of humanized A69 antibody, BiAb, a heterodimer of humanized A69 antibody and humanized B26 antibody, and B-Homo, a homodimer of humanized B26 antibody were calculated.
Column: ProPac WCX-10, 4×250 nm, (Dionex)
Mobile phase: A: 10 mmol/L NaH$_2$PO$_4$/Na$_2$HPO$_4$, pH6.25
  B: 10 mmol/L NaH$_2$PO$_4$/Na$_2$HPO$_4$, 500 mmol/L NaCl, pH6.25
Flow rate: 1.0 mL/min
Gradient: 10% B (5 min)-->(40 min)-->60% B-->(5 min)-->100% B (5 min)
Detection: 220 nm For Wild type, KiH, s2, s3, s1C, s2C, s3C, w3C, and w3C2, BiAbs were purified by collecting BiAb peak fractions from the IEX analyses described above. The BiAb fractions were concentrated using Amicon Ultra, MWCO 10000 (Millipore), then dialyzed overnight against 20 mM sodium acetate, 150 mM NaCl, pH6.0 while cooling, and then recovered. BiAb concentrations were made uniform at 0.1 mg/mL, initial samples and samples at 60° C. for one week (60° C.-1 week) were individually dispensed into vials in duplicates, and stability tests were performed on the 60° C.-1 week samples. Gel filtration chromatographic (SEC) analysis was performed, and the rate of recovery of the monomer peak was calculated (60° C.-1 week sample monomer peak area/initial sample monomer peak area×100). Conditions for the gel filtration chromatographic analyses were as follows:

Column: Super3000 (TOSOH)
Mobile phase: 50 mM sodium phosphate, 300 mM KCl, pH7.0
Flow rate: 0.2 mL/min
Detection: 220 nm The IEX chromatograms of the IgG4-type wild type, s1, s2, s3, and w1 are shown in FIG. 28, and the percentages of formation of A-Homo, BiAb, and B-Homo by the wild type, KiH, s1, s2, s3, w1, w2, w3, s1C, s2C, s3C, w3C, and w3C2 are shown in FIG. 29. The monomer recovery rates after 60° C. for one week are shown in FIG. 30.

As shown in FIGS. 28 and 29, efficiency of the intended BiAb formation improved greatly as compared to the wild type for every one of the CH3 interface-modified variants found in the present Example. Since CH3 is in the constant region, when making modifications to the native amino acids, the modified positions are desirably kept to minimum from the viewpoint of antigenicity. For introduction of knobs and holes, in KiH, a total of four positions in the both H chains are modified and in addition two positions are modified for disulfide bond introduction, and a total of six positions are modified. Therefore, as shown in FIG. 29, the efficiency of BiAb formation is high. However, the results of stability tests shown in FIG. 30 shows that thermal stability is significantly lowered compared to the wild type even though a disulfide bond is introduced. To develop antibodies into medical pharmaceuticals, stable formulations are necessary and thus, a higher thermal stability is more desirable.

On the other hand, every one of the CH3 interface-modified variants found in the present Example was successful in greatly improving the efficiency of the intended BiAb formation as compared to the wild type. Among these variants, for example, high BiAb formation efficiency of 90% or more was achieved by modification of s2, s3, w1, w2, w3, and s1C at a total of two or four positions which is fewer compared to KiH (six modified positions), which the risk of antigenicity is considered to be low. Furthermore, the results of stability tests shown in FIG. 30 showed that among the variants, for example, s2, s3, w3, w3C, and w3C2 have high BiAb formation efficiency of 90% or more and also have higher thermal stability (higher percentage of monomer recovery) than KiH, and s3, s2c, s3C, w3C, and w3C2 have much higher thermal stability than the wild type, and they will be useful for developing stable pharmaceutical formulations.

The present Example demonstrated that by modifying the amino acids at H-chain positions 356, 357, 370, 399, 409, and 439 in the CH3 interface to introduce charge-induced molecular repulsion, efficiency of the intended BiAb formation could be greatly improved. It also showed that by introducing disulfide bonds and such modifications individually or in combination, BiAb formation efficiency could be greatly improved with fewer modifications than in KiH, and that BiAb formation efficiency could be greatly improved with higher stability than in KiH, and even more with a higher thermal stability than in the wild type.

Figure 31:
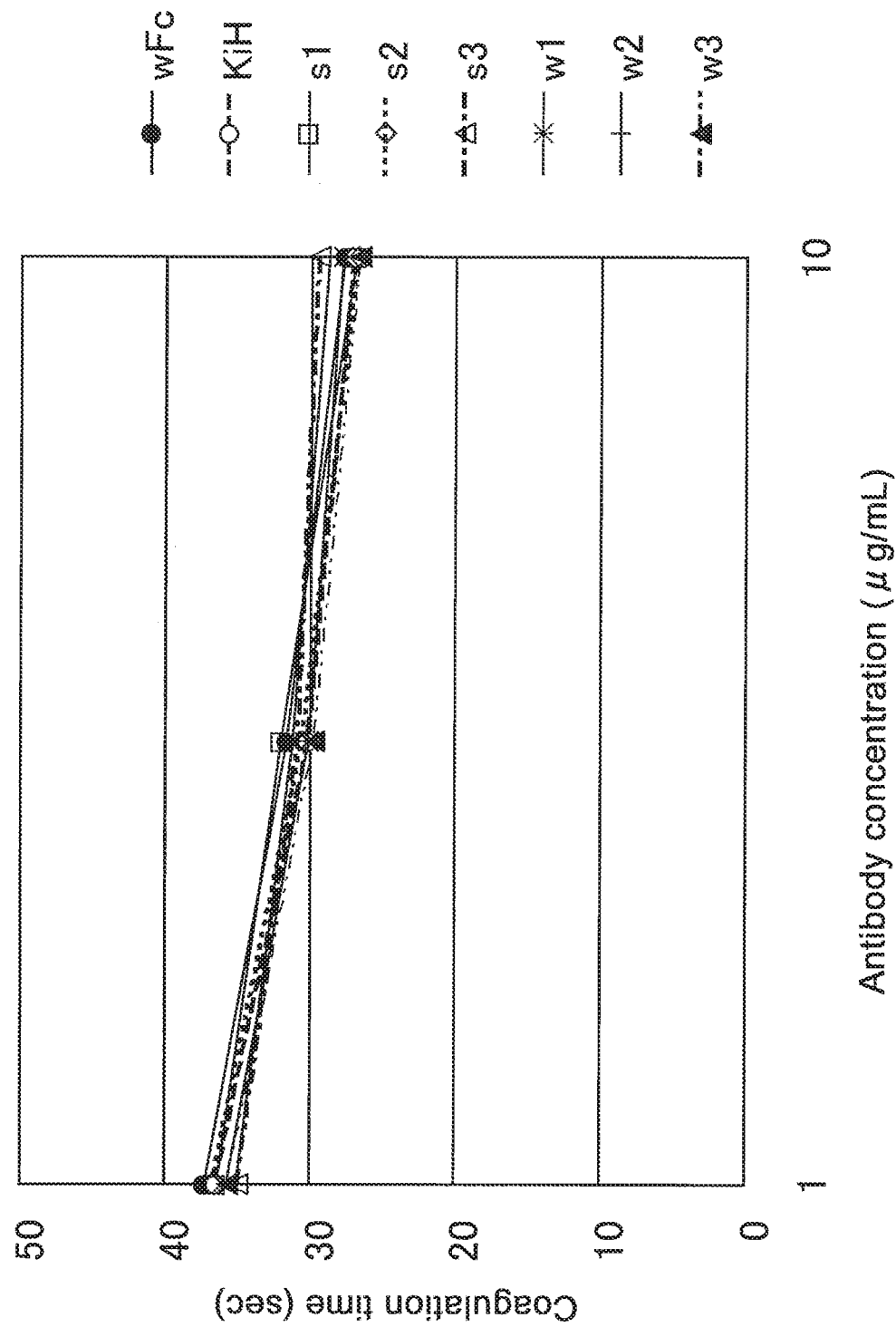
FIG. 31 depicts the results of an assay evaluating coagulation activity of humanized bispecific antibodies (IgG4-type) whose CH3 interface has been modified. The results demonstrate that the coagulation activities are equivalent to that of the unmodified bispecific antibody.

[Example 18] Coagulation Activity Assessment of CH3 Interface-Modified Bispecific Antibodies Coagulation activity was assessed according to the method described in Example 5, using CH3 interface-modified IgG4-type bispecific antibodies (s1, s2, s3, w1, w2, and w3) purified in Example 16. As shown in FIG. 31, since coagulation activity did not change even when the amino acids at the constant region CH3 interface was modified, modification of CH3 interface amino acids were shown not to affect the structure of the variable regions involved in reacting with the antigens.

[Example 19] Assessment of the Formation Efficiency of CH3 Interface-Modified Bispecific Antibodies (IgG1-Type)

IgG1-type wild type, KiH, w1, w2, and w3 were analyzed by cation exchange chromatography (IEX), and BiAb formation efficiency was evaluated. The conditions of the cation exchange chromatographic analysis are as follows, and the ratio of the peak areas of A-Homo, a homodimer of humanized A69 antibody, BiAb, a heterodimer of humanized A69 antibody and humanized B26 antibody, and B-Homo, a homodimer of humanized B26 antibody were calculated.

Column: ProPac WCX-10, 4×250 nm, (Dionex)
Mobile phase: A: 10 mmol/L $NaH_2PO_4/Na_2HPO_4$, pH6.25
 B: 10 mmol/L $NaH_2PO_4/Na_2HPO_4$, 500 mmol/L NaCl, pH6.25
Flow rate: 1.0 mL/min
Gradient: 10% B (5 min)-->(40 min)-->60% B-->(5 min)-->100% B (5 min)
Detection: 220 nm The percentages of formation of A-Homo, BiAb, and B-Homo by the IgG1-type wild type, KiH, w1, w2, and w3 are shown in FIG. 32. Alike IgG4-type, the efficiency of the intended BiAb formation greatly improved in every one of them as compared to the wild type. As in the IgG4-types, high BiAb formation efficiency of 90% or more was achieved by modification at four positions, which is less than that of KiH, and the risk of antigenicity is considered to be small. The present Example showed that the method of modifying the amino acids at H-chain positions 356, 357, 370, 399, 409, and 439 in the CH3 interface can be applied not only to antibody constant region subclass IgG4, but also to the IgG1, and is applicable to IgG antibodies in general.

INDUSTRIAL APPLICABILITY

In that the present invention requires only a small number of amino acid substitutions, the methods of the present invention find exceptional utility in regulating association without changing the structure and function (activity) of the original polypeptides. Thus, there is little effect on antigenicity. Accordingly, bispecific antibodies that actually maintain activity can be obtained efficiently by following the methods of the present invention.

The invention claimed is:

1. A method for producing a desired multi-specific antibody, the method comprising
    (a) identifying a first polypeptide that forms part of a multi-specific antibody by associating directly with either (i) a second polypeptide different from the first polypeptide or (ii) a third polypeptide different from the first and second polypeptides, wherein the first polypeptide comprises an antibody heavy chain CH1 region, wherein each of the second and third polypeptides respectively comprises an antibody light chain CL region, wherein the amino acid residue at position 221 (Kabat numbering) ("H221") of the heavy chain CH1 region of the first polypeptide and the amino acid residue at position 123 (Kabat numbering) ("L123") of the light chain CL region of the second or third polypeptide can form part or all of an interface in the multi-specific antibody, wherein the residue at L123 of the second polypeptide is a charged residue and the residue at H221 of the first polypeptide is either uncharged or has a charge different from that of the residue at L123 of the second polypeptide, wherein the multi-specific antibody contains a fourth polypeptide comprising an antibody heavy chain CH1 region, and wherein the fourth polypeptide is different from the first, second, and third polypeptides;
- (b) producing a nucleic acid encoding a modified first polypeptide in which the residue at H221 is substituted with a substitute residue of the same charge as the residue at L123 of the second polypeptide, wherein the like charges of the substitute residue and the residue at L123 of the second polypeptide inhibit direct association between the modified first polypeptide and the second polypeptide;
- (c) expressing the nucleic acid of (b), a nucleic acid encoding the second polypeptide, a nucleic acid encoding the third polypeptide, and a nucleic acid encoding the fourth polypeptide, thereby producing an expression product, wherein the residue at H221 of the heavy chain CH1 region of the fourth polypeptide has either no charge or a charge that is opposite to that of the substitute residue; and
- (d) collecting the expression product of (c), the expression product comprising the desired multi-specific antibody comprising (1) the modified first polypeptide associated directly with the third polypeptide, and (2) the second polypeptide associated directly with the fourth polypeptide.

2. The method of claim 1, wherein the amino acid residue at L123 of the third polypeptide is not glutamic acid (E), and has a charge that is opposite to that of the substitute residue.

3. The method of claim 1, wherein the amino acid residue at H221 of the fourth polypeptide has a charge that is opposite to that of the substitute residue.

4. The method of claim 1, wherein the substitute residue at H221 of the modified first polypeptide is glutamic acid (E) and the amino acid residue at L123 of the second polypeptide is glutamic acid (E).

5. The method of claim 1, wherein the amino acid residue at L123 of the third polypeptide is arginine (R) and the amino acid residue at H221 of the fourth polypeptide is lysine (K).

6. The method of claim 1, wherein the modified first polypeptide comprises an antibody heavy chain CH3 region and the fourth polypeptide comprises an antibody heavy chain CH3 region that is different from the CH3 region of the modified first polypeptide, and wherein the two CH3 regions associate together by a knobs-into-holes arrangement, with a "knob" in one of the CH3 regions associating with a "hole" in the other.

7. The method of claim 6, wherein the CH3 region of the modified first polypeptide comprises at least one of: a cysteine at position 356 (EU numbering), a serine at position 366 (EU numbering), an alanine at position 368 (EU numbering), and a valine at position 407 (EU numbering); and
the CH3 region of the fourth polypeptide comprises one or both of a cysteine at position 349 (EU numbering) and a tryptophan at position 366 (EU numbering).

8. The method of claim 1, wherein the multi-specific antibody of (d) is a bispecific antibody.

9. A method for producing a desired multi-specific antibody, the method comprising
- (a) identifying a first polypeptide that forms a multi-specific antibody by associating directly with either (i) a second polypeptide different from the first polypeptide or (ii) a third polypeptide different from the first and second polypeptides, wherein the first polypeptide comprises an antibody light chain CL region, wherein each of the second and third polypeptides respectively comprises an antibody heavy chain CH1 region, wherein the amino acid residue at position 123 (Kabat numbering) ("L123") of the light chain CH1 region of the first polypeptide and the amino acid residue at position 221 (Kabat numbering) ("H221") of the heavy chain CH1 region of the second or third polypeptide can form part or all of an interface in the multi-specific antibody, wherein the residue at H221 of the second polypeptide is a charged residue, wherein the residue at L123 of the first polypeptide is either uncharged or has a charge different from that of the residue at H221 of the second polypeptide, wherein the multi-specific antibody contains a fourth polypeptide comprising an antibody light chain CL region, and wherein the fourth polypeptide is different from the first, second, and third polypeptides;
- (b) producing a nucleic acid encoding a modified first polypeptide in which the residue at L123 is substituted with a substitute residue of the same charge as the residue at H221 of the second polypeptide, wherein the like charges of the substitute residue and the residue at H221 of the second polypeptide inhibit direct association between the modified first polypeptide and the second polypeptide;
- (c) expressing the nucleic acid of (b), a nucleic acid encoding the second polypeptide, a nucleic acid encoding the third polypeptide, and a nucleic acid encoding the fourth polypeptide, thereby producing an expression product, wherein the residue at L123 of the light chain CL region of the fourth polypeptide has either no charge or a charge that is opposite to that of the substitute residue; and
- (d) collecting the expression product of (c), the expression product comprising the desired multi-specific antibody comprising (1) the modified first polypeptide associated directly with the third polypeptide, and (2) the second polypeptide associated directly with the fourth polypeptide.

10. The method of claim 9, wherein the amino acid residue at H221 of the third polypeptide is not lysine (K), and has a charge that is opposite to that of the substitute residue.

11. The method of claim 9, wherein the amino acid residue at L123 of the fourth polypeptide has a charge that is opposite to that of the substitute residue.

12. The method of claim 9, wherein the substitute residue at L123 of the modified first polypeptide is arginine (R) and the amino acid residue at H221 of the second polypeptide is lysine (K).

13. The method of claim 9, wherein the amino acid residue at H221 of the third polypeptide is glutamic acid (E) and the amino acid residue at L123 of the fourth polypeptide is glutamic acid (E).

14. The method of claim 9, wherein the second polypeptide comprises an antibody heavy chain CH3 region and the third polypeptide comprises an antibody heavy chain CH3 region that is different from the CH3 region of the second polypeptide, and wherein the two CH3 regions associate together by a knobs-into-holes arrangement, with a "knob" in one of the CH3 regions associating with a "hole" in the other.

15. The method of claim 14, wherein
the CH3 region of the second polypeptide comprises one or both of a cysteine at position 349 (EU numbering) and a tryptophan at position 366 (EU numbering); and
the CH3 region of the third polypeptide comprises at least one of: a cysteine at position 356 (EU numbering), a serine at position 366 (EU numbering), an alanine at position 368 (EU numbering), and a valine at position 407 (EU numbering).

16. The method of claim 9, wherein the multi-specific antibody of (d) is a bispecific antibody.

17. A method for producing a desired multi-specific antibody, the method comprising
(a) identifying a first polypeptide that forms part of a multi-specific antibody by associating directly with either (i) a second polypeptide different from the first polypeptide or (ii) a third polypeptide different from the first and second polypeptides,
wherein the first polypeptide comprises an antibody heavy chain CH1 region, wherein each of the second and third polypeptides respectively comprises an antibody light chain CL region,
wherein the amino acid residue at position 221 (Kabat numbering) ("H221") of the heavy chain CH1 region of the first polypeptide and the amino acid residue at position 123 (Kabat numbering) ("L123") of the light chain CL region of the second or third polypeptide can form part or all of an interface in the multi-specific antibody,
wherein the residue at L123 of the second polypeptide is a charged residue, the residue at H221 of the first polypeptide is either uncharged or has a charge different from that of the residue at L123 of the second polypeptide, and the residue at L123 of the third polypeptide is either uncharged or has a charge that is same as the residue at L123 of the second polypeptide,
wherein the multi-specific antibody contains a fourth polypeptide comprising an antibody heavy chain CH1 region, and
wherein the fourth polypeptide is different from the first, second, and third polypeptides;
(b) producing a nucleic acid encoding a modified first polypeptide in which the residue at H221 is substituted with a first substitute residue of the same charge as the residue at L123 of the second polypeptide, wherein the like charges of the first substitute residue and the residue at L123 of the second polypeptide inhibit direct association between the modified first polypeptide and the second polypeptide;
(c) producing a nucleic acid encoding a modified third polypeptide in which the residue at L123 is substituted with a second substitute residue, wherein the second substitute residue has a charge that is opposite to that of the first substitute residue;
(d) expressing the nucleic acids of (b) and (c), a nucleic acid encoding the second polypeptide, and a nucleic acid encoding the fourth polypeptide, thereby producing an expression product comprising the desired multi-specific antibody comprising (1) the modified first polypeptide associated directly with the modified third polypeptide, and (2) the second polypeptide associated directly with the fourth polypeptide, wherein the residue at H221 of the heavy chain CH1 region of the fourth polypeptide has either no charge or a charge that is opposite to that of the first substitute residue; and
(e) collecting the expression product of (d).

18. The method of claim 17, wherein the amino acid residue at H221 of the fourth polypeptide has a charge that is opposite to that of the first substitute residue.

19. The method of claim 17, wherein the first substitute residue is glutamic acid (E) and the amino acid residue at L123 of the second polypeptide is glutamic acid (E).

20. The method of claim 17, wherein the second substitute residue is arginine (R) and the amino acid residue at H221 of the fourth polypeptide is lysine (K).

21. The method of claim 17, wherein the multi-specific antibody is a bispecific antibody.

22. The method of claim 21, wherein the modified first polypeptide comprises an antibody heavy chain CH3 region and the fourth polypeptide comprises an antibody heavy chain CH3 region that is different from the CH3 region of the modified first polypeptide, and wherein the two CH3 regions associate together by a knobs-into-holes arrangement, with a "knob" in one of the CH3 regions associating with a "hole" in the other.

23. The method of claim 22, wherein the CH3 region of the modified first polypeptide comprises at least one of: a cysteine at position 356 (EU numbering), a serine at position 366 (EU numbering), an alanine at position 368 (EU numbering), and a valine at position 407 (EU numbering); and the CH3 region of the fourth polypeptide comprises one or both of a cysteine at position 349 (EU numbering) and a tryptophan at position 366 (EU numbering).

24. A method for producing a desired bispecific antibody, the method comprising
(a) expressing a nucleic acid encoding a first antibody heavy chain, a nucleic acid encoding a second antibody heavy chain, a nucleic acid encoding a first antibody light chain, and a nucleic acid encoding a second antibody light chain, thereby producing an expression product comprising the desired bispecific antibody in which (1) the first antibody heavy chain is associated directly with the first antibody light chain and (2) the second antibody heavy chain is associated directly with the second antibody light chain,
wherein the first antibody heavy chain has a charged amino acid residue at position 221 (Kabat numbering) ("H1-221"), and the second antibody heavy chain has a charged amino acid residue at position 221 (Kabat numbering) ("H2-221") that is opposite in charge to the amino acid residue at H1-221,
wherein the first antibody light chain has a charged amino acid residue at position 123 (Kabat numbering) ("L1-123"), and the second antibody light chain has a charged amino acid residue at position 123 (Kabat numbering) ("L2-123") that is opposite in charge to the amino acid residue at L1-123,
wherein the amino acid residue at H1-221 has the same charge as the amino acid residue at L2-123, thereby inhibiting direct association between the first antibody heavy chain and the second antibody light chain, but has a charge opposite to that of the amino acid residue at L1-123, thereby permitting the first antibody heavy chain to associate directly with the first antibody light chain,
wherein the amino acid residue at H2-221 has the same charge as the amino acid residue at L1-123, thereby inhibiting direct association between the second antibody heavy chain and the first antibody light chain, but has a charge opposite to that of the amino acid residue at L2-123, thereby permitting the second antibody heavy chain to associate directly with the second antibody light chain; and (b) collecting the expression product of (a).

25. The method of claim 24, wherein the amino acid residue at H1-221 is glutamic acid (E), and the amino acid residue at L2-123 is glutamic acid (E).

26. The method of claim 24, wherein the amino acid residue at L1-123 is arginine (R) and the amino acid residue at H2-221 is lysine (K).

27. The method of claim 24, wherein the first antibody heavy chain comprises a CH3 region and the second antibody heavy chain comprises a CH3 region that is different from the CH3 region of the first antibody heavy chain, and wherein the two CH3 regions associate together by a knobs-into-holes arrangement, with a "knob" in one of the CH3 regions associating with a "hole" in the other.

28. The method of claim 26, wherein
one of the CH3 regions comprises at least one of: a cysteine at position 356 (EU numbering), a serine at position 366 (EU numbering), an alanine at position 368 (EU numbering), and a valine at position 407 (EU numbering); and
the other CH3 region comprises one or both of a cysteine at position 349 (EU numbering) and a tryptophan at position 366 (EU numbering).

29. A bispecific antibody comprising
a first polypeptide comprising an antibody heavy chain CH1 region;
a second polypeptide comprising an antibody light chain CL region;
a third polypeptide comprising an antibody light chain CL region different from the CL region of the second polypeptide; and
a fourth polypeptide comprising an antibody heavy chain CH1 region different from the CH1 region of the first polypeptide,
wherein the amino acid residue at position 221 (Kabat numbering) ("H221") of the heavy chain CH1 region of the first polypeptide and the amino acid residue at position 123 (Kabat numbering) ("L123") of the light chain CL region of the third polypeptide form part or all of an interface in the multi-specific antibody,
wherein the amino acid residue at position 221 (Kabat numbering) ("H221") of the heavy chain CH1 region of the fourth polypeptide and the amino acid residue at position 123 (Kabat numbering) ("L123") of the light chain CL region of the second polypeptide form part or all of an interface in the multi-specific antibody,
wherein the amino acid residue at H221 of the first polypeptide and the amino acid residue at L123 of the second polypeptide either both have a positive charge or both have a negative charge,
wherein the amino acid residue at L123 of the third polypeptide is either uncharged or has a charge that is opposite to that of the amino acid residue at H221 of the first polypeptide, and
wherein the amino acid residue at H221 of the fourth polypeptide is either uncharged or has a charge that is opposite to the charge of the amino acid residue at L123 of the second polypeptide.

30. The antibody of claim 29, wherein the amino acid residue at H221 of the first polypeptide has a charge that is opposite to that of the amino acid residue at L123 of the third polypeptide.

31. The antibody of claim 29, wherein the amino acid residue at H221 of the first polypeptide is glutamic acid (E) and the amino acid residue at L123 of the second polypeptide is glutamic acid (E).

32. The antibody of claim 29, wherein the amino acid residue at L123 of the third polypeptide is arginine (R) and the amino acid residue at H221 of the fourth polypeptide is lysine (K).

33. The antibody of claim 29, wherein the first polypeptide comprises an antibody heavy chain CH3 region and the fourth polypeptide comprises an antibody heavy chain CH3 region that is different from the CH3 region of the first polypeptide, and wherein the two CH3 regions associate together by a knobs-into-holes arrangement, with a "knob" in one of the CH3 regions associating with a "hole" in the other.

34. The antibody of claim 33, wherein
the CH3 region of the first polypeptide comprises at least one of: a cysteine at position 356 (EU numbering), a serine at position 366 (EU numbering), an alanine at position 368 (EU numbering), and a valine at position 407 (EU numbering); and
the CH3 region of the fourth polypeptide comprises one or both of a cysteine at position 349 (EU numbering) and a tryptophan at position 366 (EU numbering).

35. A bispecific antibody comprising
a first antibody heavy chain, a second antibody heavy chain, a first antibody light chain, and a second antibody light chain, wherein the first antibody heavy chain is associated directly with the first antibody light chain and the second antibody heavy chain is associated directly with the second antibody light chain,
wherein the first antibody heavy chain has a charged amino acid residue at position 221 (Kabat numbering) ("H1-221"), and the first antibody light chain has a charged amino acid residue at position 123 (Kabat numbering) ("L1-123") that is opposite in charge to the amino acid residue at H1-221,
wherein the second antibody heavy chain has a charged amino acid residue at position 221 (Kabat numbering) ("H2-221") and the second antibody light chain has a charged amino acid residue at position 123 (Kabat numbering) ("L2-123") that is opposite in charge to the amino acid residue at H2-221, and
wherein the amino acid residue at H1-221 has the same charge as the amino acid residue at L2-123, and the amino acid residue at H2-221 has the same charge as the amino acid residue at L1-123.

36. The bispecific antibody of claim 35, wherein the amino acid residue at H1-221 is glutamic acid (E), and the amino acid residue at L2-123 is glutamic acid (E).

37. The bispecific antibody of claim 35, wherein the amino acid residue at L1-123 is arginine (R) and the amino acid residue at H2-221 is lysine (K).

38. The bispecific antibody of claim 35, wherein the first antibody heavy chain comprises a CH3 region and the second antibody heavy chain comprises a CH3 region that is different from the CH3 region of the first antibody heavy chain, and wherein the two CH3 regions associate together by a knobs-into-holes arrangement, with a "knob" in one of the CH3 regions associating with a "hole" in the other.

39. The bispecific antibody of claim 38, wherein
one of the CH3 regions comprises at least one of: a cysteine at position 356 (EU numbering), a serine at position 366 (EU numbering), an alanine at position 368 (EU numbering), and a valine at position 407 (EU numbering); and
the other CH3 region comprises one or both of a cysteine at position 349 (EU numbering) and a tryptophan at position 366 (EU numbering).

* * * * *